(12) United States Patent
Furusako et al.

(10) Patent No.: US 8,252,905 B2
(45) Date of Patent: Aug. 28, 2012

(54) ANTI-CD14 ANTIBODY FUSION PROTEIN

(75) Inventors: Shoji Furusako, Tokyo (JP); Kazuyuki Nakayama, Tokyo (JP); Yoshitaka Hosaka, Tokyo (JP); Tetsushi Kawahara, Tokyo (JP); Masaki Nakamura, Tokyo (JP); Takashi Takeuchi, Tokyo (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 383 days.

(21) Appl. No.: 11/791,888

(22) PCT Filed: Jun. 5, 2006

(86) PCT No.: PCT/JP2006/311255
§ 371 (c)(1),
(2), (4) Date: May 30, 2007

(87) PCT Pub. No.: WO2006/129849
PCT Pub. Date: Dec. 7, 2006

(65) Prior Publication Data
US 2008/0286290 A1 Nov. 20, 2008

(30) Foreign Application Priority Data
Jun. 3, 2005 (JP) .................................. 2005-164901

(51) Int. Cl.
*C07K 16/24* (2006.01)
*C07K 16/46* (2006.01)
(52) U.S. Cl. ............... 530/387.3; 530/388.23; 530/388.1
(58) Field of Classification Search ......................... None
See application file for complete search history.

(56) References Cited

U.S. PATENT DOCUMENTS

| | | |
|---|---|---|
| 5,256,770 A | 10/1993 | Glaser et al. |
| 5,409,895 A | 4/1995 | Morishita et al. |
| 5,451,659 A | 9/1995 | Morishita et al. |
| 5,466,668 A | 11/1995 | Glaser et al. |
| 5,589,360 A | 12/1996 | Morishita et al. |
| 5,679,770 A | 10/1997 | Morishita et al. |
| 5,730,980 A | 3/1998 | Ulevitch et al. |
| 5,792,629 A | 8/1998 | Morishita et al. |
| 5,820,858 A | 10/1998 | Leturcq et al. |
| 5,827,824 A | 10/1998 | Light et al. |
| 5,851,983 A | 12/1998 | Sugiyama et al. |
| 5,863,760 A | 1/1999 | Light et al. |
| 5,869,055 A | 2/1999 | Juan et al. |
| 6,063,763 A | 5/2000 | Light et al. |
| 2004/0091478 A1 | 5/2004 | Furusako et al. |
| 2004/0092712 A1 | 5/2004 | Furusako et al. |

FOREIGN PATENT DOCUMENTS

| | | |
|---|---|---|
| JP | 4-505554 A | 10/1992 |
| JP | 5-84083 A | 4/1993 |
| JP | 5-308988 A | 11/1993 |
| JP | 6-25289 A | 2/1994 |
| JP | 6-80697 A | 3/1994 |
| JP | 6-321989 A | 11/1994 |
| JP | 2744130 B2 | 3/1998 |
| JP | 10-512142 A | 2/1999 |
| WO | WO-94/28025 A1 | 12/1994 |
| WO | WO-01/72993 A1 | 10/2001 |
| WO | WO-02/42333 A1 | 5/2002 |
| WO | WO-03/092602 A2 | 11/2003 |

OTHER PUBLICATIONS

Rudikoff et al. PNAS 1982 79:1979.*
Attwood Science 290: 471-473, 2000.*
Skolnick et al. Trends in Biotech. 18: 34-39, 2000.*
MacCallum et al. J. Mol. Biol. (1996) 262, 732-745.*
Pascalis et al. The Journal of Immunology (2002) 169, 3076-3084.*
Casset et al. BBRC 2003, 307:198-205.*
Vajdos et al. J. Mol. Biol. (2002) 320, 415-428.*
Chen et al. J. Mol. Bio. (1999) 293, 865-881.*
Wu et al. J. Mol. Biol. (1999) 294, 151-162.*
Padlan et al. PNAS 1989, 86:5938-5942.*
Lamminmaki et al. JBC 2001, 276:36687-36694.*
The Merck Manuals Online Medical Library, [online]. Whitehouse Station, NJ: Merck Research Laboratories, 2006-2007. [retrieved on Nov. 19, 2007]. Retrieved from the Internet: < URL: http://www.merck.com/mmpe/print/sec06/ch068/ch068a.html>. Sepsis and Septic Shock. see pp. 1-5.*
Inoue, K. et al., Mol. Pharmacol., Mar. 2005, vol. 67, No. 3, pp. 673 to 680.
Kenji Okajima, Shinshu to Men'eki, 2002, vol. 11, No. 4, pp. 114 to 117.
Mitsuhiro Uchiba, Kokyu, 2002, vol. 21, No. 8, pp. 691 to 697.
Toru Kojima et al., The Japanese Journal of Gastroenter ological Surgery, 2003, vol. 36, No. 7, pp. 1102 (pp. 3-106).
Yutaka Eguchi, Igaku no Ayumi, 2003, vol. 206, No. 1, pp. 19 to 22.
Inoue, K. et al., Mol. Pharmacol.., Mar. 2005, vol. 67, No. 3, pp. 673 to 680.
Haziot A. et al., J. Immunol., 1995, 154, 6529-6532.
Rivard G.E. et al., J. Pediatr., 1995, 126, 646-652.
Fourrier F. et al., Chest, 1993, 104, 882-888.
Abraham E., Crit. Care Med., 2000, 28, S31-33.
Bernard, G.R. et al., N. Engl. J. Med., 2001, 344, 699-709.
Latureq D.J., et al., J Clin Invest, 1996, 98, 1533-1538.
Reinhart K., et al., Crit Care Med, 2004, 32, 1100-1108.
Murata A., et al., Inflammation, 1994, 18, 337-347.

* cited by examiner

*Primary Examiner* — Sharon Wen
(74) *Attorney, Agent, or Firm* — Birch, Stewart, Kolasch & Birch, LLP

(57) ABSTRACT

A protein comprising (I) an anti-CD14 antibody or its active fragment, or a derivative thereof and (II) an inhibitor for a protease, or its active fragment, or a derivative thereof is provided.

53 Claims, 60 Drawing Sheets

FIG. 1

DNA sequence SEQ ID NO:123
PRT sequence SEQ ID NO:124

ATGGATTGGTTGTGGAACTTGCTATTCCTGATGGTAGTTGCCCAAAGTGCTCAAGCACAG
METAspTrpLeuTrpAsnLeuLeuPheLeuMETValValAlaGlnSerAlaGlnAlaGln

ATCCAGTTGGTACAGTCTGGACCTGAACTGAAGAAGCCTGGAGAGTCAGTGAAGATCTCC
IleGlnLeuValGlnSerGlyProGluLeuLysLysProGlyGluSerValLysIleSer

TGCAAGGCTTCTGGGTATACCTTCACAGACTATGCAATGAACTGGGTGAAACAGGCTCCA
CysLysAlaSerGlyTyrThrPheThrAspTyrAlaMETAsnTrpValLysGlnAlaPro

GGAAATGGCTTGAAGTGGATGGGCTGGATCAACACCCAAACTGGAAAGCCAACATATGCG
GlyAsnGlyLeuLysTrpMETGlyTrpIleAsnThrGlnThrGlyLysProThrTyrAla

GATGATTTCAAACAACGGTTTGTCTTCTCTTTGGAAACTTCTGCCAGCACTGCATACTTG
AspAspPheLysGlnArgPheValPheSerLeuGluThrSerAlaSerThrAlaTyrLeu

CAGATCAACAACCTCAATATTGAGGACACAGCTACATATTTCTGTACAAGATCCACTTTT
GlnIleAsnAsnLeuAsnIleGluAspThrAlaThrTyrPheCysThrArgSerThrPhe

TACTATAGCAGCTATATCTACGGGTGGTACTTTGACTTCTGGGGCCCAGGAACCATGGTC
TyrTyrSerSerTyrIleTyrGlyTrpTyrPheAspPheTrpGlyProGlyThrMETVal

ACCGTGTCCTCAGCTGAAACAACA
ThrValSerSerAlaGluThrThr

FIG. 2

DNA sequence SEQ ID NO:125
PRT sequence SEQ ID NO:126

ATGGAGTCACATACTAGGGTCTTCATATTCCTGCTGCTCTGGTTGTCTGGTGCTGATGGG
METGluSerHisThrArgValPheIlePheLeuLeuLeuTrpLeuSerGlyAlaAspGly

GACATTGTGATGACTCAGTCTCCCACATCCATTTCCATATCAGTAGGAGAGAGGGTCACC
AspIleValMETThrGlnSerProThrSerIleSerIleSerValGlyGluArgValThr

ATGAACTGCAAGGCCAGTCAGAATGTGGGTTCTAATGTAGACTGGTACCAACAGAAAACA
METAsnCysLysAlaSerGlnAsnValGlySerAsnValAspTrpTyrGlnGlnLysThr

GGGCAGTCTCCTAAACTGCTTATCTACAAGGCATCCAACCGGTACACTGGCGTCCCTGAT
GlyGlnSerProLysLeuLeuIleTyrLysAlaSerAsnArgTyrThrGlyValProAsp

CGCTTCACAGGCAGTGGATCTGGAACAGATTTCACTTTCACCATCAGCAACATGCAGGCT
ArgPheThrGlySerGlySerGlyThrAspPheThrPheThrIleSerAsnMETGlnAla

GTGGACCTGGCTGTTTATTACTGTATGCAGTCTAACACCAATCCTCCGTGGACGTTCGGT
ValAspLeuAlaValTyrTyrCysMETGlnSerAsnThrAsnProProTrpThrPheGly

GGAGGCACCAAGCTGGAATTGAAACGGGCTGATGCTGCACCAACTGTATCT
GlyGlyThrLysLeuGluLeuLysArgAlaAspAlaAlaProThrValSer

FIG. 3

DNA sequence SEQ ID NO:127
PRT sequence SEQ ID NO:128

| | |
|---|---:|
| tgaacacaga ccactcacc atg gaa tgt aac tgg ata ctt cct ttt att ctg<br>                            Met Glu Cys Asn Trp Ile Leu Pro Phe Ile Leu<br>                             1            5                  10 | 52 |
| tcg gta att tca gga gtc tac tca gag gtt cag ctc cag cag tct ggg<br>Ser Val Ile Ser Gly Val Tyr Ser Glu Val Gln Leu Gln Gln Ser Gly<br>              15                20              25 | 100 |
| act gtg ctg gca agg cct ggg gct tcc gtg aag atg tcc tgc aag gct<br>Thr Val Leu Ala Arg Pro Gly Ala Ser Val Lys Met Ser Cys Lys Ala<br>        30                35                40 | 148 |
| tct ggc tac agg tat acc aac tac tgg ttg cac tgg gta aaa cag agg<br>Ser Gly Tyr Arg Tyr Thr Asn Tyr Trp Leu His Trp Val Lys Gln Arg<br>        45                50              55 | 196 |
| cct gga cag ggt cta gag tgg att ggt gct att tat cct gga aat agt<br>Pro Gly Gln Gly Leu Glu Trp Ile Gly Ala Ile Tyr Pro Gly Asn Ser<br>60              65              70              75 | 244 |
| gat tct agc tac aac cag aac ttc aag ggc aag gcc aaa ctg act gca<br>Asp Ser Ser Tyr Asn Gln Asn Phe Lys Gly Lys Ala Lys Leu Thr Ala<br>              80                85              90 | 292 |
| gtc aca tcc gcc agc act gcc tac atg gag ctc agc agc ctg aca aat<br>Val Thr Ser Ala Ser Thr Ala Tyr Met Glu Leu Ser Ser Leu Thr Asn<br>        95                100             105 | 340 |
| gag gac tct gcg gtc tat tac tgt aca aga tgg ggc cct tat ggc atc<br>Glu Asp Ser Ala Val Tyr Tyr Cys Thr Arg Trp Gly Pro Tyr Gly Ile<br>        110               115            120 | 388 |
| tat gct atg gac tac tgg ggt caa gga acc tca gtc acc gtc tcc tca<br>Tyr Ala Met Asp Tyr Trp Gly Gln Gly Thr Ser Val Thr Val Ser Ser<br>125              130             135 | 436 |
| gcc aaa aca aca ccc cca tca gtc tat cca ctg gcc c<br>Ala Lys Thr Thr Pro Pro Ser Val Tyr Pro Leu Ala<br>140              145             150 | 473 |

FIG. 4

DNA sequence SEQ ID NO:129
PRT sequence SEQ ID NO:130

| | | | | | | | | | | | | | | |
|---|---|---|---|---|---|---|---|---|---|---|---|---|---|---|
| gac | atc | gtg | atg | acc | cag | tct | cca | gct | tct | ttg | gct | gtg | tct | ctg | ggg | 48 |
| Asp | Ile | Val | Met | Thr | Gln | Ser | Pro | Ala | Ser | Leu | Ala | Val | Ser | Leu | Gly |
| 1 | | | | 5 | | | | | 10 | | | | | 15 | |

| cag | agg | gcc | acc | atc | tcc | tgc | aga | gcc | agc | gaa | agt | gtt | gat | tat | tct | 96 |
|---|---|---|---|---|---|---|---|---|---|---|---|---|---|---|---|---|
| Gln | Arg | Ala | Thr | Ile | Ser | Cys | Arg | Ala | Ser | Glu | Ser | Val | Asp | Tyr | Ser |
| | | | 20 | | | | 25 | | | | 30 | | | | |

| ggc | att | agt | ttt | atg | aac | tgg | ttc | caa | cag | aaa | cca | gga | cag | cca | ccc | 144 |
|---|---|---|---|---|---|---|---|---|---|---|---|---|---|---|---|---|
| Gly | Ile | Ser | Phe | Met | Asn | Trp | Phe | Gln | Gln | Lys | Pro | Gly | Gln | Pro | Pro |
| | | | 35 | | | | 40 | | | | 45 | | | | |

| aaa | ctc | ctc | atc | tat | gct | gca | tcc | aac | caa | gga | tcc | ggg | gtc | cct | gcc | 192 |
|---|---|---|---|---|---|---|---|---|---|---|---|---|---|---|---|---|
| Lys | Leu | Leu | Ile | Tyr | Ala | Ala | Ser | Asn | Gln | Gly | Ser | Gly | Val | Pro | Ala |
| | 50 | | | | 55 | | | | 60 | | | | | | |

| agg | ttt | agt | ggc | agt | ggg | tct | ggg | aca | gac | ttc | agc | ctc | aac | atc | cat | 240 |
|---|---|---|---|---|---|---|---|---|---|---|---|---|---|---|---|---|
| Arg | Phe | Ser | Gly | Ser | Gly | Ser | Gly | Thr | Asp | Phe | Ser | Leu | Asn | Ile | His |
| 65 | | | | | 70 | | | | | 75 | | | | | 80 |

| cct | atg | gag | gag | gat | gat | act | gca | atg | tat | ttc | tgt | cag | cac | agt | aag | 288 |
|---|---|---|---|---|---|---|---|---|---|---|---|---|---|---|---|---|
| Pro | Met | Glu | Glu | Asp | Asp | Thr | Ala | Met | Tyr | Phe | Cys | Gln | His | Ser | Lys |
| | | | | 85 | | | | | 90 | | | | | 95 | |

| gag | ctt | ccg | tac | acg | ttc | gga | ggg | ggg | acc | aag | ctg | gaa | a | | | 328 |
|---|---|---|---|---|---|---|---|---|---|---|---|---|---|---|---|---|
| Glu | Leu | Pro | Tyr | Thr | Phe | Gly | Gly | Gly | Thr | Lys | Leu | Glu | | | |
| | | | 100 | | | | 105 | | | | | | | | |

FIG. 5

DNA sequence SEQ ID NO:131
PRT sequence SEQ ID NO:132

| | | | | | | | | | | | | |
|---|---|---|---|---|---|---|---|---|---|---|---|---|
| gaattcc atg | gaa | tgt | aac | tgg | ata | ctt | cct | ttt | att | ctg | tcg gta att | 49 |
| Met | Glu | Cys | Asn | Trp | Ile | Leu | Pro | Phe | Ile | Leu | Ser Val Ile | |
| 1 | | | | 5 | | | | 10 | | | | |

| | | | | | | | | | | | | |
|---|---|---|---|---|---|---|---|---|---|---|---|---|
| tca | gga | gtc | tac | tca | gag | gtt | cag | ctc | cag | cag | tct ggg act gtg ctg | 97 |
| Ser | Gly | Val | Tyr | Ser | Glu | Val | Gln | Leu | Gln | Gln | Ser Gly Thr Val Leu | |
| 15 | | | | 20 | | | | 25 | | | 30 | |

| | | | | | | | | | | | | |
|---|---|---|---|---|---|---|---|---|---|---|---|---|
| gca | agg | cct | ggg | gct | tcc | gtg | aag | atg | tcc | tgc | aag gct tct ggc tac | 145 |
| Ala | Arg | Pro | Gly | Ala | Ser | Val | Lys | Met | Ser | Cys | Lys Ala Ser Gly Tyr | |
| | | | 35 | | | | 40 | | | | 45 | |

| | | | | | | | | | | | | |
|---|---|---|---|---|---|---|---|---|---|---|---|---|
| agg | tat | acc | aac | tac | tgg | ttg | cac | tgg | gta | aaa | cag agg cct gga cag | 193 |
| Arg | Tyr | Thr | Asn | Tyr | Trp | Leu | His | Trp | Val | Lys | Gln Arg Pro Gly Gln | |
| | | | 50 | | | | 55 | | | | 60 | |

| | | | | | | | | | | | | |
|---|---|---|---|---|---|---|---|---|---|---|---|---|
| ggt | cta | gag | tgg | att | ggt | gct | att | tat | cct | gga | aat agt gat tct agc | 241 |
| Gly | Leu | Glu | Trp | Ile | Gly | Ala | Ile | Tyr | Pro | Gly | Asn Ser Asp Ser Ser | |
| | 65 | | | | 70 | | | | 75 | | | |

| | | | | | | | | | | | | |
|---|---|---|---|---|---|---|---|---|---|---|---|---|
| tac | aac | cag | aac | ttc | aag | ggc | aag | gcc | aaa | ctg | act gca gtc aca tcc | 289 |
| Tyr | Asn | Gln | Asn | Phe | Lys | Gly | Lys | Ala | Lys | Leu | Thr Ala Val Thr Ser | |
| | 80 | | | | 85 | | | | 90 | | | |

| | | | | | | | | | | | | |
|---|---|---|---|---|---|---|---|---|---|---|---|---|
| gcc | agc | act | gcc | tac | atg | gag | ctc | agc | agc | ctg | aca aat gag gac tct | 337 |
| Ala | Ser | Thr | Ala | Tyr | Met | Glu | Leu | Ser | Ser | Leu | Thr Asn Glu Asp Ser | |
| 95 | | | | 100 | | | | 105 | | | 110 | |

| | | | | | | | | | | | | |
|---|---|---|---|---|---|---|---|---|---|---|---|---|
| gcg | gtc | tat | tac | tgt | aca | aga | tgg | ggc | cct | tat | ggc atc tat gct atg | 385 |
| Ala | Val | Tyr | Tyr | Cys | Thr | Arg | Trp | Gly | Pro | Tyr | Gly Ile Tyr Ala Met | |
| | | | 115 | | | | 120 | | | | 125 | |

| | | | | | | | | | | | | |
|---|---|---|---|---|---|---|---|---|---|---|---|---|
| gac | tac | tgg | ggt | caa | gga | acc | tca | gtc | acc | gtc | tcc agc gct agc | 430 |
| Asp | Tyr | Trp | Gly | Gln | Gly | Thr | Ser | Val | Thr | Val | Ser Ser Ala Ser | |
| | | | 130 | | | | 135 | | | | 140 | |

FIG. 6

DNA sequence SEQ ID NO:133
PRT sequence SEQ ID NO:134

| gaattcc atg gag aca gac aca ctc ctg cta tgg gtc ctg ctt ctc tgg | 49 |
|---|---|
|         Met Glu Thr Asp Thr Leu Leu Leu Trp Val Leu Leu Leu Trp | |
|         1                 5              10 | |

| gtt cca ggt tcc aca ggt gac att gtg ctg acc caa tct cca gct tct | 97 |
|---|---|
| Val Pro Gly Ser Thr Gly Asp Ile Val Leu Thr Gln Ser Pro Ala Ser | |
| 15             20            25            30 | |

| ttg gct gtg tct ctg ggg cag agg gcc acc atc tcc tgc aga gcc agc | 145 |
|---|---|
| Leu Ala Val Ser Leu Gly Gln Arg Ala Thr Ile Ser Cys Arg Ala Ser | |
|          35            40              45 | |

| gaa agt gtt gat tat tct ggc att agt ttt atg aac tgg ttc caa cag | 193 |
|---|---|
| Glu Ser Val Asp Tyr Ser Gly Ile Ser Phe Met Asn Trp Phe Gln Gln | |
|          50            55              60 | |

| aaa cca gga cag cca ccc aaa ctc ctc atc tat gct gca tcc aac caa | 241 |
|---|---|
| Lys Pro Gly Gln Pro Pro Lys Leu Leu Ile Tyr Ala Ala Ser Asn Gln | |
|          65            70              75 | |

| gga tcc ggg gtc cct gcc agg ttt agt ggc agt ggg tct ggg aca gac | 289 |
|---|---|
| Gly Ser Gly Val Pro Ala Arg Phe Ser Gly Ser Gly Ser Gly Thr Asp | |
|          80            85              90 | |

| ttc agc ctc aac atc cat cct atg gag gag gat gat act gca atg tat | 337 |
|---|---|
| Phe Ser Leu Asn Ile His Pro Met Glu Glu Asp Asp Thr Ala Met Tyr | |
| 95            100          105          110 | |

| ttc tgt cag cac agt aag gag ctt ccg tac acg ttc gga ggg ggg acc | 385 |
|---|---|
| Phe Cys Gln His Ser Lys Glu Leu Pro Tyr Thr Phe Gly Gly Gly Thr | |
|            115           120          125 | |

| aag ctg gaa atc aaa cgt acg | 406 |
|---|---|
| Lys Leu Glu Ile Lys Arg Thr | |
|          130 | |

FIG. 32

```
            PRT sequence SEQ ID NOS:10(residues 474-543),12(residues 474-543), 46 through 49, and 27 through 45)
                     1         10        20        30        40        50        60        70
                     TVAACNLPIVRGPCRAFIQLWAFDAVKGKCVLFPYGGCQGNGNKFYSEKECREYCGVPGDGDEELLRFSN
pTK-2355             ......................................................................
pTK-2370             ..................S..........................D.......................

pTK-2824             ..................S...I..K...................D.......................
pTK-2825             ..................S...L..K...................D.......................
pTK-2826             ..................S...T..K...................D.......................
pTK-2827             ..................S...V..K...................D.......................

pTK-2730             ......................A...............................................
pTK-2731             ......................C...............................................
pTK-2732             ......................D...............................................
pTK-2733             ......................E...............................................
pTK-2734             ......................F...............................................
pTK-2735             ......................G...............................................
pTK-2736             ......................H...............................................
pTK-2737             ......................I...............................................
pTK-2738             ......................K...............................................
pTK-2739             ......................L...............................................
pTK-2740             ......................M...............................................
pTK-2741             ......................N...............................................
pTK-2742             ......................P...............................................
pTK-2743             ......................Q...............................................
pTK-2744             ......................S...............................................
pTK-2745             ......................T...............................................
pTK-2746             ......................V...............................................
pTK-2747             ......................W...............................................
pTK-2748             ......................Y...............................................
```

FIG. 33

PRT sequence SEQ ID NOS:10(residues 474-543), 12(residues 474-543), 50 through 68)

```
                 1           10          20          30          40          50          60          70
          TVAACNLPIVRGPCRAFIQLWAFDAVKGKCVLFPYGGCQGNGNKFYSEKECREYCGVPGDGDEELLRFSN
pTK-2355  ......................................................................
pTK-2370  ...........S..................................D......................

pTK-2866  ...........S...T....A.........................D......................
pTK-2867  ...........S...T....C.........................D......................
pTK-2868  ...........S...T....D.........................D......................
pTK-2869  ...........S...T....E.........................D......................
pTK-2870  ...........S...T....F.........................D......................
pTK-2871  ...........S...T....G.........................D......................
pTK-2872  ...........S...T....H.........................D......................
pTK-2873  ...........S...T....I.........................D......................
pTK-2874  ...........S...T....L.........................D......................
pTK-2875  ...........S...T....M.........................D......................
pTK-2876  ...........S...T....N.........................D......................
pTK-2877  ...........S...T....P.........................D......................
pTK-2878  ...........S...T..............................D......................
pTK-2879  ...........S...T....R.........................D......................
pTK-2880  ...........S...T....S.........................D......................
pTK-2881  ...........S...T....T.........................D......................
pTK-2882  ...........S...T....V.........................D......................
pTK-2883  ...........S...T....W.........................D......................
pTK-2884  ...........S...T....Y.........................D......................
```

FIG. 34

PRT sequence SEQ ID NOS:10(residues 474-543), 12(residues 474-543), 69 through 87)

```
              1         10         20         30         40         50         60         70
              TVAACNLPIVRGPCRAFIQLWAFDAVKGKCVLFPYGGCQGNGNKFYSEKECREYCGVPGDGDEELLRFSN
pTK-2355      ......................................................................
pTK-2370      ........S.........K...................D..............................

pTK-2889      ........S........T.A..................................................
pTK-2890      ........S........T.C..................D...............................
pTK-2891      ........S........T.D..................D...............................
pTK-2892      ........S........T.E..................D...............................
pTK-2893      ........S........T.G..................D...............................
pTK-2894      ........S........T.H..................D...............................
pTK-2895      ........S........T.I..................D...............................
pTK-2896      ........S........T.K..................D...............................
pTK-2897      ........S........T.L..................D...............................
pTK-2898      ........S........T.M..................D...............................
pTK-2899      ........S........T.N..................D...............................
pTK-2900      ........S........T.P..................D...............................
pTK-2901      ........S........T.Q..................D...............................
pTK-2902      ........S........T.R..................D...............................
pTK-2903      ........S........T.S..................D...............................
pTK-2904      ........S........T.T..................D...............................
pTK-2905      ........S........T.V..................D...............................
pTK-2906      ........S........T.W..................D...............................
pTK-2907      ........S........T.Y..................D...............................
```

FIG. 35

PRT sequence SEQ ID NOS:10(residues 474-543), 12(residues 474-543), 88 through 106)

```
            1          10         20         30         40         50         60         70
            TVAACNLPIVRGPCRAFIQLWAFDAVKGKCVLFPYGGCQGNGNKFYSEKECREYCGVPGDGDEELLRFSN
pTK-2355    ......................................................................
pTK-2370    ........S......K......................................D..............

pTK-2932    .........A.......T....................................D..............
pTK-2933    .........C.......T....................................D..............
pTK-2934    .........D.......T....................................D..............
pTK-2935    .........E.......T....................................D..............
pTK-2936    .........F.......T....................................D..............
pTK-2937    .........G.......T....................................D..............
pTK-2938    .........H.......T....................................D..............
pTK-2939    .........I.......T....................................D..............
pTK-2940    .........K.......T....................................D..............
pTK-2941    .........L.......T....................................D..............
pTK-2942    .........M.......T....................................D..............
pTK-2943    .........N.......T....................................D..............
pTK-2944    .........P.......T....................................D..............
pTK-2945    .........Q.......T....................................D..............
pTK-2946    .................T....................................D..............
pTK-2947    .........T.......T....................................D..............
pTK-2948    .........V.......T....................................D..............
pTK-2949    .........W.......T....................................D..............
pTK-2950    .........Y.......T....................................D..............
```

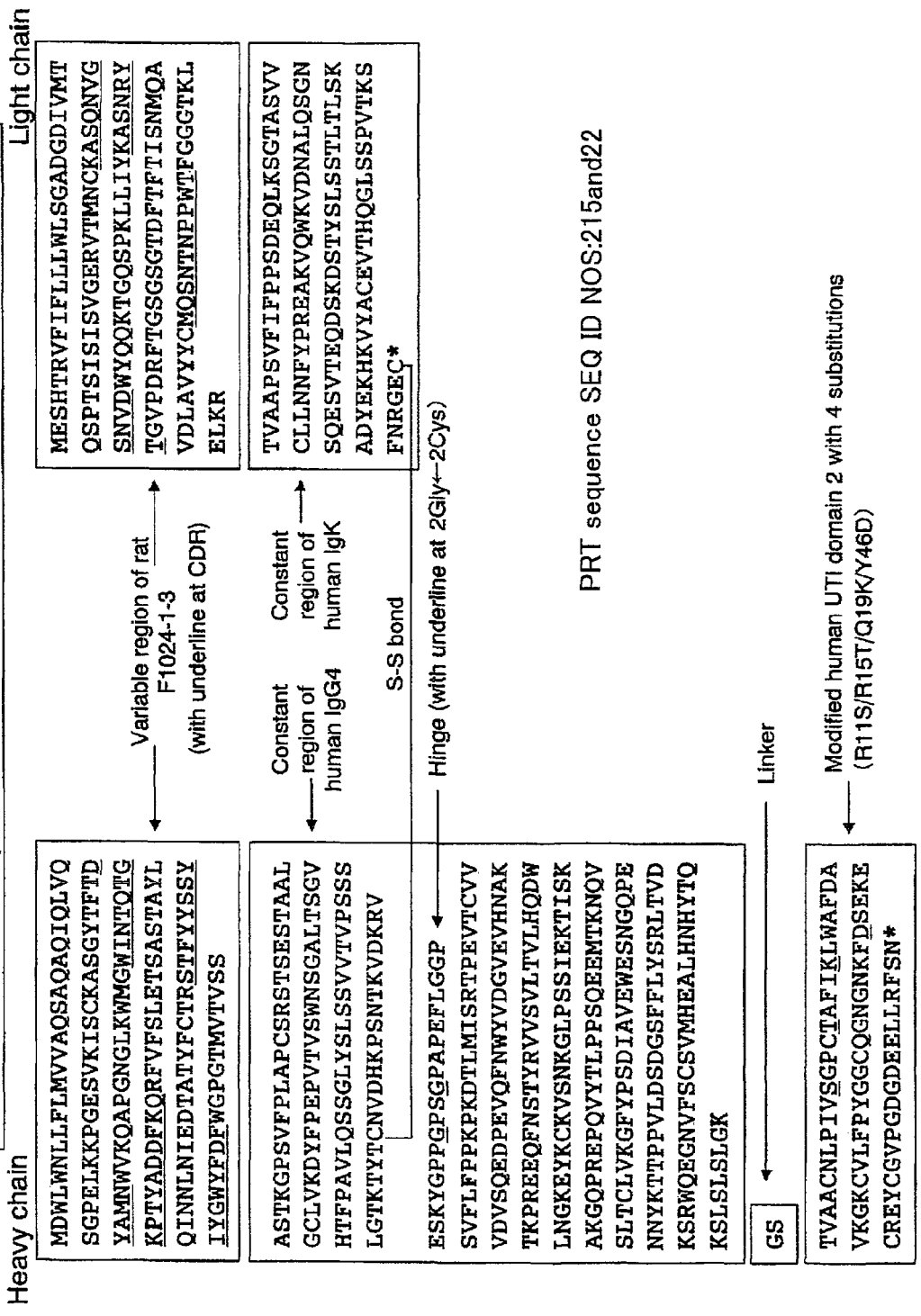

FIG. 37

PRT sequence SEQ ID NOS:107-108

F1024S-TM123456M (pTK-2754)

CSVENGGCEHACNAIPGAPRCQCPAGAALQADGRSC
TASATQSCNDLCEHFCVPNPDQPGSYSCMCETGYRLAADQHRC
EDVDDCILEPSPCPQRCVNTQGGFECHCYPNYDLVDGEC
VEPVDPCFRANCEYQCQPLNQTSYLCVCAEGFAPIPHEPHRCQMF
CNQTACPADCDPNTQASCECPEGYILDDGFICTDIDE
CENGGFCSGVCHNLPGTFECICGPDSALARHIGTDC

F1024S-TM123456L (pTK-2762)

CSVENGGCEHACNAIPGAPRCQCPAGAALQADGRSC
TASATQSCNDLCEHFCVPNPDQPGSYSCMCETGYRLAADQHRC
EDVDDCILEPSPCPQRCVNTQGGFECHCYPNYDLVDGEC
VEPVDPCFRANCEYQCQPLNQTSYLCVCAEGFAPIPHEPHRCQLF
CNQTACPADCDPNTQASCECPEGYILDDGFICTDIDE
CENGGFCSGVCHNLPGTFECICGPDSALARHIGTDC

FIG. 38

PRT sequence SEQ ID NOS:109-110

F1024S-TM1234567M (pTK-2755)

CSVENGGCEHACNAIPGAPRCQCPAGAALQADGRSC
TASATQSCNDLCEHFCVPNPDQPGSYSCMCETGYRLAADQHRC
EDVDDCILEPSPCPQRCVNTQGFECHCYPNYDLVDGEC
VEPVDPCFRANCEYQCQPLNQTSYLCVCAEGFAPIPHEPHRCQMF
CNQTACPADCDPNTQASCECPEGYILDDGFICTDIDE
CENGGFCSGVCHNLPGTFECICGPDSALARHIGTDC
DSGKVDGGDSGSGEPPPSPTPGSTLTPPAVGLVHS

F1024S-TM1234567L (pTK-2763)

CSVENGGCEHACNAIPGAPRCQCPAGAALQADGRSC
TASATQSCNDLCEHFCVPNPDQPGSYSCMCETGYRLAADQHRC
EDVDDCILEPSPCPQRCVNTQGFECHCYPNYDLVDGEC
VEPVDPCFRANCEYQCQPLNQTSYLCVCAEGFAPIPHEPHRCQLF
CNQTACPADCDPNTQASCECPEGYILDDGFICTDIDE
CENGGFCSGVCHNLPGTFECICGPDSALARHIGTDC
DSGKVDGGDSGSGEPPPSPTPGSTLTPPAVGLVHS

FIG. 39

PRT sequence SEQ ID NOS:111-112

F1024S-TM23456M (pTK-2756)

TASATQSCNDLCEHFCVPNPDQPGSYSCMCETGYRLAADQHRC
EDVDDCILEPSPCPQRCVNTQGGFECHCYPNYDLVDGEC
VEPVDPCFRANCEYQCQPLNQTSYLCVCAEGFAPIPHEPHRCQMF
CNQTACPADCDPNTQASCECPEGYILDDGFICTDIDE
CENGGFCSGVCHNLPGTFECICGPDSALARHIGTDC

F1024S-TM23456L (pTK-2764)

TASATQSCNDLCEHFCVPNPDQPGSYSCMCETGYRLAADQHRC
EDVDDCILEPSPCPQRCVNTQGGFECHCYPNYDLVDGEC
VEPVDPCFRANCEYQCQPLNQTSYLCVCAEGFAPIPHEPHRCQLF
CNQTACPADCDPNTQASCECPEGYILDDGFICTDIDE
CENGGFCSGVCHNLPGTFECICGPDSALARHIGTDC

FIG. 40

PRT sequence SEQ ID NOS:113-114

F1024S-TM234567M
(pTK-2757)

TASATQSCNDLCEHFCVPNPDQPGSYSCMCETGYRLAADQHRC
EDVDDCILEPSPCPQRCVNTQGGFECHCYPNYDLVDGEC
VEPVDPCFRANCEYQCQPLNQTSYLCVCAEGFAPIPHEPHRCQMF
CNQTACPADCDPNTQASCECPEGYILDDGFICTDIDE
CENGGFCSGVCHNLPGTFECICGPDSALARHIGTDC
DSGKVDGGDSGSGEPPPSPTPGSTLTPPAVGLVHS

F1024S-TM234567L
(pTK-2765)

TASATQSCNDLCEHFCVPNPDQPGSYSCMCETGYRLAADQHRC
EDVDDCILEPSPCPQRCVNTQGGFECHCYPNYDLVDGEC
VEPVDPCFRANCEYQCQPLNQTSYLCVCAEGFAPIPHEPHRCQLF
CNQTACPADCDPNTQASCECPEGYILDDGFICTDIDE
CENGGFCSGVCHNLPGTFECICGPDSALARHIGTDC
DSGKVDGGDSGSGEPPPSPTPGSTLTPPAVGLVHS

FIG. 41

PRT sequence SEQ ID NOS:115-116

F1024S-TM3456M
(pTK-2758)

EDVDDCILEPSPCPQRCVNTQGGFECHCYPNYDLVDGEC
VEPVDPCFRANCEYQCQPLNQTSYLCVCAEGFAPIPHEPHRCQMF
CNQTACPADCDPNTQASCECPEGYILDDGFICTDIDE
CENGGFCSGVCHNLPGTFECICGPDSALARHIGTDC

F1024S-TM3456L
(pTK-2766)

EDVDDCILEPSPCPQRCVNTQGGFECHCYPNYDLVDGEC
VEPVDPCFRANCEYQCQPLNQTSYLCVCAEGFAPIPHEPHRCQLF
CNQTACPADCDPNTQASCECPEGYILDDGFICTDIDE
CENGGFCSGVCHNLPGTFECICGPDSALARHIGTDC

FIG. 42

PRT sequence SEQ ID NOS:117-118

F1024S-TM34567M
(pTK-2759)

EDVDDCILEPSPCPQRCVNTQGGFECHCYPNYDLVDGEC
VEPVDPCFRANCEYQCQPLNQTSYLCVCAEGFAPIPHEPHRCQMF
CNQTACPADCDPNTQASCECPEGYILDDGFICTDIDE
CENGGFCSGVCHNLPGTFECICGPDSALARHIGTDC
DSGKVDGGDSGSGEPPPSPTPGSTLTPPAVGLVHS

F1024S-TM34567L
(pTK-2767)

EDVDDCILEPSPCPQRCVNTQGGFECHCYPNYDLVDGEC
VEPVDPCFRANCEYQCQPLNQTSYLCVCAEGFAPIPHEPHRCQLF
CNQTACPADCDPNTQASCECPEGYILDDGFICTDIDE
CENGGFCSGVCHNLPGTFECICGPDSALARHIGTDC
DSGKVDGGDSGSGEPPPSPTPGSTLTPPAVGLVHS

FIG. 43

PRT sequence SEQ ID NOS:119-120

F1024S-TM456M
(pTK-2760)

VEPVDPCFRANCEYQCQPLNQTSYLCVCAEGFAPIPHEPHRCQMF
CNQTACPADCDPNTQASCECPEGYILDDGFICTDIDE
CENGGFCSGVCHNLPGTFECICGPDSALARHIGTDC

F1024S-TM456L
(pTK-2768)

VEPVDPCFRANCEYQCQPLNQTSYLCVCAEGFAPIPHEPHRCQLF
CNQTACPADCDPNTQASCECPEGYILDDGFICTDIDE
CENGGFCSGVCHNLPGTFECICGPDSALARHIGTDC

FIG. 44

PRT sequence SEQ ID NOS:121-122

F1024S-TM4567M (pTK-2761)

VEPVDPCFRANCEYQCQPLNQTSYLCVCAEGFAPIPHEPHRCQMF
CNQTACPADCDPNTQASCECPEGYILDDGFICTDIDE
CENGGFCSGVCHNLPGTFECICGPDSALARHIGTDC
DSGKVDGGDSGSGEPPPSPTPGSTLTPPAVGLVHS

F1024S-TM4567L (pTK-2769)

VEPVDPCFRANCEYQCQPLNQTSYLCVCAEGFAPIPHEPHRCQLF
CNQTACPADCDPNTQASCECPEGYILDDGFICTDIDE
CENGGFCSGVCHNLPGTFECICGPDSALARHIGTDC
DSGKVDGSGSGEPPPSPTPGSTLTPPAVGLVHS

FIG. 48 PRT sequence (SEQ ID NOS:219), (SEQ ID NOS:223), (SEQ ID NOS:220-222), (SEQ ID NOS:224-226)

V_H

```
F1024-1-3     QIQLVQSGPELKKPGESVKISCKASGYTFTDYAMNWVKQAPGNGLKWMGWINTQTGKPTYAD
IGHV7-81-HA   .V......H.V.Q..A...V......S..........P...Q..E...............
NEW-HA        .V..QE...G.VR.SQTLSLT.TV..S..S........R.P..R..E.I...........
Eu-HA         .V..........A.V....S......V......G..S........R....Q..E.......

F1024-1-3     DFKQRFVFSLETSASTAYLQINNLNIEDTATYFCTRSTFYYSSYIYGWYFDWGPGTSVTVSS
IGHV7-81-HA   ............MD...........SS.KA..M.M.Y.A....................Q.
NEW-HA        ....VTMLVD..KNQFS.RLSSVTAA...V.Y.A..........................Q.SL
Eu-HA         ....VTITADE.TN...MELSS..RS.....I.Y.A........................Q...L
```

V_L

```
F1024-1-3     DIVMTQSPTSISISVGERVTMNCKASQNVGSNVDWYQQKTGQSPKLLIYKASNRYT
RF-KA         E......ATL.V.P...A.LS......................P..A.R.......
REI-KA        ..Q........S...A...D...IT..................P.KA.........
Eu-KA         ..Q.....STL.A...D...IT......................P.KA...M....

F1024-1-3     GVPDRFTGSGSGTDFTFTISNMQAVDLAVYYCMQSNTNPPWTFGGGTKLELKRT
RF-KA         .I.A..S......E.L...SL.SE.F................Q...V.I....
REI-KA        ...S.S........SL.PE.I.T...................Q...V.I....
Eu-KA         ...S..I.....E.L...SL.PD.F.T................Q...V.V....
```

FIG. 49

PRT sequence SEQ ID NOS:219, 227-233

VH

| | | |
|---|---|---|
| F1024-1-3 | QIQLVQSGPELKKPGESVKISCKASGYTFTDYAMNWVKQAPGNGLKWMGWINTQTGKPTYAD |
| IGHV7-81-HA | .V........H.V.Q..A.....V..........S..........P....Q..E........ |
| IGHV7-81-HC | .V........H.V.Q..A.....V..........S..........K....N..K........ |
| IGHV7-81-HX | .V........H.V.Q..A.....V..........S..........K....Q..E........ |
| NEW-HA | .V..QE....G.VR.SQTLSLT.TV.....S....S........R.P..R...E.I...... |
| NEW-HB | .I..VQ....E.KK.GESVKIS.KA.....S....S........R.P..R...E.I...... |
| Eu-HA | .V........A.V.....S....V.........G..S..........R.....Q..E..... |
| Eu-HB | .I........P.L.....E..I........Y..T..........R.....Q..E....... |

| | | |
|---|---|---|
| F1024-1-3 | DFKQRFVFSLETSASTAYLQINNLNIEDTATYFCTRSTFYYSSYIYGWYFDWGPGTSVTVSS |
| IGHV7-81-HA | .........MD................SS..KA....M.M.Y.A...............Q.SL...... |
| IGHV7-81-HC | .........MD................SS..KA....M.M.Y.A...............Q.SL...... |
| IGHV7-81-HX | .........MD................SS..KA....M.M.Y.A...............Q........ |
| NEW-HA | ....VTMLVD..KNQFS.RLSSVTAA.....V.Y.A...............Q.SL...... |
| NEW-HB | ....VTMLVD..KNQFS.RLSSVTAA.....V.Y.A...............Q.SL...... |
| Eu-HA | ....VTITADE.TN...MELSS..RS.....I.Y.A...............Q..L...... |
| Eu-HB | ....VTITADE.TN...MELSS..RS.....I.Y.A...............Q..L...... |

Human

Rabbit

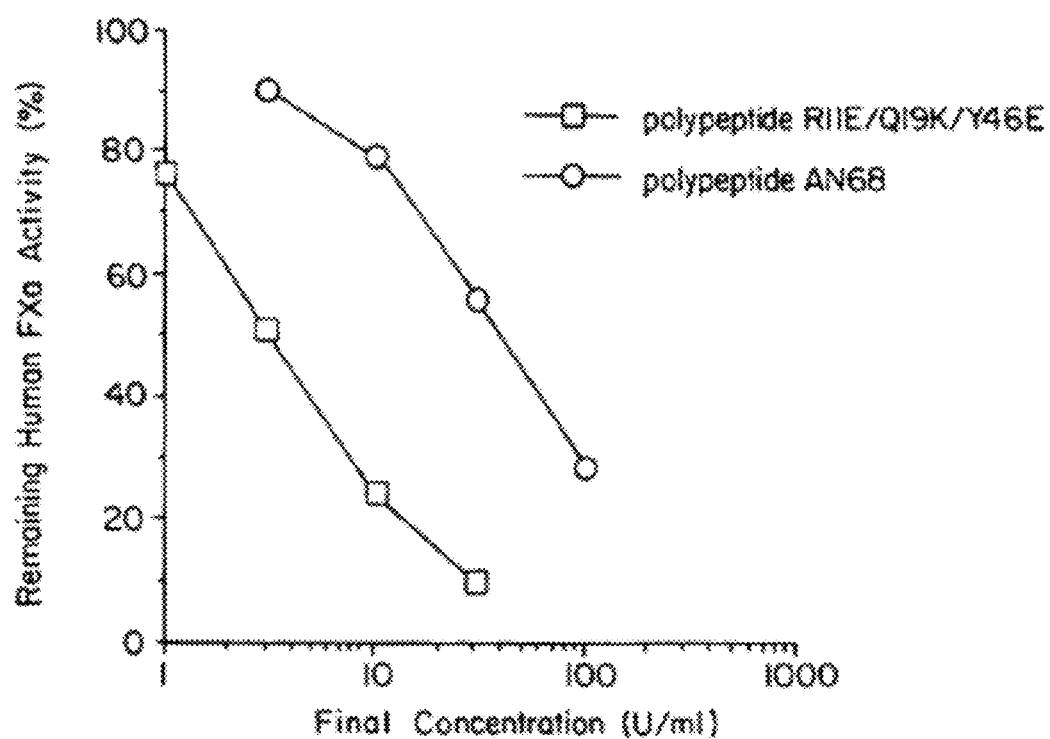

ANTI-CD14 ANTIBODY FUSION PROTEIN

TECHNICAL FIELD

The present invention relates to a novel protein comprising an anti-CD14 antibody and a protease inhibitor; a polynucleotide coding for the novel protein; a method for producing the novel protein; and medical use of the novel protein for sepsis and the like.

BACKGROUND ART

Sepsis is defined as a disease which has infectious cause and which shows the pathology of systemic inflammatory response syndrome (SIRS) (see Non-Patent Document 1). Initial symptoms found include ague, sweating, fever, and decrease in the blood pressure, and when various inflammatory mediators and blood coagulation factors increase in the whole body, disturbance in the microcirculation occurs, and this results in the worsening of the pathological conditions including tissue and organ failures, which often lead to continuous onset of multiple organ failure or septic shock resulting in the death.

Onset of the sepsis is triggered by action of the components constituting the infectious bacteria, for example, lipopolysaccharide (LPS) of Gram-negative bacteria and lipoteichoic acid (LTA) in Gram-positive bacteria with leukocyte (monocyte/macrophage and neutrophil) or vascular endothelial cell, which in turn causes production of various inflammatory mediators. Recent studies revealed that CD14 which was first found as a differentiation antigen of leukocyte (see Non-Patent Document 2) and Toll-like-receptors (TLR) which are accepted to be pattern recognition molecules in the innate immune system (see Non-Patent Document 3) play an important role in such activation of the target cell by the bacterial constituent components.

CD14 is present in two forms, namely, in membrane-bound form and soluble form. The membrane-bound form CD14 is anchored to cell membrane by glycosylphosphatidyl-inositol, and the soluble form CD14 includes the one synthesized in liver and the one present in blood after cleavage on leukocyte by phosphatidylinositol-specific phospholipase (see Non-Patent Document 4). For example, activation of the target cell by LPS is caused by binding of the LPS to the CD14 promoted by catalytic action of LPS-binding protein (LBP) in blood and the subsequent binding to the TLR on the cell membrane which results in the transduction of the activation signal to the target cell. The target cell which has received the activation signal produces and expresses various mediators related to inflammatory response, for example, cytokines such as TNF-α, IL-1, IL-6, and IL-8 and tissue factors. The cytokine which is a typical mediator activates neutrophil and macrophage, and this causes adhesion to vascular endothelium, migration in the tissue, release of neutral proteases such as neutrophil elastase, and production of reactive oxygen species. Activation of the coagulation and fibrinolytic system, activation of the complement system, and activation of kallikrein also contribute for this process. As described above, a large number of mediator molecules and effector molecules are involved at the molecular level and the cell level with the formation of the pathology, and excessive promotion of these reactions results in the systemic damage, which leads worsening of the pathology from the microcirculatory disturbance to the tissue failure and organ failure as described above.

In order to cope with the sepsis exhibiting such complicated pathology, many studies have been conducted on the therapeutic agents. The approaches employed in developing the therapeutic agents may be divided into two major categories, namely, the approach of inhibiting the action of the bacterial constituent component which is the substance responsible for the onset of the sepsis, and the approach of inhibiting various factors which are expressed as the biological response to the signal of the substance responsible for the onset of the sepsis.

The therapeutic approaches of inhibiting the action of the endotoxin from Gram-negative bacteria include (1) the method using an anti-endotoxin antibody (see Non-Patent Documents 5 and 6); (2) the method using an endotoxin antagonist (see Non-Patent Document 7); (3) a method using polymixin B (see Non-Patent Document 8); and (4) a method using BPI (see Non-Patent Document 9). Endotoxin is a component constituting Gram-negative bacteria, which is not found in the Gram-positive bacteria and fungi which are responsible for the sepsis. Accordingly, sepsis agents targeting the endotoxin are associated with the problem that they cannot cope with the bacteria and fungi other than the Gram-negative bacteria.

A sepsis agent which targets on CD14 which functions as a receptor for LPS which is a substance constituting Gram-negative bacteria has also been proposed. Since CD14 has been found to be not only the receptor for the LPS but also a receptor for a bacterial constituent such as lipoteichoic acid and peptidoglycan which are the constituents of Gram-positive bacteria (see Non-Patent Document 10), it is indicated that the sepsis agent targeting the CD14 is applicable not only to the Gram-negative sepsis. The agents that have been proposed include anti-CD14 antibodies (See Patent Documents 1 and 2) and soluble CD14 (see Non-Patent Document 11 and Patent Documents 3 and 4). These agents, however, are not yet used in practice. The pathology of sepsis has been estimated to be sequential and complex development from the stage triggering the inflammatory response with the constituent of the pathogen to a more serious stage. The drawback of the CD14 targeting agents is that, since action of these agents focuses on the early triggering stage of the pathology formation, dubiousness remains on the effects on the more serious late stage of the pathology.

In the meanwhile, of the therapeutic approaches of targeting the excessively produced factors, the therapeutic methods of inhibiting a cytokine or other inflammatory mediators include (1) the method using an anti-TNF antibody (see Non-Patent Document 12), (2) the method using a soluble TNF receptor (see Non-Patent Document 13), (3) the method using an IL-1 receptor antagonist (see Non-Patent Document 14), (4) the method using an PAF inhibitor (see Non-Patent Document 15), and (5) the method using an NO inhibitor (see Non-Patent Document 16). Although these therapeutic methods have demonstrated their effectiveness in the stage of experimental animals or in small scale clinical tests, their effectiveness and usefulness are not clearly revealed in the stage of large scale clinical test. As described above, cytokine and other inflammatory mediators each have a plurality of activities, and these mediators constitute a complicated network and various events occur in this network in which each mediator complements other mediators and induces the expression of other mediators. Therefore, it has been estimated that treatment made by inhibiting one factor has some limitation (see Non-Patent Document 17).

Also proposed is the therapeutic approach which targets blood coagulation factors whose production is enhanced in the process of the interaction of mediators associated with the generation of the pathology of the sepsis. The blood coagulation factors are believed to be included among the important targets of the therapeutic agent since enhancement of the blood coagulation invites disturbance in the blood microcirculation system, which in turn invites decrease in the amount of oxygen supplied to the peripheral tissue, tissue failure, and even multiple organ failure. Exemplary methods include (1) a therapeutic method using an activated protein C (see Non-Patent Document 18), (2) a therapeutic method using an antithrombin III (see Non-Patent Document 19), and (3) a therapeutic method using a TFPI (see Non-Patent Document 20). Among these, the treatment of severe sepsis using activated protein C has been demonstrated to have a significant therapeutic effect in a large scale clinical test (see Non-Patent Document 21), and this treatment has been offered for clinical use. However, this treatment has great clinical limitation that it is contraindicated for patients having bleeding tendency.

[Patent Document 1] JP 2744130 B
[Patent Document 2] WO 02/42333
[Patent Document 3] JP 10-512142 A
[Patent Document 4] WO 01/72993
[Non-Patent Document 1] The ACCP/SCCM Consensus Conference Committee. Chest, 1992, 101, 1644-1655.
[Non-Patent Document 2] Goyert S. M. and Ferrero E., in McMichael A. (ed.): Leukocyte Typing III. Oxford, Oxford University Press, 1987.
[Non-Patent Document 3] Zhang G. and Ghosh S., Endotoxin Res., 2000, 6, 453-457.
[Non-Patent Document 4] Stelter F., Structure/Function relationship of CD14; in Jack R. S. (ed.): CD14 in the Inflammatory Response. Chem. Immunol. Basl, Karger, 2000, 74, pp. 25-41.
[Non-Patent Document 5] Ziegler E. J., et al., New Engl. J. Med., 1991, 324, 429-436.
[Non-Patent Document 6] Greenman R. L. et al., JAMA, 1991, 266, 1097-1102.
[Non-Patent Document 7] Kawata T. et al., Prog Clin Biol Res., 1995, 392, 499-509.
[Non-Patent Document 8] Tani T. et al., Artif. Organs, 1998, 22, 1038-1045.
[Non-Patent Document 9] Lin Y. et al., Antimicrob. Agents Chemother., 1996, 40, 65-69.
[Non-Patent Document 10] Cleveland, Infect Immun., 1996, 64, 1906-1912.
[Non-Patent Document 11] Goyert S. M., J. Immunol., 1995, 154, 6529-6532.
[Non-Patent Document 12] Fischer C. J. et al., Crit. Care Med., 1993, 21, 318-327.
[Non-Patent Document 13] Fischer C. J. et al., N. Engl. J. Med., 1996, 334, 1697-1702.
[Non-Patent Document 14] Fischer C. J. et al., JAMA, 1994, 271, 1836-1843.
[Non-Patent Document 15] Dhainaut J. F. et al., Crit. Care Med., 1994, 22, 1720-1728.
[Non-Patent Document 16] Gachot B., Intensive Care Med., 1995, 21, 1027-1031.
[Non-Patent Document 17] Vincent J. L. et al., CID, 2002, 34, 1984-1093.
[Non-Patent Document 18] Rivard G. E. et al., J. Peditr., 1995, 126, 646-652.
[Non-Patent Document 19] Fourrier F. et al., Chest, 1993, 104, 882-888.
[Non-Patent Document 20] Abraham E. et al., Crit. Care Med., 2000, 28, S31-33.
[Non-Patent Document 21] Bernard, G. R. et al., N. Engl. J. Med., 2001, 344, 699-709.

DISCLOSURE OF THE INVENTION

Problems to be Solved by the Invention

In view of such situation, the inventors of the present invention noticed that a novel protein produced by binding an anti-CD14 antibody and a protease inhibitor would solve the problems associated with prior art techniques, and confirmed its effectiveness by producing such novel protein. An object of the present invention is to provide a novel protein comprising an anti-CD14 antibody and a protease inhibitor; a polynucleotide coding for such novel protein; a method for producing such novel protein; a preventive and/or therapeutic agent for sepsis comprising such novel protein.

Means for Solving the Problems

Next, typical aspects of the present invention are described below. A first aspect of the present invention is a novel protein comprising (I) an anti-CD14 antibody or its active fragment, or a derivative thereof and (II) an inhibitor for a protease or its active fragment, or a derivative thereof. More specifically, the novel protein of this aspect is (1) a protein comprising (I) an anti-CD14 antibody or its active fragment, or a derivative thereof and (II) an inhibitor for a protease, or its active fragment, or a derivative thereof,
(2) the protein according to (1) wherein the inhibitor in (II) is a protein inhibitor,
(3) the protein according to (1) or (2) wherein the inhibitor in (II) is a multivalent enzyme inhibitor,
(4) the protein according to any one of (1) to (3) wherein the protease in (II) is a blood coagulation factor (a blood coagulation protease) or an inflammatory protease,
(5) the protein according to any one of (1) to (4) wherein the protease in (II) is FXa and/or FXIa,
(6) the protein according to any one of (1) to (4) wherein the protease in (II) is thrombin,
(7) the protein according to any one of (1) to (6) wherein the inhibitor in (II) is derived from UTI,
(8) the protein according to any one of (1) to (6) wherein the inhibitor in (II) is derived from thrombomodulin,
(9) the protein according to any one of (1) to (6) wherein the inhibitor in (II) is derived from UTI domain 2,
(10) the protein according to any one of (1) to (8) wherein the inhibitor in (II) is derived from functional domain, especially EGF-like domain, of thrombomodulin,
(11) the protein according to any one of (1) to (4) wherein the protease in (II) is elastase,
(12) the protein according to any one of (1) to (4) and (11) wherein the inhibitor in (II) is a secretory leukocyte protease inhibitor,
(13) the protein according to any one of (1) to (11) wherein the inhibitor in (II) is a mutant of UTI domain 2 with 1 to 4 amino acid substitutions,
(14) the protein according to any one of (1) to (13) wherein the anti-CD14 antibody in (I) is an antibody which has neutralizing activity,
(15) the protein according to any one of (1) to (14) wherein the anti-CD14 antibody in (I) is one which recognizes at least a part of amino acid Nos. 269-315 of human CD14,
(16) the protein according to any one of (1) to (15) wherein the anti-CD14 antibody in (I) is a chimeric antibody,
(17) the protein according to any one of (1) to (16) wherein the anti-CD14 antibody in (I) is a humanized antibody, or
(18) the protein according to any one of (1) to (17) wherein the anti-CD14 antibody in (I) is one comprising CDR1, CDR2, and CDR3 of the heavy chain described in Table 2 as the CDR1, CDR2, and CDR3 in the heavy chain variable region, or CDR1, CDR2, and CDR3 of the light chain described in Table 2 as the CDR1, CDR2, and CDR3 of the light chain variable region.

A second aspect of the present invention is a polynucleotide which codes for at least a part of the protein according to the first aspect. More specifically, the polynucleotide of this aspect is
(19) a polynucleotide which codes for at least a part of the protein according to any one of (1) to (18).

A third aspect of the present invention is a vector which comprises the polynucleotide according to the second aspect of the present invention. More specifically, the vector of this aspect is
(20) a vector which comprises the polynucleotide of (19).

A fourth aspect of the present invention is a cell which comprises the polynucleotide according to the second aspect of the present invention or the vector according to the third aspect of the present invention. More specifically, the cell of this aspect is
(21) a cell which comprises the polynucleotide of (19) or the vector of (20).

A fifth aspect of the present invention is a method for producing the protein according to the first aspect of the present invention which uses at least one of the polynucleotide according to the second aspect of the present invention, the vector according to the third aspect of the present invention, and the cell according to the fourth aspect of the present invention. More specifically, the method of this aspect is
(22) a method for producing the protein according to any one of (1) to (18) which uses at least one of the polynucleotide of (19), the vector of (20), and the cell of (21).

A sixth aspect of the present invention is a preventive and/or therapeutic agent for a disease comprising at least one of the protein according to the first aspect of the present invention, the polynucleotide according to the second aspect of the present invention, the vector according to the third aspect of the present invention, and the cell according to the fourth aspect of the present invention. More specifically, the preventive and/or therapeutic agent of this aspect is
(23) a preventive and/or therapeutic agent for a disease comprising at least one of the protein of any one of (1) to (18), the polynucleotide of (19), the vector of (20), and the cell of (21), or
(24) the preventive and/or therapeutic agent according to (23) wherein the disease is sepsis, severe sepsis or septic shock, SIRS related disease, endotoxin shock, or ARDS.

EFFECTS OF THE INVENTION

The novel protein of the present invention is effective for a disease or a pathology, or a specific symptom or therapeutic index associated with such disease or pathology, to which use of the anti-CD14 antibody or the protease inhibitor alone is ineffective or insufficiently effective. This protein simultaneously exhibits a stable in vivo anti-inflammatory action, anticoagulant action, and/or elastase inhibitory action, and therefore, it is useful as a preventive and/or therapeutic agent for sepsis.

BRIEF DESCRIPTION OF THE DRAWINGS

FIG. 1 shows the DNA sequence (SEQ ID NO: 123) and the amino acid sequence (SEQ ID NO: 124) of the heavy chain variable region of antibody F1024.

FIG. 2 shows the DNA sequence (SEQ ID NO: 125) and the amino acid sequence (SEQ ID NO: 126) of the light chain variable region of antibody F1024.

FIG. 3 shows the DNA sequence (SEQ ID NO: 127) and the amino acid sequence (SEQ ID NO: 128) of the heavy chain variable region of antibody F1031-13-2.

FIG. 4 shows the DNA sequence (SEQ ID NO: 129) and the amino acid sequence (SEQ ID NO: 130) of the light chain variable region of antibody F1031-13-2.

FIG. 5 shows the DNA sequence (SEQ ID NO: 131) and the amino acid sequence (SEQ ID NO: 132) of the heavy chain variable region of antibody F1031-13-2.

FIG. 6 shows the DNA sequence (SEQ ID NO: 133) and the amino acid sequence (SEQ ID NO: 134) of the light chain variable region of antibody F1031-13-2.

FIG. 32 shows the amino acid sequences (SEQ ID NOS: 10 (residues 474-543), 12 (residues 474-543), 46 through 49, and 27 through 45) of modified UTI domain 2 of fusion protein F1024-D2.

FIG. 33 shows the amino acid sequences (SEQ ID NOS: 10 (residues 474-543), 12 (residues 474-543), 50 through 68) of modified UTI domain 2 of fusion protein F1024-D2.

FIG. 34 shows the amino acid sequences (SEO ID NOS: 10 (residues 474-543), 12 (residues 474-543), 69 through 87) of modified UTI domain 2 of fusion protein F1024-D2.

FIG. 35 shows the amino acid sequences (SEQ ID NOS: 10 (residues 474-543), 12 (residues 474-543), 88 through 106) of modified UTI domain 2 of fusion protein F1024-D2.

FIG. 36 is a view showing the structure of the total amino acid sequences (SEQ ID NOS: 215 and 22) of fusion protein F1024S-D2(4)(R11S/R15T/Q19K/Y46D).

FIG. 37 shows the amino acid sequences (SEQ ID NOS: 107-108) of modified functional domain of TM in fusion protein F1024-TM.

FIG. 38 shows the amino acid sequences (SEQ ID NOS: 109-110) of modified functional domain of TM in fusion protein F1024-TM.

FIG. 39 shows the amino acid sequences (SEQ ID NOS: 111-112) of modified functional domain of TM in fusion protein F1024-TM.

FIG. 40 shows the amino acid sequences (SEQ ID NOS: 113-114) of modified functional domain of TM in fusion protein F1024-TM.

FIG. 41 shows the amino acid sequences (SEO ID NOS: 115-116) of modified functional domain of TM in fusion protein F1024-TM.

FIG. 42 shows the amino acid sequences (SEQ ID NOS: 117-118) of modified functional domain of TM in fusion protein F1024-TM.

FIG. 43 shows the amino acid sequences (SEQ ID NOS: 119-120) of modified functional domain of TM in fusion protein F1024-TM.

FIG. 44 shows the amino acid sequences (SEQ ID NOS: 121-122) of modified functional domain of TM in fusion protein F1024-TM.

FIG. 48 is a view showing the amino acid sequences of the heavy (SEQ ID NO: 219) and light (SEQ ID NO: 223) chain variable regions of F1024-1-3 rat antibody; and the amino acid sequences of human antibodies having a high homology with the heavy (SEQ ID NOS: 220-222) and light (SEQ ID NOS: 224-226) chain variable regions of humanized F1024S-D2(3).

FIG. 49 is a view showing the amino acid sequences (SEQ ID NOS: 219, 227-233) which are capable of expressing the heavy chain of the humanized antibody and maintaining the binding activity.

FIG. 66 is a graph showing FXa-inhibiting activity of polypeptide R11E/Q19K/Y46E of the present invention.

BEST MODE FOR CARRYING OUT THE INVENTION

Figure 7:
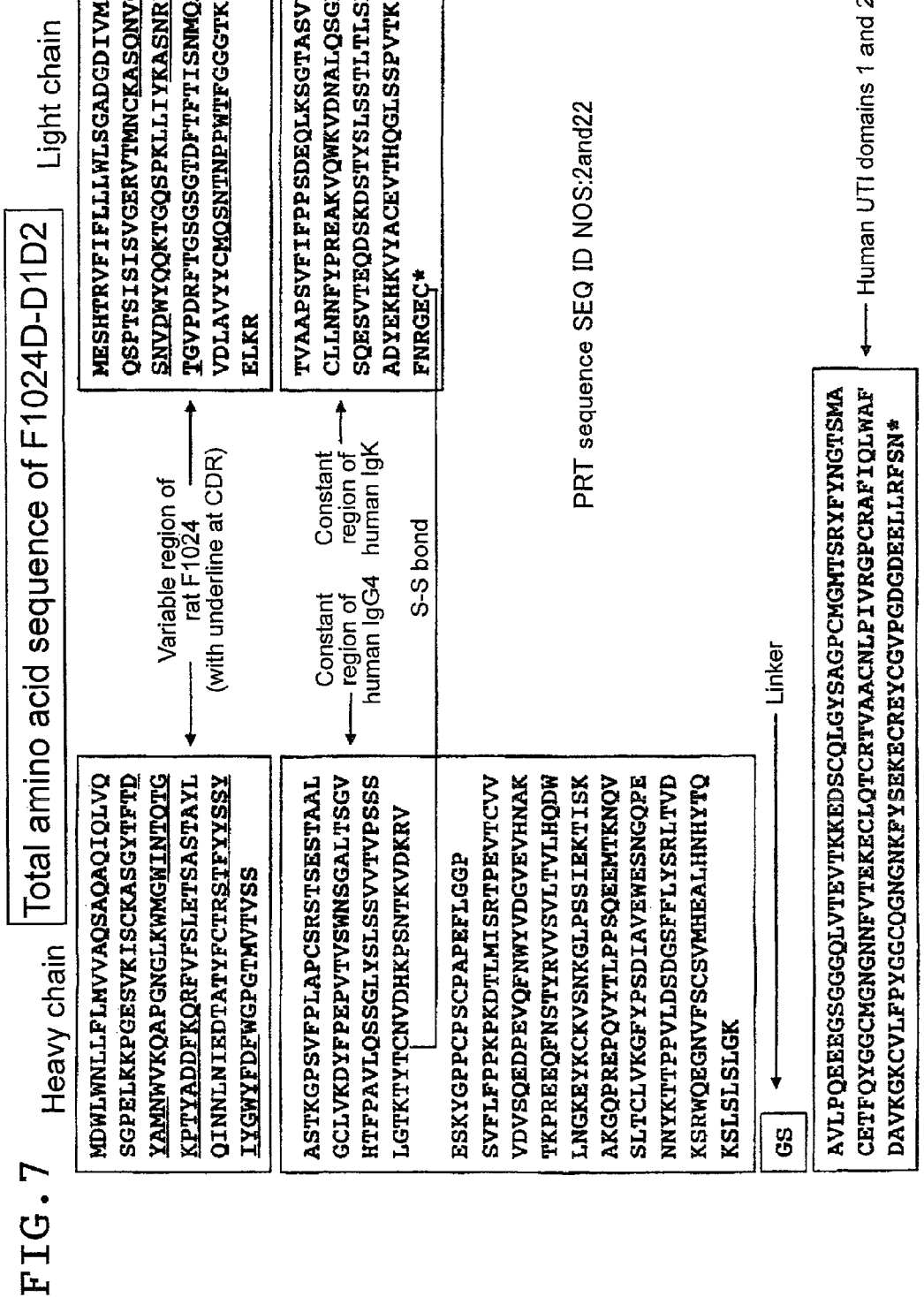
FIG. 7 is a view showing the structure of the total amino acid sequences (SEQ ID NOS: 2 and 22) of fusion protein F1024D-D1D2.
Figure 8:
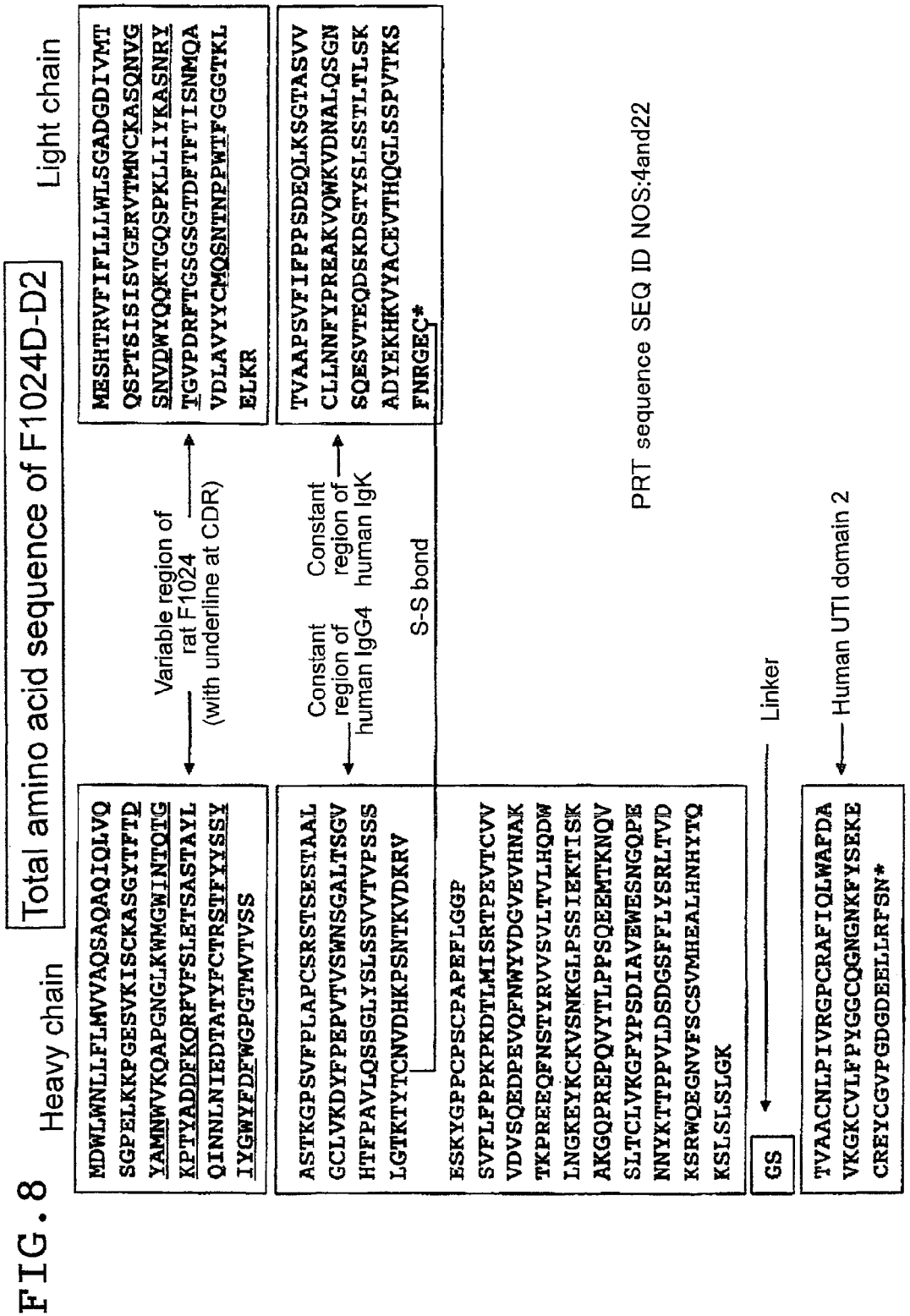
FIG. 8 is a view showing the structure of the total amino acid sequences (SEQ ID NOS: 4 and 22) of fusion protein F1024D-D2.
Figure 9:
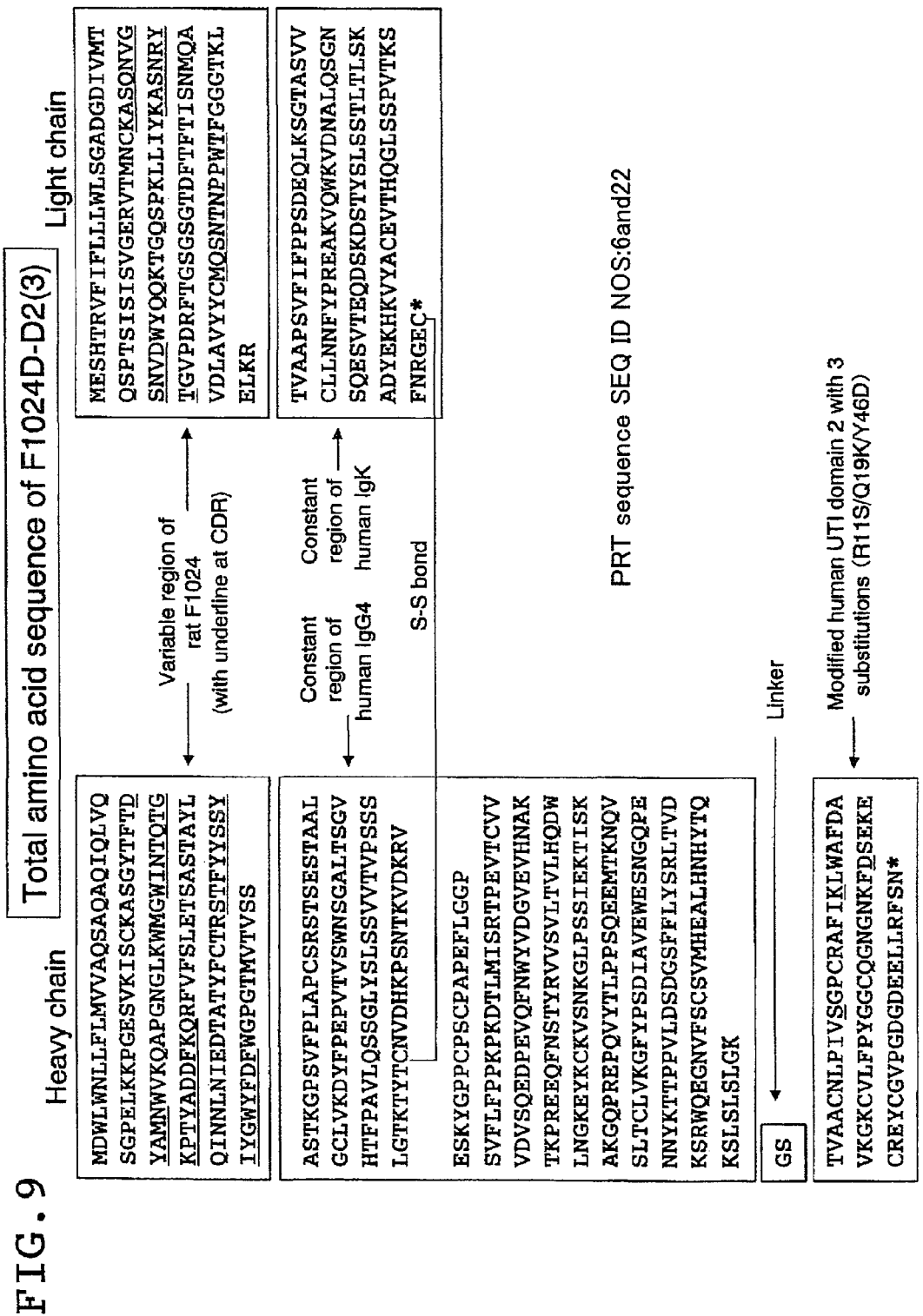
FIG. 9 is a view showing the structure of the total amino acid sequences (SEQ ID NOS: 6 and 22) of fusion protein F1024D-D2(3).
Figure 10:
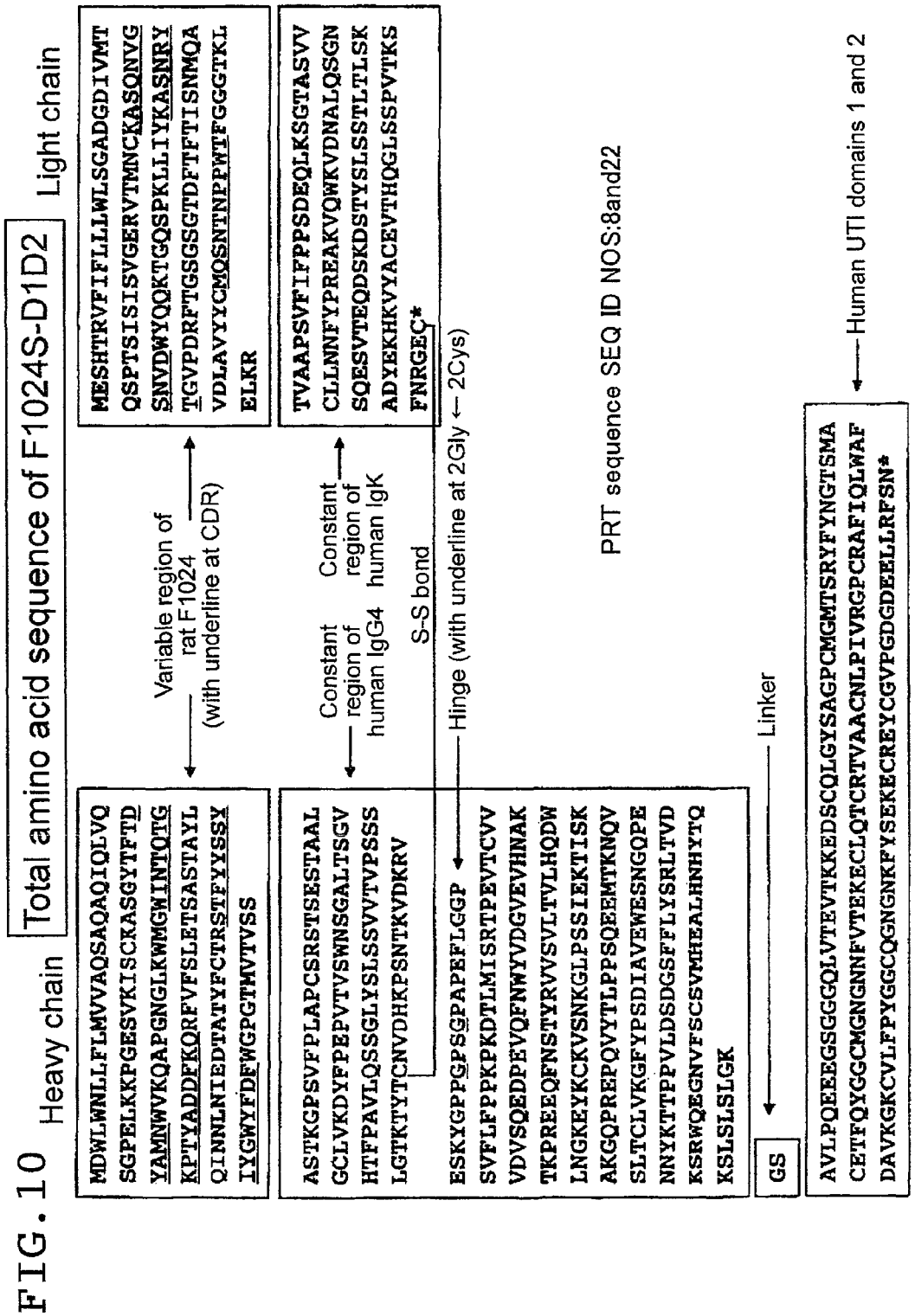
FIG. 10 is a view showing the structure of the total amino acid sequences (SEQ ID NOS: 8 and 22) of fusion protein F1024S-D1D2.
Figure 11:
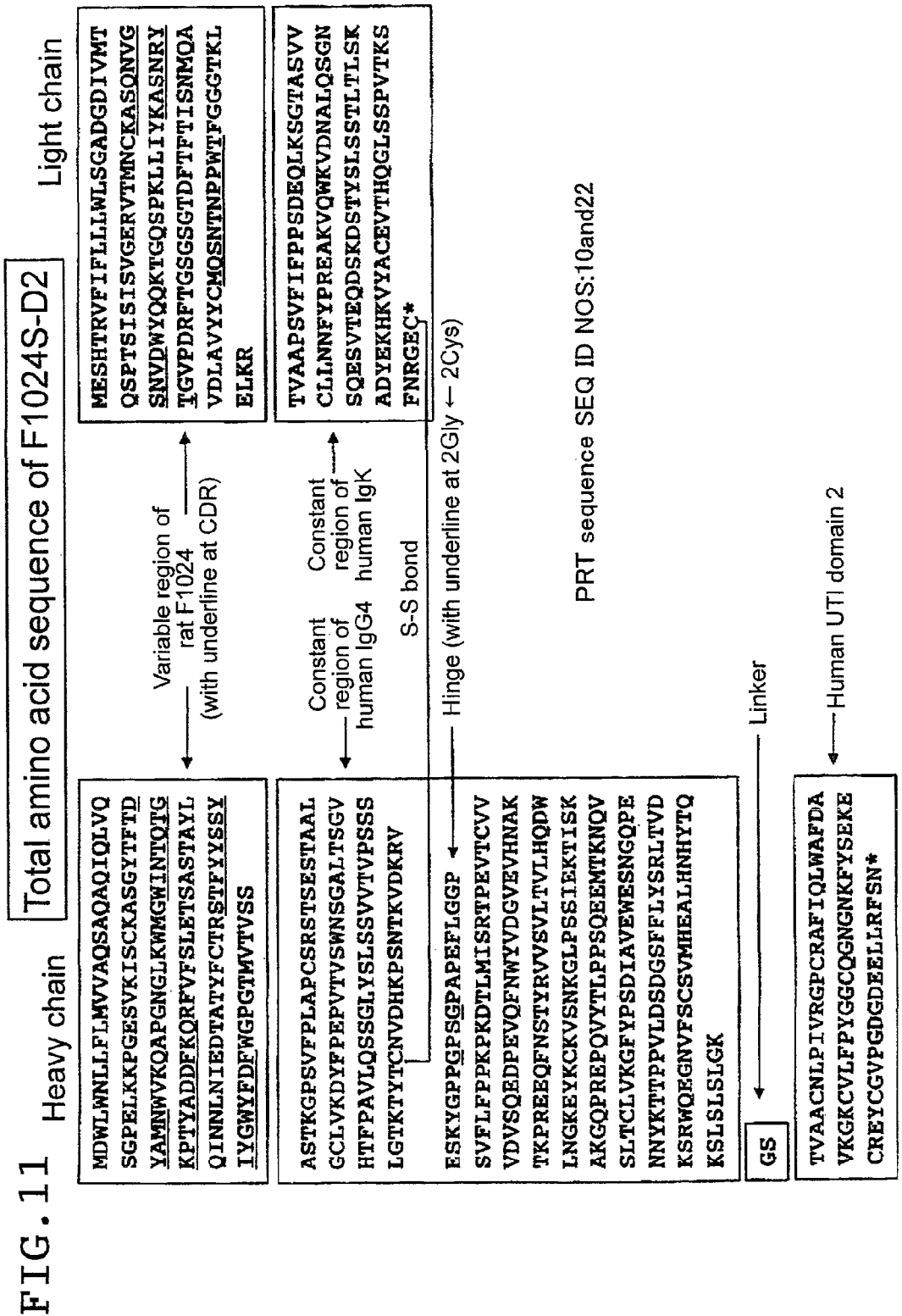
FIG. 11 is a view showing the structure of the total amino acid sequences (SEQ ID NOS: 10 and 22) of fusion protein F1024S-D2.
Figure 12:
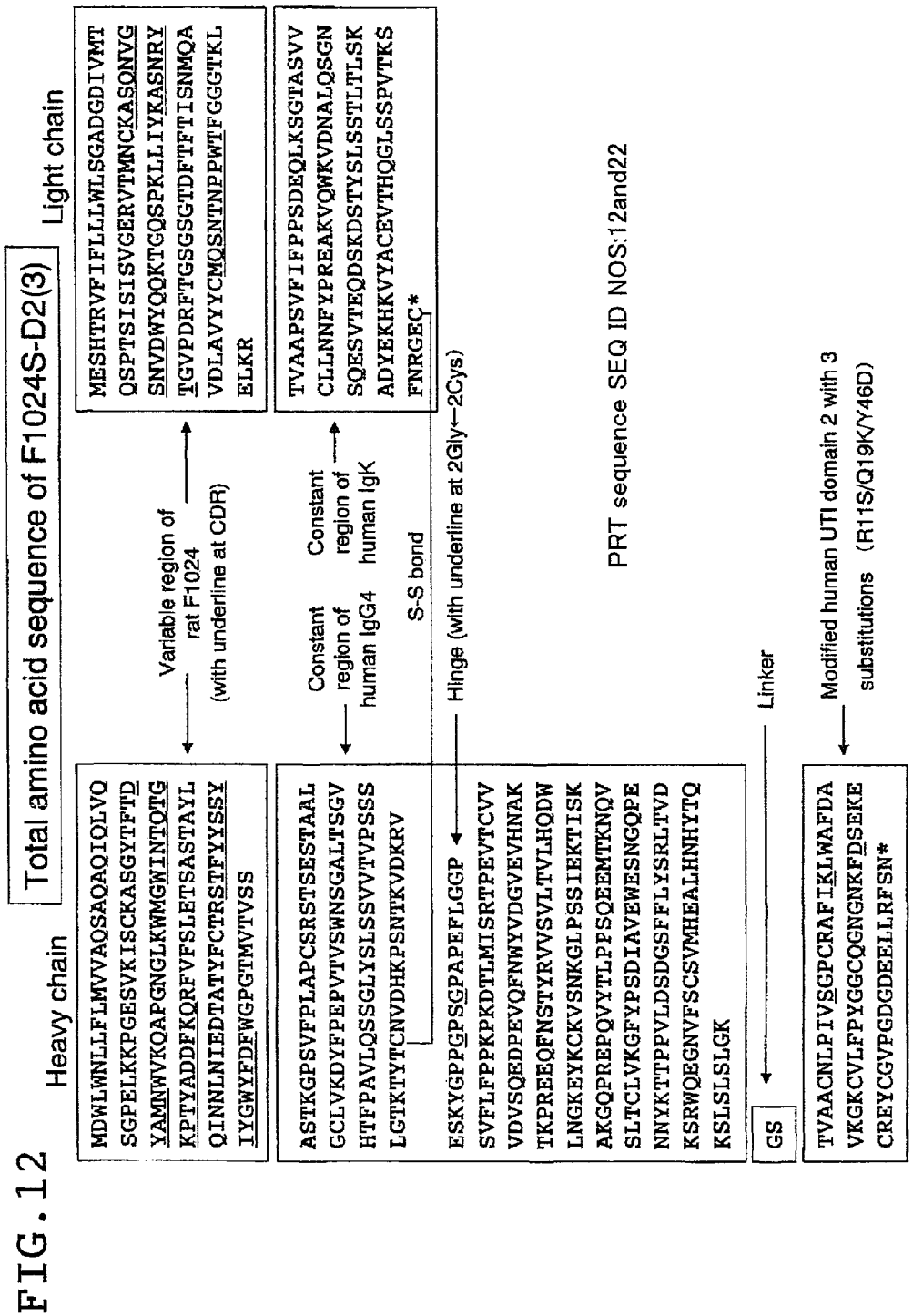
FIG. 12 is a view showing the structure of the total amino acid sequences (SEQ ID NOS: 12 and 22) of fusion protein F1024S-D2(3).
Figure 13:
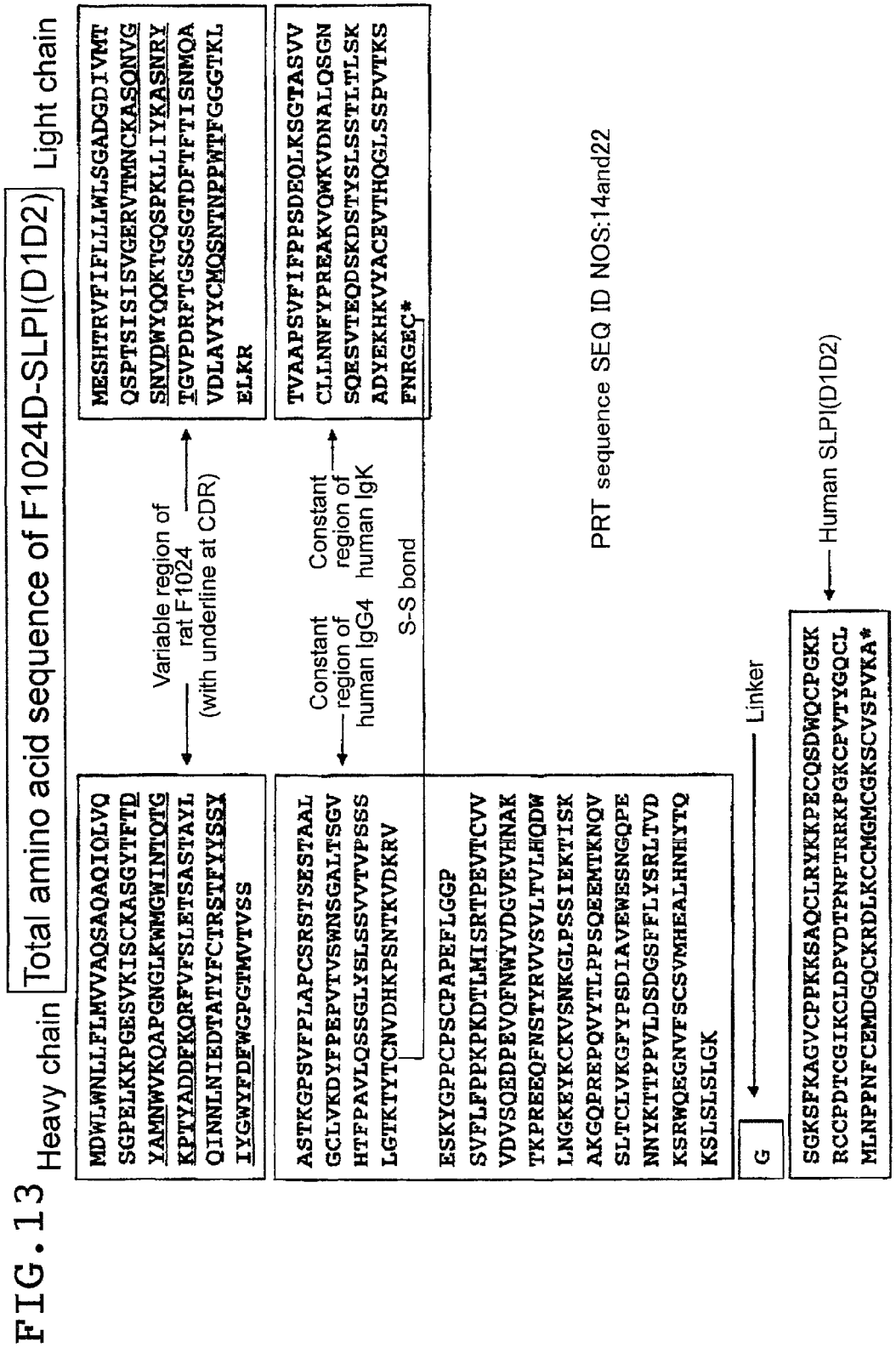
FIG. 13 is a view showing the structure of the total amino acid sequences (SEQ ID NOS: 14 and 22) of fusion protein F1024D-SLP1(D1D2).
Figure 14:
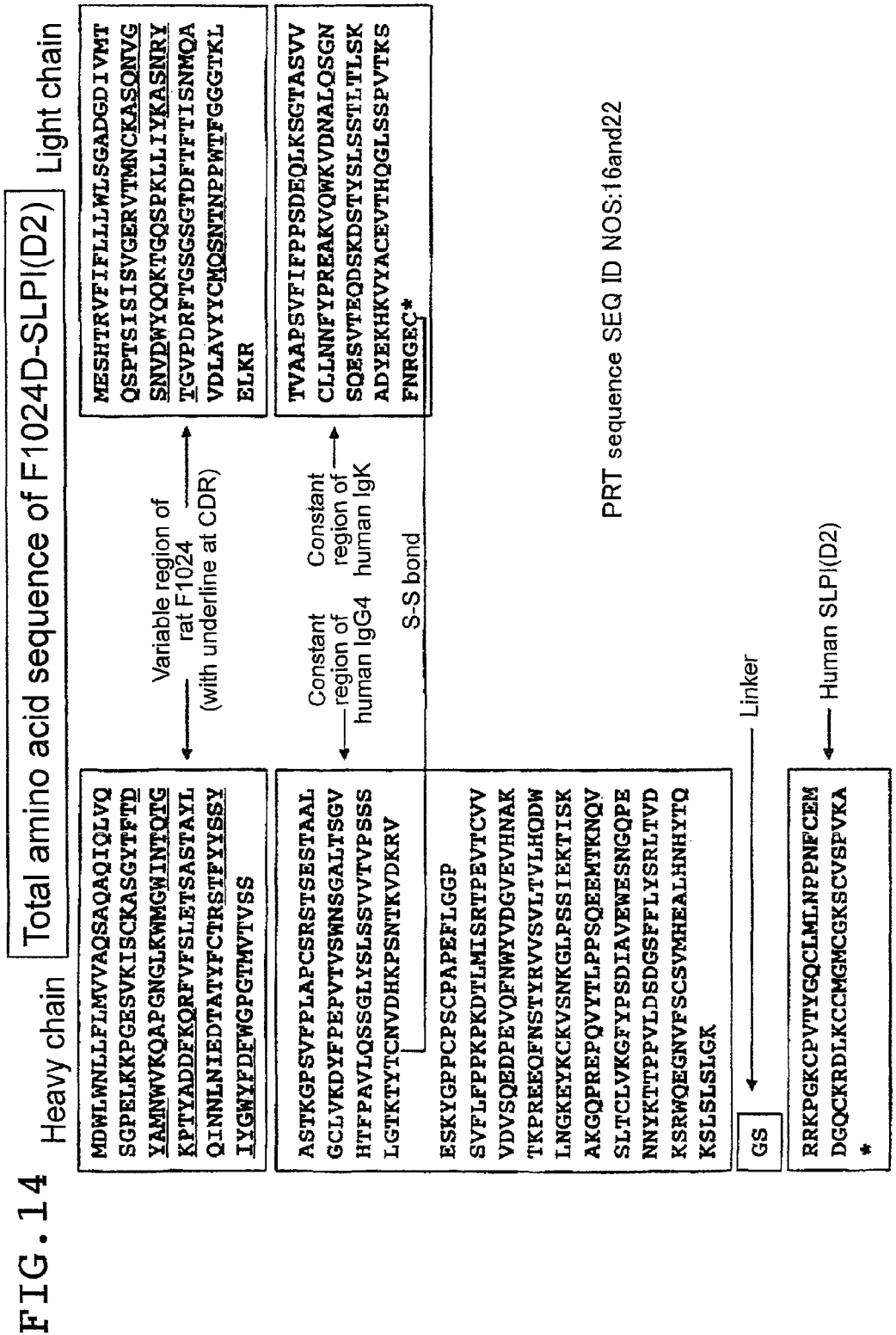
FIG. 14 is a view showing the structure of the total amino acid sequences (SEQ ID NOS: 16 and 22) of fusion protein F1024D-SLP1(D2).
Figure 15:
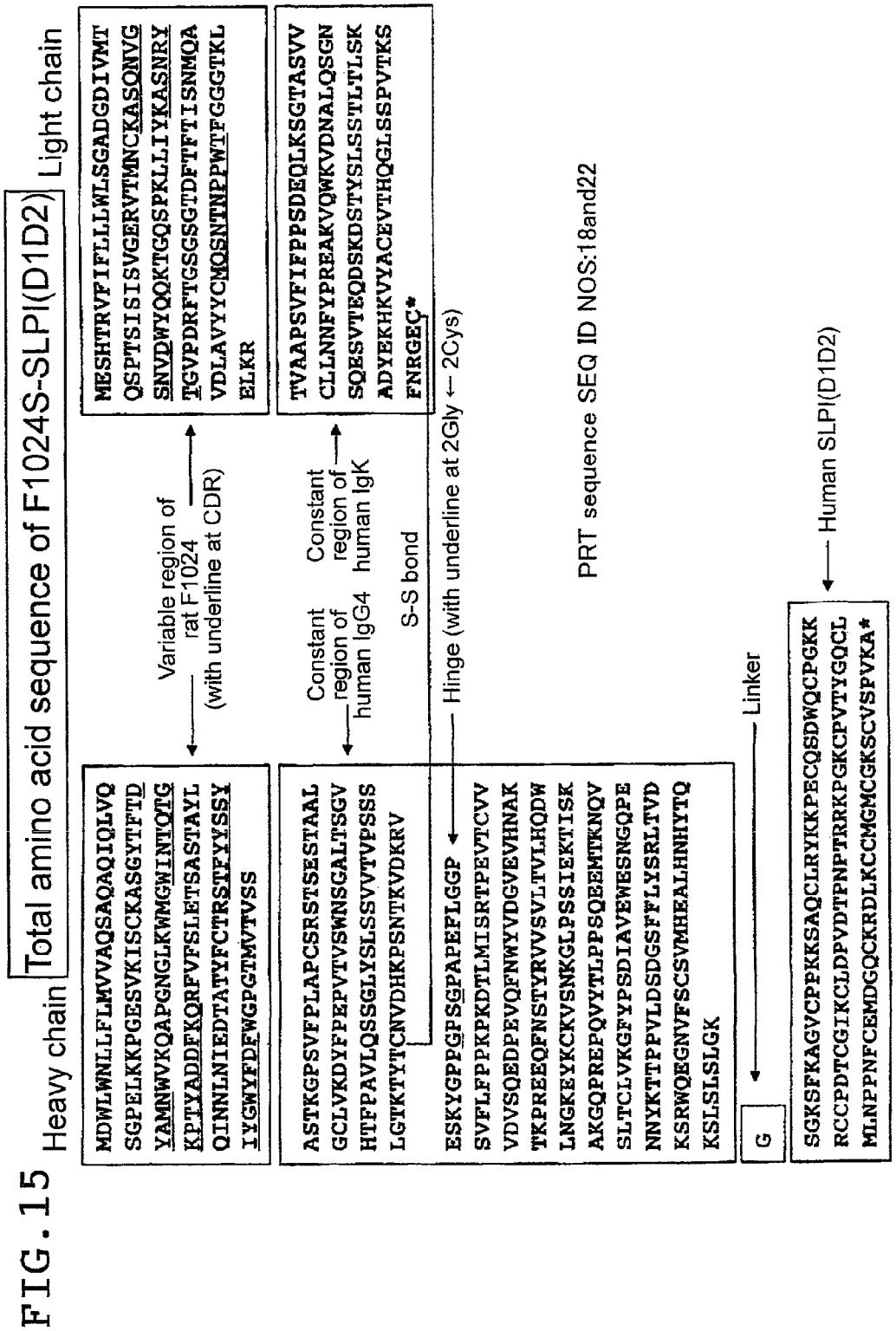
FIG. 15 is a view showing the structure of the total amino acid sequences (SEQ ID NOS: 18 and 22) of fusion protein F1024S-SLP1(D1D2).
Figure 16:
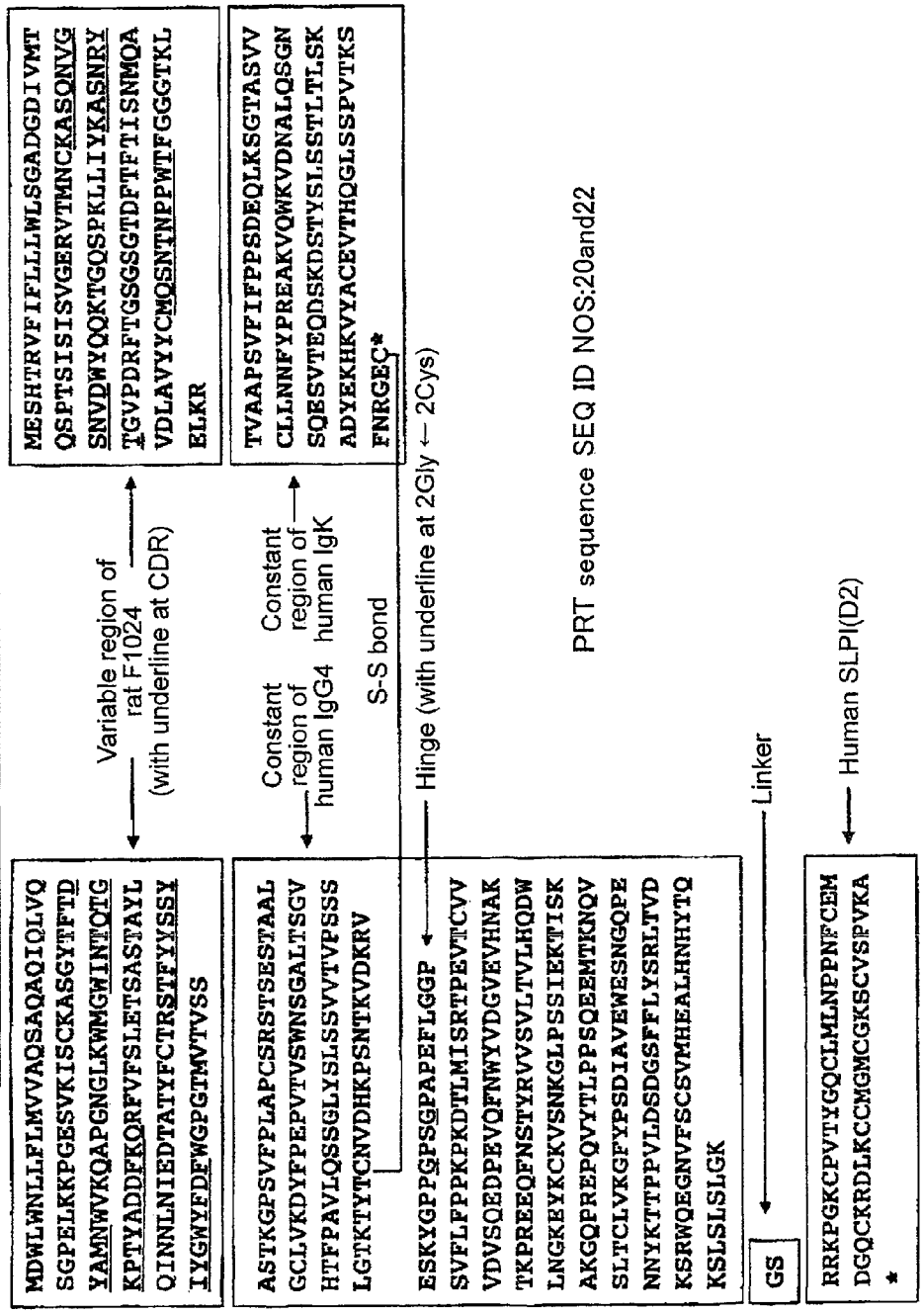
FIG. 16 is a view showing the structure of the total amino acid sequences (SEQ ID NOS: 20 and 22) of fusion protein F1024S-SLP1(D2).
Figure 17:
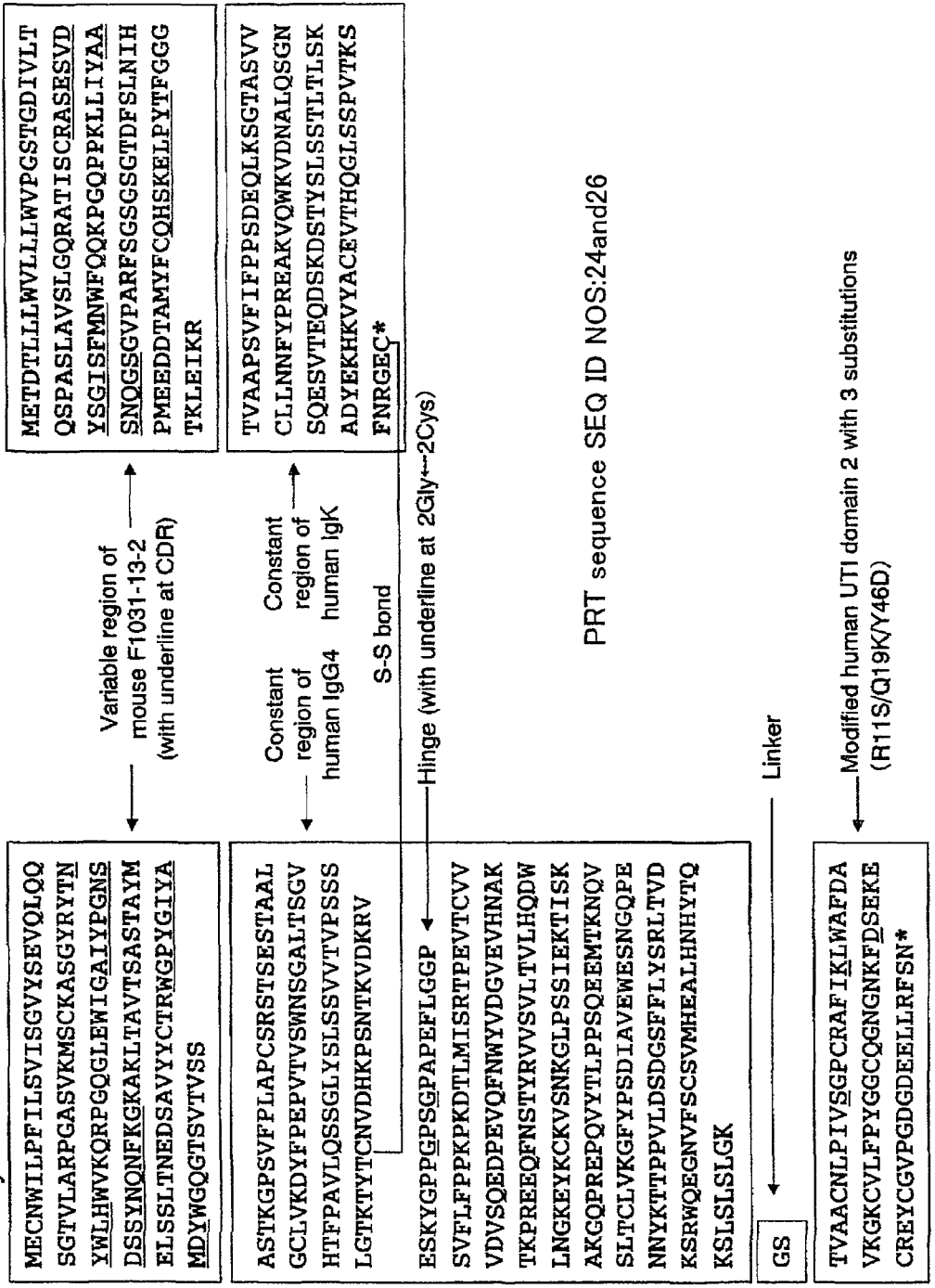
FIG. 17 is a view showing the structure of the total amino acid sequences (SEQ. ID NOS: 24 and 26) of fusion protein F1031-13S-D2(3).

Next, the present invention is described in further detail.

The protein according to the first aspect of the present invention is not particularly limited for its type. Exemplary proteins include simple protein (or polypeptide) and complex protein (for example, glycoprotein).

In the protein according to the first aspect of the present invention, the binding mode between (I) an anti-CD14 antibody or its active fragment, or a derivative thereof and (II) an inhibitor for a protease or its active fragment, or a derivative thereof is not particularly limited. Although (I) and (II) are generally linked by covalent bond, they may be linked, for example, by chemical means (chemical synthesis or chemical conjugation) or genetic engineering. The protein according to the first aspect of the present invention is preferably a fusion protein produced by genetic engineering.

The protease inhibitor (II) may be the one which binds to either one or both of the heavy chain and the light chain of the antibody. Typically, the protease inhibitor (II) is fused to the heavy chain, especially C terminal side of the heavy chain of the antibody. The number of protease inhibitor (II) molecules linked to the antibody is not particularly limited, and either one or two or more molecules may be linked to the antibody. If desired, the linkage may be accomplished by using an appropriate linker or spacer. Such method, the linker, the spacer, and the like are well known to those skilled in the art, and typical examples are described in the Examples.

In the protein of the present invention, active fragment of the anti-CD14 antibody (I) or the protease inhibitor (II) is a fragment which comprises a part which is capable of expressing or retaining at least one of the activities or functions inherent in the anti-CD14 antibody (I) or the protease inhibitor (II), and comprises the active region or functional domain. In the protein of the present invention, the derivative of the anti-CD14 antibody (I), the protease inhibitor (II), or the active fragment thereof is the anti-CD14 antibody (I), the protease inhibitor (II), or the active fragment thereof which includes some modification, mutation, or addition, for example, the one which comprises other chemical substance (such as polyethylene glycol), or the one which is associated with mutation such as addition, deletion, insertion or substitution of at least one, and preferably one to several amino acids. In other words, the derivatives of (I), (II), and active fragments thereof include mutants, modified forms, and modification products of the (I), (II), and active fragments thereof, and they are capable of expressing or retaining at least one, and preferably all of the activities or functions inherent in the anti-CD14 antibody (I), the protease inhibitor, or the active fragment thereof.

The protein according to the first aspect of the present invention expresses or retains at least one, and preferably all of the activities inherent in each of the anti-CD14 antibody (I), and the protease inhibitor (II). Since the protein according to the first aspect of the present invention has at least one, and preferably all of the activities inherent in each of the anti-CD14 antibody (I), and the protease inhibitor (II), it is effective in the disease or the pathology, or the specific symptom or therapeutic index associated with such disease or pathology, to which use of the anti-CD14 antibody (I) or the protease inhibitor (II) alone is ineffective or insufficiently effective.

In the protein according to the first aspect of the present invention, the protease inhibitor (II) is not particularly limited, and it may be a nonprotein inhibitor or a low molecular weight compound. The protease inhibitor (II), however, is preferably a protein inhibitor.

Although the protease inhibitor (II) may also be the one which is specific to a particular enzyme, the protease inhibitor (II) is preferably a multivalent enzyme inhibitor which inhibits two or more enzymes. Exemplary substances having multivalent enzyme inhibitory action include Kunitz-type protease inhibitors such as urinary trypsin inhibitor (UTI), secretory leukocyte protease inhibitor (SLPI), tissue factor pathway inhibitor (TFPI), and aprotinin, among which the preferred are UTI, SLPI, and TFPI.

UTI is a protease inhibitor which is the same as bikunin or ulinastatin, and it is an inhibitor for proteases such as trypsin, plasmin, and neutrophil elastase.

SLPI is an inhibitor for proteases such as neutrophil elastase and cathepsin.

TFPI is a protease inhibitor which is also referred to as lipoprotein-associated coagulation inhibitor (LACI) or extrinsic pathway inhibitor (EPI). TFPI binds to blood coagulation factor Xa (FXa) to inhibit factor VIIa-tissue factor (factor III) complex to thereby suppress the initiation of the extrinsic blood coagulation.

Other multivalent enzyme inhibitors include α2-macroglobulin (α2-MG), antithrombin III (ATIII), and α1-antitrypsin (α1-AT). α2-MG is a plasma protein with a huge molecular weight of about 770,000, and inhibits thrombin, FXa, plasmin, trypsin, chymotrypsin, elastase, and the like. ATIII forms a complex with a serine protease such as FXa or thrombin at a ratio of 1:1, to thereby control the coagulation. ATIII has a heparin binding domain at its N terminal and a reactive site with thrombin at its C terminal, and the anti-thrombin activity of the ATIII increases by a factor of about 1000 by binding to the heparin. α1-AT is a glycoprotein comprising 394 amino acids, and the molecular weight is 51000. α1-AT inhibits various serine proteases including thrombin, plasmin, trypsin, chymotrypsin, and elastase.

The protease inhibitor (II) in the protein of the present invention is preferably an inhibitor which has an inhibitory action for a blood coagulation factor (blood coagulation protease) including the factor which induces anticoagulant action or bradykinin production, especially an inhibitory action for activated blood coagulation factor, or an anti-inflammatory action or an inhibitory action for inflammatory protease. Typical blood coagulation factors include kallikrein, thrombin, FVa, FVIIa, FVIIIa, FIXa, FXa, FXIa, FXIIa, and FXIIIa, and among these, kallikrein, thrombin, FVa, FVIIIa, FIXa, FXa, FXIa, and FXIIIa are the important factors, and thrombin, or FXa and FXIa are the most important target enzymes. Typical inflammatory proteases include elastase, trypsin, chymotrypsin, and cathepsin, and among these, elastase, and in particular, neutrophil elastase and pancreatic elastase, especially neutrophil elastase, are the important target enzymes. The protease inhibitory activity of the protein of the present invention or the inhibitor (II) in the protein of the present invention may be measured by various known materials and methods, and typical examples are described in the Examples.

The inhibitor having the anticoagulant action or the inhibitory action for a blood coagulation factor may be a substance known in the art. Examples include TFPI, ATIII, α1-AT, and α2-MG; and UTI and thrombomodulin (TM); their active fragments, and derivatives thereof, and the preferred are TM or UTI, their active fragments or derivatives thereof, and the more preferred are the functional domain of TM or the UTI domain 2 (UTI-D2) having inhibitory activity for FXa and/or FXIa, or their modified forms, especially the mutant with 3 amino acid substitutions (UTI-D2(3)). The amino acid sequences and the nucleotide sequences of the UTI, UTI-D2, and UTI-D2(3) and their production methods are described in JP 5-84083 A, JP 5-308988 A, JP 6-25289 A, and JP 6-321989 A, and they can be produced by referring to such documents.

Thrombomodulin (TM) is one of the anticoagulants produced by vascular endothelial cell, and when TM forms a complex with thrombin on the cell membrane, protein C will subsequently be activated and the blood coagulation will be suppressed. TM was discovered in 1981, and this substance which is present on the vascular endothelial cell converts thrombin from the coagulation enzyme to an anticoagulation enzyme. TM also directly inhibits the thrombin activity and promotes the activation of the protein C (PC), and the resulting activated protein C (APC) contributes for the negative feedback of the blood coagulation cascade by inactivating activated blood coagulation factor V (FVa) and factor VIII (FVIIIa) to thereby suppress the generation of the thrombin. In other words, TM inhibits both the coagulation activity and the fibrinolytic activity in a manner dependent on the thrombin. Since this action does not require antithrombin III in contrast to the case of heparin, this process is understood to involve less risk of promoting the bleeding tendency.

Since the amino acid sequence of the TM and the nucleotide sequence coding for such amino acid sequence, and the domain structure and the function of the TM are known (for example, Kurosawa, S, Supplementary volume of Progress in Medicine (in Japanese), "Blood Disease—State of Arts (Ver. 2)", 1998, pp. 205-207), preparation of the TM, its active fragments and derivatives used in the present invention and evaluation of their activity may be carried out by referring to such publications as JP 1-6219 A and WO 88/5053. TM comprises 5 domains, namely, lectin-like domain, Epidermal growth factor (EGF)-like domain, O-linked glycosylation domain, transmembrane domain, and cytoplasmic domain from the extra-cellular N terminal (Kurosawa, S. et al., J. Biol. Chem., 263, 5993, 1988), and among these, the EGF-like domain comprises 6 repeating units (this domain is sometimes also referred to as EGF1-6 or TM123456 in the present invention). The minimal active unit is assumed to be the fourth to sixth repeating units of the EGF-like domain, namely, the EGF4-6.

Examples of the preferable active fragments, the derivatives, and the functional domains of the TM include EGF-like domain; active fragments of TM comprising the EGF-like domain or their derivatives; active fragments of the EGF-like domain or their derivatives, which may preferably be EGF4-6, more preferably EGF3-6, and most preferably EGF2-6; active fragments of TM comprising such part or their derivatives, for example, active fragments of the TM or their derivatives prepared in the Examples, especially TM23456M, TM234567M, or their active fragments or derivatives. Preferable examples of the derivatives include a mutant (M388L) in which methionine at amino acid No. 388 of TM has been replaced with leucine, and these are TM23456L and TM234567L. The production and the evaluation of such derivatives may be accomplished by the methods known in the art, and typical examples are described in the Examples.

Various inhibitors are known to have anti-inflammatory action or inhibitory action for inflammatory protease. Although various known inhibitors may be used, the most preferred is elastase inhibitor. Typical examples include UTI, UTI-D2, SLPI, α1-AT and α2-MG and their active fragments or derivatives; and preferable examples are UTI, especially modified UTI domain 2 having elastase inhibitory activity, for example, a mutant of UTI-D2 with 3 amino acid substitutions, a mutant of UTI-D2 with 4 amino acid substitutions (also referred to as UTI-D2(4)), and SLPI, especially the downstream part of the SLPI (the polypeptide at the C terminal). The amino acid sequence, the nucleotide sequence, and the production method of SLPI and the downstream part (the polypeptide at the C terminal) are described in JP 6-80697 A, and the like, and the publication may be used as a reference.

Typical examples of the mutants of the UTI-D2 with 3 or 4 amino acid substitutions are shown in Table 9 of Example 7, and the most preferred is UTI-D2(4) (R11S/R15T/Q19K/Y46D).

The modified UTI domain 2 having the inhibitory activity for FXa and/or FXIa and the elastase inhibitory activity, specifically UTI-D2(3), is most preferred.

In the protein according to the first aspect of present invention, the anti-CD14 antibody is not particularly limited as long as it binds to CD14, and preferably, to human CD14. In the protein of the present invention, the anti-CD14 antibody (I) acts synergistically with the protease inhibitor, and improves the function or the effect of the protein or the inhibitor. The anti-CD14 antibody (I) in the protein according to the first aspect of present invention is not limited by the presence or the absence of the CD14 inhibitory action. However, the anti-CD14 antibody (I) is preferably an antibody which has the CD14 inhibitory action. The term "CD14 inhibitory action" used herein is the action of inhibiting at least one of the functions of the CD14, for example, binding ability with LPS, interaction with TLR, and activation of the TLR expressing cell, and more specifically, activation of NF-κB, production of IL-8, or production of cytokine such as IL-6 by the endothelial cell; and preferably, the action of inhibiting the binding between the CD14 and the TLR, especially the binding between the CD14 and the TLR2 or the TLR4.

Exemplary preferable antibodies include known anti-CD14 antibodies, especially the antibodies disclosed in WO02/42333 or the like and those produced by a known method, for example, a method disclosed in WO02/42333 or the like. The chimeric antibody and the humanized antibody produced from such antibody are also included in the anti-CD14 antibody (I) of the protein of the present invention.

In the protein of the present invention, the anti-CD14 antibody (I) is not particularly limited for its recognition region or binding region as long as it binds to the CD14, and preferably, to the human CD14. However, the anti-CD14 antibody (I) is preferably the one which recognizes or binds to at least a part of the C terminal region of the human CD14, especially to amino acid Nos. 269 to 315, and more preferably amino acid Nos. 285 to 307, and most preferably to the amino acid Nos. 294 to 296. More specifically, the anti-CD14 antibody (I) is the antibody which recognizes or binds to the part of the CD14 or the antigenic determinant on the CD14. Among the CD14 amino acid substitution mutants of CD14 shown in Table 5 (hereinafter sometimes referred to as amino acid substitution product, amino acid substitution modified form, or an amino acid modified form), the preferred is the one which has significantly reduced binding ability to at least one and preferably all of P294H, Q295A, P296H, and P294/296A compared to the binding ability to the human CD14, and the more preferred is the antibody whose binding ability with other mutants has not substantially changed despite such reduced binding ability. The recognition region or the binding region of the anti-CD14 antibody (I) in the protein of the present invention can be confirmed by using the known material and method, for example, by using the material and method described in WO02/42333. The preferable example, however, is described in the Examples.

Furthermore, of the mutants described in Table 5, the anti-CD14 antibody having the CD14 inhibitory activity can be easily screened, identified, or prepared by using the significant reduction of the binding ability to at least one and preferably all of P294H, Q295A, P296H, and P294/296A compared to the binding ability to the human CD14 for the index, and more preferably, by using absence of the substantial change in the binding ability with other mutants in addition to such reduced binding ability with the said specified mutants for the index. The present invention also provides such method.

In the protein according to the first aspect of the present invention, the antibody (I) is preferably a monoclonal antibody although the antibody may be a polyclonal antibody, and its source is not limited to a particular species. In view of ease of preparing the antibody, the source is preferably a mouse or a rat. In view of constituting a pharmaceutical composition, the antibody is preferably a chimeric antibody, a CDR-grafted antibody, a humanized antibody, or human antibody. The human antibody also includes a human antibody prepared by immunizing a transgenic mouse expressing human antibody gene. Also included in the antibody of the present invention is a phage antibody or the like. The humanized antibody is a CDR-grafted antibody in which the constant region and the framework region (FR) are from human and the complementarity determining region (CDR) is from non-human, or an antibody which has further mutation introduced in its FR. The phage antibody is an antibody produced by fusing an antibody with the coat protein of a filamentous phage for presentation of the antibody on a phage particle, and single chain Fv (scFv) form or Fab form is mainly used. The chimeric antibody is an antibody comprising the variable region of a monoclonal antibody from a mammal other than human, for example, a rat or a mouse and the constant region of a human antibody. In the protein according to the first aspect of the present invention, the antibody (I) is not particularly limited for its molecular species, and the antibody may be the one belonging to any class (for example, IgG, IgM, and IgA, especially IgG), subclass (for example, IgG1, IgG2, IgG3, and IgG4, especially IgG4) or isotype. With regard to the light chain of the antibody, either one of the kappa chain and the lambda chain may be used. Also included within the present invention are active fragments and derivatives, such as biologically active Fab (fragment of antigen binding), Fab', F(ab')$_2$, antibody active fragments linked by a linker or the like, such as a single chain antibody (single chain Fv: scFv) (Bird, R. E. et al., Science, 1988; 242: 423-426), a disulfide stabilized antibody (disulfide stabilized Fv: dsFv) (Reiter et al., Protein Engineering, 1994; 7: 697) and a diabody (Holliger P. et al., Proc Natl. Acad Sci USA 1993; 90: 6444-8), a single domain antibody (dAb) (Ward E. S. et al., Nature., 1989; 341:544-6) and the like. These antibodies may be produced by techniques known in the art such as genetic engineering technique and treatment of an antibody with an appropriate protease.

The chimeric antibody is an antibody which has been typically produced by genetic engineering means in which the light chain gene and the heavy chain gene are constituted from the antibody gene segments belonging to different species. For example, the variable (V) segment in the gene from a rat or a mouse monoclonal antibody may be linked to a human constant (C) segment, for example, γ1 and γ4. Therefore, a typical chimeric antibody used for therapeutic purposes is a hybrid protein comprising a V or antigen-binding domain from a rat or a mouse antibody and a C or effector domain from human antibody although other mammalian species may be used.

Preferable examples of the variable region sequence of the antibody (I) in the protein according to the first aspect of the present invention are shown in FIGS. 1 and 2 (SEQ ID NOS: 123 to 126), and the preferable examples of the fusion protein in which the antibody is a chimeric antibody are shown in FIGS. 7 to 17 and Examples.

While an antibody is typically polyvalent in the binding to an antigen (and divalent in the case of IgG), the antibody (I) in the protein of the present invention is preferably monovalent in some phase. A typical such antibody is a monovalent antibody produced by introducing an amino acid mutation in Fab, or in the constant region of an antibody, especially in the constant region of the heavy chain (CH), so that normal formation of the disulfide bond between the heavy chains is prevented, and typically, by substituting Cys residue, especially Cys residue in the hinge region of the antibody heavy chain, with another amino acid residue. Preferable examples are described in the Examples.

A plurality of definitions of the "complementarity determining region (CDR)" and methods for determining its location have been reported and any one may be employed in the present invention. Typical examples include definition by Kabat (Sequences of proteins of immunological interest, 5th ed., U.S. Department of Health and Human Services, 1991) and definition by Chothia (Chothia and Lesk, J. Mol. Biol., 1987; 196: 901-917). In the present invention, the preferable CDR is the one according to the definition of Kabat, while the CDR is not limited to such type. In some cases, the CDR may be determined by considering both the definition of Kabat and the definition of Chothia. For example, the CDR may be an overlapping region of the CDR according to both the definitions or a region covering the CDR according to both the definitions. Typical example of such method is the method of Martin et al. (Proc. Natl. Acad. Sci. USA, 1989; 86: 9268-9272) using Oxford Molecular's AbM antibody modeling software, which is a compromise between the definition of Kabat and the definition of Chothia.

The "framework region" is a region in the light chain and heavy chain variable regions which is considerably conserved among various antibodies in a single species as in the case of the definition by Kabat et al (namely, the region other than the CDR). In the present invention, "human framework region" means the framework region which is substantially the same (with a homology of about 85% or higher) as the framework region of the naturally occurring human antibody or common sequence between some of such antibodies.

The "humanized antibody" is an antibody comprising human framework and at least one CDR derived from a non-human antibody, the constant region of the humanized antibody is substantially the same as the constant region of the human antibody, namely, with the homology at a level of at least about 85 to 90%, and preferably at least 95%. Accordingly, it is likely that the every part of the humanized antibody except the CDR is substantially the same as the corresponding part of at least one natural human antibody sequence. For example, the humanized antibody does not include chimeric antibody comprising the mouse variable region/human constant region.

Such humanized antibody, and more specifically, the antibody (I) of the present invention is a humanized antibody comprising at least one, preferably all (4) of one chain, and more preferably all (4 for each chain), of the framework regions (FRs) from the human acceptor antibodies, preferably from a single human acceptor antibody; and at least one, and preferably all (3 for each chain) of the complementarity determining regions (CDRs) from the antibody F1024. Such antibody may comprise 2 pairs of the light chain/heavy chain complexes, and at least one chain, especially the heavy chain, comprise at least one, and preferably all (3) of the complementarity determining regions from the donor antibody (for example, the rat or mouse antibody, and this applies to the following description) which are functionally linked to the human framework region segment. For example, the complementarity determining region of the donor may be introduced in the human framework region with or without the additional naturally accompanying donor amino acid residues. More illustratively, the humanized antibody of the present invention is the one comprising at least one, and preferably all (3 for each chain) of the CDRs comprising or consisting of any one of the amino acid sequences of the CDRs shown in Table 2. In the humanized antibody, each CDR and the framework are preferably located at positions corresponding to their positions in the original donor antibody.

The humanized antibody used as the antibody (I) of the present invention generally has a homology (percentage of the sequence consistency) of from 65% to 95%, and preferably 70% to 90% between the framework of the heavy chain variable region of the humanized antibody and the framework of the heavy chain variable region of the donor antibody. In the standard procedure, the framework sequences are derived from the heavy chain and the light chain of the same human antibody in order to reduce the risk of incompatibility in the combination of the two chains. The framework sequences, however, may be derived from two or more different human antibodies.

With regard to the human framework region, the sequences are obtained by comparing the amino acid sequences of the frameworks or the variable regions of the non-human antibody from which the CDRs are obtained, with the corresponding sequences in the human antibody sequence collection, and selecting the sequences having a high homology. Preferably, the homology of the framework amino acid sequence is at least 60%, and more preferably at least 65%. In addition, the amino acid sequence of the heavy chain variable region of the acceptor antibody is selected from 5, and more preferably 3 sequences in a typical collection of the sequence of the heavy chain variable region of the human antibody which have the highest homology with the amino acid sequence of the heavy chain variable region of the donor antibody. The designing of the humanized antibody may be accomplished as described below.

1) When the particular amino acid corresponds to the following categories (a) to (c), this particular amino acid in the framework of the human antibody (acceptor antibody) may be substituted with the amino acid from the non-human antibody (donor antibody).

(a) the particular amino acid in the human framework region of the acceptor antibody is rarely found at the position of the human antibody, while this corresponding amino acid in the donor antibody is typically found at the position of the human antibody;

(b) the particular amino acid is close or adjacent to one of the CDRs in the primary sequence; or (c) the particular amino acid has an atom at a distance within about 5, preferably 4, and more preferably 3 angstroms in the three-dimensional model of the donor antibody or the humanized antibody (Co et al., Proc. Natl. Acad. Sci. USA, 1991; 88: 2869).

2) When a particular amino acid in the human framework region of the acceptor antibody and the corresponding amino acid in the donor antibody are rare at the corresponding position of the human antibody, the amino acid is substituted with the amino acid which is typically found at the corresponding position of the human framework.

For detailed description of the production of the humanized antibody, Queen et al., Proc, Natl. Acad. Sci. USA, 1989; 86: 10029, WO90/07861, WO92/11018, Co et al., Proc, Natl. Acad. Sci. USA, 1991; 88: 2869, Co and Queen, Nature, 1991; 351: 501, and Co et al., J. Immunol., 1992; 148: 1149 may be referred to, which are herein incorporated by reference.

It is generally desirable that all or most of the amino acid substitutions fulfill the criteria as described above. However, since uncertainty is associated with the judgment whether the individual amino acid is actually consistent with the criteria as described above, and various antibodies produced include those with and without the substitution at the particular position, optimization of the CDR and the FR may be conducted by computer modeling.

When the V region of the human antibody having a high homology is found, the CDR sequences of the donor antibody, especially antibody F1024, are transplanted into the framework portion of such V region, and the conformation is simulated by computer molecular modeling. The programs used in this step include ABMOD and ENCAD (Biochemistry, 1990; 29: 10032). By this simulation of the conformation, optimization is accomplished by substituting an amino acid in the FR near the CDR with another amino acid so that the amino acid arrangement of the CDR region will realize optimized binding activity with the CD14.

Alternatively, the optimization of the CDR and FR may be accomplished by using the amino acid sequence of a part of the FR of the donor antibody, especially antibody F1024, without any change in the sequence and transplanting such sequence into the V region of the human antibody. In this case, the sequence of a part of the CDR and the FR of the antibody F1024 is transplanted into the V region of the human antibody, and the conformation is simulated by computer molecular modeling. Exemplary programs which may be used in this step include Modeler and QUANTA/CHARMm (Molecular Simulations).

When 3 to 4 sites in the light chain and 7 to 8 sites in the heavy chain are replaced with the amino acids from a donor, for example rat, FR will have a structure resembling the rat antibody and the arrangement of the amino acids in the CDR region may facilitate optimization of the binding activity with the CD14.

As long as the binding activity as an anti-CD14 antibody is retained, deletion, substitution, insertion, or addition of a single or 2 or more amino acids may be conducted in the amino acids of the CDR region. In this case, binding activity as an anti-CD14 antibody is more likely to be retained when the substitution takes place between the amino acids classified as the same group, for example, between Gly and Ala; Val, Leu and Ile; Asn and Gln; Cys and Met; or Lys and Arg. In addition, the amino acids at some positions of the framework region are involved in the direct interaction with the antigen, for example, contact with the antigen in a noncovalent binding mode, and such positions are also subject to the substitution as described above. Especially, the amino acids at 26th to 30th of the heavy chain are described to be a part of the hypervariable loop in terms of the conformation (Chothia and Lesk, J. Mol. Biol., 1987; 196: 901-917), and such region may also be transplanted as in the case of the CDR.

The humanized antibody is prepared based on the resulting amino acid sequence. For example, the nucleotide sequence of the humanized antibody may be determined from the thus determined amino acid sequence, and the gene coding for the humanized monoclonal antibody is thereby produced. More specifically, DNA coding for the CDR is deleted from the gene coding for the human V region, and instead, the DNA coding for the CDR from the donor such as the rat is inserted. According to the changed amino acid based on the results of the molecular modeling, the corresponding DNA sequence is altered, for example, by site-directed mutagenesis using PCR to thereby produce the recombinant human V gene. This gene is cloned into the vector comprising the C regions of the heavy chain and the light chain of the human antibody to produce the expression vector. By changing the sequence from the human used in this stage, antibodies of the desired subclass, for example, human IgG1 or IgG3, and preferably IgG4 and the like may be produced. The expression vector may be introduced and expressed in mouse myeloma cell Sp2-O-ag14 (ATCC CRL1581) or hamster ovary cell CHO.

The humanized antibody has at least three latent advantages when used for therapeutic treatment of human compared to the non-human antibody, for example, the mouse or rat antibody, and in some cases, chimeric antibody.

1) Since the effector part is of human origin, the antibody undergoes better interaction with other parts of the human immune system (for example, a more efficient destruction of the target cell by complement-dependent cytotoxicity (CDC) or antibody-dependent cellular cytotoxicity (ADCC)).

2) Human immune system does not recognize the framework or the C region of the humanized antibody as a foreign substance, and therefore, response by the antibody upon administration of the antibody is reduced compared to the mouse antibody which is totally foreign or the chimeric antibody which is partly foreign.

3) Administered rat and mouse antibodies are reported to have an in vivo half life in the circulation in blood of human which is extremely shorter than the normal antibodies (Shaw, D. et al., J. Immunol., 1987; 138: 4534-4538). The humanized antibody after the administration probably has a half life more or less resembling that of the naturally occurring human antibody, and effective administration will be accomplished by using a smaller amount or by administering at a lower frequency.

The anti-CD14 antibody (I) may include the antibodies, especially humanized antibodies, having at least one of the CDRs of the antibody described in the Examples, especially F1024, preferably having 3 CDRs in the heavy chain variable region (VH) or the light chain variable region (VL) of the antibody, and more preferably having all of the 6 CDRs of the antibody, positioned at the corresponding positions. More specifically, the anti-CD14 antibody (I) is an antibody, especially a humanized antibody, comprising the CDR1, CDR2, and CDR3 of the heavy chain described in Table 2 as the CDR1, CDR2, and CDR3 of the heavy chain variable region and/or the CDR1, CDR2, and CDR3 of the light chain described in Table 2 as the CDR1, CDR2, and CDR3 of the light chain variable region.

When the anti-CD14 antibody (I) is a human antibody, exemplary methods used in the production include a method in which a hybridoma is produced by using activation of human lymphocyte by in vitro immunization; a method carried out by using a human antibody phage library; and a method in which a hybridoma is produced by using a non-human animal having the recombinant human antibody gene, especially a transgenic mouse such as KM mouse (WO2002/070648 (JP 2005-504507 A) and WO2002/043478 (JP 2004-515230 A)).

The human antibody phage library is a library produced by inserting the antibody gene prepared from human B cell in a phage gene to promote expression of the active fragments of the antibody such as the Fab and the single chain antibody on the surface of the phage. The antibody of the present invention can also be obtained by screening such libraries. These and other methods are well known to those skilled in the art (Huse et al., Science, 246: 1275-1281 (1989), Winter and Harris, Immunol. Today 14: 243-246 (1993), Ward et al., Nature 341: 544-546 (1989), Harlow and Lane (1988), supra, Hilyard et al., Protein Engineering: A practical approach (IRL Press 1992), Borrabeck, Antibody Engineering, 2nd ed. (Oxford University Press 1995), Barbas, C. F. I., Burton, D. R., Scott, J. K., and Silverman, G. J. 2001. Phage display: a laboratory manual. Cold Spring Harbor Laboratory Press. Cold Spring Harbor, N.Y., USA. 736 pp.). A phage expressing the active fragment of the antibody having the desired antigen binding activity may be collected from the library by using the binding activity to a substrate having an antigen immobilized thereto for the index. The active fragment of the antibody may also be converted to a human antibody molecule comprising two complete H chains and two complete L chains by genetic engineering.

The polynucleotide according to the second aspect of the present invention may be any molecular species including the nucleic acid. The polynucleotide may include DNA and RNA as well as polydeoxyribonucleotide and polyribonucleotide. The polynucleotide may be a mixture or a modification product thereof as long as it codes for at least a part of the protein according to the first aspect of the present invention. The polynucleotide according to the second aspect of the present invention can be produced from the cell producing the (I) and/or (II) as described above by a method known in the art, and particularly by genetic engineering. Typical examples are described in the Examples.

The second aspect of the present invention is a polynucleotide coding for the protein, preferably the fusion protein, and more specifically, the fusion protein comprising an antibody of the first aspect. However, since the antibody is a protein inherently comprising a plurality of polypeptide chains, the polynucleotide of the present invention includes the case in which the single molecule polynucleotide codes for the protein of the present invention and the case in which 2 or more molecules, for example, 2 or 3 molecules of polynucleotide codes for the protein of the present invention. Typical examples are described in the Examples. With regard to at least a part of the protein according to the first aspect of the present invention, typical polynucleotide is the polynucleotide coding for the heavy chain, especially the heavy chain variable region (VH) part of the antibody, or the heavy chain part and the inhibitor part, or preferably their fusion protein; or the polynucleotide coding for the light chain, especially the light chain variable region (VL) part of the antibody, or the light chain part and the inhibitor part, or preferably their fusion protein. Preferable examples of the polynucleotide include those shown by SEQ ID NOS: 1, 3, 5, 7, 9, 11, 13, 15, 17, 19, 21, 23, and 25 in the Sequence Listing.

The vector according to the third aspect of the present invention includes a case in which the polynucleotide according to the second aspect is present on a single vector, and a case in which the polynucleotide is present on 2 or more vectors, for example, 2 or 3 vectors. The vector according to the third aspect of the present invention may also include components required for replication of the vector and components required for controlling the expression of the polynucleotide according to the second aspect in addition to the polynucleotide according to the second aspect. Such additional components are well known to those skilled in the art.

The vector used for the incorporation of the polynucleotide according to the second aspect is not particularly limited. The vector, however, is preferably a vector which is generally used for the expression of a protein gene, especially a vector which is adapted for expression of an antibody or a fusion protein comprising an antibody, or a vector for overexpression. Exemplary preferable vectors include a vector comprising human elongation factor (EF) 1α promoter and/or CMV enhancer, for example, pEF-BOS or the vector used in the Examples. While the general practice is such that an expression vector having incorporated therein a polynucleotide coding for the VH part, or the VH and the inhibitor part, and preferably, the fusion protein of the VH and the inhibitor part, and an expression vector having incorporated therein a polynucleotide coding for the VL part, or the VL part and the inhibitor part, and preferably, the fusion protein of the VL part and the inhibitor part are separately prepared, and these vectors are cotransfected in a host cell, it is also possible to incorporate both polynucleotides in a single expression vector. The procedure as described above may be carried out by using known materials and methods, and typical examples are described in the Examples.

The cell according to the fourth aspect of the present invention can be prepared by introducing the vector according to the third aspect of the present invention in an adequate host cell by the method known in the art. Examples of such cells include hybridoma, transformant, and genetically modified cell having the polynucleotide or the vector of the present invention introduced therein. The host cell used is not particularly limited, and the preferred are those which are generally used in the expression of a protein gene or the like, especially the cells which are adapted for use in the expression of an antibody, a fusion protein comprising an antibody or the like. Exemplary host cells include bacteria (for example, E. coli), actinomycete, yeast, insect cell (for example, SF9), and mammalian cell (for example, COS-1, CHO, and myeloma cell), and the preferred is the mammalian cell. The procedure as described above may be carried out by using known materials and methods, and typical examples are described in the Examples.

The protein according to the first aspect of the present invention can be produced by the in vitro translation using the polynucleotide according to the second aspect or the vector according to the third aspect of the present invention, or by cultivating the cell according to the fourth aspect of the present invention under appropriate conditions (fifth aspect of the present invention). The protein produced may be isolated by combining appropriate known purification methods. Preferable examples are described in the Examples.

The preventive and/or therapeutic agent for a disease according to the sixth aspect of the present invention is a pharmaceutical composition comprising at least one of the protein according to the first aspect of the present invention, the polynucleotide according to the second aspect of the present invention, the vector according to the third aspect of the present invention, and the cell according to the fourth aspect of the present invention as its effective component, and the polynucleotide and the vector of the present invention can be used, for example, in gene therapy, and the transformant can be used in cell therapy with optional addition of pharmaceutically acceptable additives.

The preventive and/or therapeutic agent for a disease according to the sixth aspect of the present invention can be applied to various diseases or pathologies, or particular therapeutic indexes associated with such diseases or pathology. Although such disease, pathology, and therapeutic index are not limited to any particular types, they are preferably diseases related to distribution or function of the CD14, distribution or function of the protease, or bacterial infection. Accordingly, the preventive and/or therapeutic agent of the present invention may be used for sepsis and related diseases, systemic or cardiovascular disease, infectious disease, inflammatory disease, respiratory disease or respiratory failure, autoimmune disease, multiple organ dysfunction syndrome (MODS) or failure or dysfunction of individual organ. More specifically, the preventive and/or therapeutic agent of the present invention may be used for sepsis and related diseases such as severe sepsis, septic ARDS and septic shock; SIRS related disease; shocks such as endotoxin shock, exotoxin shock, hemorrhagic shock, and intraoperative or postoperative shock; systemic or cardiovascular diseases such as ischemic reperfusion organ failure, ischemic encephalopathy, acute ischemic stroke, acute stage cerebral thrombosis, acute coronary microvascular embolus, vascular embolus resulting from shock, disseminated intravascular coagulation (DIC), myocardial infarction and its aftereffect, and hypotension; infectious diseases such as periodontal disease, acute bacterial meningitis, invasive staphylococcal infection, infectious endocarditis, acute viral encephalitis, and AIDS; inflammatory diseases such as psoriasis, gastritis, peptic ulcer, pancreatitis, nephritis, myocarditis, pneumonia, hepatitis, liver cirrhosis, encephalitis, osteoarthritis, atopic dermatitis, allergic contact dermatitis, allergic rhinitis, reflux esophagitis, and ankylosing spondylitis; respiratory diseases or respiratory failures such as acute respiratory distress syndrome (ARDS), infantile respiratory distress syndrome (IRDS), chronic obstructive pulmonary disease (COPD), pulmonary emphysema, and asthma; autoimmune diseases such as chronic rheumatoid arthritis, intractable colitis, ulcerative colitis, Crohn's disease, glomerulonephritis, SLE, scleroderma, multiple sclerosis and Sjoegren's syndrome; multiple organ failure; organ failure or rejection after organ transplantation; and individual organ dysfunctions such as cardiac failure, unstable angina, valvulitis, renal failure, cardiomyopathy, nephratonia, hepatic insufficiency, and fulminant hepatic failure.

Preferable diseases for application of the preventive and/or therapeutic agent are diseases such as sepsis, severe sepsis, septic ARDS or septic shock, SIRS, endotoxin shock, and ARDS.

The preventive and/or therapeutic agent of the present invention is also useful for improving or preventing the conditions associated with the increase in the inflammatory cytokine, especially increase in the blood TNF concentration. Furthermore, the agent of the present invention is expected to have therapeutic and preventive effects on Gram-negative bacterial infection in which LPS is involved, Gram-positive bacterial infection in which LTA or peptidoglycan is involved, and sepsis associated with mycoplasma infection, namely, therapeutic effects after emergence or progress of the conditions associated with such diseases as well as preventive effects for patients exhibiting high value of blood LPS, LTA, or mycoplasma, patients exhibiting high blood concentration of certain CD14 molecular species (see WO01/22085 and WO2004/44005), and those who are expected to develop such conditions.

Exemplary pharmaceutically acceptable additives which may be incorporated as desired include carrier, excipient, stabilizer, lubricant, colorant, disintegrant, antiseptic, isotonic agent, stabilizer, dispersant, antioxidant, buffer agent, preservative, suspending agent, emulsifier, appropriate solvents generally used in the art (for example, sterile water and vegetable oil), and physiologically acceptable solubilizer.

The pharmaceutical composition of the present invention may also comprise an antibiotic, steroid, various cytokine antibodies, or anticoagulants. These agents will exhibit additive effects or synergistic effects with the protein of the present invention, and the pharmaceutical composition will have an improved effectiveness.

The dose when the pharmaceutical composition of the present invention is administered as a agent is not particularly limited, and the dose may be adequately determined by taking the conditions, body weight, age, sex, and the like of a patient into consideration. In a typical case of administering the protein of the present invention as the effective component, the dose is preferably at least 0.1 mg/kg, and more preferably 1 to 10 mg/kg.

The dosage form used in administering the pharmaceutical composition of the present invention as a agent is not particularly limited, and preferable dosage forms include tablet, injection, powder, suppository, inhalant, and the more preferred are injection and inhalant. While various administration routes are possible, the preferred is parenteral administration. Parenteral administration is commonly performed with an injection such as intravenous administration (bolus administration, continuous infusion, intermittent infusion), intraarterial administration, subcutaneous administration, and intramuscular administration, and inhalation is also preferably used. Other administration routes include intrarectal administration, percutaneous absorption, intraarticular administration, transnasal administration, and transmucosal administration. The administration method may include prophylactic administration, single administration, and continuous administration while actual timing and frequency of the administration depends on the conditions of the patient.

Also provided is a therapeutic method using the agent comprising the pharmaceutical composition of the present invention as its main ingredient for the disease or the pathology to which the preventive and/or therapeutic agent according to the sixth aspect of the present invention is applied.

EXAMPLES

Next, the present invention is described in further detail by referring to the Examples which by no means limit the scope of the present invention.

Example 1

Construction of Chimeric Antibody and Antibody Fusion Protein 1-1) Construction of Chimeric Antibody and Antibody Fusion Protein (F1024)

(1) Materials

Major materials and apparatus used were as described below.

Primer: primers shown in Table 1 (synthesized by Sigma Genosys Japan, K.K.),

Enzyme for PCR: Ex Taq (TAKARA BIO INC.),

Restriction enzymes: EcoRI, BamHI, NotI, NheI, EcoRV, StuI, BglII, and others (TAKARA BIO INC.), Genomic DNA: HeLa genome (lot. N34707-1, BD Biosciences Clontech), PCR apparatus: DNA Engine (MJ RESEARCH, INC.), Agarose electrophoresis gel: SeaKem GTG Agarose (TAKARA BIO INC.), 50×TAE (2 mol/L Tris-acetate, 0.05 mol/L EDTA) (NIPPON GENE CO., LTD.), Molecular weight marker (λ DNA fragment digested with StyI), Kit used for extraction of DNA fragment from the gel (QIAEX II, QIAGEN K.K.), Expression vector for mammalian cell: pEF2cew (a vector produced by improving pEF-BOS), Plasmid comprising human IgG4 heavy chain constant region (Cγ4) gene: pTK-2232, TA cloning vector: pT7BlueT (NOVAGEN) and ligation reagent: TaKaRa ligation Kit ver. 2 (TAKARA BIO INC.), E. coli competent cell: JM109 (TAKARA BIO INC.), Plasmid DNA and genomic DNA purification kit (QIAGEN K.K.), Sequencing kit: DYEnamic ET Terminator Cycle Sequencing Premix Kit lot. 1767 (Amersham Biosciences) and analyzer: ABI3100 genetic analyzer (Applied Biosystems), Total RNA isolation reagent: TRIzol (GIBCO BRL), 5'RACE kit: 5'RACE system for Rapid Amplification of cDNA Ends, v. 2.0 (Invitrogen Corporation), Dulbecco's MEM (SIGMA), Transfection reagent: FuGENE6 (Roche Diagnostics K.K.)

TABLE 1

Sequence of primers

| Primer Name | Base Sequence | SEQ ID |
|---|---|---|
| M4 | 5'-GTTTTCCCAGTCACGACG-3' | 135 |
| T7 | 5'-CTGTTGTTTCAGCTGAGGACAC-3' | 136 |
| rIgH-b | 5'-CTGTTGTTTCAGCTGAGGACAC-3' | 137 |
| rIgH-c | 5'-AGGGTCACCATGGAGTTACTT-3' | 138 |
| rIgK-a | 5'-AGATACAGTTGGTGCAGCATCAGC-3' | 139 |
| rIgK-b | 5'-GACACTGATGTCTCTGGGATAGA-3' | 140 |
| 1024H-a | 5'-GAATTCCATGGATTGGTTGTGGAACTT-3' | 141 |
| 1024K-a | 5'-GAATTCCATGGAGTCACATACTAG-3' | 142 |
| HchainEco47NheI | 5'-CCCCCGCTAGCGCTGGAGACGGTGACC-3' | 143 |
| rIgK-BsiWI | 5'-CGTACGTTTCAATTCCAGCTTGGT-3' | 144 |
| IgG4-m | 5'-AGCGCTAGCACCAAGGGCCCATCCGTCTTC-3' | 145 |
| IgG4-v | 5'-GGATCCTTTACCCAGAGACAGGGA-3' | 146 |
| IgG4-s | 5'-TTACCTGGGCCTGATGGGCCTGGGGACCA-3' | 147 |
| IgG4-r | 5'-TGGTCCCCCAGGCCCATCAGGCCCAGGTAA-3' | 148 |
| IgK-e | 5'-GCACTTCTCCCTCTAACACT-3' | 149 |
| BsiWI-hIgK | 5'-CGTACGGTGGCTGCACCATCTGTC-3' | 150 |
| UTI-a | 5'-GGATCCGCTGTGCTACCCCAAGAA-3' | 151 |
| UTI-b | 5'-GGATCCACTGTGGCGGCCTGCAAT-3' | 152 |
| UTI-c | 5'-GCGGCCGCTCAGTTGGAGAAGCGCAGCAG-3' | 153 |
| UTI-f | 5'-GATATCACCACCACCACCGTTGGAGAAGCGCAGCA-3' | 154 |
| UTI-g | 5'-AGGCCTACCACCACCACCGTTGGAGAAGCGCAGCA-3' | 155 |
| UTI-h | 5'-GATATCGGAGGAGGAGGAGCTGTGCTACCCCAAGA-3' | 156 |
| UTI-i | 5'-GATATCGGAGGAGGAGGAACTGTGGCGGCCTGCAA-3' | 157 |
| SLPI-a | 5'-CAGAGTCACTCCTGCCTTCA-3' | 158 |
| SLPI-c | 5'-AGATCTGGAAAGTCCTTCAAAGCTGGGAGTC-3' | 159 |
| SLPI-d | 5'-ACACCCCAAACCCAACAAGGAGAAGCCTG-3' | 160 |
| SLPI-e | 5'-CAGGCTTCCTCCTTGTTGGGTTTGGGGTGT-3' | 161 |

TABLE 1-continued

Sequence of primers

| Primer Name | Base Sequence | SEQ ID |
|---|---|---|
| SLPI-g | 5'-GCGGCCGCTCAAGCTTTCACAGGG GAAACG-3' | 162 |
| 1031H-a | 5'-GGG GAA TTC CAT GGG ATG GAG CCG GAT C-3' | 163 |
| mIgG2b-c | 5'-TGA ACA CAG ACC ACT CAC CAT G-3' | 164 |
| mIgG2b-a | 5'-GGG CCA GTG GAT AGA CTG ATG-3' | 165 |
| IGKV4-1-a | 5'-GCA TTG TGA ACT GAG CTA CAA C-3' | 166 |
| IgK-d | 5'-GAC ATC GTG ATG ACC CAG TCT C-3' | 167 |
| rIgK-a | 5'-AGA TAC AGT TGG TGC AGC ATC AGC-3' | 168 |
| 13HcS-EcoR | 5'-GGA ATT CCA TGG AAT GTA ACT GGA TAC TTC-3' | 169 |
| 13HcA-Nhe | 5'-CTA GCT AGC GCT GGA GAC GGT GAC TGA GGT-3' | 170 |
| 13LcS-EcoR | 5'-GGA ATT CCA TGG AGA CAG ACA CAC TCC TG-3' | 171 |
| 13LcA-BsiW | 5'-CAC CGT ACG TTT GAT TTC CAG CTT GGT CCC-3' | 172 |

(2) Experimental Methods

Major experimental methods employed are as described below.

PCR

PCR was conducted according to the instruction manual of the enzyme.

Agarose Gel Electrophoresis

Agarose gel at a concentration of 0.8% was prepared, and this gel was placed in an electrophoresis tank filled with 1×TAE, and after applying 5 µL of the sample to the well, electrophoresis was conducted at 135 V for 15 minutes. After completion of the electrophoresis, the gel was stained with ethidium bromide, and the band was detected with UV.

Extraction of DNA Fragments from the Gel

The band of interest was cut with a razor, and the DNA fragment was extracted from the gel piece using QIAEX II kit according to the attached instruction manual. The thus extracted DNA fragment was dissolved in 20 µL sterile water.

Ligation Reaction

1 µL of the extracted DNA fragment, 1 µL of the cloning vector (pT7BlueT), and 2 µL of I solution of the ligation kit ver. 2 were mixed, and the mixture was allowed to stand at room temperature for 15 minutes to promote the ligation.

Transformation of E. coli

50 µL of competent E. coli was allowed to thaw on ice, and 4 µL of the ligation product was added. After allowing to stand on ice for 30 minutes, heat shock was applied at 42° C. for 45 seconds, and the solution was coated on an ampicillin-containing LB plate (final concentration, 50 µg/mL), and the plate was incubated overnight at 37° C.

Purification of Plasmid and Sequencing Reaction

The procedure was conducted according to the instruction manual attached to the kit.

Separation of Total RNA from Hybridoma and 5'RACE

The procedure was conducted according to the instruction manual attached to the kit. The number of hybridoma cells used was $5 \times 10^7$.

Transfection

The transfection was conducted according to the instruction manual attached to the FuGENE6. In the case of 6-well plate, 2 mL of COS-1 cell was inoculated in each well at a density of $1.5 \times 10^5$ cells/mL on the day before the transfection. On the next day, 3 µL of FuGENE6 and 1 µg of the expression plasmid were added to 97 µL of Dulbecco's MEM, and after allowing the mixture to stand for at least 15 minutes, 2 mL of this mixture was added dropwise to the serum free Dulbecco's MEM. The transfection was accomplished by the replacement of the culture medium.

(3) Cloning of the Variable Region of the Hybridoma Antibody Gene and Determination of the Sequence (F1024)

The hybridoma F1024 ($1 \times 10^7$ cells) produced by the method described in WO02/42333 was washed with PBS⁻ (SIGMA), and total RNA was extracted by using TRIzol (GIBCO BRL). Next, 5 µg of the total RNA was subjected to 5' RACE by using 5'RACE system for Rapid Amplification of cDNA Ends, ver. 2.0 (Invitrogen Corporation), and gene fragments coding for the heavy and light chain variable regions were respectively amplified. The procedure was conducted as described in the manual attached to the kit, and the heavy chain variable region was subjected to reverse transcription using rIgH-c primer, dC addition on the terminal using terminal deoxynucleotide transferase, and first PCR using the rIgH-c primer and AAP primer (attached to the kit). The light chain variable region was similarly subjected to the reverse transcription using rIgK-b primer, and first PCR using the rIgK-b primer and the AAP primer. Subsequently, second PCR was conducted using the reaction product for the template by using the rIgH-b primer and AUAP primer (attached to the kit) for the heavy chain variable region, and rIgH-a primer and AUAP primer (attached to the kit) for the light chain variable region, and each of the thus specifically amplified DNA fragments were confirmed by agarose gel electrophoresis. After extracting the DNA fragment from the gel, the nucleotide sequence was determined, and amino acid sequence of the corresponding region was also determined (FIGS. 1 and 2). The CDR sequences according to the definition of Kabat are shown in Table 2. The sequences shown in Table 2 are described in SEQ ID NOS: 173 to 178.

TABLE 2

CDR amino acid sequence of antibody F1024

| F1024 | CDR1 | CDR2 | CDR3 |
|---|---|---|---|
| Heavy chain | DYAMN (SEQ ID No: 173) | WINTQTGKPTYADDFKQ (SEQ ID No: 174) | STFYYSSYIYGWYFDF (SEQ ID No: 175) |
| Light chain | KASQNVGSNVD (SEQ ID No: 176) | KASNRYT (SEQ ID No: 177) | MQSNTNPPWT (SEQ ID No: 178) |

(4) Construction of Expression Plasmid of Chimeric Antibody Fusion Protein

Production of a chimeric antibody in which the variable region having the antigen binding activity is the one from the hybridoma antibody, namely, the one from the rat antibody and the constant region is the one from human antibody enables provision of an antibody with reduced antigenicity for human. A large number of chimeric antibodies have been developed since the report of Morrison et al. in 1984 (Proc, Natl. Acad. Sci. USA, 81: 6851, 1984).

5' primers respectively having a recognition sequence for restriction enzyme EcoRI attached immediately upstream of the initiation codon of the variable region (1024H-a for the heavy chain, 1024K-a for the light chain) and 3' primers (HchainEco47NheI for the heavy chain and rIgK-BsiWI for the light chain) having attached thereto a restriction enzyme (NheI recognition sequence for the heavy chain and BsiWI recognition sequence for the light chain) which can be ligated with the human constant region without altering the amino acid sequence of the 3' side sequence of the variable region were designed. With these primers, PCR was conducted again by using the heavy chain and the light chain samples prepared in Example 1-1)-(3) after the reverse transcription for the template. The thus amplified PCR product was mixed with pT7BlueT vector (NOVAGEN), and ligation reaction was conducted using TaKaRa Ligation Kit, ver. 2 (TAKARA BIO INC.) at room temperature for 15 minutes. Competent cell *E. coli* (JM109, TAKARA BIO INC.) was transformed by using the reaction solution.

The colony formed was picked up, and the insertion of the insert in the vector was confirmed by colony direct PCR by using Ex Taq polymerase (TAKARA BIO INC.), M4 primer, and T7 primer.

Next, the colony which had been confirmed for the insertion of the insert was cultivated overnight in LB medium, and the plasmid was purified by using QIAGEN plasmid midi kit (QIAGEN) (The plasmid having the gene fragment coding for the heavy chain variable region was designated pT7-1024H, and the plasmid having the gene fragment coding for the light chain variable region was designated pT7-1024K). The nucleotide sequence of the purified plasmid was checked by using the M4 primer and the T7 primer.

pT7-1024H was cleaved with restriction enzymes EcoRI and NheI to prepare gene fragment A coding for the heavy chain variable region. In a similar manner, pT7-1024K was cleaved with restriction enzymes EcoRI and BsiWI to prepare gene fragment B coding for the light chain variable region.

PCR was conducted by using plasmid pTK-2232 (see WO2005/7800) comprising the gene for human IgG4 heavy chain constant region (Cγ4) for the template and the primer pair (IgG4-m and IgG4-v) to amplify a gene fragment having the recognition sequence for restriction enzyme NheI at the 5' terminal of the Cγ4, and having the recognition sequence for restriction enzyme BamHI at the 3' terminal of the Cγ4 in place of the stop codon that had been deleted. This fragment was cleaved with restriction enzymes NheI and BamHI to prepare gene fragment C.

PCR was conducted by using pTK-2232 for the template and 2 primer pairs (IgG4-m and IgG4-s) and (IgG4-r and IgG4-v) to thereby amplify each gene fragment. These gene fragments were mixed for use as a template, and PCR was conducted again by using another primer pair (IgG4-m and IgG4-v) to amplify a gene fragment which has 2 cysteine residues required for the dimerization of the heavy chains replaced with glycine residues, and which has the recognition sequence for restriction enzyme NheI at the 5' terminal, and the recognition sequence for restriction enzyme BamHI at the 3' terminal in place of the stop codon. This fragment was cleaved with restriction enzymes NheI and BamHI to prepare gene fragment D.

PCR was conducted by using HeLa genomic DNA for the template and the primers (BsiWI-hIgK and IgK-e) to thereby amplify human light chain constant region (Cκ), and this amplification product was cloned into pT7BlueT vector to construct pT7-hIgK. Fragment E was then prepared by using adequate restriction enzymes (BsiWI and BamHI) which were capable of cleaving the human light chain constant region from the plasmid.

PCR was conducted by using plasmid pM1213 comprising human UTI domain 1 and domain 2 (D1D2) for the template and the primer pair (UTI-a and UTI-c) to amplify a gene fragment having the recognition sequence for restriction enzyme BamHI at the 5' terminal of the D1D2, and the recognition sequence for restriction enzyme NotI immediately downstream of the stop codon at the 3' terminal. This fragment was cleaved with restriction enzymes BamHI and NotI to prepare gene fragment F.

PCR was conducted by using pM1213 for the template and the primer pair (UTI-b and UTI-c) to amplify a gene fragment having the recognition sequence for the restriction enzyme BamHI at the 5' terminal of D2, and the recognition sequence for restriction enzyme NotI immediately downstream of the stop codon at the 3' terminal. This fragment was cleaved with restriction enzymes BamHI and NotI to prepare gene fragment G.

PCR was conducted by using plasmid pM765 comprising 3 amino acids modified form of human UTI domain 2 {D2(3)} (see JP 6-321989 A) for the template and the primer pair (UTI-b and UTI-c), and a gene fragment having the recognition sequence for restriction enzyme BamHI at the 5' terminal of D2(3), and the recognition sequence for restriction enzyme NotI immediately downstream of the stop codon at the 3' terminal. This fragment was cleaved with restriction enzymes BamHI and NotI to prepare gene fragment H.

PCR was conducted by using pM1213 for the template and the primer pair (UTI-a and UTI-f) to amplify a gene fragment having the recognition sequence for restriction enzyme BamHI at the 5' terminal of the D1D2, and having a linker comprising 4 glycine residues added after removing the stop codon at the 3' terminal and further having recognition sequence for restriction enzyme EcoRV immediately downstream of the linker. This fragment was cleaved with restriction enzymes BamHI and EcoRV to prepare gene fragment I.

PCR was conducted by using pM1213 for the template and the primer pair (UTI-b and UTI-f) to amplify a gene fragment having the recognition sequence for restriction enzyme BamHI at the 5' terminal of D2 and having a linker comprising 4 glycine residues added after removing the stop codon at the 3' terminal and further having recognition sequence for restriction enzyme EcoRV immediately downstream of the linker. This fragment was cleaved with restriction enzymes BamHI and EcoRV to prepare gene fragment J.

PCR was conducted by using pM1213 for the template and the primer pair (UTI-h and UTI-c) to amplify a gene fragment having a linker comprising 4 glycine residues added at the 5' terminal of D1D2 and having the recognition sequence for the restriction enzyme EcoRV immediately upstream of the linker, and having the recognition sequence for restriction enzyme NotI immediately downstream of the stop codon at the 3' terminal. This fragment was cleaved with restriction enzymes EcoRV and NotI to prepare gene fragment K.

PCR was conducted by using pM1213 for the template and the primer pair (UTI-i and UTI-c) to amplify a gene fragment having a linker comprising 4 glycine residues added at the 5' terminal of D2 and the recognition sequence for restriction enzyme EcoRV immediately before the linker, and having the recognition sequence for restriction enzyme NotI immediately downstream of the stop codon at the 3' terminal. This fragment was cleaved with restriction enzymes EcoRV and NotI to prepare gene fragment L.

PCR was conducted by using pM1213 for the template and the primer pair (UTI-h and UTI-g) to amplify a gene fragment having a linker comprising 4 glycine residues added at the 5' terminal of D1D2 and the recognition sequence for restriction enzyme EcoRV immediately before the linker, and having a linker comprising 4 glycine residues added after removing the stop codon at the 3' terminal and further having recognition sequence for restriction enzyme StuI immediately downstream of the linker. After cloning this fragment in pT7BlueT vector, the vector was cleaved with EcoRV and BamHI, and gene fragment I was ligated to construct an intermediate plasmid comprising D1D2D1D2 sequence. This plasmid was cleaved with BamHI and StuI to prepare gene fragment M.

PCR was conducted by using pM1213 for the template and the primer pair (UTI-i and UTI-g) to amplify a gene fragment having a linker comprising 4 glycine residues added at the 5' terminal of D2 and having the recognition sequence for restriction enzyme EcoRV immediately upstream of the linker, and having a linker comprising 4 glycine residues added after removing the stop codon at the 3' terminal and further having recognition sequence for restriction enzyme StuI immediately downstream of the linker. After cloning this fragment in pT7BlueT vector, the vector was cleaved with EcoRV and BamHI, and gene fragment J was ligated to construct an intermediate plasmid comprising D2D2 sequence. This plasmid was cleaved with BamHI and StuI to prepare gene fragment N.

PCR was conducted by using HeLa genomic DNA for the template and the following primer pair. As a consequence, PCR amplification product O was obtained by SLPI-c and SLPI-e, PCR amplification product P was obtained by SLPI-d and SLPI-g, and PCR amplification product R was obtained by SLPI-a and SLPI-g.

When PCR was conducted again by using a mixture of O and P for the temperate using primers SLPI-c and SLPI-g, amplification product Q, which is ligation product of both fragments was obtained.

The amplification products Q and R were respectively cloned in pT7BlueT vector, and Q and R were confirmed to be the sequences coding for $Ser^1$-$Ala^{107}$ of human SLPI (also referred to as SLPI(D1D2)) and $Arg^{58}$-$Ala^{107}$ of human SLPI (also referred to as SLPI(D2)), and they were designated pT7-SLPI(D1D2) and pT7-SLPI(D2), respectively. Both were constructed such that the recognition sequence for restriction enzyme BglII was located on the 5' side of the SLPI, NotI recognition sequence was located immediately downstream of the stop codon on the 3' side. These plasmids were respectively cleaved with restriction enzymes BglII and NotI, respectively, to prepare SLPI(D1D2) fragment S and SLPI(D2) fragment T.

The gene fragments as described above were ligated in the downstream of the EF1α promoter of the expression vector pEF2cew prepared by cleaving with EcoRI and NotI, or EcoRI and BamHI in appropriate combinations to construct respective expression plasmids. The names of the expression plasmids and the names of the gene fragments incorporated in the vector are together shown in Table 3. The same plasmid pTK-2344 expressing the light chain of the chimeric antibody was used for all types of heavy chains. The structure, the nucleotide sequence, and the deduced amino acid sequence of each fusion protein are shown in FIGS. 7 to 17 and Sequence Listing (SEQ ID NOS: 1 to 26). In each of the amino acid sequences of SEQ ID NOS: 2, 4, 6, 8, 10, 12, 14, 16, 18, 20, and 24, Amino Acid Nos. 1 to 19 correspond to the signal peptide sequence, and in the amino acid sequences of SEQ ID NOS: 22 and 26, Amino Acid Nos. 1 to 20 correspond to the signal peptide sequence. Accordingly, the deduced amino acid sequence of the fusion protein of the present invention is the amino acid sequence from which the signal peptide has been excluded.

TABLE 3 chimeric antibody - heavy chain fusion protein and plasmid expressing light chain of the chimeric antibody

| Antibody Fusion Protein | Plasmid Name | Insert Fragment | FIG. No. | SEQ ID |
|---|---|---|---|---|
| F1024D-D1D2 | pTK-2348 | A + C + F | 7 | 1 to 2 |
| F1024D-D2 | pTK-2349 | A + C + G | 8 | 3 to 4 |
| F1024D-D2(3) | pTK-2368 | A + C + H | 9 | 5 to 6 |
| F1024S-D1D2 | pTK-2354 | A + D + F | 10 | 7 to 8 |
| F1024S-D2 | pTK-2355 | A + D + G | 11 | 9 to 10 |
| F1024S-D2(3) | pTK-2370 | A + D + H | 12 | 11 to 12 |
| F1024D-D1D2D1D2 | pTK-2356 | A + C + I + K | — | — |
| F1024D-D2D2 | pTK-2357 | A + C + J + L | — | — |
| F1024S-D1D2D1D2 | pTK-2360 | A + D + I + K | — | — |
| F1024S-D2D2 | pTK-2361 | A + D + J + L | — | — |
| F1024D-D1D2D1D2D1D2 | pTK-2362 | A + C + M + K | — | — |
| F1024D-D2D2D2 | pTK-2363 | A + C + N + L | — | — |
| F1024S-D1D2D1D2D1D2 | pTK-2366 | A + D + M + K | — | — |
| F1024S-D2D2D2 | pTK-2367 | A + D + N + L | — | — |
| F1024D-SLPI(D1D2) | pTK-2397 | A + C + S | 13 | 13 to 14 |
| F1024D-SLPI(D2) | pTK-2394 | A + C + T | 14 | 15 to 16 |
| F1024S-SLPI(D1D2) | pTK-2399 | A + D + S | 15 | 17 to 18 |
| F1024S-SLPI(D2) | pTK-2396 | A + D + T | 16 | 19 to 20 |
| F1024 light chain of chimeric antibody | pTK-2344 | B + E | 7 to 16 | 21 to 22 |
| F1031-13S-D2(3) | pF31-13HU | | 17 | 23 to 24 |
| F1031-13 light chain of chimeric antibody | pF31-13L | | 17 | 25 to 26 |

(5) Expression of Each Fusion Protein in Small Scale and Purification of Expressed Fusion Protein COS-1 cell was subcultured in Dulbecco's MEM supplemented with 10% fetal bovine serum, and on the day before the transfection, the cell was inoculated in the cultivation vessel at a density of $1.5 \times 10^5$ cells/mL. On the next day, light chain expression plasmid (pTK-2344) was mixed with each heavy chain expression plasmid at a weight ratio of 1:1, and then, with an adequate amount of the transfection reagent (FuGENE6, Rosch Diagnostics). This mixture was added dropwise to serum free Dulbecco's MEM, and the cell was transfected by replacing this medium with the culture medium. The cell was incubated in the presence of 5% $CO_2$ at 37° C. for 2 to 3 days, and the supernatant was collected. The purification was conducted using Prosep-A column (MILLIPORE), and after dialyzing with PBS (pH 7.4), concentration was calculated from the absorbance at 280 nm.

1-2) Construction of Chimeric Antibody and Antibody Fusion Protein (F1031)

(1) Cloning of Variable Region of Hybridoma Antibody Gene and Determination of Sequence (F1031)

CDR sequence of antibody F1031-13-2 (mouse IgG2b/κ) which is an anti-human CD14 antibody that binds to CD14 but that has no CD14 inhibitory activity was determined by the procedure as described below.

First, total RNA was prepared from the hybridoma expressing F1031-13-2 by using TRIzol, and single chain cDNA was synthesized by using SuperScript III First-Strand Synthesis System for RT-PCR (Invitrogen Corporation).

In the meanwhile, sense primers 1031H-a and mIgG2b-c and antisense primer mIgG2b-a were synthesized for use in the amplification of the variable region of the mouse IgG2b heavy chain, and sense primers IGKV4-1-a and IgK-d and antisense primer rIgK-a were synthesized for use in the amplification of the variable region of κ chain (see Table 1).

Next, PCR was conducted by using the thus synthesized single chain cDNA of the hybridoma for the template. The primers used were the combinations of 1031H-a and mIgG2b-a for heavy chain (i), mIgG2b-c and mIgG2b-a for heavy chain (ii), IGKV4-1-a and rIgK-a for light chain (i), and IgK-d and rIgK-a for light chain (ii). PCR was conducted by heating the reaction solution at 96° C. for 2 minutes and then repeating 25 cycles of heating at 96° C. for 30 seconds, 55° C. for 30 seconds, and 72° C. for 30 seconds.

The resulting products were directly determined for their sequence, and it was found that the heavy chains (i)(ii), and the light chains (i)(ii) respectively had the same sequence. With regard to the light chain, 5' terminal was incomplete, and the translation initiation codon could not be identified. Accordingly, sequence showing homology in the frame region was searched in the mouse K chain whose sequence has already been reported. FIGS. 3 and 4 (SEQ ID NOS: 127 to 130) show sequences (the nucleotide sequence and the amino acid sequence) of the heavy chain and the light chain of variable region of antibody F1031-13-2. In the sequence, the underlined part is the sequence from the primers.

(2) Construction of Plasmid Expressing Chimeric Antibody (F1031)

Plasmid expressing chimeric antibody F1031-13-2 was constructed by the method similar to that of Example 1-1) (construction of plasmid expressing F1024 chimeric antibody). More specifically, by referring to the sequence obtained in 1-2)(1), primers for constructing the heavy chain expressing plasmid, namely, primer 13HcS-EcoR of the 5' side having the recognition sequence for restriction enzyme EcoRI added immediately upstream of the initiation codon of the variable region, and primer 13HcA-Nhe of the 3' having the recognition site for restriction enzyme NheI which can be ligated to the human constant region added without altering the amino acid sequence of the 3' side of the variable region were synthesized. Although the sequence on the 5' side of the light chain was not identified, the sequence on the 5' terminal side was estimated by homology search, and primer 13LcS-EcoR of the 5' side having the recognition sequence for restriction enzyme EcoRI added immediately upstream of the initiation codon of the variable region, and primer 13LcA-BsiW of the 3' side having the recognition site for restriction enzyme BsiWI which can be ligated to the human constant region added without altering the amino acid sequence of the 3' side of the variable region were synthesized (see Table 1).

Next, PCR was conducted by using the single strand cDNA synthesized in 1-2) (1) for the template. The reaction was conducted by heating at 90° C. for 2 minutes, and then repeating 30 cycles of (1) heating at 94° C. for 30 seconds, (2) 50° C. for 30 seconds, and (3) 72° C. for 1 minute. The resulting PCR product for constructing the heavy chain was digested with EcoRI and NheI, and the PCR product for constructing the light chain was digested with EcoRI and BsiWI, and the fragments of about 0.4 kb were collected from the respective digestion products.

Next, the plasmid pTK-2370 for expressing the heavy chain and the plasmid pTK-2344 for expressing the light chain of the F1024 chimeric antibody constructed in Example 1-1) were digested with EcoRI and NheI, and EcoRI and BsiWI, respectively, to collect the fragments of about 5.7 kb and 4.8 kb. The fragments from the PCR product were then inserted in these fragments, and *E. coli* competent cell JM109 was transformed by the standard method to obtain plasmid pF31-13HU for expressing the heavy chain and plasmid pF31-13L for expressing the light chain of the F1031-13-2. Since the 5' terminal sequence of the light chain of the F1031-13-2 includes the sequence newly confirmed in the construction of the present invention, the sequences of the heavy chain variable region and the light chain variable region of the expression plasmid are shown again in FIGS. 5 and 6 (SEQ ID NOS: 131 to 134). In the sequence, the underlined part is the sequence from the construction primers.

(3) Confirmation of Expression of Chimeric Antibody Fusion Protein

The heavy chain expression plasmid and the light chain expression plasmid constructed in 1-2)(2) were introduced in COS-1 cells to confirm the expression of the chimeric antibody fusion protein.

First, COS-1 cells were inoculated in DMEM supplemented with 10% inactivated FBS in 6-well plate at 2.0 to $2.4 \times 10^5$ cells/well, and the cells were incubated overnight at 37° C. and in the presence of 5% $CO_2$. On the next day, 6 μL of FuGENE6 was mixed with 1 μg of the heavy chain expression plasmid and 1 μg of the light chain expression plasmid, and the mixture was added dropwise to the COS-1 cells according to the protocol attached to the FuGENE6. In the procedure as described above, the following treatment was conducted before the dropwise addition of the FuGENE/plasmid mixture to the cells in order to prevent contamination of the immunoglobulin from FBS. Namely, after incubating the COS-1 cells overnight and removing the cell supernatant, the cells were washed twice with the production medium (Hybridoma-SFM (Invitrogen Corporation) or Cellgro Complete Serum Free Medium (Mediatech)), and subsequently, 2 mL/well of the production medium was added to the plate. The FuGENE/plasmid mixture was then added dropwise to the cells. After incubating the cells at 37° C. and in the presence 5% $CO_2$ for 3 to 4 days, the supernatant was recovered and the amount of the chimeric antibody fusion protein in the supernatant was confirmed by the procedure similar to the EIA procedure described in Example 2 except that the HRP-labeled antibody used in the detection was HRP-labeled anti human κ light chain antibody (DAKO) instead of the peroxidase-labeled UTI antibody. It was then found that the chimeric antibody was expressed at approximately 10-20 μg/mL. The culture supernatant produced in this experiment was used in the experiment examining inhibitory activity for IL-6 production in Example 1-3)(1).

1-3) Confirmation Tests of Activities (1) Confirmation Test of IL-6 Production Inhibitory Activity The following experiments were conducted to examine activity of the antibody functional domains of the antibody fusion proteins prepared in Examples 1-1) and 1-2).

Cell line U-373 MG from human glioma was inoculated in MEM (SIGMA) containing 2% inactivated FBS in a 96-well plate at $1 \times 10^4$ cells/well, and the cells were incubated overnight at 37° C. and in the presence of 5% $CO_2$. The following solutions were prepared on the next day.

1) Physiological saline (Otsuka Pharmaceutical Co., Ltd.) containing 0.2% human serum albumin (SIGMA) (hereinafter referred to as 0.2% HSA/physiological saline)

2) MEM containing 0.2% human serum albumin (SIGMA) (hereinafter referred to as 0.2% HSA/MEM)

3) A solution prepared by mixing 0.2% HSA/physiological saline and 0.2% HSA/MEM at a ratio of 1:1 (hereinafter referred to as 0.1% HSA/1/2MEM)

4) MEM containing 4% human serum (hereinafter referred to as 4% HS/MEM)

5) A solution prepared by diluting LPS (*E. coli* 0111:B4, SIGMA) with physiological saline to 1 mg/mL, sonicating for 10 minutes, and diluting with 0.2% HSA/MEM to 200 ng/mL (hereinafter referred to as 200 ng/mL LPS B4)

6) A solution prepared by mixing 4% HS/MEM and 200 ng/mL LPS B4 at a ratio of 9:1 (hereinafter referred to as 2×(HS+LPS))

Figure 18:
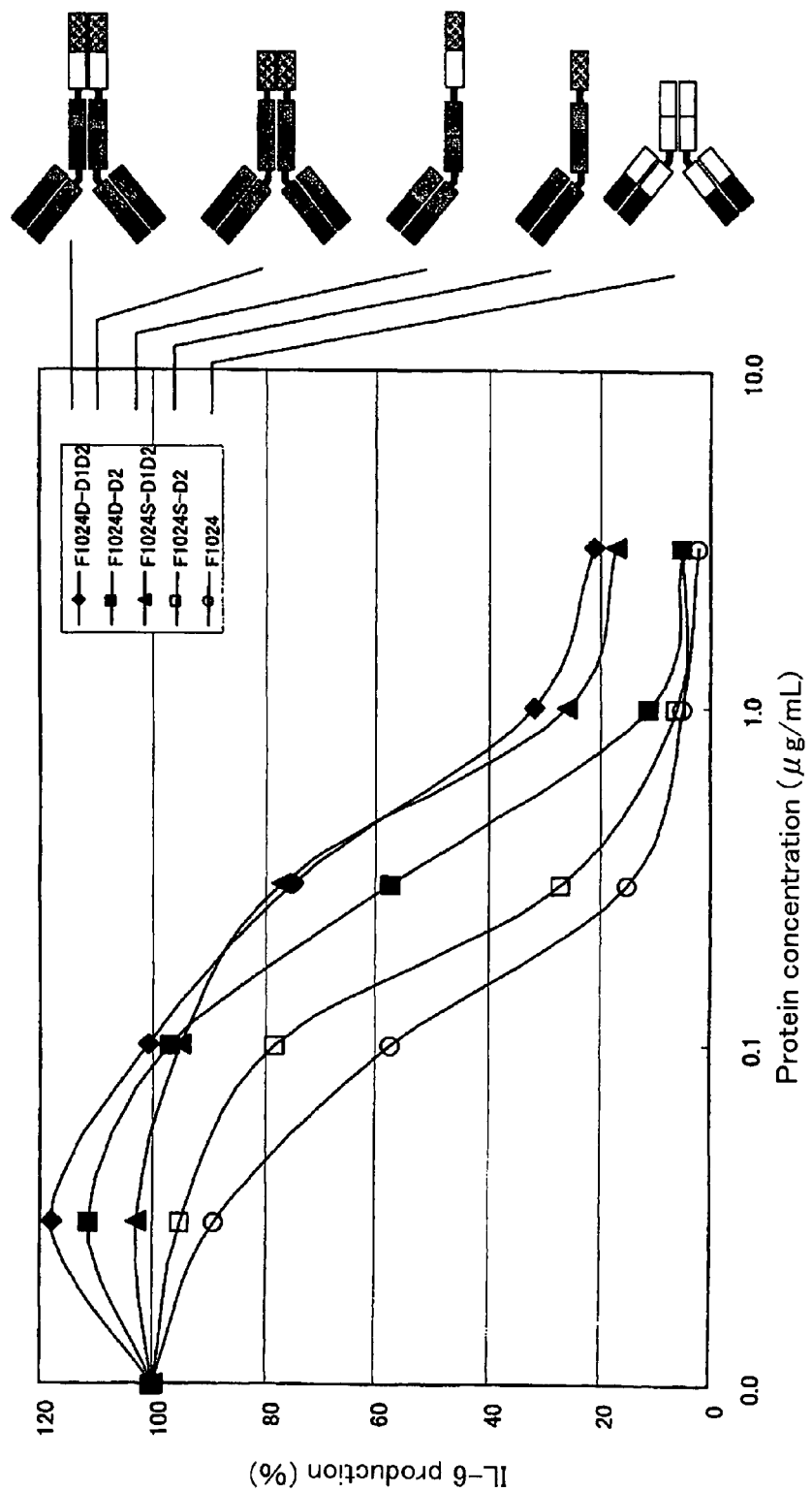
FIG. 18 is a view showing suppressive activity of F1024 (anti-CD14 antibody) or antibody fusion proteins in the production of IL-6 by the LPS-stimulated U373MG cell.
Figure 19:
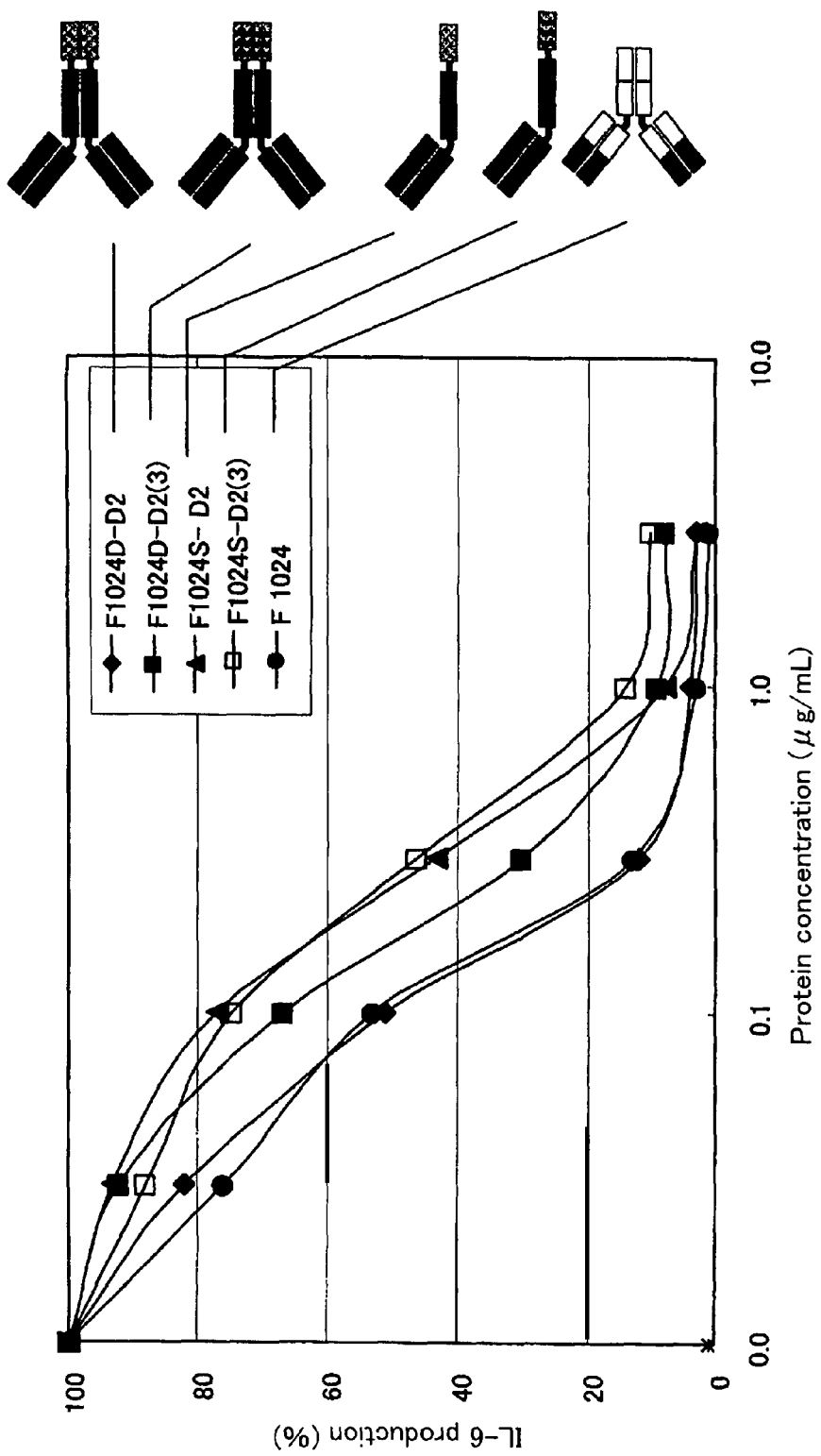
FIG. 19 is a view showing suppressive activity of F1024 (anti-CD14 antibody) or antibody fusion proteins in the production of IL-6 by the LPS-stimulated U373MG cell.
Figure 20:
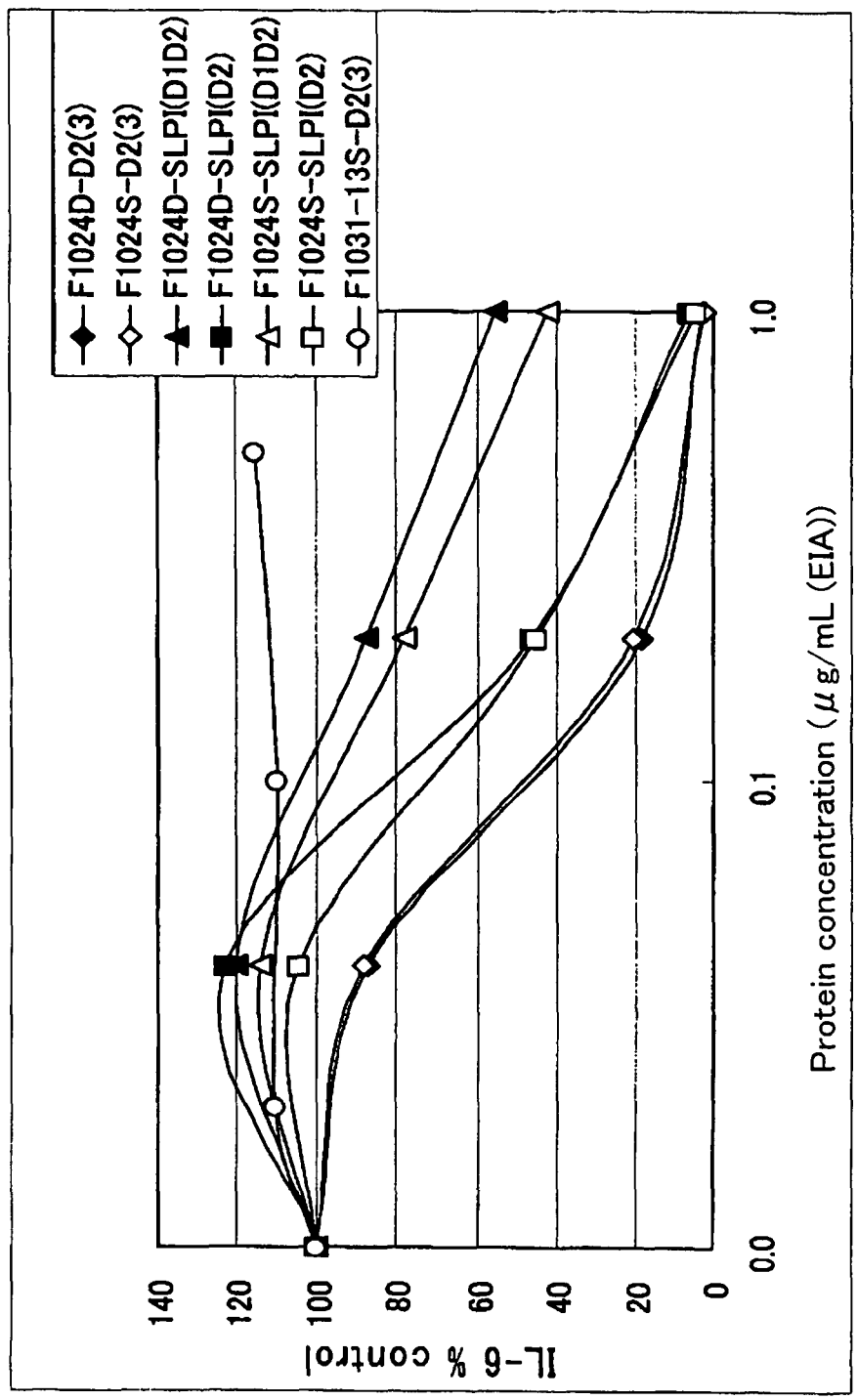
FIG. 20 is a view showing suppressive activity of antibody fusion proteins in the production of IL-6.

The analyte sample was diluted to twice the target concentration with 0.2% HSA/physiological saline to prepare the sample. Culture supernatant of the overnight culture of U-373MG cells was discarded, and the cells were washed twice with 0.1% HSA/1/2MEM. To these cells, 100 µL/well of a mixture of equal amounts of the analyte sample and 2×(HS+LPS) was added, and the cells were incubated in the presence of 5% $CO_2$ at 37° C. for about 18 hours. Amount of the IL-6 in the culture supernatant was then detected using human IL-6 detection kit (Eli-PAIR hIL-6; Invitorgen Corporation). FIGS. 18 to 20 show typical test results.

It was then demonstrated that the antibody activity was maintained in the chimeric antibody fusion proteins in the case of the antibodies exhibiting the CD14 inhibitory activity, whereas the F1031-13-2 antibody exhibiting no CD14 inhibitory activity did not show the inhibitory activity when it was produced in the form of a chimeric antibody fusion protein. In FIG. 20, the results are shown in relation to the IL-6 production (100%) of the control having no sample added (IL-6% Control).

(2) Confirmation Test of Enzyme Inhibitory Activity

Trypsin inhibitory activity was measured in order to confirm the activity of the domain having the enzyme inhibitory function of the antibody fusion proteins produced in Examples 1-1) and 1-2).

The analyte sample was diluted to ten times the target concentration with 0.1 mol/L NaCl/5 mmol/L $CaCl_2$/20 mmol/L Tris-HCl (pH 7.4) (hereinafter referred to as dilution solution). In the meanwhile, 1 µg/mL of trypsin from human pancreas (Athens Research and Technology) was prepared with 0.1 w/v % BSA/1 mmol/L HCl, and synthetic substrate S2222 (TESTZYM, Daiichi Pure Chemicals Co., Ltd.) was diluted with water to 4 mmol/L.

Figure 21:
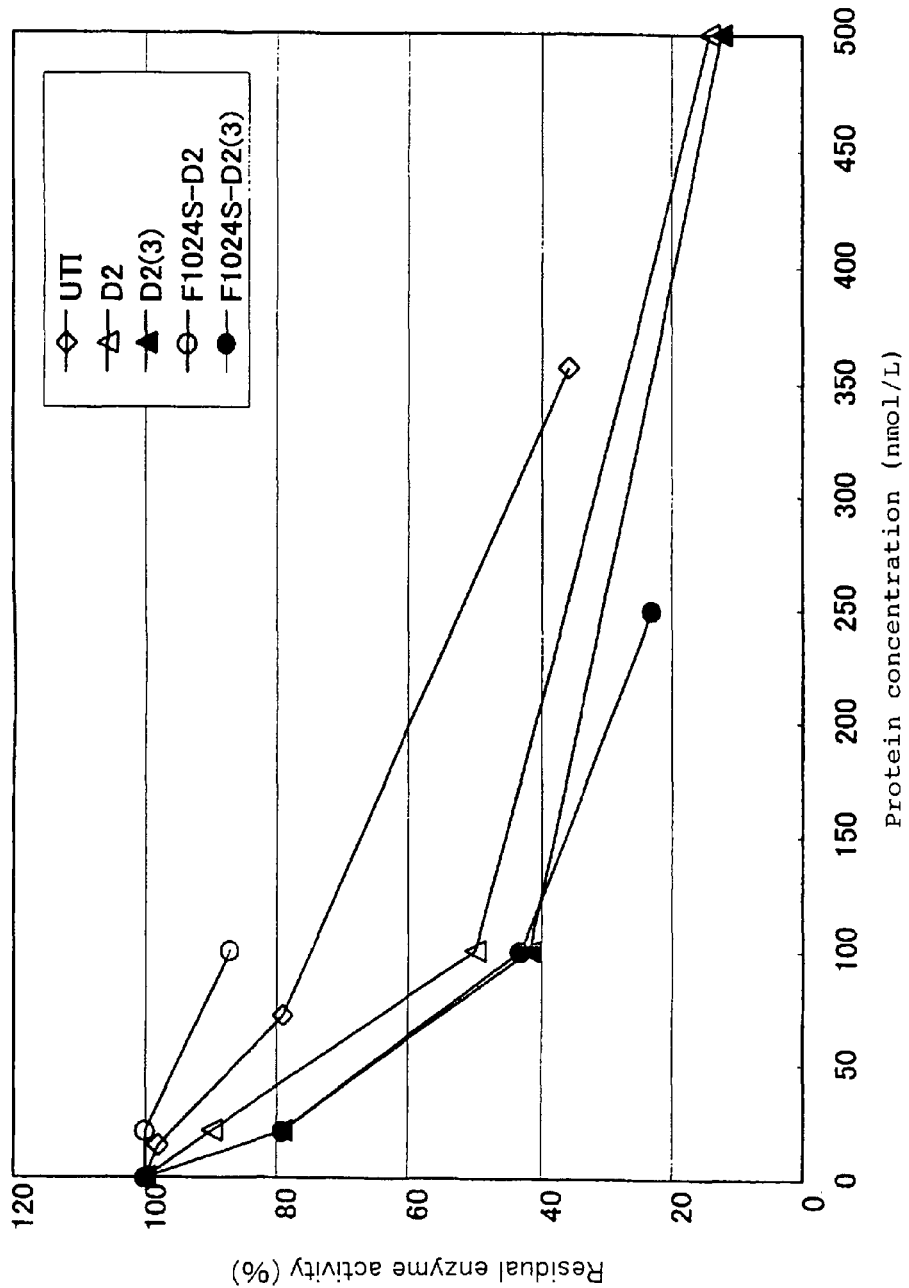
FIG. 21 is a view showing trypsin inhibitory activity of the proteins derived from UTI and anti-CD14 antibody fusion proteins.
Figure 22:
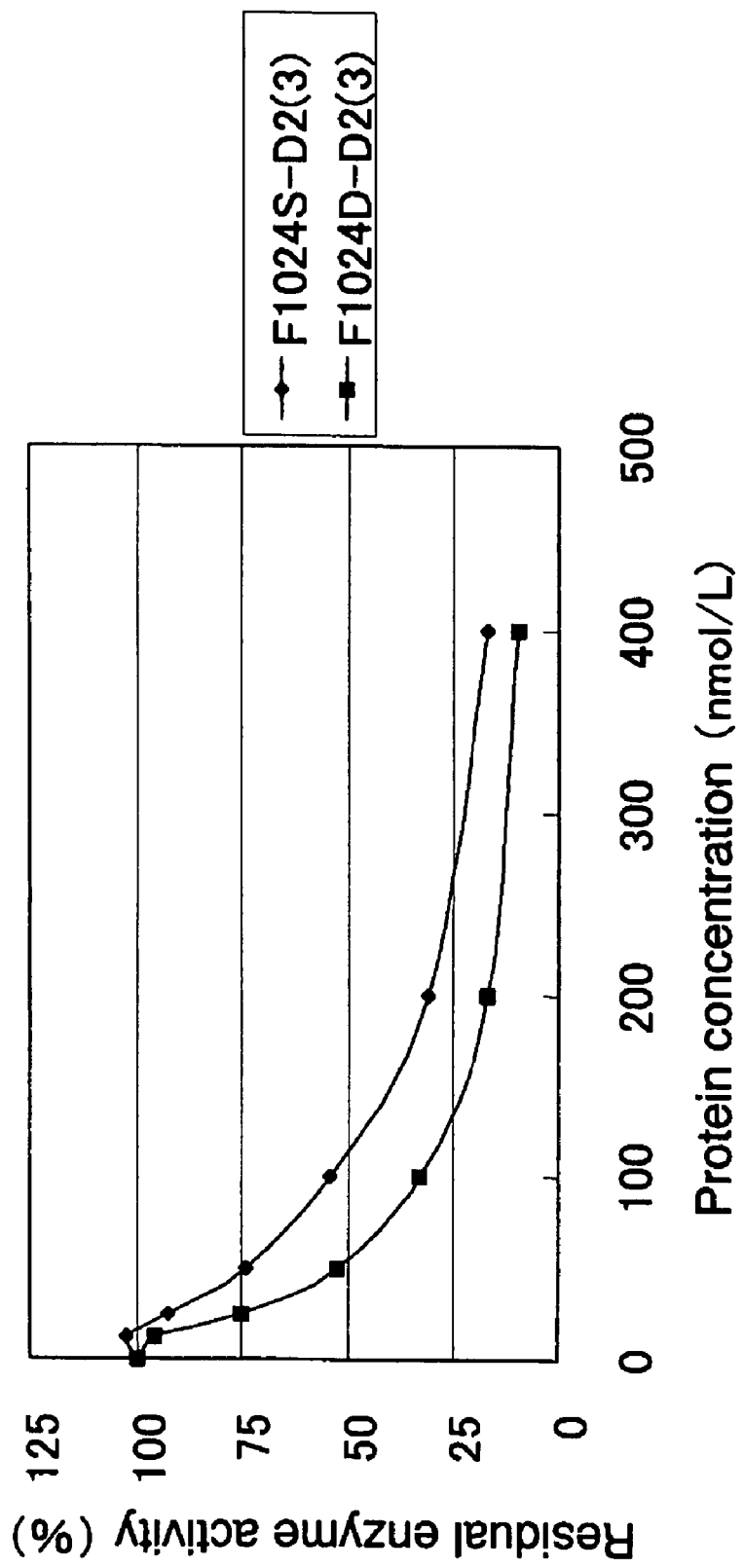
FIG. 22 is a view showing Factor Xa inhibitory activity of anti-CD14 antibody fusion proteins.

After preparation of the reagents, 70 µL of the dilution solution, 10 µL of 1 µg/mL human trypsin solution, and 10 µL of analyte sample solution were placed in 96-well microtiter plate (Nunc), and the solution was incubated at 37° C. for 3 minutes. Next, 10 µL of synthetic substrate S2222 solution was added to the well, and the solution was incubated at 37° C. for another 60 minutes. The reaction was then terminated with 20 v/v % aqueous solution of acetic acid, and absorbance of the reaction solution at 405 nm was measured. FIG. 21 shows the typical results. It was then found that enzyme inhibitory activity was substantially retained in the chimeric antibody fusion protein.

Example 2

Mass Production of Antibody Fusion Protein (1) Mass Production of F1024S-D2(3) and F1031-13S-D2 (3)

In order to conduct the mass production of F1024S-D2(3), transient expression system using COS-1 cell was employed. More specifically, 1700 mL of DMEM containing 10% inactivated FBS and 10 mM HEPES (pH 7.0 to 7.6) was added to CellsTACK-10 Chamber (Corning), and 21×10⁶ COS-1 cells were inoculated in this medium. The interior of the CellsTACK-10 Chamber was replaced with a gas mixture containing 5% $CO_2$, and after sealing the container, the medium was incubated at 37° C.

Transfection was conducted 4 days after the inoculation by the following procedure.

First, 2.12 mL of FuGENE6 transfection reagent (Rosch Diagnostics K.K.) was added to 63.6 mL of DMEM, and stirred. After 5 minutes, 530 µg each of the plasmid pTK2370 coding for the heavy chain and the plasmid pTK2344 coding for the light chain prepared in Example 1 were added, and after stirring, the culture was allowed to stand for 15 minutes at room temperature. In the meanwhile, the medium of the CellsTACK-10 Chamber was replaced with 1300 mL of Hybridoma-SFM (Invitrogen Corporation) containing 10 mM HEPES (pH 7.0-7.6) (hereinafter referred to as production medium), and the thus prepared mixture of the transfection reagent and the plasmid was added. After incubating at 37° C. for 3 days, the production medium was collected. 1300 mL of new production medium was added to the CellsTACK-10 Chamber, and the production medium was again collected after 4 days.

Production of F1031-13S-D2(3) was similarly conducted by using the plasmid pF31-13HU coding for the heavy chain and the plasmid F31-13L coding for the light chain prepared in Example 1.

(2) Assay System (EIA) of F1024S-D2(3) and F1031-13S-D2(3)

Concentration of the F1024S-D2(3) was measured by sandwich EIA.

A sandwich EIA system was prepared by using a recombinant human CD14 comprising the full length 356 amino acids of the human CD14 prepared by the procedure similar to that in Example 6 for the immobilized protein, and peroxidase-labeled UTI antibody produced by the procedure described in JP 2002-14104 A for the labeled antibody.

F1024S-D2(3) prepared in Example 1 was used for the standard. More specifically, recombinant human CD14 was diluted with PBS (pH 7.4) to 4 µg/mL, and 50 µL was added to each well of NUNC-Immuno plate Maxisorp (NUNC). After allowing to react overnight at 4° C., the well was washed three times with 0.05% Tween 20/0.9% sodium chloride solution, and 100 µL of PBS (pH 7.4) containing 2% StabilGuard (SurModics, Inc.) was added to the well for blocking. Next, diluted specimens of the analytes and the standard were prepared by using PBS (pH 7.4) containing 0.1% BSA for the dilution solution. In the meanwhile, peroxidase-labeled UTI antibody diluted with PBS (pH 7.4) containing 10% rabbit serum was prepared. 25 µL of the diluted peroxidase-labeled antibody and 25 µL of the diluted specimen were added to the well, and the reaction was allowed to take place at 37° C. for 1 hour. After the termination of the reaction, the well was washed three times with 0.05% Tween 20/0.9% sodium chloride solution, and 50 µL of tetramethylbenzidine solution (BioFX) was added to each well. After allowing the reaction to take place at room temperature for about 20 minutes, the reaction was terminated by adding 50 µL of 1 mol/L hydrochloric acid solution, and absorbance at 450 nm was measured with a plate spectrophotometer.

The concentration was measured for F1031-13S-D2(3) in the same manner. In the measurement, F1031-13S-D2(3) having known concentration was used for the standard.

(3) Mass Purification of F1024S-D2(3)

Unless otherwise noted, the following procedure was conducted at 4° C.

The COS culture supernatant produced in Example 2(1) was applied to 1 μm capsule cartridge filter (Advantec Toyo Kaisha, Ltd.) connected to 0.22 μm Fluorodyne II DFLP Filter (Nihon Pall Ltd.) to thereby remove the insoluble content in the culture supernatant. The filtrate was applied to ProSep-vA column (Nihon Millipore K.K.) which had been preliminarily equilibrated with PBS (SIGMA), and the non-adsorbed contents were washed off with PBS. Then, non-specifically adsorbed contents were washed off with 10×PBS (SIGMA) and eluted with 25 mM Glycine-HCl (pH 2.5) to recover F1024S-D2(3). The resulting eluted fraction was adjusted to pH 5 by adding MacIlvaine buffer solution. The precipitate in the eluted fraction was removed by centrifugation, and the supernatant after the centrifugation was passed through a dialysis tube (SPECTRUM) having a cut-off molecular weight of 10,000 for dialysis against physiological saline. The dialyzate was used as the purified standard.

(4) Mass Purification of F1031-13S-D2(3)

Unless otherwise noted, the following procedure was conducted at 4° C.

The COS culture supernatant produced in Example 2(1) was applied to 1 μm capsule cartridge filter (Advantec Toyo Kaisha, Ltd.) connected to 0.22 μm Fluorodyne II DFLP Filter (Nihon Pall Ltd.) to thereby remove the insoluble content in the culture supernatant. The filtrate was applied to ProSep-vA column which had been preliminarily equilibrated with PBS (SIGMA), and the non-adsorbed contents were washed off with PBS. Then, non-specifically adsorbed contents were washed off with 1M sodium chloride solution and eluted with 100 mM Glycine-HCl (pH 2.7) to recover F1031-13S-D2(3). The resulting eluted fraction was neutralized by adding 1M Tris-hydrochloric acid (pH 8.0), and this solution was passed through a dialysis tube (SPECTRUM) having a cut-off molecular weight of 3,500 for dialysis against physiological saline. The dialysate was concentrated using YM10 ultrafiltration membrane (Nihon Millipore K.K.), and the concentrate was used as the purified standard.

Example 3

Evaluation of Efficacy (In Vitro)

3-1) Confirmation of Antibody Activity (1) Confirmation of Inhibitory Activity for LPS-Induced IL-6 Production in Human Vascular Endothelial Cell Endothelial cells of the human umbilical cord vein (HUVEC, Sanko Junyaku Co., Ltd.) separated by PBS(−) containing 0.05% trypsin and 0.02% EDTA were suspended in RPMI 1640 medium (SIGMA) containing 10% of human serum (TENNESSEE BLOOD SERVICE CORPORATION), and inoculated in 96-well plate at $2 \times 10^4$ cells/well. The cells were incubated overnight at 37° C. in the presence of 5% $CO_2$. After the incubation, LPS (WE. coli 055:B5, DIFCO) was added to a final concentration of 10 ng/mL, and simultaneously, F1024S-D2(3) was added to final concentrations of 0.03, 0.1, 0.3, 1, 3, and 10 μg/mL. After incubating at 37° C. in the presence of 5% $CO_2$ for 6 hours, the IL-6 in the culture supernatant was measured by using human IL-6 EIA kit (Diaclone Research) according to the attached protocol. $IC_{50}$ value for the inhibition of the IL-6 production by the F1024S-D2(3) was 0.38 μg/mL. This result revealed that F1024S-D2(3) inhibits cytokine production of the human vascular endothelial cell induced by LPS which is a component constituting the Gram-negative bacteria.

The inhibitory activity of the F1031-13S-D2(3) and F1024D-SLPI(D1D2), F1024D-SLPI(D2), F1024S-SLPI(D1D2), or F1024S-SLPI(D2) is evaluated by using a similar assay system.

(2) Confirmation of Inhibitory Activity for LPS-Induced Expression of E-Selectin in Human Vascular Endothelial Cell Endothelial cells of human umbilical cord vein (HUVEC, Sanko Junyaku Co., Ltd.) were inoculated by the procedure described in Example 3-1)(1), and after incubation, LPS (WE. coli 055:B5, DIFCO) was added to a final concentration of 10 ng/mL simultaneously with the addition of F1024S-D2(3) to final concentrations of 0.03, 0.1, 0.3, 1, 3, and 10 μg/mL. After incubating at 37° C. in the presence of 5% $CO_2$ for 6 hours, the culture medium was removed, and the cells were washed twice with PBS(−).

After drying with a dryer, 100 μL/well of PBS(−) containing 2% paraformaldehyde was added. After incubating at room temperature for 20 minutes, the cells were washed three times with PBS(−), and 100 μL/well of biotinylated anti-human E-Selectin antibody (Cosmo Bio Co., Ltd.) diluted with RPMI 1640 containing 1% human serum was added, and the cells were incubated at room temperature for 60 minutes. The cells were then washed 3 times with PBS(−), and after adding 100 μL/well of peroxidase-labeled streptavidin solution (Dako Cytomation), the cells were incubated at room temperature for another 30 minutes. After washing, 100 μL/well of chromogenic substrate (TMB) was added, and the reaction was allowed to proceed at room temperature for 30 minutes, and the reaction was terminated by adding 100 μL/well of 2N sulfuric acid. Absorbance was measured at wavelengths of 450 nm and 650 nm, ΔOD (450 nm-650 nm) was used for the amount of E-Selectin expressed. $IC_{50}$ value for the inhibition of the E-Selectin expression by the F1024S-D2(3) was 0.43 μg/mL. This result revealed that LPS-induced expression of the adhesion molecule in the human vascular endothelial cell is inhibited by the F1024S-D2(3).

The inhibitory activity of the F1031-13S-D2(3) and F1024D-SLPI(D1D2), F1024D-SLPI(D2), F1024S-SLPI(D1D2) or F1024S-SLPI(D2) is evaluated by using a similar assay system.

(3) Confirmation of Inhibitory Activity for LPS Induced TNF-α Production in Human Peripheral Blood Mononuclear Cell Normal human peripheral blood mononuclear cells (hPBMC, BioWhittaker Inc.) were suspended in RPMI 1640 containing 10% human serum and 25 mM HEPES (SIGMA), and inoculated in 96-well plate at $2.5 \times 10^5$ cells/well. F1024S-D2(3) was added to final concentrations of 0.1, 0.3, 1, 3, 10, and 30 μg/mL, and after allowing to stand at room temperature for 20 minutes, LPS (WE. coli 055:B5, DIFCO) was added to a final concentration of 0.1 ng/mL. After incubating at 37° C. in the presence of 5% $CO_2$ for 6 hours, TNF-α in the culture supernatant was measured using human TNF-α EIA kit (Diaclone Research) according to the protocol attached to the kit.

$IC_{50}$ value for the inhibition of the TNF-α production by F1024S-D2(3) was 0.58 μg/mL. This result revealed that LPS-induced cytokine production in the human leukocyte is inhibited by the F1024S-D2(3).

The inhibitory activity of the F1031-13S-D2(3) and F1024D-SLPI(D1D2), F1024D-SLPI(D2), F1024S-SLPI(D1D2) or F1024S-SLPI(D2) is evaluated by using a similar assay system.

(4) Confirmation of Inhibitory Activity for Enhancement of LPS-Induced Procoagulant Activity (PCA) in Human Peripheral Blood Mononuclear Cell Mononuclear cells of normal human peripheral blood (hPBMC, BioWhittaker Inc.) were inoculated by the procedure described in Example 3-1)(3), and F1024S-D2(3) was added to final concentrations of 0.1, 0.3, 1, 3, 10, and 30 µg/mL, and after allowing the cells to stand at room temperature for 20 minutes, LPS (WE. coli O55:B5, DIFCO) was added to a final concentration of 0.1 ng/mL. After incubating at 37° C. in the presence of 5% $CO_2$ for 6 hours, PCA of the cell suspension was measured by using normal human plasma (DADE BEHRING INC.). More specifically, after diluting the suspension 2.5 folds with 50 mM Tris-HCl (pH 7.4) solution containing 0.15M NaCl and 0.1% BSA, the cells were lysed by ultrasonication (SIMAZU) for 20 seconds. This sample was placed in a coagulometer (AMAX CS190, MC Medical, Inc.). 20 µL of the sample was collected from the coagulometer, and after adding 20 µL of 25 mM $CaCl_2$, the sample was incubated at 37° C. for 3 minutes. Coagulation reaction was started by adding 90 µL of normal human plasma, and coagulation time was measured. The $IC_{50}$ value for the PCA inhibition by F1024S-D2(3) calculated from the coagulation time was 20.86 µg/mL. This result revealed that F1024S-D2(3) inhibits enhancement of the LPS-induced PCA in human leucocyte.

The inhibitory activity of the F1031-13S-D2(3) and F1024D-SLPI(D1D2), F1024D-SLPI(D2), F1024S-SLPI (D1D2) or F1024S-SLPI(D2) is evaluated by using a similar assay system.

(5) Confirmation of Inhibitory Activity for LPS-Induced TNF-α Production in Rabbit Whole Blood The blood was collected from auricular artery of male rabbit (New Zealand white, 3.4 kg, Kitayama Labes Co., Ltd.), and after adding 10 unit/mL of heparin (Mochida Pharmaceutical Co., Ltd.) to the collected whole blood, it was transferred to microtubes and F1024S-D2(3) was added to final concentrations of 0.3, 1, 3, 10, and 30 µg/mL. After incubating at room temperature for 30 minutes, LPS (WE. coli O55:B5, DIFCO) was added to a final concentration of 0.1 ng/mL.

After incubating at 37° C. for 6 hours, plasma was separated by centrifuging at 4° C. and at 8000 rpm (TOMY) for 10 minutes, and TNF-α in the plasma was measured by sandwich ELISA using anti-rabbit TNF-α antibody. More specifically, 100 µL of plasma diluted with PBS(−) containing 1% BSA was moved to a plate having 4 µg/mL of anti-rabbit TNF-α antibody (BD Biosciences) immobilized thereon, and the plate was incubated at room temperature for 2 hours. The well was washed three times with 400 µL/well of PBS(−) containing 0.05% Tween 20, and 100 µL/well of biotinylated anti-rabbit TNF-α antibody solution (2 µg/mL, BD Biosciences) was added. After incubating at room temperature for 1 hour and washing, 100 µL/well of peroxidase labeled streptavidin solution (Invitrogen Corporation) was added, and the well was incubated at room temperature for 30 minutes. After washing, 100 µL/well of chromogenic substrate (TMB) was added, and the reaction was allowed to proceed at room temperature for 30 minutes and 100 µL/well of 2N sulfuric acid was added to terminate the reaction. Absorbance was measured at 450 nm and 650 nm, and amount of the TNF-α produced in the sample was calculated. $IC_{50}$ value for the inhibition of the TNF-α production by F1024S-D2(3) was 0.83 µg/mL. This result revealed that LPS-induced cytokine production in the rabbit whole blood is inhibited by F1024S-D2(3).

The inhibitory activity of the F1031-13S-D2(3) and F1024D-SLPI(D1D2), F1024D-SLPI(D2), F1024S-SLPI (D1D2) or F1024S-SLPI(D2) is evaluated by using a similar assay system.

3-2) Confirmation of Enzyme Inhibitory Activity

In order to confirm the activity of enzyme inhibitory functional domains of F1024S-D2(3) and F1024D-D2(3), inhibitory activities for various enzymes were measured as described below. In the assay system, the protein concentration of the analyte sample was measured by using bovine γ globulin (Nippon Bio-Rad Laboratories K.K.) for the standard and using protein assay staining solution (Nippon Bio-Rad Laboratories K.K.), and the molar concentration was calculated from the deduced molecular weight of the antibody fusion protein. The test results are shown in FIGS. 22 to 25 in which the y axis represents the residual activity of the enzyme, and the x axis represents protein concentration of the analyte sample in the reaction solution.

(1) Inhibitory Activity for Factor Xa

F1024S-D2(3) and F1024D-D2(3) were serially diluted with a dilution solution prepared by mixing 0.14M sodium chloride/5 mM calcium chloride/20 mM Tris-hydrochloric acid buffer solution (pH 7.4) and 10% BSA at a ratio of 99:1 (this solution being hereinafter referred to as the dilution solution) to prepare the samples for measuring inhibitory activity. In the meanwhile, Human Factor Xa (Enzyme Research Laboratories Ltd.) was diluted with the dilution solution to 0.1 U/mL, and this solution was used as the Factor Xa solution. Synthetic substrate S-2222 (Daiichi Pure Chemicals Co., Ltd.) was also diluted with the dilution solution to 2 mM, and this solution was used as the S-2222 solution. After the preparation of the reagents, 10 µL of sample for measuring the inhibitory activity, 50 µL of the dilution solution, and 20 µL of the Factor Xa solution were placed in the wells of 96-well microtiter plate (Nunc). After incubating at 37° C. for 5 minutes, the S-2222 solution was added in 20 µL/well, and incubation at 37° C. was continued for another 30 minutes. The reaction was then terminated by adding 50 µL of 20% solution of acetic acid to each well, and absorbance at a wavelength of 405 nm was measured.

The control was prepared by mixing 20 µL of the Factor Xa solution with 60 µL of the diluting solution, incubating the mixture at 37° C. for 5 minutes, adding 20 µL of the S-2222 solution, incubating the mixture at 37° C. for 30 minutes, and adding 50 µL of the 20% solution of acetic acid. The results shown in FIG. 22 confirmed retention of the FXa inhibitory activity.

Inhibitory activity of F1031-13S-D2(3) is evaluated by using a similar assay system.

(2) Inhibitory Activity for Factor XIa

F1024S-D2(3) and F1024D-D2(3) were serially diluted with the dilution solution (as described above) to prepare the samples for measuring inhibitory activity. In the meanwhile, Human Factor XIa (American Diagnostica Inc.) was diluted with the dilution solution to 750 ng/mL, and this solution was used as the Factor XIa solution. Synthetic substrate S-2366 (Daiichi Pure Chemicals Co., Ltd.) was also diluted with water to 5 mM, and this solution was used as the S-2366 solution.

After the preparation of the reagents, 10 µL of the sample for inhibitory activity measurement, 60 µL of the dilution solution, and 10 µL of the Factor XIa solution were placed in the wells of 96-well microtiter plate (Nunc). After incubating at 37° C. for 5 minutes, 20 µL of the S-2366 solution was added to the well, and incubation at 37° C. was continued for another 30 minutes. Next, the reaction was terminated by adding 100 μL of 20% acetic acid solution to the well, and the reaction solution was measured for absorbance at a wavelength of 405 nm.

The control used was the one prepared by mixing 70 μL of the dilution solution with 10 μL of the Factor XIa solution, incubating the mixture at 37° C. for 5 minutes, adding 20 μL of the S-2366 solution to the mixture, incubating at 37° C. for 30 minutes, and adding 100 μL of 20% acetic acid solution.

Figure 23:
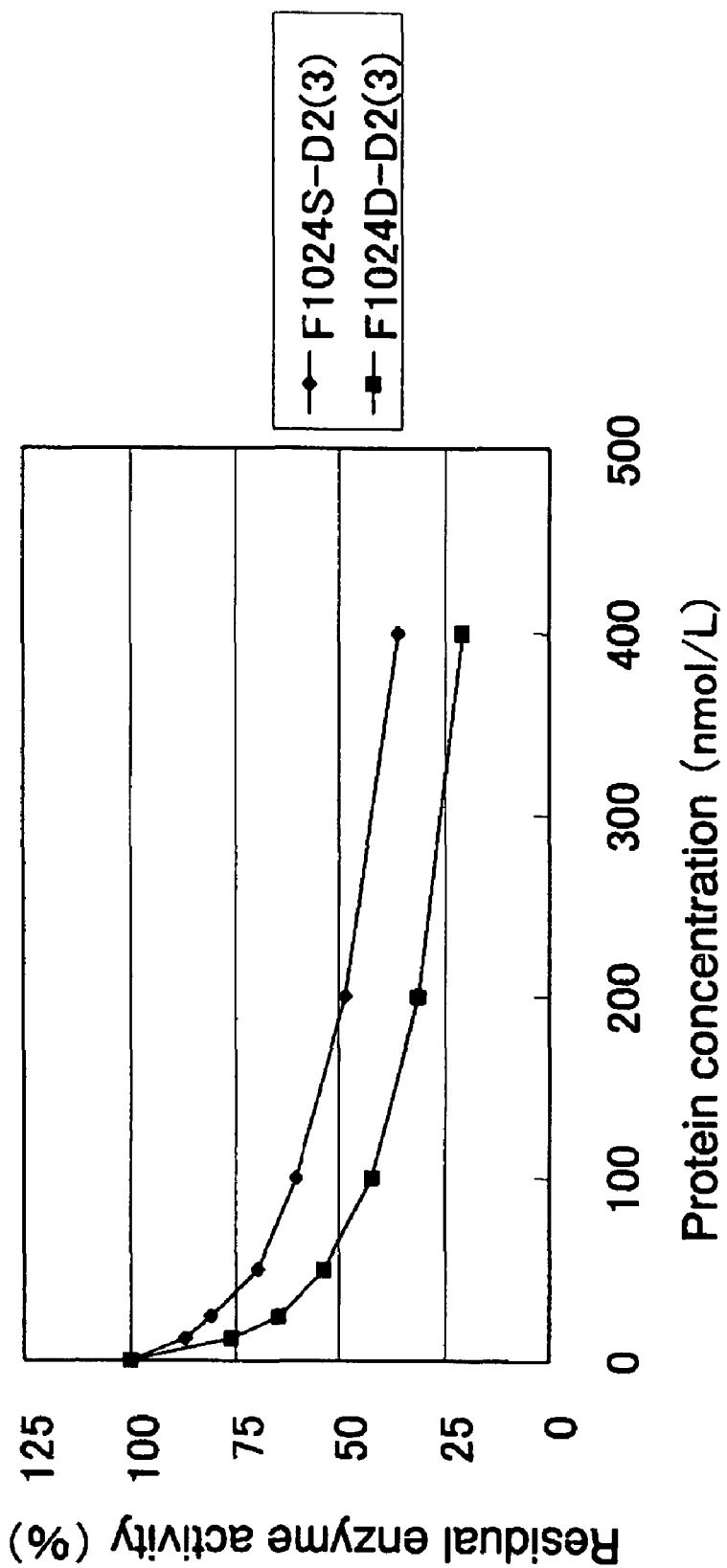
FIG. 23 is a view showing Factor XIa inhibitory activity of anti-CD14 antibody fusion proteins.
Figure 24:
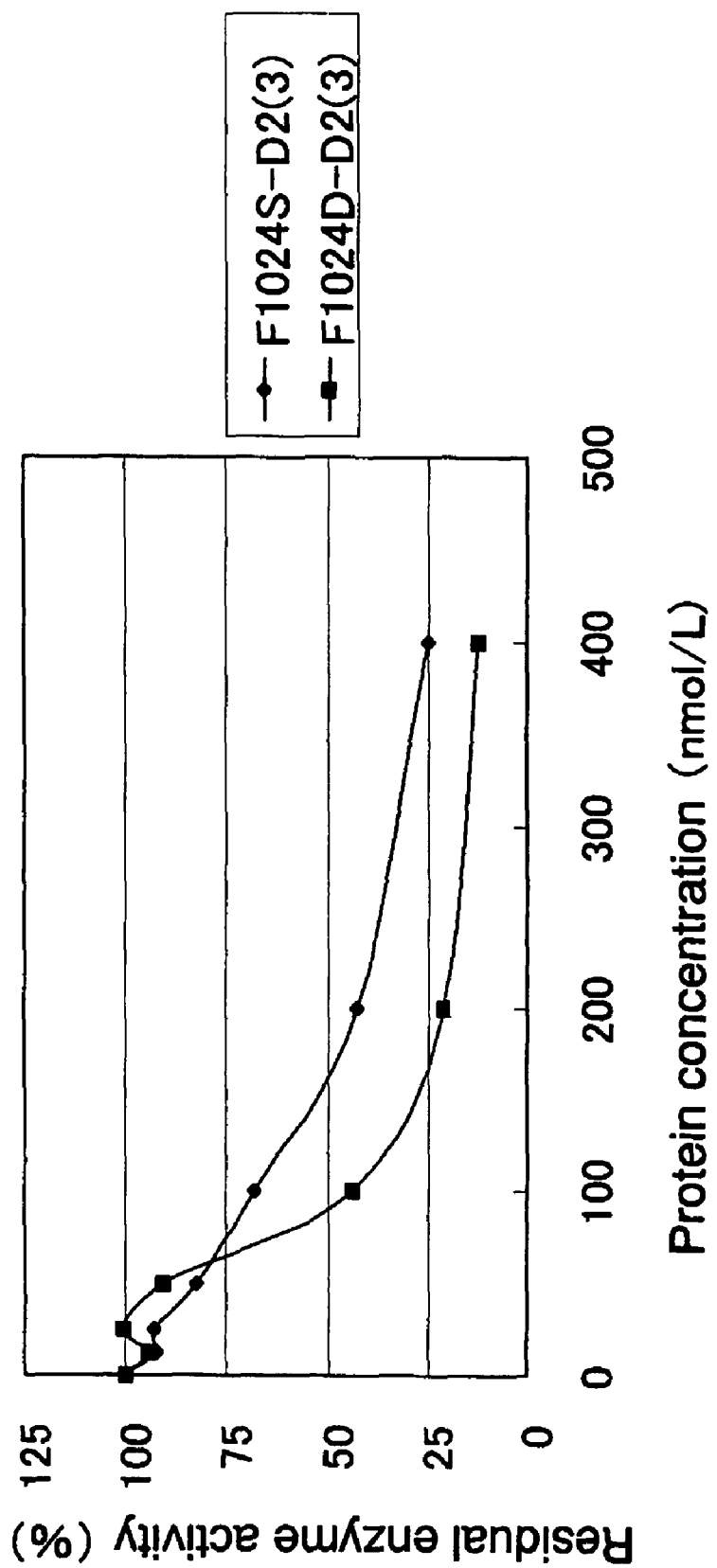
FIG. 24 is a view showing elastase inhibitory activity of anti-CD14 antibody fusion proteins.

The results shown in FIG. 23 reveal FXIa inhibitory activity of D2(3).

Inhibitory activity of F1031-13S-D2(3) is evaluated by using a similar assay system.

(3) Inhibitory Activity for Elastase

F1024S-D2(3) and F1024D-D2(3) were serially diluted with the dilution solution (as described above) to prepare the samples for measuring inhibitory activity. In the meanwhile, Elastase, Human Neutrophil (Athens Research & Technology) which has been dissolved in 500 mM sodium chloride/50 mM sodium acetate (pH 5.5) and cryopreserved was diluted with the dilution solution to 20 μg/mL, and this solution was used as the elastase solution. Synthetic substrate S-2484 (Daiichi Pure Chemicals Co., Ltd.) was diluted with dimethylsulfoxide and stored at a low temperature, and diluted with water to 2 mM immediately before use as the S-2484 solution.

After the preparation of the reagents, 10 μL of the sample for inhibitory activity measurement, 70 μL of the dilution solution, and 10 μL of the elastase solution were placed in the wells of 96-well microtiter plate (Nunc). After incubating at 37° C. for 3 minutes, 10 μL of the S-2484 solution was added to the well, and incubation at 37° C. was continued for exactly 10 minutes. Next, the reaction was terminated by adding 50 μL of 20% acetic acid solution to the well, and the reaction solution was measured for absorbance at a wavelength of 405 nm.

The control was prepared by mixing 10 μL of the elastase solution with 80 μL of the diluting solution, incubating the mixture at 37° C. for 3 minutes, adding 10 μL of the S-2484 solution, incubating at 37° C. for exactly 10 minutes, and adding 50 μL of 20% solution of acetic acid. The results shown in FIG. 24 confirmed retention of the elastase inhibitory activity.

Inhibitory activity of fusion proteins F1031-13S-D2(3) and F1024D-SLPI(D1D2), F1024D-SLPI(D2), F1024S-SLPI(D1D2), or F1024S-SLPI(D2) is evaluated by using a similar assay system.

(4) Plasma Kallikrein

F1024S-D2(3) and F1024D-D2(3) were serially diluted with the dilution solution (as described above) to prepare the samples for measuring inhibitory activity. In the meanwhile, Kalliklein from human plasma (Sigma-Aldrich Co.) was diluted with the dilution solution to 20 mU/mL, and this solution was used as the plasma kallikrein solution. Synthetic substrate S-2302 (Daiichi Pure Chemicals Co., Ltd.) was also diluted with water to 4 mM, and this solution was used as the S-2302 solution.

After the preparation of the reagents, 10 μL of the sample for inhibitory activity measurement, 70 μL of the dilution solution, and 10 μL of the plasma kallikrein solution were placed in the wells of 96-well microtiter plate (Nunc). After incubating at 37° C. for 3 minutes, 10 μL of the S-2302 solution was added to the well, and incubation at 37° C. was continued for another 30 minutes. Next, the reaction was terminated by adding 50 μL of 20% acetic acid solution to the well, and the reaction solution was measured for absorbance at a wavelength of 405 nm.

Figure 25:
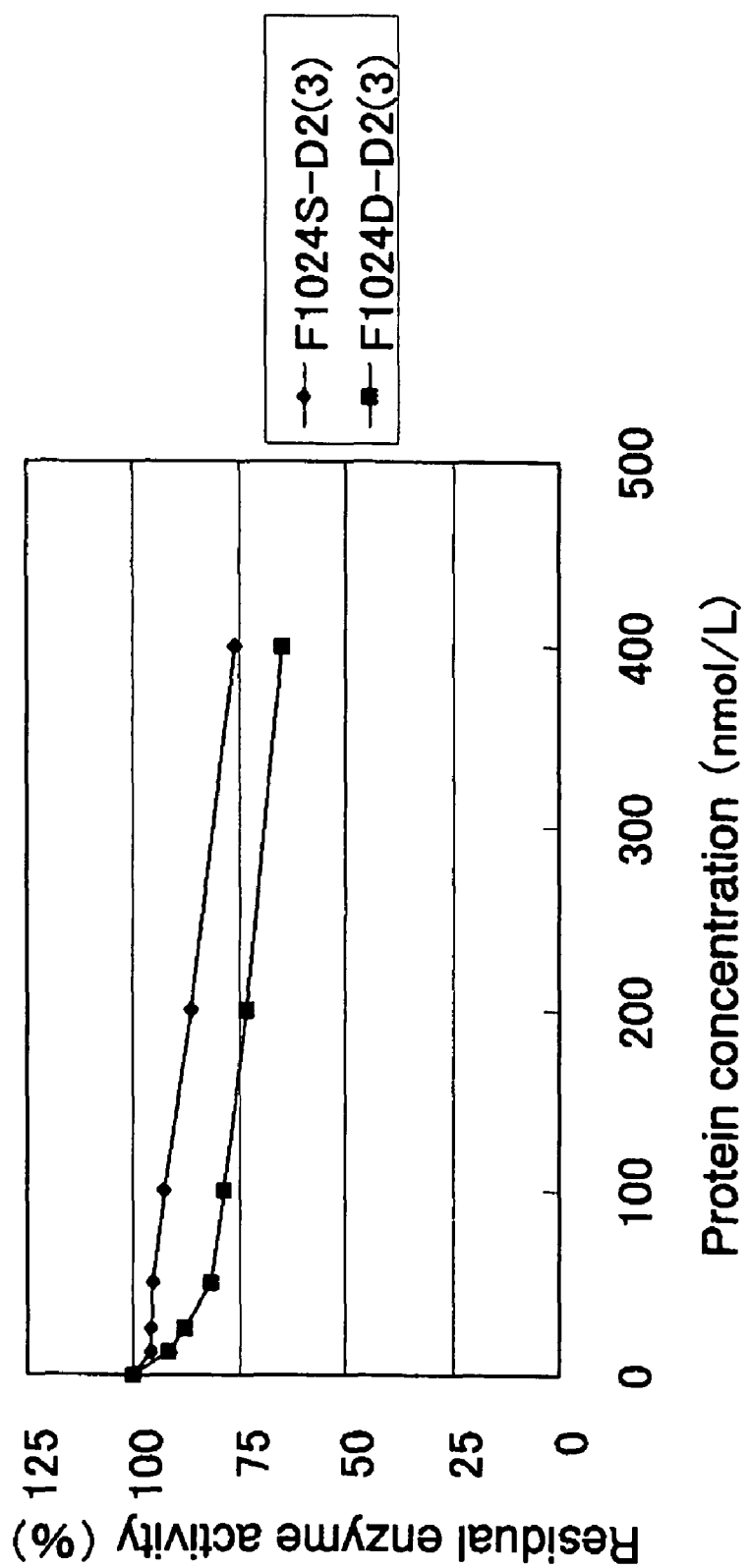
FIG. 25 is a view showing plasma kallikrein inhibitory activity of anti-CD14 antibody fusion proteins.
Figure 26:
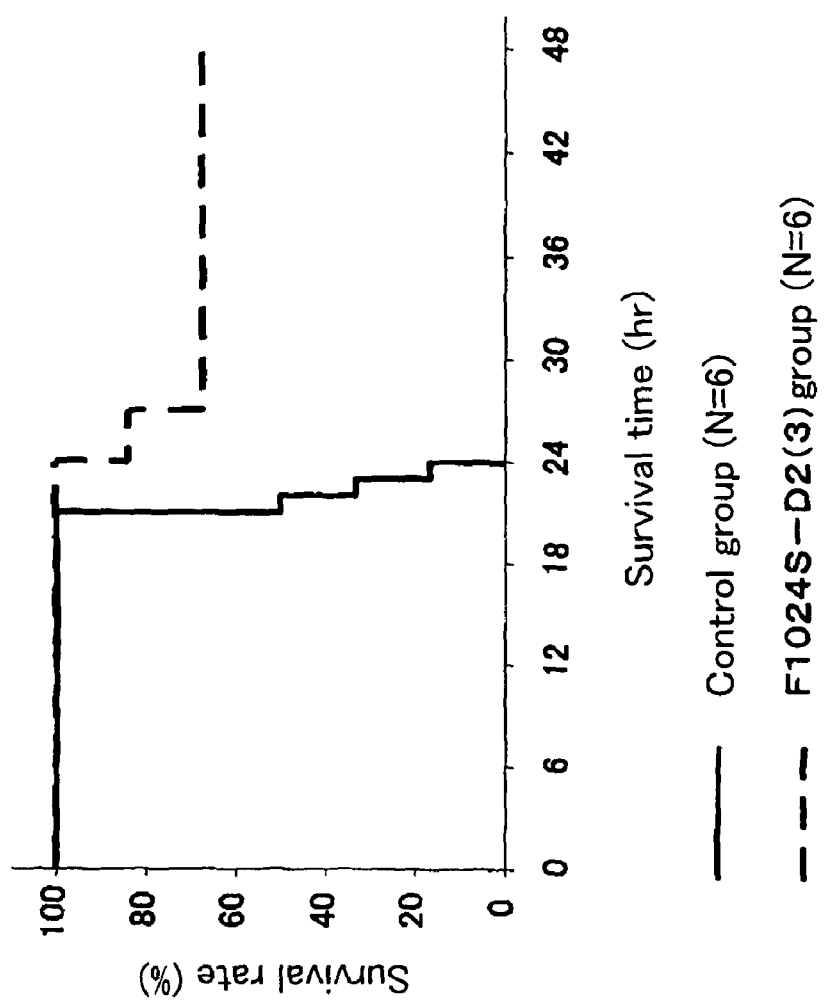
FIG. 26 is a view showing the effect of fusion protein F1024S-D2(3) on improving the survival rate of the LPS-induced rabbit sepsis model.

The control was prepared by mixing 10 μL of the plasma kallikrein solution with 80 μL of the diluting solution, incubating at 37° C. for 3 minutes, adding 10 μL of the S-2302 solution, incubating at 37° C. for 30 minutes, and adding 50 μL of 20% solution of acetic acid. The results are shown in FIG. 25.

Inhibitory activity of F1031-13S-D2(3) is evaluated by using a similar assay system.

3-3) Confirmation of Inhibitory Action for Coagulation (1) Confirmation of Extension of Activated Partial Thromboplastin Time (APTT) in Human and Rabbit The normal human plasma used was Dade Ci-Trol Level 1 (DADE BEHRING INC.). The rabbit plasma was obtained by collecting blood from auricular artery of male rabbit (New Zealand white, 2.6 to 2.7 kg, Kitayama Labes Co., Ltd.) using a syringe containing 1/10 volume of 3.8% sodium citrate (sodium citrate for measuring erythrocyte sedimentation rate, Iwaki Seiyaku Co., Ltd.), and centrifuging at 4° C. and at 3000 rpm (05PR-22, Hitachi) for 10 minutes.

To 113 μL of human or rabbit plasma, 20 μL of F1024S-D2(3)) solution was added to final concentrations of 0, 1.56, 3.13, 6.25, 12.5, 25, 50, and 100 μg/mL, and the plasma was placed in a coagulometer (AMAX CS190, MC Medical, Inc.). 50 μL was collected from the coagulometer, and after addition of 50 μL of APTT measurement reagent (DADE BEHRING INC.) and 2 minute incubation, 50 μL of 25 mM CaCl$_2$ was added to measure the coagulation time. It was then found that F1024S-D2(3) extends the human and rabbit APTT in a concentration dependent manner, and extension of the human and rabbit APTT of 1.5 folds was attained at a concentration of 9.06 μg/mL and 40.96 μg/mL, respectively.

F1031-13S-D2(3) is evaluated for extension of APTT by using a similar assay system.

Example 4

Evaluation of In Vivo Effectiveness 4-1) Effect of the Fusion Protein on Improving Survival Rate of LPS-Induced Rabbit Sepsis Model LPS-induced rabbit sepsis fatal model was prepared, and improvement in the survival rate by post-administration of the fusion protein was examined.

The LPS-induced rabbit sepsis model was prepared according to the method of Schimke et al. (Proc. Natl. Acad. Sci. USA, 95: 13875, 1998) by administering LPS (*Salmonella Minnesota* Re595, SIGMA) to auricular vein of a rabbit (New Zealand white, 1.8 to 2.6 kg, Kitayama Labes Co., Ltd.) at a dose of 15 μg/kg at 0, 5, and 24 hours. F1024S-D2(3) was administered to the auricular vein at a dose of 1 mg/kg at 2, 8, and 23 hours. Control group was administered with human immunoglobulin instead of the fusion protein. The survival was monitored until 48 hours after the administration, and Kaplan-Meier survival curve was depicted. It was then found that administration of F1024S-D2(3) improves the survival rate compared to the control group.

In the same assay system, administration of F1024D-SLPI (D1D2), F1024D-SLPI(D2), F1024S-SLPI(D1D2), and F1024S-SLPI(D2) also had the action of improving the survival rate.

4-2) Effect of the Fusion Protein on Improving Inflammation and Coagulation Parameters of LPS-Induced Rabbit Sepsis Model LPS-induced rabbit sepsis model was prepared, and the effect on inflammation and coagulation parameters by the post-administration of the fusion protein was examined.

The LPS-induced rabbit sepsis model was prepared according to the method of Schimke et al. (Proc. Natl. Acad. Sci. USA, 95: 13875, 1998) by administering LPS (*Salmonella Minnesota* Re595, SIGMA) to auricular vein of a rabbit (New Zealand white, 1.8 to 2.6 kg, Kitayama Labes Co., Ltd.) at a dose of 10 μg/kg at 0, 5, and 24 hours. F1024S-D2(3) was administered to the auricular vein at a dose of 0.3, 1, and 3 mg/kg at 2, 8, and 23 hours. Control group was administered with 3 mg/kg of human immunoglobulin instead of the fusion protein.

Blood was collected (with addition of citric acid) from auricular artery before the LPS administration and at 1.5, 25, 26, 28 hours post administration to measure the inflammatory parameters and the coagulation parameters.

The inflammatory parameters used were leukocyte count and plasma TNF concentration, and the coagulation parameter used were platelet count and plasma antithrombin III activity.

The leukocyte count was measured by Sysmex F-820 (Sysmex Corporation). The TNF-α concentration was measured by sandwich ELISA using Purified Goat Anti-rabbit TNF Polyclonal Antibody (BD Biosciences) and Biotinylated Mouse Anti-rabbit TNF-α Monoclonal Antibody (BD Biosciences).

The antithrombin III activity was measured by TESTZYM ATIII 2 kit (Daiichi Pure Chemicals Co., Ltd.).

Figure 27:
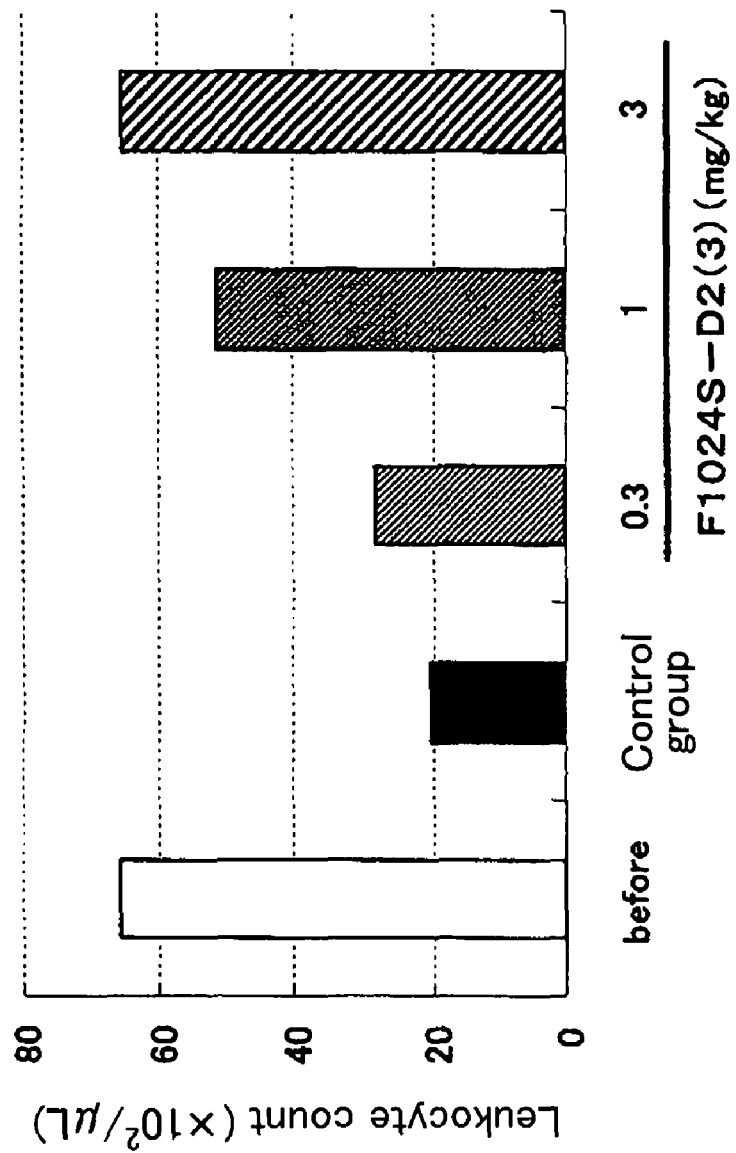
FIG. 27 is a view showing the effect of fusion protein F1024S-D2(3) on leukocyte count in LPS-induced rabbit sepsis model (leukocyte count at 28 hours after the initial administration of the LPS in the LPS-induced rabbit sepsis model).
Figure 28:
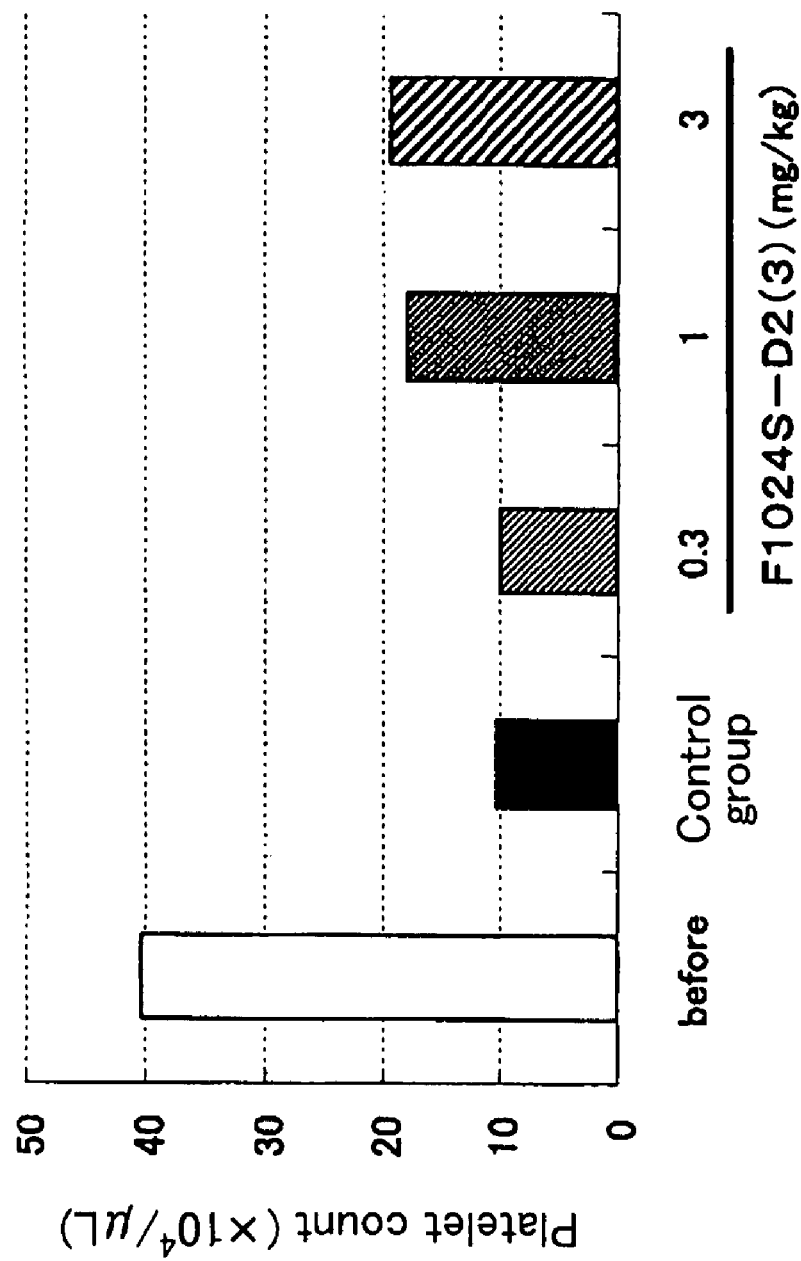
FIG. 28 is a view showing the effect of fusion protein F1024S-D2(3) on platelet count in LPS-induced rabbit sepsis model (platelet count at 26 hours after the initial administration of the LPS in the LPS-induced rabbit sepsis model).
Figure 29:
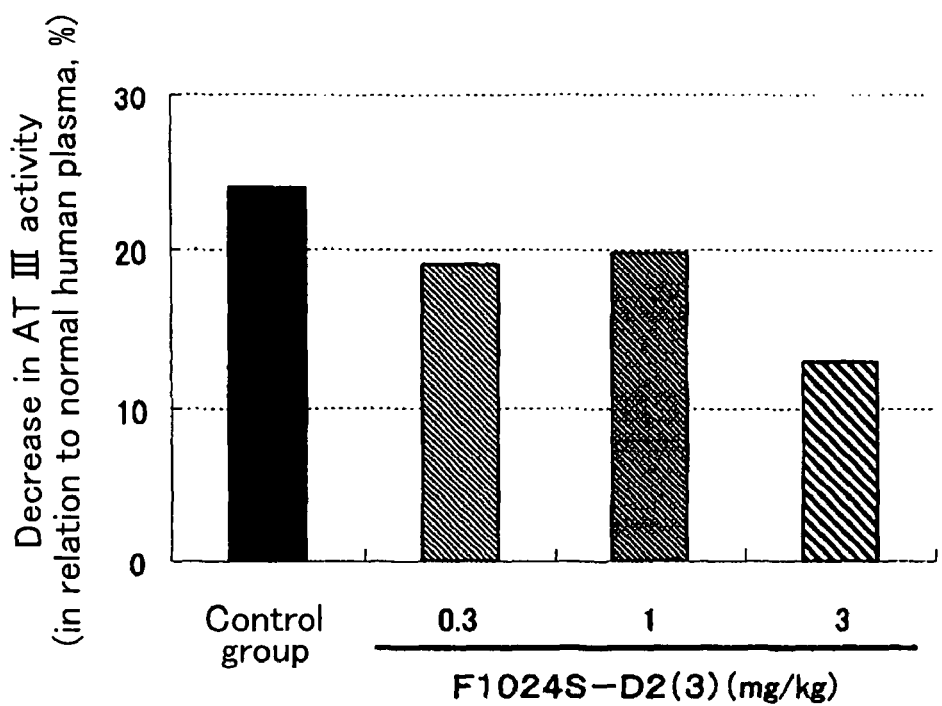
FIG. 29 is a view showing the effect of fusion protein F1024S-D2(3) on decrease in antithrombin (AT)III activity in LPS-induced rabbit sepsis model (decrease in antithrombin (AT)III activity at 28 hours after the initial administration of the LPS in the LPS-induced rabbit sepsis model).

The TNF-α concentration in plasma was evaluated "positive" when the concentration measured was equal to or higher than 0.4 ng/mL which is the detection limit of the sandwich ELISA, and "negative" when the measured value was less than 0.4 ng/mL. It was then found that the group administered with F1024S-D2(3) showed dose dependent improvement of the decrease of the leukocyte count (FIG. 27), increase of the TNF-α concentration in the plasma (Table 4), decrease of the platelet count (FIG. 28), and decrease of the antithrombin III activity (FIG. 29) compared to the control group. These results demonstrated improvement of the inflammation and coagulation parameters by the F1024S-D2(3).

In the same assay system, the group administered with the F1031-13S-D2(3) shows the effects of improving the decrease of the leukocyte count, increase of the TNF-α concentration in the plasma, decrease of the platelet count, and decrease of the antithrombin III activity compared to the control group.

TABLE 4

| TNF-α concentration in plasma at 25 hours after the initial administration of LPS in LPS-induced rabbit sepsis model | |
|---|---|
| Dose of F1024S-D2(3) (mg/kg) | Positive rate |
| Control group | 4/6 |
| 0.3 | 3/6 |
| 1 | 1/6 |
| 3 | 0/6 |

4-3) Effect of the Fusion Protein on Improving Decrease in Blood Pressure of LPS-Induced Rabbit Sepsis Model LPS-induced rabbit sepsis model was prepared, and the effect of improving the decrease in blood pressure by the post-administration of the fusion protein was examined.

The LPS-induced rabbit sepsis model was prepared according to the method of Schimke et al. (Proc. Natl. Acad. Sci. USA, 95: 13875, 1998) by administering LPS (*Salmonella Minnesota* Re595, SIGMA) to auricular vein of a rabbit (New Zealand white, 1.8 to 2.6 kg, Kitayama Labes Co., Ltd.) at a dose of 5 μg/kg at 0 and 5 hours. F1024S-D2(3) was administered to the auricular vein at a dose of 1 mg/kg at 2 hours after the initial administration of the LPS. Control group was administered with 1 mg/kg of human immunoglobulin instead of the fusion protein.

Figure 30:
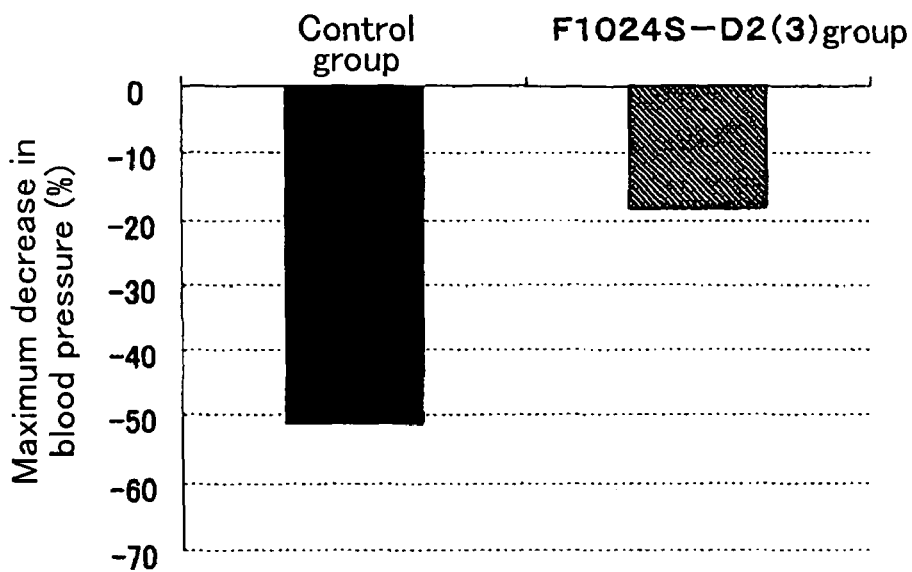
FIG. 30 is a view showing the improvement of decrease in blood pressure by the fusion protein F1024S-D2(3) in the LPS-induced rabbit sepsis model.

Before the LPS administration and at 4, 6, and 8 hours post administration, a catheter inserted in the carotid artery was connected to a blood pressure transducer (DT-XX, Japan BD Medical Systems) to measure the average arterial blood pressure. It was then found that the group administered with F1024S-D2(3) showed improvement in the decrease of the blood pressure compared to the control group (FIG. 30).

In the same assay system, the group administered with the F1031-13S-D2(3) shows the effects of improving the decrease in the blood pressure compared to the control group.

Example 5

Establishment of Strain Stably Producing Antibody Fusion Protein 5-1) Construction of Plasmid Expressing Strain Producing F1024S-D2(3) or F1024D-D2(3)

The expression plasmid used in establishing the strain which is capable of stably producing the F1024S-D2(3) or the F1024D-D2(3) was constructed by the procedure as described below.

The plasmid pTK-2370 expressing the heavy chain of F1024S-D2(3) and the plasmid pTK-2368 expressing the heavy chain of F1024D-D2(3) constructed in Example 1 were respectively digested with EcoRI and KpnI to recover the fragment of about 1.7 kb. The expression plasmid pM1103 having mouse DHFR expression unit and EF1α promoter (see WO97/42319) was also digested with EcoRI and KpnI to recover the fragment having about 7.9 kb. The fragment obtained by digesting the plasmid expressing heavy chain and the fragment obtained by digesting pM1103 were ligated, and plasmid pEFD2370 expressing the heavy chain of F1024S-D2(3) and plasmid pEFD2368 expressing the heavy chain of F1024D-D2(3) for producing the production strain were produced by transforming JM109 competent cell by the method commonly used in the art. In the meanwhile, the light chain expression plasmid is common to F1024S-D2(3) and F1024D-D2(3), and this plasmid was constructed by the following procedure. Plasmid pTK-2344 for transient expression was digested by BamHI, and blunt-ended, and further digested with EcoRI to recover the fragment of 0.7 kb. pM1103 was digested with KpnI, and after blunt ending, it was digested with EcoRI to recover the fragment of about 7.9 kb. The fragment obtained by digesting pTK-2344 and the fragment obtained by digesting pM1103 were ligated, and plasmid pEFD2344 expressing the light chain for producing the production strain was produced by transforming JM109 competent cell by the method commonly used in the art.

5-2) Establishment of Transformant Strain Producing F1024S-D2(3) and F1024D-D2(3)

The plasmids expressing the heavy chain and the light chain constructed in Example 5-1) were co-transfected in DHFR gene-deleted CHO cell to establish the CHO transformant producing the chimeric antibody fusion protein. More specifically, CHO DXB11 derived from the conditioned medium of EX-CELL 325 PF CHO (JRH Bioscience) containing HT media Supplement (50×) Hybri-Max (SIGMA, used at a final concentration of 1×) and 200 mM L-Glutamine (SIGMA, used at a final concentration of 4 mM) was centrifuged on the day of the transfection, and inoculated in a flask at a concentration of 8×10$^6$ cells/150 Roux. 12.5 µg of the plasmid expressing the heavy chain and 12.5 µg of the plasmid expressing the light chain (namely, pEFD2370+ pEFD2344, or pEFD2368+pEFD2344) were prepared according to the protocol attached to FuGENE6 by using 125 µL of FuGENE6 (Roche Diagnostics K.K.), and they were co-transfected in the CHO DXB11 as described above. After incubating at 37° C. in the presence of 5% $CO_2$ for 2 days, the cells were collected, and the cells were washed once with HT-free EX-CELL 325 PF CHO medium containing 4 mM L-Glutamine (hereinafter referred to as EX-CELL(HT-), and then once with PBS$^-$, and suspended again in EX-CELL (HT-). Next, the cells were newly inoculated in a 96-well plate at 3,000 to 48,000 cells/well, the cells were incubated at 37° C. in the presence of 5% $CO_2$, and half of the medium was replaced with a new EX-CELL(HT-) at intervals of 3 days or 4 days. After incubating for about 1 month, the cells of the well in which the colony had formed were transferred to a new plate, and amount of the chimeric antibody in the culture supernatant was measured by the EIA procedure described in Example 2. The cell for which expression of the chimeric antibody in the supernatant had been confirmed was obtained as the transformant strain producing the chimeric antibody fusion protein.

5-3) Gene Amplification Using Methotrexate

Gene amplification was conducted by selectively cultivating the CHO transformant strain expressing the chimeric antibody fusion protein produced in Example 5-2) on EX-CELL(HT-) medium containing methotrexate (hereinafter referred to as MTX) to select the clone producing the chimeric antibody fusion protein of interest at a high yield.

(1) Establishment of CHO-F1024SC93t3L1

The transformant strain producing F1024S-D2(3) produced in the above 5-2) was suspended in EX-CELL (HT-) medium containing 100 nM MTX, and inoculated in 96-well plate, and half of the medium was changed with a fresh EX-CELL(HT-) containing 100 nM MTX in every 3 or 4 days. Incubation was continued at 37° C. in the presence of 5% $CO_2$ until colonies were formed. The resulting colonies were evaluated by EIA for their expression, and the increasingly produced clones were selected. The selected clones were subsequently suspended in EX-CELL(HT-) medium containing 300 nM MTX, and inoculated in 96-well plate for selective cultivation. A process similar to the selective cultivation using 100 nM MTX was conducted to thereby obtain a transformant strain having an about 20 times higher production rate. Clones having even higher production rate can also be obtained by repeating the process of selective cultivation by using cultures having 3 to 10 times higher MTX concentration.

(2) Establishment of CHO-F1024DC78u1

The transformant strain producing the F1024D-D2(3) produced in the above 5-2) was treated by the procedure similar to that of Example 5-2) to produce a strain with high production rate. The selective cultivation using MTX was conducted first at the MTX concentration of 100 nM, and then at the concentration of 1000nM to thereby obtain a clone which produces the F1024D-D2(3) at about 60 µg/mL as measured by EIA.

Example 6

Analysis of Sequence Required for Binding to F1024 Antibody 6-1) Construction of Plasmid Expressing Amino Acid-Substituted Soluble Human CD14

In order to analyze the region recognized by the F1024 antibody, 31 types of amino acid-substituted soluble human CD14 shown in Table 5 were prepared. It is to be noted that the 1 amino acid-substituted CD14 having the 263rd Asn calculated from N terminal of the soluble CD14 molecule substituted with Gln is designated "N263Q", and other 1 amino acid-substituted CD4 were designated in the same manner. In the meanwhile, the 2 amino acid-substituted CD14 having both the 294th Pro and the 296th Pro substituted with Ala is designated "P294/296A". The plasmid expressing these substituted CD14 was constructed by the procedure as described below.

First, the plasmids expressing the modified sCD14(1-307) with amino acid substitution(s) were constructed by the method similar to that in the construction of the plasmid expressing the amino acid-substituted polypeptide described in WO02/42333 or US2004/0092712. For example, the plasmid expressing the modified sCD14(1-307) having the amino acid substitution P294H, P294/296A, Q295A, or P296H introduced therein was constructed by designing the primer set which was shown in Table 6 and coded for the amino acid substitution sequence, and using the primer set for the PCR. The codon coding for the amino acid-substituted part is shown in bold (underline) (Table 6).

Next, a DNA fragment having introduced therein an amino acid substitution (codon substitution) was produced by using recombinant PCR to construct a plasmid expressing soluble human amino acid-substituted CD14. More specifically, P294H, P294/296A, Q295A and P296H expression plasmids were constructed by the procedure as described below. Sense primer S1 (5'-GCG GCA GTA TGC TGA CAC GG-3'), SEQ ID NO: 209, sense primer S2 (5'-GAT AAC CTG ACA CTG GAC GGG AAT CCC TTC-3'), SEQ ID NO: 210, and sense primer S3 (5'-GCC ATC CAG AAT CTA GCG CT-3'); SEQ ID NO: 211, and antisense primer A1 (5'-GAA GGG ATT CCC GTC CAG TGT CAG GTT ATC-3'), SEQ ID NO: 212, antisense primer A2(5'-ATT AGC CAG AAG TCA GAT GCT C-3'), SEQ ID NO: 213, and antisense primer A3 (5'-GGG CAT TGG CCA CAC CAG C-3'), SEQ ID NO: 214, were synthesized. PCR was conducted by using each of the above-mentioned plasmids expressing the amino acid-substituted modified sCD14(1-307) for the template and using sense primers S1 and A1. The amplification product was separated and purified by electrophoresis (PCR product A). PCR was also conducted by using pCAG356 for the template, and using sense primers S2 and A2, and the amplification product was separated and purified by electrophoresis (PCR product B). PCR was also conducted by using the mixture of PCR product A and PCR product B for the template and using sense primers S3 and A3, the PCR product was separated and purified by electrophoresis (PCR product C). Next, PCR product C was digested with PvuII and KpnI, and the fragment of about 0.2 kb was separated by electrophoresis and collected. In the meanwhile, pCAG356 was similarly digested with PvuII and KpnI, and the fragment of about 5.8 kb was collected by electrophoresis, and this fragment was ligated to the fragment of about 0.2 kb as described above. E. coli XL1-Blue (STRATGENE) was transformed by the method commonly used in the art to produce the desired expression plasmid. It is to be noted that pCAG356 is a plasmid produced by inserting CD14 gene (having a mutation introduced at the GPI anchoring site) derived from sCD14 expression plasmid pM1656 described in WO02/42333 in pCAGGS (GENE, Vol. 15 (1989) pp. 269-277).

TABLE 5

Amino acid-substituted soluble human CD4

| Substituted human CD4 | Substitution Amino acid | Nucleotide (codon) |
|---|---|---|
| N263Q | 263rd Asn → Gln | AAT → CAG |
| L269A | 269th Leu → Ala | CTG → GCT |
| L276A | 276th Leu → Ala | CTG → GCT |
| K279A | 279th Lys → Ala | AAG → GCT |
| L280A | 280th Leu → Ala | CTC → GCT |
| V282A | 282nd Val → Ala | GTG → GCT |
| L283A | 283rd Leu → Ala | CTC → GCT |
| D284A | 284th Asp → Ala | GAT → GCT |
| L285A | 285th Leu → Ala | CTC → GCT |
| S286C | 286th Ser → Cys | AGC → TGT |
| C287A | 287th Cys → Ala | TGC → GCT |
| N288A | 288th Asn → Ala | AAC → GCT |
| R289A | 289th Arg → Ala | AGA → GCT |
| L290A | 290th Leu → Ala | CTG → GCT |
| N291A | 291st Asn → Ala | AAC → GCT |
| R292A | 292nd Arg → Ala | AGG → GCT |
| A293S | 293rd Ala → Ser | GCG → AGC |
| P294H | 294th Pro → His | CCG → CAC |
| P294/296A | 294th and 296th Pro → Ala | CCG, CCT → GCG, GCT |
| Q295A | 295th Gln → Ala | CAG → GCT |
| P296H | 296th Pro → His | CCT → CAC |
| D297A | 297th Asp → Ala | GAC → GCT |
| E298A | 298th Glu → Ala | GAG → GCT |
| L299A | 299th Leu → Ala | CTG → GCT |
| P300H | 300th Pro → His | CCC → CAC |
| E301A | 301st Glu → Ala | GAG → GCT |
| V302A | 302nd Val → Ala | GTG → GCT |
| D303A | 303rd Asp → Ala | GAT → GCT |
| N304A | 304th Asn → Ala | AAC → GCT |
| L305A | 305th Leu → Ala | CTG → GCT |
| L307A | 307th Leu → Ala | CTG → GCT |

TABLE 6

Primer sequence

| Product | Primer | | Sequence | SEQ ID |
|---|---|---|---|---|
| P294H | Sense | P294H-S1 | 5'-AGA CTG AAC AGG GCG CAC CAG CCT GAC GAG-3' | 179 |
| | Antisense | P294H-A1 | 5'-CAG CTC GTC AGG CTG GTG CGC CCT GTT CAG-3' | 180 |
| P294/296A | Sense | H1043Sdmt | 5'-C AGG GCG GCG CAG GCT GAC GA-3' | 181 |
| | Antisense | H1043Admt | 5'-TC GTC AGC CTG CGC CGC CCT G-3' | 182 |
| Q295A | Sense | Q295A-S1 | 5'-AGG GCG CCG GCT CCT GAC GAG CTG CCC GAG-3' | 183 |
| | Antisense | Q295A-A1 | 5'-CTC GTC AGG AGC CGG CGC CCT GTT CAG TCT-3' | 184 |
| P296H | Sense | P296H-S1 | 5'-AAC AGG GCG CCG CAG CAC GAC GAG CTG CCC-3' | 185 |
| | Antisense | P296H-A1 | 5'-CTC GGG CAG CTC GTC GTG CTG CGG CGC CCT-3' | 186 |

6-2) Expression of Amino Acid-Substituted Soluble Human CD14

The expression plasmid prepared in the above 7-1) was introduced in the COS-1 cell by the procedure as described below. 50 µL of FuGENE6 (Roche Diagnostics K.K.) was mixed with 12.5 µg of each plasmid DNA according to the attached protocol, and the mixture was added to the COS-1 cell grown to semiconfluency in 150 cm² flask. The cell was incubated for 3 to 4 days at 37° C. in the presence of 5% $CO_2$ for expression of the human amino acid-substituted CD14 in the supernatant. The expression was confirmed by EIA using the CD14 antibody described in WO02/42333. The expression was then confirmed for all of substitution products described in Table 5 except N263Q, L276A, L283A, N288A, and L290A.

6-3) Purification of Amino Acid-Substituted Soluble Human CD14

The soluble human amino acid-substituted CD14 was purified by the procedure as described below. The culture supernatant produced in the above 6-2) was passed through an affinity purification column (NHS-activated Sepharose4 Fast Flow; Amersham Biosciences) having anti-human CD14 antibody (3C10) immobilized for selective adsorption, and the column was eluted with 10 mM HCl. The eluted fraction was immediately neutralized by adding 10×PBS⁻ (SIGMA) to a concentration twice higher than the final concentration. The solution was subsequently dialyzed against physiological saline, and the dialysate was used as the purified specimen.

6-4) Competitive Experiment for F1024 Antibody

A competitive experiment was conducted by the following procedure to confirm the reactivity of each soluble human amino acid-substituted CD14 with the F1024 antibody. First, soluble CD14 molecule (356(CHO); production method is described below in 6-5)) was diluted with PBS⁻ to 4 µg/mL and placed in 96-well plate (F8 MaxiSorp; NUNC) at 50 µL/well. After allowing to stand overnight at 4° C. and washing 3 times with the PBS-containing 0.05% Tween 20, 200 µL/well of PBS⁻ containing 2% StabilGuard (SurModics, Inc.) was added to the well, and the solution was incubated at 37° C. for 30 minutes and stored at 4° C. In the meanwhile, amino acid-substituted soluble human CD14 that had been purified in Example 6-3) was diluted to 2 to 0.02 µg/mL with PBS⁻ containing 0.1% BSA. HRP-labeled F1024 antibody was diluted to 2 µg/mL with PBS⁻ containing 0.1% BSA, and the diluted HRP-labeled F1024 antibody was mixed with an equal amount of the human amino acid-substituted CD14 (25 µL+25 µL). Next, the solution was discarded from the wells of the plate having the soluble CD14 immobilized, and 50 µL/well of a mixed solution of amino acid-substituted CD14 and HRP-labeled F1024 was added. After the incubation at 37° C. for 2 hours, the plate was washed 5 times with PBS⁻ containing 0.05% Tween 20, and 50 µL/well of TMB solution (BioFX) was added to the well as the chromogenic substrate. The reaction was allowed to proceed at room temperature for 0.5 minutes, the reaction was terminated by adding 50 µL/well of 1M hydrochloric acid solution. Absorbance at 450 nm was measured with a plate spectrophotometer.

Figure 31:
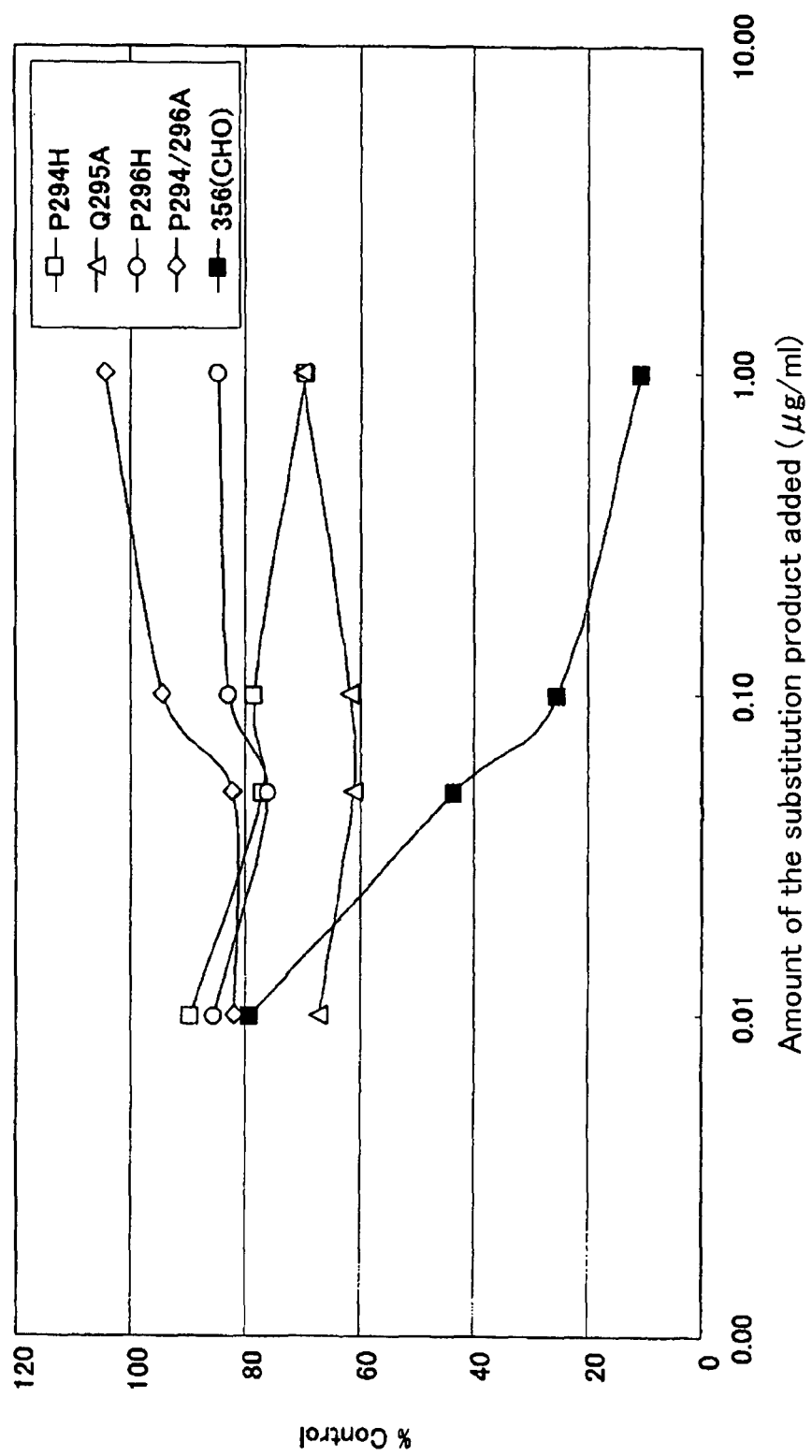
FIG. 31 is a view showing the experimental results of competitive binding to antibody F1024.

The results are shown in FIG. 31 in relation to the absorbance without the addition of the amino acid-substituted CD-14 (100%). In FIG. 31, 356(CHO) shows the absorbance when the soluble CD14 molecule used for the immobilization was added.

The absorbance decreased in many cases of the amino acid-substituted CD14 in a manner dependent on the concentration, and this confirmed their binding with the F1024 antibody in a manner competitive with the 356(CHO). However, in the cases of P294H, P294/296A, Q295A, and P296H, decrease in the absorbance was not confirmed irrespective of their concentration, and it was determined that binding to the F1024 antibody had not occurred (FIG. 31). These results demonstrated that 294th, 295th, and 296th Pro, Gln, and Pro in the CD14 are the regions critical in the binding to the F1024 antibody.

6-5) Preparation of Soluble Human CD14 Molecule (356 (CHO))

Soluble human CD14 molecule (356(CHO)) was prepared by using CHO cell by the procedure as described below.

(1) Construction of Expression Plasmid pM1656 described in WO02/42333 was digested with HindIII, and the fragment was blunt-ended with DNA Blunting Kit (TAKARA BIO INC.). It was digested with XbaI, and the fragment of about 1.4 kb was separated by electrophoresis and recovered. The expression plasmid pM1103 having mouse DHFR expression unit and EF1α promoter was digested with NotI, and the fragment was blunt-ended with DNA Blunting Kit (TAKARA BIO INC.). This fragment was subsequently digested with XbaI, and the fragment of about 8.0 kb was separated by electrophoresis and recovered. The fragment of about 1.4 kb from pM1656 was inserted for ligation in the fragment of about 8.0 kb, and the fragment was then used in transforming $E.\ coli$ JM109 to thereby produce a plasmid expressing 356(CHO).

(2) Establishment of 356(CHO) Expressing Transformant Strain

This expression plasmid was introduced in DHFR gene-deleted CHO cell to establish the transformant strain expressing the 356(CHO). More specifically, 50 µL of FuGENE6 (Roche Diagnostics K.K.) was mixed with 12.5 µg of plasmid DNA according to the protocol attached to the FuGENE6, and the mixture was added to CHO DXB11 cell that had been grown by using Ham's F-12 medium (Invitrogen Corporation) containing 10% inactivated FBS to semiconfluency in 150 cm² flask. After incubating overnight at 37° C. in the presence of 5% $CO_2$, the cells were separated and recovered on the next day by using trypsin, and the cells were re-inoculated in the 96-well plate by using α-MEM containing 10% inactivated dialyzed FBS (not containing ribonucleoside or deoxyribonucleoside) (Invitrogen Corporation) (hereinafter referred to as selective medium). The incubation was continued at 37° C. in the presence of 5% $CO_2$, and half of the medium was replaced in every 3 or 4 days with a fresh selective medium. After continuing the incubation for 3 to 4 weeks, the cells in the well where colony development was observed was transferred to a new plate, and the amount of the soluble CD14 produced in the culture supernatant was assayed by EIA which used CD14 antibody described in WO02/42333. Clone No. P3 exhibiting high amount of expression was established as the soluble CD14-expressing strain.

(3) Gene Amplification Using Methotrexate (MTX)

In order to enhance expression of 356(CHO), selective cultivation of P3 clone was conducted in a selective medium containing MTX to thereby increase its production amount by gene amplification. More specifically, P3 clone produced in Example 6-5)(2) was suspended in the selective medium containing 15 nM MTX, and the cells were inoculated in 10 cm culture dish. Half of the medium was replaced in every 3 or 4 days with a fresh selective medium containing 15 nM MTX, and the incubation was continued at 37° C. in the presence of 5% $CO_2$ until colony formation was observed. The resulting colony was subcultured in the plate and the amount of 356 (CHO) in the supernatant was confirmed by EIA to obtain clone P3-54 with an increase amount of expression.

(4) Production and Purification of 356(CHO)

The P3-54 clone produced in the above 6-5)(3) was incubated in a selective medium, and the 356(CHO) expressed in the supernatant was purified by repeating the procedure of Example 6-3).

Example 7

Modification of UTI Domain 2 of Antibody Fusion Protein (F1024S-D2)

7-1) Preparation of Modified Forms of UTI Domain 2 of F1024S-D2

For example, in the case of replacing 15th arginine in UTI domain with alanine (indicated as R15A), primers coding for about 10 amino acids at and near the part to which the mutation is to be introduced were designed and synthesized.

TABLE 7

| Primer Name | | Base Sequence | SEQ ID |
|---|---|---|---|
| Sense | D2-R15A-s | 5' GGC CCC TGC GCA GCC TTC ATC CAG CTC 3' | 187 |
| Anti-sense | D2-R15A-a | 5' GAT GAA GGC TGC GCA GGG GCC CCG GAC 3' | 188 |

Next, PCR was conducted again by using pTK-2355 for the template and using each of the primer pairs [IgG4-w and D2-R15A-s] and [pEF2ce-27 and D2-R15A-a]. The resulting amplification products were mixed and again subjected to PCR using primer pair [IgG4-w and pEF2ce-27] (Table 8).

The amplification product was cleaved with restriction enzymes BamHI and NotI, and subjected to agarose gel electrophoresis. After extracting the fragments, they were ligated by T4 DNA ligase to the vector part of the pTK-2355 which had been similarly cleaved with the BamHI and NotI to thereby construct plasmid (pTK-2730) which was capable of expressing the heavy chain of modified F1024S-D2 having the R15A mutation introduced therein. This plasmid was cotransfected in COS-1 cell with the light chain expression plasmid (pTK-2344) for expression of modified F1024S-D2 (R15A) in the culture supernatant. After confirming the expression in the culture supernatant, the expressed product was purified by Prosep-A column.

By using a similar procedure, 80 modified forms of UTI domain 2 of the F1024S-D2 shown in Table 9 were prepared, and they were confirmed to retain their ability to bind to CD14 antigen. The amino acid sequences of the modified UTI domain 2 shown in Table 9 are shown in FIGS. 32 to 35.

TABLE 8

| Primer Name | Base Sequence | SEQ ID |
|---|---|---|
| IgG4-w | 5' AATGTCTTCTCATGCTCCGTG 3' | 189 |
| pEF2ce-27 | 5' CATCAATGTATCTTATCATCTCT 3' | 190 |

TABLE 9

| Modified UTI domain 2 of F1024S-D2 | FIG. ID | SEQ ID |
|---|---|---|
| pTK-2730 (R15A) | 32 | 27 |
| pTK-2731 (R15C) | 32 | 28 |
| pTK-2732 (R15D) | 32 | 29 |
| pTK-2733 (R15E) | 32 | 30 |
| pTK-2734 (R15F) | 32 | 31 |
| pTK-2735 (R15G) | 32 | 32 |
| pTK-2736 (R15H) | 32 | 33 |
| pTK-2737 (R15I) | 32 | 34 |
| pTK-2738 (R15K) | 32 | 35 |
| pTK-2739 (R15L) | 32 | 36 |
| pTK-2740 (R15M) | 32 | 37 |
| pTK-2741 (R15N) | 32 | 38 |
| pTK-2742 (R15P) | 32 | 39 |
| pTK-2743 (R15Q) | 32 | 40 |
| pTK-2744 (R15S) | 32 | 41 |
| pTK-2745 (R15T) | 32 | 42 |
| pTK-2746 (R15V) | 32 | 43 |
| pTK-2747 (R15W) | 32 | 44 |
| pTK-2748 (R15Y) | 32 | 45 |
| pTK-2824 (R11S/R15I/Q19K/Y46D) | 32 | 46 |
| pTK-2825 (R11S/R15L/Q19K/Y46D) | 32 | 47 |
| pTK-2826 (R11S/R15T/Q19K/Y46D) | 32 | 48 |
| pTK-2827 (R11S/R15V/Q19K/Y46D) | 32 | 49 |
| pTK-2866 (R11S/R15T/Q19A/Y46D) | 33 | 50 |
| pTK-2867 (R11S/R15T/Q19C/Y46D) | 33 | 51 |
| pTK-2868 (R11S/R15T/Q19D/Y46D) | 33 | 52 |
| pTK-2869 (R11S/R15T/Q19E/Y46D) | 33 | 53 |
| pTK-2870 (R11S/R15T/Q19F/Y46D) | 33 | 54 |
| pTK-2871 (R11S/R15T/Q19G/Y46D) | 33 | 55 |
| pTK-2872 (R11S/R15T/Q19H/Y46D) | 33 | 56 |
| pTK-2873 (R11S/R15T/Q19I/Y46D) | 33 | 57 |
| pTK-2874 (R11S/R15T/Q19L/Y46D) | 33 | 58 |
| pTK-2875 (R11S/R15T/Q19M/Y46D) | 33 | 59 |
| pTK-2876 (R11S/R15T/Q19N/Y46D) | 33 | 60 |
| pTK-2877 (R11S/R15T/Q19P/Y46D) | 33 | 61 |
| pTK-2878 (R11S/R15T/Y46D) | 33 | 62 |
| pTK-2879 (R11S/R15T/Q19R/Y46D) | 33 | 63 |
| pTK-2880 (R11S/R15T/Q19S/Y46D) | 33 | 64 |

TABLE 10

| Modified UTI domain 2 of F1024S-D2 | FIG. ID | SEQ ID |
|---|---|---|
| pTK-2881 (R11S/R15T/Q19T/Y46D) | 33 | 65 |
| pTK-2882 (R11S/R15T/Q19V/Y46D) | 33 | 66 |
| pTK-2883 (R11S/R15T/Q19W/Y46D) | 33 | 67 |
| pTK-2884 (R11S/R15T/Q19Y/Y46D) | 33 | 68 |
| pTK-2889 (R11S/R15T/F17A/Y46D) | 34 | 69 |
| pTK-2890 (R11S/R15T/F17C/Y46D) | 34 | 70 |
| pTK-2891 (R11S/R15T/F17D/Y46D) | 34 | 71 |
| pTK-2892 (R11S/R15T/F17E/Y46D) | 34 | 72 |
| pTK-2893 (R11S/R15T/F17G/Y46D) | 34 | 73 |
| pTK-2894 (R11S/R15T/F17H/Y46D) | 34 | 74 |
| pTK-2895 (R11S/R15T/F17I/Y46D) | 34 | 75 |
| pTK-2896 (R11S/R15T/F17K/Y46D) | 34 | 76 |
| pTK-2897 (R11S/R15T/F17L/Y46D) | 34 | 77 |
| pTK-2898 (R11S/R15T/F17M/Y46D) | 34 | 78 |
| pTK-2899 (R11S/R15T/F17N/Y46D) | 34 | 79 |
| pTK-2900 (R11S/R15T/F17P/Y46D) | 34 | 80 |
| pTK-2901 (R11S/R15T/F17Q/Y46D) | 34 | 81 |
| pTK-2902 (R11S/R15T/F17R/Y46D) | 34 | 82 |
| pTK-2903 (R11S/R15T/F17S/Y46D) | 34 | 83 |
| pTK-2904 (R11S/R15T/F17T/Y46D) | 34 | 84 |
| pTK-2905 (R11S/R15T/F17V/Y46D) | 34 | 85 |
| pTK-2906 (R11S/R15T/F17W/Y46D) | 34 | 86 |

TABLE 10-continued

| Modified UTI domain 2 of F1024S-D2 | FIG. ID | SEQ ID |
|---|---|---|
| pTK-2907 (R11S/R15T/F17Y/Y46D) | 34 | 87 |
| pTK-2932 (R11A/R15T/Y46D) | 35 | 88 |
| pTK-2933 (R11C/R15T/Y46D) | 35 | 89 |
| pTK-2934 (R11D/R15T/Y46D) | 35 | 90 |
| pTK-2935 (R11E/R15T/Y46D) | 35 | 91 |
| pTK-2936 (R11F/R15T/Y46D) | 35 | 92 |
| pTK-2937 (R11G/R15T/Y46D) | 35 | 93 |
| pTK-2938 (R11H/R15T/Y46D) | 35 | 94 |
| pTK-2939 (R11I/R15T/Y46D) | 35 | 95 |
| pTK-2940 (R11K/R15T/Y46D) | 35 | 96 |
| pTK-2941 (R11L/R15T/Y46D) | 35 | 97 |
| pTK-2942 (R11M/R15T/Y46D) | 35 | 98 |
| pTK-2943 (R11N/R15T/Y46D) | 35 | 99 |
| pTK-2944 (R11P/R15T/Y46D) | 35 | 100 |
| pTK-2945 (R11Q/R15T/Y46D) | 35 | 101 |
| pTK-2946 (R15T/Y46D) | 35 | 102 |
| pTK-2947 (R11T/R15T/Y46D) | 35 | 103 |
| pTK-2948 (R11V/R15T/Y46D) | 35 | 104 |
| pTK-2949 (R11W/R15T/Y46D) | 35 | 105 |
| pTK-2950 (R11Y/R15T/Y46D) | 35 | 106 |

7-2) Elastase Inhibitory Activity of Modified F1024S-D2

The 80 modified forms of F1024S-D2 prepared as described above and F1024-D2(3) were evaluated for their elastase inhibitory activity by repeating the procedure of Example 3-2)(3) except that incubation was made for 5 minutes at 37° C. after the addition of the S-2484 solution. It was then confirmed that the fusion proteins (modified F1024S-D2) from the following expression plasmids exhibit elastase inhibitory activity equivalent to that of the F1024S-D2 (3).

pTK-2730(R15A), pTK-2737(R15I), pTK-2739(R15L), pTK-2740(R15M), pTK-2745(R15T), pTK-2746(R15V), pTK-2866(R11S/R15T/Q19A/Y46D), pTK-2867(R11S/R15T/Q19C/Y46D), pTK-2868(R11S/R15T/Q19D/Y46D), pTK-2869(R11S/R15T/Q19E/Y46D), pTK-2870(R11S/R15T/Q19F/Y46D), pTK-2871(R11S/R15T/Q19G/Y46D), pTK-2872(R11S/R15T/Q19H/Y46D), pTK-2873(R11S/R15T/Q19I/Y46D), pTK-2874(R11S/R15T/Q19L/Y46D), pTK-2875(R11S/R15T/Q19M/Y46D), pTK-2876(R11S/R15T/Q19N/Y46D), pTK-2877(R11S/R15T/Q19P/Y46D), pTK-2878(R11S/R15T/Y46D), pTK-2879(R11S/R15T/Q19R/Y46D), pTK-2880(R11S/R15T/Q19S/Y46D), pTK-2881(R11S/R15T/Q19T/Y46D), pTK-2882(R11S/R15T/Q19V/Y46D), pTK-2883(R11S/R15T/Q19W/Y46D), pTK-2884(R11S/R15T/Q19Y/Y46D), PTK-2889(R11S/R15T/F17A/Y46D), pTK-2890(R11S/R15T/F17C/Y46D), pTK-2891(R11S/R15T/F17D/Y46D), pTK-2892(R11S/R15T/F17E/Y46D), pTK-2932(R11A/R15T/Y46D), pTK-2893(R11S/R15T/F17G/Y46D), pTK-2933(R11C/R15T/Y46D), pTK-2895(R11S/R15T/F17H/Y46D), pTK-2934(R11D/R15T/Y46D), pTK-2896(R11S/R15T/F17I/Y46D), pTK-2935(R11E/R15T/Y46D), pTK-2897(R11S/R15T/F17L/Y46D), pTK-2936(R11F/R15T/Y46D), pTK-2898(R11S/R15T/F17M/Y46D), pTK-2937(R11G/R15T/Y46D), pTK-2899(R11S/R15T/F17N/Y46D), pTK-2938(R11H/R15T/Y46D), pTK-2900(R11S/R15T/F17P/Y46D), pTK-2939(R11I/R15T/Y46D), PTK-2901(R11S/R15T/F17Q/Y46D), pTK-2940(R11K/R15T/Y46D), pTK-2902(R11S/R15T/F17R/Y46D), pTK-2941(R11L/R15T/Y46D), pTK-2903(R11S/R15T/F17S/Y46D), pTK-2942(R11M/R15T/Y46D), pTK-2904(R11S/R15T/F17T/Y46D), pTK-2943(R11N/R15T/Y46D), pTK-2905(R11S/R15T/F17V/Y46D), pTK-2944(R11P/R15T/Y46D), pTK-2906(R11S/R15T/F17W/

Y46D), pTK-2945(R11Q/R15T/Y46D), PTK-2907(R11S/R15T/F17Y/Y46D), pTK-2946(R15T/Y46D), pTK-2947(R11T/R15T/Y46D), pTK-2948(R11V/R15T/Y46D), pTK-2949(R11W/R15T/Y46D), pTK-2950(R11Y/R15T/Y46D), pTK-2824(R11S/R15I/Q19K/Y46D), pTK-2825(R11S/R15L/Q19K/Y46D), pTK-2826(R11S/R15T/Q19K/Y46D), pTK-2827(R11S/R15V/Q19K/Y46D)

In particular, the fusion protein from the expression plasmid pTK-2826 (R11S/R15T/Q19K/Y46D) exhibited a 50% inhibitory concentration of 4.43 µg/mL in contrast to the 50% inhibitory concentration of F1024S-D2(3) which was 8.90 µg/mL, demonstrating the enhanced elastase inhibitory activity provided by the replacement of the 15th arginine of D2(3) portion with threonine.

FIG. 36 is a view explaining the total amino acid sequence of fusion protein F1024-D2(4) (R11S/R15T/Q19K/Y46D).

Example 8

Antibody Fusion Protein (F1024S-Thrombomodulin (TM) Functional Domain)

8-1) Construction of F1024S-TM Expression Plasmid

In order to produce fusion proteins of anti-CD14 antibody (F1024S) with various functional domains of TM, PCR was conducted by using HeLa genomic DNA for the template and the primer pair (TM-b and TM-g) to amplify full gene length of the human thrombomodulin (hereinafter referred to as TM), and the amplification product was cloned in pT7-Blue vector by TA cloning. After confirming the sequence, this plasmid was designated pT7-TM.

Next, PCR was conducted by using pT7-TM for the template and the primer pair (TMD123456 and TM domain 2-Not1 Bgl2), and after cleaving the thus amplified fragment with restriction enzymes BamHI and BglII and mixing with the preliminarily prepared vector (prepared by cleaving the pTK-2354 described in Example 1, Table 3 with restriction enzyme BamHI, followed by dephosphorylation), and the fragment was ligated using T4 DNA ligase to thereby produce plasmid pTK-2754 which was capable of expressing the heavy chain of fusion protein (designated F1024S-TM123456M) comprising F1024S having the region of 227th cysteine to 462nd cysteine ($Cys^{227}$ to $Cys^{462}$) in the amino acid sequence of TM added thereto. This procedure was repeated by using the primer pair (TMD123456 and TM domain 3-Not1 Bgl2) to prepare a plasmid pTK-2755 which was capable of expressing the heavy chain of fusion protein (designated F1024S-TM1234567M) having the region of 227th cysteine to 497th serine ($Cys^{227}$ to $Ser^{497}$) of the amino acid sequence added thereto; by using the primer pair (TMD23456 and TM domain 2-Not1 Bgl2) to prepare plasmid pTK-2756 which was capable of expressing the heavy chain of fusion protein (designated F1024S-TM23456M) having the region of 263rd threonine to 462nd cysteine ($Thr^{263}$ to $Cys^{462}$) of the amino acid sequence added thereto; by using the primer pair (TMD23456 and TM domain 3-Not1 Bgl2) to prepare plasmid pTK-2757 which was capable of expressing the heavy chain of fusion protein (designated F1024S-TM234567M) having the region of 263rd threonine to 497th serine ($Thr^{263}$ to $Ser^{497}$) added thereto; by using the primer pair (TMD3456 and TM domain 2-Not1 Bgl2) to prepare plasmid pTK-2758 which was capable of expressing the heavy chain of fusion protein (designated F1024S-TM3456M) having the region of 306th glutamine to 462nd cysteine ($Glu^{306}$ to $Cys^{462}$) added thereto; by using the primer pair (TMD3456 and TM domain 3-Not1 Bgl2) to prepare plasmid pTK-2759 which was capable of expressing the heavy chain of fusion protein (designated F1024S-TM34567M) having the region of 306th glutamine to 497th serine ($Glu^{306}$ to $Ser^{497}$) added thereto; by using the primer pair (TMD456 and TM domain 2-Not1 Bgl2) to prepare plasmid pTK-2760 which was capable of expressing the heavy chain of fusion protein (designated F1024S-TM456M) having the region of 345th valine to 462nd cysteine ($Val^{345}$ to $Cys^{462}$) added thereto; and by using the primer pair (TMD456 and TM domain 3-Not1 Bgl2) to prepare plasmid pTK-2761 which was capable of expressing the heavy chain of fusion protein (designated F1024S-TM4567M) having the region of 345th valine to 497th serine ($Val^{345}$ to $Ser^{497}$) added thereto.

In the meanwhile, in order to prevent decrease in the activity by the oxidation of TM, the mutant (M388L) in which 388th methionine ($Met^{388}$) in the amino acid sequence has been substituted with leucine (Leu) was also produced by the procedure as described below (Clarke, J H. et al., J. Biol. Chem. 268, 6309-6315 (1993)), namely, by conducting PCR using pT7-TM for the template and each of the primer pairs [TMD123456 and TM(M388L)-a] and [TM domain 2-Not1 Bgl2 and TM(M388L)-s], mixing each of the amplification products, and again conducting PCR using the primer pair (TMD123456 and TM domain 2-Not1 Bgl2). The gene fragment coding for the region of 227th cysteine to 462nd cysteine ($Cys^{227}$ to $Cys^{462}$) which included the M388L mutation was thereby amplified. As in the case described above, this fragment was cleaved with restriction enzymes BamHI and BglII and ligated to the vector using a ligase to construct plasmid pTK-2762 which was capable of expressing the heavy chain of fusion protein (designated F1024S-TM123456L) comprising the antibody molecule F1024S having added thereto the region of the TM from 227th cysteine to 462nd cysteine ($Cys^{227}$ to $Cys^{462}$) including the M388L mutation. The plasmids finally constructed were pTK-2763 which was capable of expressing the heavy chain of the fusion protein (F1024S-TM1234567L) including the mutation of M388L introduced in the pTK-2755; pTK-2764 which was capable of expressing the heavy chain of the fusion protein (designated F1024S-TM23456L) including the mutation of M388L introduced in the pTK-2756; pTK-2765 which was capable of expressing the heavy chain of the fusion protein (designated F1024S-TM234567L) including the mutation of M388L introduced in the pTK-2757; pTK-2766 which was capable of expressing the heavy chain of the fusion protein (designated F1024S-TM3456L) including the mutation of M388L introduced in the pTK-2758; pTK-2767 which was capable of expressing the heavy chain of the fusion protein (designated F1024S-TM34567L) including the mutation of M388L introduced in the pTK-2759; and pTK-2768 which was capable of expressing the heavy chain of the fusion protein (designated F1024S-TM456L) including the mutation of M388L introduced in the pTK-2760; and pTK-2769 which was capable of expressing the heavy chain of the fusion protein (designated F1024S-TM4567L) including the mutation of M388L introduced in the pTK-2761.

The sequences of the primers used are shown in Table 10, and the fusion proteins of the anti-CD14 antibody (F1024S) and the expression plasmids are shown in Table 11.

The amino acid sequences of the fusion proteins of the anti-CD14 antibody (F1024S) are shown in FIGS. 37 to 44 and Sequence Listing.

Figure 45:
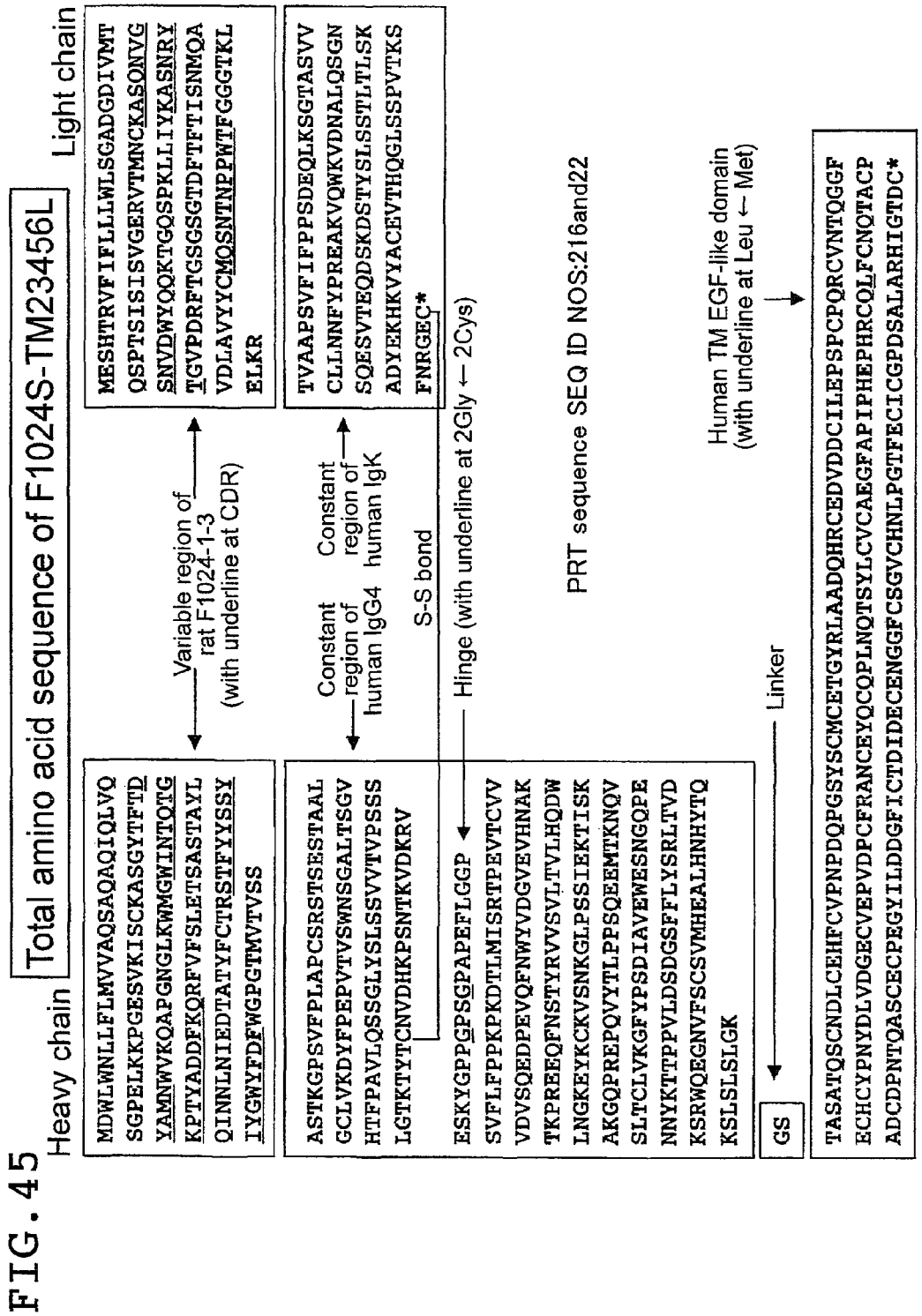
FIG. 45 is a view showing the structure of the total amino acid sequences (SEQ ID NOS: 216 and 22) of fusion protein F1024S-TM23456L.

FIG. 45 is a view explaining the total amino acid sequence of fusion protein F1024-TM23456L.

TABLE 10

| Primer Name | Base Sequence | SEQ ID |
|---|---|---|
| TM-b | 5' TTTCCCCGGCGCCTGCACGC 3' | 191 |
| TM-g | 5' TCCTGGACGGAGGCCGCTCAG 3' | 192 |
| TMD123456 | 5' GGGATCCTCCAGCGTGGAGAACGGCGGCT 3' | 193 |
| TMD23456 | 5' GGGATCCACCGCATCCGCGACGCAGTCCT 3' | 194 |
| TMD3456 | 5' GGGATCCGAGGACGTGGATGACTGCATAC 3' | 195 |
| TMD456 | 5' GGGATCCGTGGAGCCCGTGGACCCGTGCT 3' | 196 |
| TMdomain2-Not1Bgl2 | 5' GGAGATCTGCGGCCGCTCAACAGTCGGTGCCAATG 3' | 197 |
| TMdomain3-Not1Bgl2 | 5' GGAGATCTGCGGCCGCTCACGAATGCACGAGCCCC 3' | 198 |
| TM (M388L)-s | 5' CCGCACAGGTGCCAGCTGTTTTGCAACCAGACT 3' | 199 |
| TM (M388L)-a | 5' AGTCTGGTTGCAAAACAGCTGGCACCTGTGCGG 3' | 200 |

TABLE 11

| F1024S Fusion Protein Name | Plasmid Name | FIG. No. | SEQ ID |
|---|---|---|---|
| F1024S-TM123456M | pTK-2754 | 37 | 107 |
| F1024S-TM123456L | pTK-2762 | 37 | 108 |
| F1024S-TM1234567M | pTK-2755 | 38 | 109 |
| F1024S-TM1234567L | pTK-2763 | 38 | 110 |
| F1024S-TM23456M | pTK-2756 | 39 | 111 |
| F1024S-TM23456L | pTK-2764 | 39 | 112 |
| F1024S-TM234567M | pTK-2757 | 40 | 113 |
| F1024S-TM234567L | pTK-2765 | 40 | 114 |
| F1024S-TM3456M | pTK-2758 | 41 | 115 |
| F1024S-TM3456L | pTK-2766 | 41 | 116 |
| F1024S-TM34567M | pTK-2759 | 42 | 117 |
| F1024S-TM34567L | pTK-2767 | 42 | 118 |
| F1024S-TM456M | pTK-2760 | 43 | 119 |
| F1024S-TM456L | pTK-2768 | 43 | 120 |
| F1024S-TM4567M | pTK-2761 | 44 | 121 |
| F1024S-TM4567L | pTK-2769 | 44 | 122 |

These plasmids were cotransfected in COS-1 cell with the light chain expression plasmid (pTK-2344) to express F1024S-TM in the culture supernatant. This supernatant was purified using Prosep-A column for use in the subsequent assay.

The binding test using EIA confirmed that the fusion proteins had the binding activity for the CD14 antigen.

8-2) Measurement of Thrombomodulin (TM) Activity

TM activity was measured by using action of the thrombomodulin (TM) forming a complex with thrombin in blood to activate protein C which is the blood coagulation inhibitory factor for the index of the activity. The measurement was conducted as described below.

Figure 46:
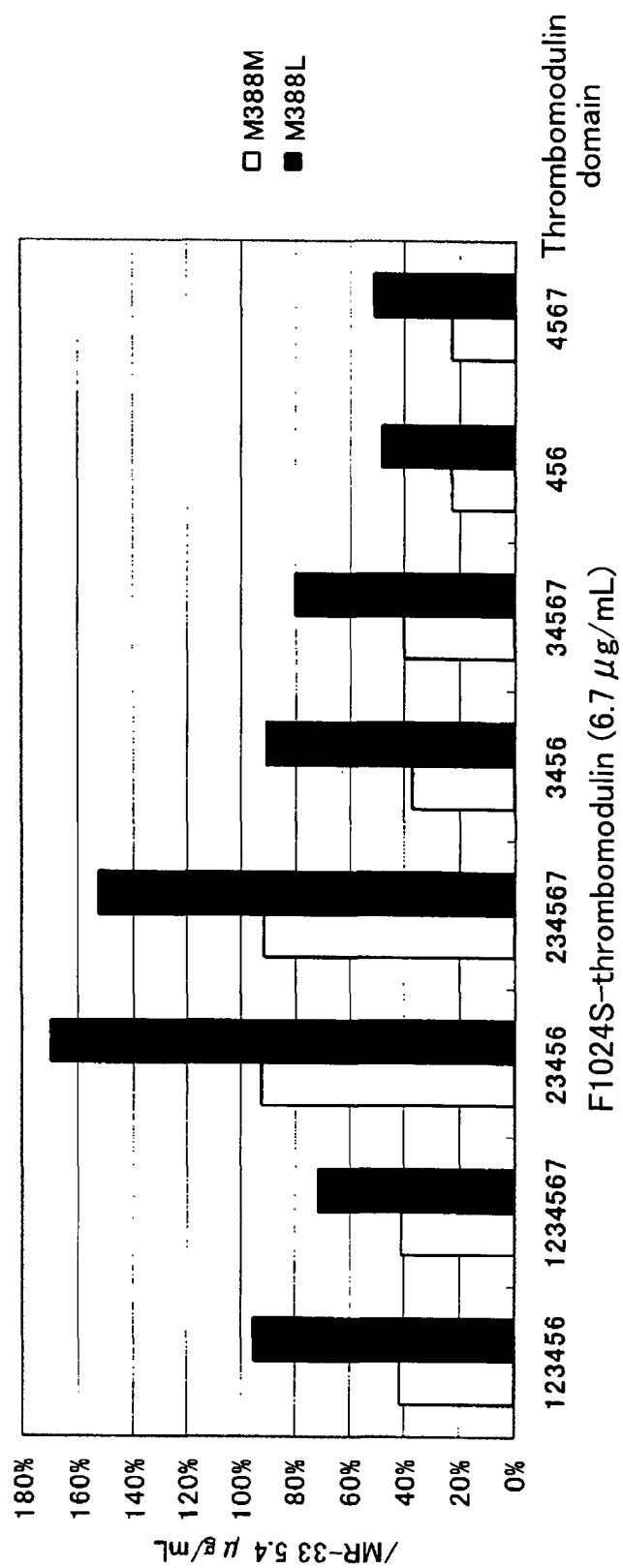
FIG. 46 is a view showing thrombomodulin activity of modified functional domains of TM in fusion protein F1024S-TM.

The reaction for the activity measurement was conducted in a multitube. The fusion protein was diluted with 25 mmol/L Tris-HCl buffer solution containing 0.14 mol/L sodium chloride, 10 mmol/L calcium chloride, and 1 mg/mL bovine serum albumin (pH 7.4). To 40 µL of the specimen, 10 µL of 6 U/mL human thrombin (SIGMA) was added and preincubation was conducted at 37° C. for 10 minutes. Next, 10 µL of 24 µg/mL protein C (American Diagnostica Inc.) was added, and the mixture was incubated at 37° C. for 5 minutes. 40 µL of the mixture of 0.15 U/mL antithrombin III (Green Cross Corporation) and 15 U/mL heparin (Mochida Pharmaceutical Co., Ltd.) was added and the mixture was incubated at 37° C. for 10 minutes. 100 µL of 3.2 mmol/L activated protein C substrate S-2366 (Daiichi Pure Chemicals Co., Ltd.) was added, and after incubating the mixture at 37° C. for 10 minutes, the reaction was terminated by adding 200 µL of 50% acetic acid. 300 µL of the reaction solution was transferred to 96-well flat plate, and absorbance at 405 nm was measured using a plate reader (Molecular Devices Corporation). Human thrombomodulin MR-33 (Mochida Pharmaceutical Co., Ltd.) was used for the positive control. It was then found that all F1024S-TM fusion proteins have the activity of promoting the protein C activation, and F1024S-TM23456M, F1024S-TM234567M, F1024S-TM23456L, and F1024S-TM234567L have high activity for promoting the protein C activation. The M388L mutants also exhibited relatively high activity (FIG. 46).

Example 9

Alteration of linker portion in antibody fusion protein (F1024S-SLPI) 9-1) Construction of expression plasmid Linker SG-4-s (5' pGATCTGGAGGTGGAG 3', SEQ ID NO: 201, with phosphorylated 5' terminal) and linker SG-4-a (5' pGATCCTCCACCTCCA 3', SEQ ID NO: 202, with phosphorylated 5' terminal) were mixed and, and the mixture was incubated at 96.degree ° C. for 2 minutes. The temperature was gradually reduced to room temperature for annealing. An adequate amount of the mixture was mixed with the preliminarily prepared vector fragment (which had been prepared by cleaving the pT7-SLPI(D2) described in Example 1 with restriction enzyme BglII, dephosphorylating, subjecting to agarose gel electrophoresis, and extracting the fragment from the gel), and the fragment was ligated with T4 DNA ligase. By this procedure, plasmid pTK-2729 comprising SLPI(D2) having 1 copy of GGGGS linker, SEQ ID NO: 203, added thereto was constructed. This pTK-2729 was cleaved with restriction enzyme BglII, and by repeating the procedure as described above, pTK-2749 comprising SLPI(D2) having 2 copies of GGGGS, SEQ ID NO: 203, linker added thereto, and pTK-2750 comprising SLPI(D2) having 3 copies of GGGGS, SEQ ID NO: 203, linker added thereto were constructed.

Next, pTK-2729, pTK-2749, and pTK-2750 were cleaved with restriction enzymes BglII and NotI to prepare gene fragments coding for the part of the linker plus SLPI(D2) (The resulting fragments are respectively designated fragment 1, fragment 2, and fragment 3). As in the case of the construction of the pTK-2396 in Example 1 (Table 3), the gene fragments A and D were ligated with each fragment by T4 DNA ligase to construct plasmids expressing heavy chain of the F1024S-SLPI(D2) with modified linker respectively having linkers GSGGGGS, SEQ ID NO: 204, GSGGGGSGGGGS, SEQ ID NO: 205, and GSGGGGSGGGGSGGGGS, SEQ ID NO: 206, between the antibody molecule and the SLPI(D2) (respectively designated pTK-2751, pTK-2752, and pTK-2753).

These plasmids were cotransfected in COS-1 cell with the light chain expression plasmid (pTK-2344) to express F1024S-SLPI(D2) with modified linker in the culture supernatant, and the supernatant was purified by Prosep-A column.

All purification products were confirmed to have the binding activity for the CD14 antigen.

Tables 12 and 13 show SEQ ID NOS of the primers and the linkers.

TABLE 12

| Primer Name | Base Sequence | SEQ ID |
|---|---|---|
| LinkerSG-4-s | 5' pGATCTGGAGGTGGAG 3' | 201 |
| LinkerSG-4-a | 5' pGATCCTCCACCTCCA 3' | 202 |

TABLE 13

| Linker Base Sequence | SEQ ID |
|---|---|
| GGGGS | 203 |
| GSGGGGS | 204 |
| GSGGGGSGGGGS | 205 |
| GSGGGGSGGGGSGGGGS | 206 |

9-2) Elastase Inhibitory Activity of F1024S-SLPI

1024D-SLPI(D1D2), F1024D-SLPI(D2), F1024S-SLPI (D1D2), and F1024S-SLPI(D2), and furthermore, the fusion protein of SLPI(D2) having 1, 2, or 3 copies of GGGGS linker added thereto were evaluated for their elastase inhibitory activity by repeating the procedure of Example 3-2)(3) except that the incubation at 37° C. after the addition of the S-2484 solution was conducted for 5 minutes.

The control was prepared by mixing 10 µL of the elastase solution to 80 µL of the diluting solution, incubating at 37° C. for 3 minutes, adding 10 µL of the S-2484 solution, and incubating at 37° C. for exactly 5 minutes, and thereafter adding 50 µL of 20% acetic acid solution. The 50% inhibitory concentrations of F1024S-SLPI(D1D2) and F1024S-SLPI (D2) were 22.5 µg/mL and 26.9 µg/mL, respectively, and the 50% inhibitory concentrations of the fusion proteins of SLPI (D2) having 1, 2, and 3 copies of GGGGS linker added thereto were 11.6 µg/mL, 11.9 µg/mL, and 11.6 µg/mL, respectively.

Example 10

Preparation of Humanized Antibody (hF1024S-D2(3))

Figure 47:
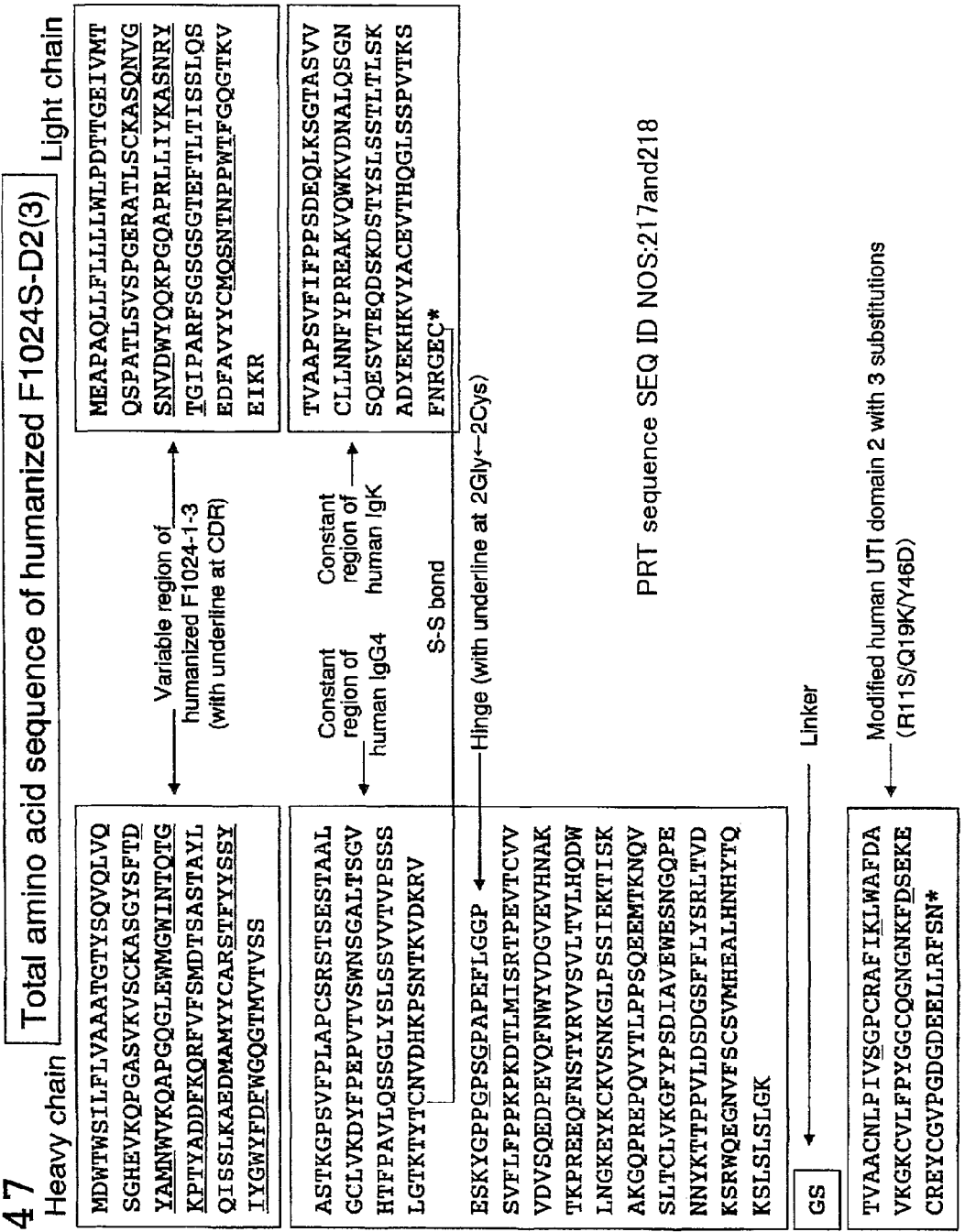
FIG. 47 is a view showing the structure of the total amino acid sequences (SEQ ID NOS: 217 and 218) of humanized F1024S-D2(3).

The amino acid sequences of the heavy chain and the light chain variable regions of the rat antibody F1024-1-3 were searched on the data base, and these sequences were respectively determined to have high homology with human antibodies IGHV7-81 (BC032733) and HUMIGRFFM (L48242). Accordingly, humanization was conducted by transplanting the 3 complementarity determining regions (CDRs) of both chains of the antibody F1024 to each framework (FR) of (1) IGHV7-81 and HUMIGRFFM (hereinafter referred to as RF) or (2) NEW, Eu, and REI which have been thoroughly analyzed by crystal structure analysis (see FIG. 47). The nucleotide sequence was designed based on each amino acid sequence (FIG. 48), and all of the 6 gene fragments were prepared by dividing the nucleotide sequence into several parts and synthesizing them. Each fragment was replaced with the variable region of the heavy chain pTK-2370 and the light chain pTK-2344 to construct the expression plasmid (heavy chain: pTK-2887 for IGHV7-81-HA, pTK-2679 for NEW-HA, and pTK-2685 for Eu-HA; light chain: pTK-2955 for RF-KA, pTK-2680 for REI-KA, and pTK-2681 for Eu-KA). COS-1 cell was cotransfected with various combinations of such plasmids and the chimeric antibody expression plasmids (pTK-2370 for heavy chain and pTK-2344 for light chain), and the antibodies secreted in the supernatant were compared for their binding activity to GPVI antigen.

With regard to the heavy chain, significant decrease in the amount of the expression by the humanization was found in all cases. In view of such situation, various mutations were introduced in the FR, and the results were examined. In the meanwhile, expression and binding activity were confirmed for the light chain.

For three humanized heavy chain expression plasmids, the sequences maintaining the expression and the binding activity (pTK-2909 for IGHV7-81-HC, pTK-3007 for IGHV7-81-HX, pTK-2803 for NEW-HB, and pTK-2811 for Eu-HB) could be finally obtained by constructing a large number of mutants in which part of the human-specific sequence in FR was returned to the sequence from the rat and precisely analyzing such constructs (FIG. 49 shows the amino acid sequence).

Finally, combinations of the humanized heavy chain and the humanized light chain were examined, and the combination exhibiting the highest expression and binding activity was the combination of IGHV7-81-HX with RF-KA or other light chain.

The antibody portion of other antibody fusion proteins are humanized by a similar procedure.

Example 11

Production of Strain which is Capable of Stably Producing Antibody Fusion Protein F1024S-D2(3) at High Yield 1-1 Production of Plasmid (pTK-2671) which is Capable of Stably Expressing F1024S-D2(3) at High Yield PCR was conducted by using a transient expression plasmid (pTK-2370, described in Example 1) for expressing heavy chain of F1024S-D2(3) for the template and using the primer pair (F1024H-kozak, IgG4-1) shown in Table 14. The amplification product was cleaved with restriction enzymes EcoRI and NheI, and after the agarose gel electrophoresis, the gene fragment (fragment U) comprising the heavy chain variable region of the antibody F1024 was extracted. SEQ ID NOS of the primers used are shown in Table 14.

TABLE 14

| Primer Name | Base Sequence | SEQ ID |
|---|---|---|
| F1024H-kozak | 5' GGGGAATTCGCCGCCACCATGGATTGGT TGTGGAA 3' | 207 |
| IgG4-1 | 5' GCTGTGCTCTCGGAGGTGCT 3' | 208 | pTK-2370 was cleaved with restriction enzymes NheI and Sse8387I, and after agarose gel electrophoresis, gene fragment (fragment V) comprising the heavy chain constant region of the F1024S-D2(3), the gene sequence coding for the D2(3), and SV40 polyA signal was extracted. Plasmid (pTK-2344 described in Example 1) expressing the light chain of F1024 was cleaved with restriction enzymes BsiWI and NcoI, and after agarose gel electrophoresis, the gene fragment (fragment W) comprising the light chain variable region of the antibody F1024 was extracted.

Plasmid (pTK-2577) comprising EF promoter, human light chain constant region, and mouse DHFR expression unit (comprising SV40 promoter (not including enhancer region)

as promoter, and polyA signal from SV40) was cleaved with restriction enzymes BsiWI and EcoRI, and after agarose gel electrophoresis, the vector fragment (fragment X) of interest was extracted. In the meanwhile, this plasmid was also cleaved with Sse8387I and NcoI, and after the agarose gel electrophoresis, gene fragment (fragment Y) comprising EF promoter region was extracted.

The gene fragments U to Y were ligated into one fragment using T4 DNA ligase (TAKARA BIO INC.) to construct plasmid (pTK-2671) for stable expression which was capable of simultaneously expressing the heavy chain and the light chain of the F1024S-D2(3), and which contained mouse DHFR expression unit serving as a marker in the cell into which the plasmid was to be introduced.

By using a similar procedure, plasmids capable of stable expression at a high yield are also constructed for other antibody fusion proteins.

Example 12

Evaluation of Efficacy (In Vitro)

Figure 50:
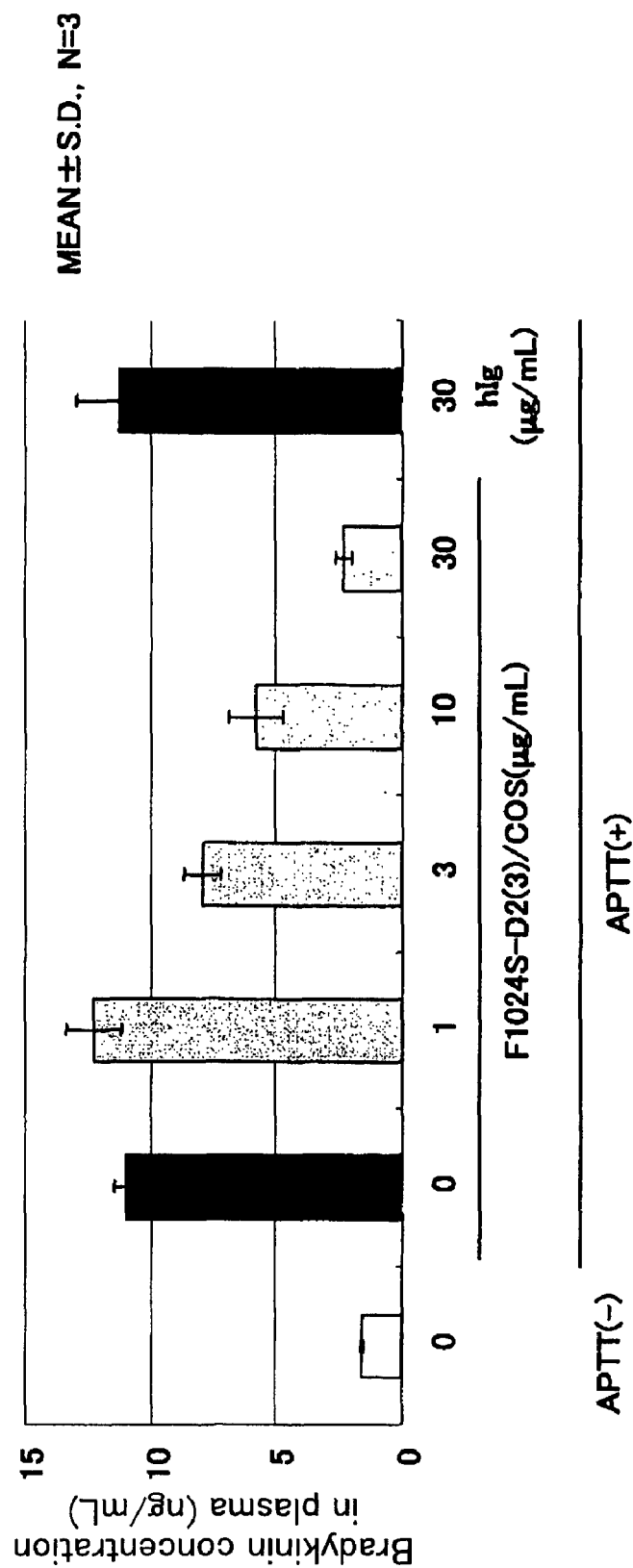
FIG. 50 is a view showing the inhibition of bradykinin production in human plasma induced by APTT reagent.
Figure 51:
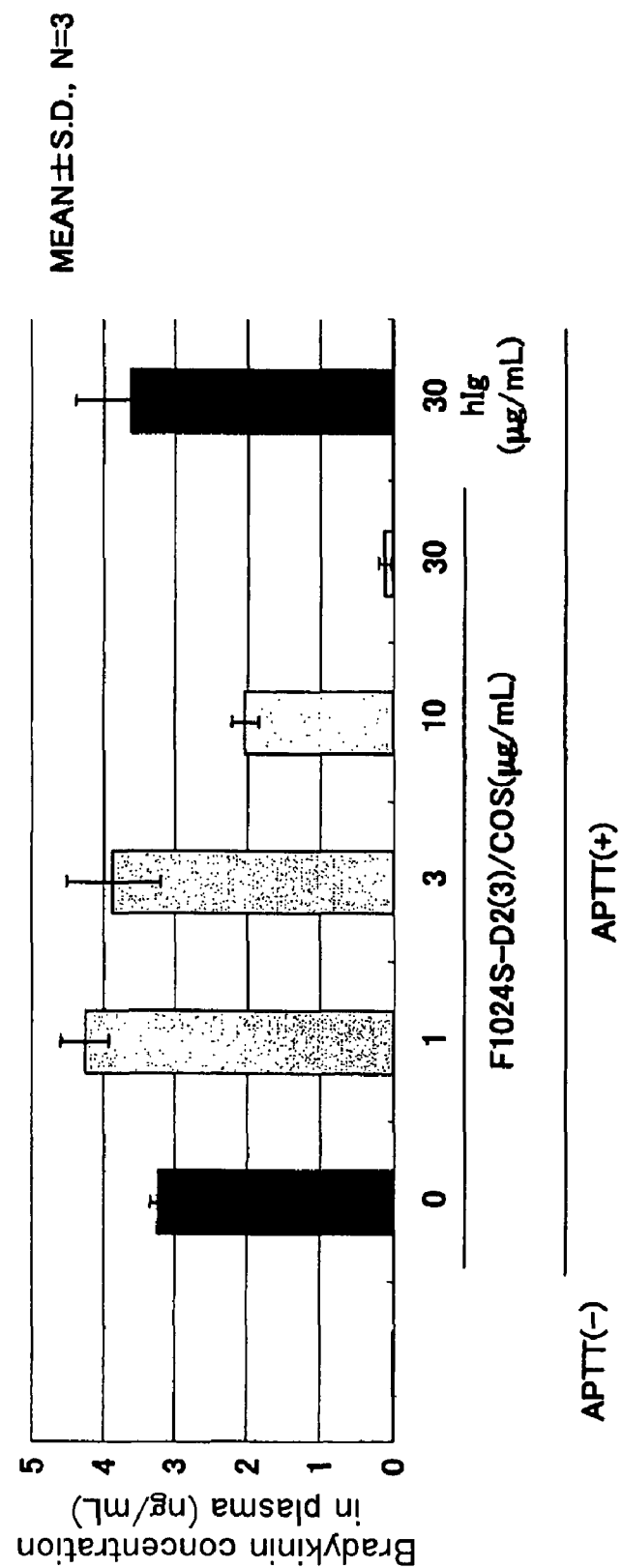
FIG. 51 is a view showing the inhibition of bradykinin production in rabbit plasma induced by APTT reagent.

12-1) Confirmation of Inhibitory Action for Bradykinin Production (1) Confirmation of Inhibitory Action for Bradykinin Production in Human and Rabbit Plasmas Induced by APTT Reagent The normal human plasma used was Dade Ci-Trol Level 1 (DADE BEHRING INC.). The rabbit plasma was prepared by collecting blood from auricular artery of male rabbit (New Zealand white, Kitayama Labes Co., Ltd.) using a syringe containing 1/10 volume of 3.8% sodium citrate (sodium citrate for measuring erythrocyte sedimentation rate, Iwaki Seiyaku Co., Ltd.), and centrifuging the blood for 10 minutes at 4° C. and 3000 rpm (05PR-22, Hitachi). After adding o-phenanthroline solution to 80 µL of human or rabbit plasma, F1024S-D2(3) solution which had been serially diluted with the diluting solution was added to final concentrations of 0, 1, 3, 10, and 30 µg/mL, or human immunoglobulin (hIg) was added to a final concentration of 30 µg/mL. After stirring, the plasma was incubated at 37° C. for 10 minutes. 80 µL of APTT reagent diluted with Milli-Q Water was added, and the plasma was further incubated at 37° C. for 10 minutes. 100 µL of the plasma was collected, and 20 µL of deproteinizing agent attached to the bradykinin measurement kit (Markit-M bradykinin, Dainippon Pharmaceutical Co., Ltd.) was added, and this plasma was centrifuged at 4° C. and 10000 rpm (MRX-150, TOMY) for 10 minutes. The resulting supernatant was measured for bradykinin concentration by using the bradykinin measurement kit. It was then found that F1024S-D2(3) inhibits bradykinin production in human and rabbit plasmas induced by APTT reagent in a concentration dependent manner (FIGS. 50 and 51).

Figure 52:
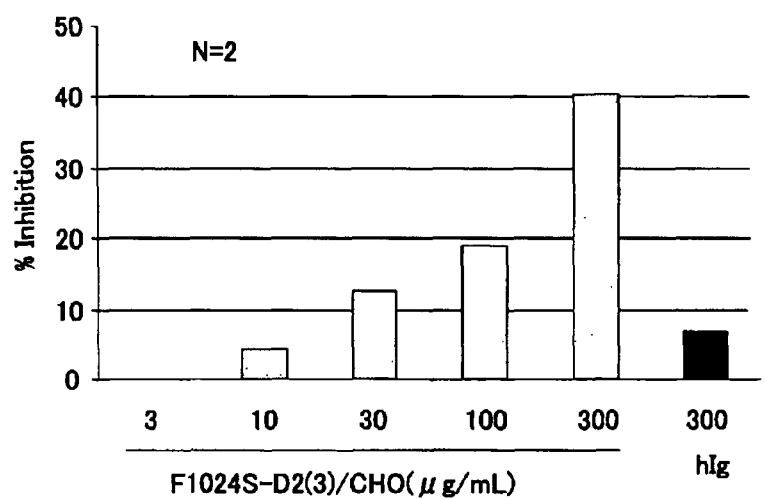
FIG. 52 is a view showing the inhibition of thrombin production in human plasma induced by thromboplastin.
Figure 53:
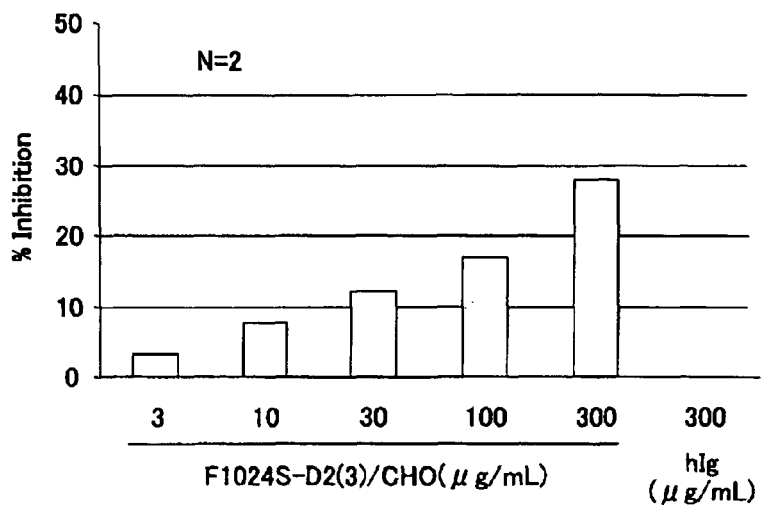
FIG. 53 is a view showing the inhibition of thrombin production in rabbit plasma induced by thromboplastin.

12-2) Confirmation of Coagulation Inhibitory Action (1) Confirmation of Inhibitory Action for (Factor XI Dependent) Thrombin Production in Human Plasma Induced by Thromboplastin To each of the human plasma containing human platelet at 3×10$^5$/µL and the rabbit plasma containing rabbit platelet at 3×10$^5$/µL, the F1024S-D2(3) solution was added to final concentrations of 0, 3, 10, 30, 100, and 300 µg/mL, or human immunoglobulin (hIg) was added to a final concentration of 300 µg/mL. The plasma was then pre-incubated at 37° C. for 10 minutes. Incubation was started at 37° C. after adding a solution of thromboplastin (Simplastin Exel, BIOMERIEUX, INC.) diluted 8000 folds with 25 mmol/L CaCl$_2$ solution. 5 µL of the incubated solution was collected before the addition of the thromboplastin solution and with time after the addition of the thromboplastin solution, and added to a mixture of 100 µL of Buffer B (50 mmol/L Tris-HCl buffer solution (pH 7.9) containing 0.5 mg/mL BSA, 0.1 mol/L NaCl, and 20 mmol/L EDTA) and 25 µL of 2 mmol/L S-2238, and the mixture was incubated at 37° C. for 10 minutes. After adding 100 µL of 50 vol % acetic acid, the reaction solution was added to a 96-well plate at 200 µL/well, and the absorbance at 405 nm was measured by a plate reader (Thermomax microplate reader, Molecular Devices Corporation). It was then found that F1024S-D2(3) inhibits thrombin production in human and rabbit plasmas induced by thromboplastin in a concentration dependent manner (FIGS. 52 to 53).

12-3) Confirmation of Coagulation Inhibitory Action (1) Confirmation of Human APTT Extending Action APTT extending actions of F1024S-TM23456M, F1024S-TM23456L, F1024S-TM234567M and F1024S-TM234567L prepared in Example 8 were respectively evaluated at final concentrations of 2.00, 2.00, 1.95, and 2.29 µg/mL by the procedure similar to that of Example 3-3) (1) using human normal human plasma. As a consequence, APTT was extended by 26, 32, 42, and 57% by the 4 fusion proteins, respectively.

Example 13

Evaluation of Effectiveness in Ex Vivo Test 13-1) Confirmation of Antiinflammatory Action of F1024S-D2(3)

Figure 54:
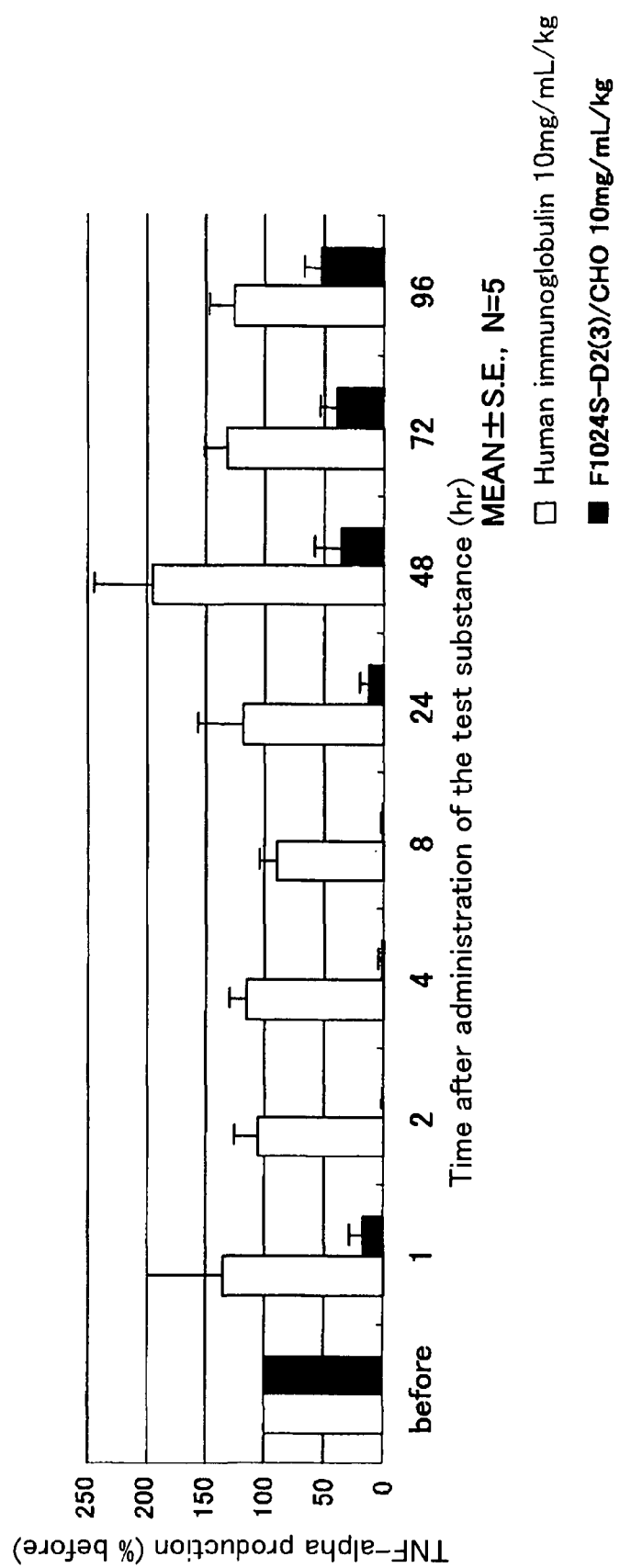
FIG. 54 is a view showing time course of the inhibitory action of F1024S-D2(3) on the LPS-induced TNF-α production in rabbit whole blood after the administration of the F1024S-D2(3).

10 mg/kg of F1024S-D2(3) was administered to rabbit (New Zealand white, 1.8 to 2.6 kg, Kitayama Labes Co., Ltd.) from auricular vein, and the blood was collected with time with addition of citric acid. LPS (WE. coli 055:B5, DIFCO) was added to the collected blood to a final concentration of 1 ng/mL, and the blood was incubated at 37° C. for 4 hours. The blood was centrifuged at 4° C. and 10000 rpm (MRX-150, TOMY) for 10 minutes, and the resulting plasma was measured for its TNF-α concentration by ELISA using anti-rabbit TNF-α antibody. It was then found that production of TNF-α was suppressed in the LPS-stimulated blood until 24 hours after the administration of the F1024S-D2(3) (FIG. 54).

13-2) Confirmation of anticoagulant action of F1024S-D2 (3)

Figure 55:
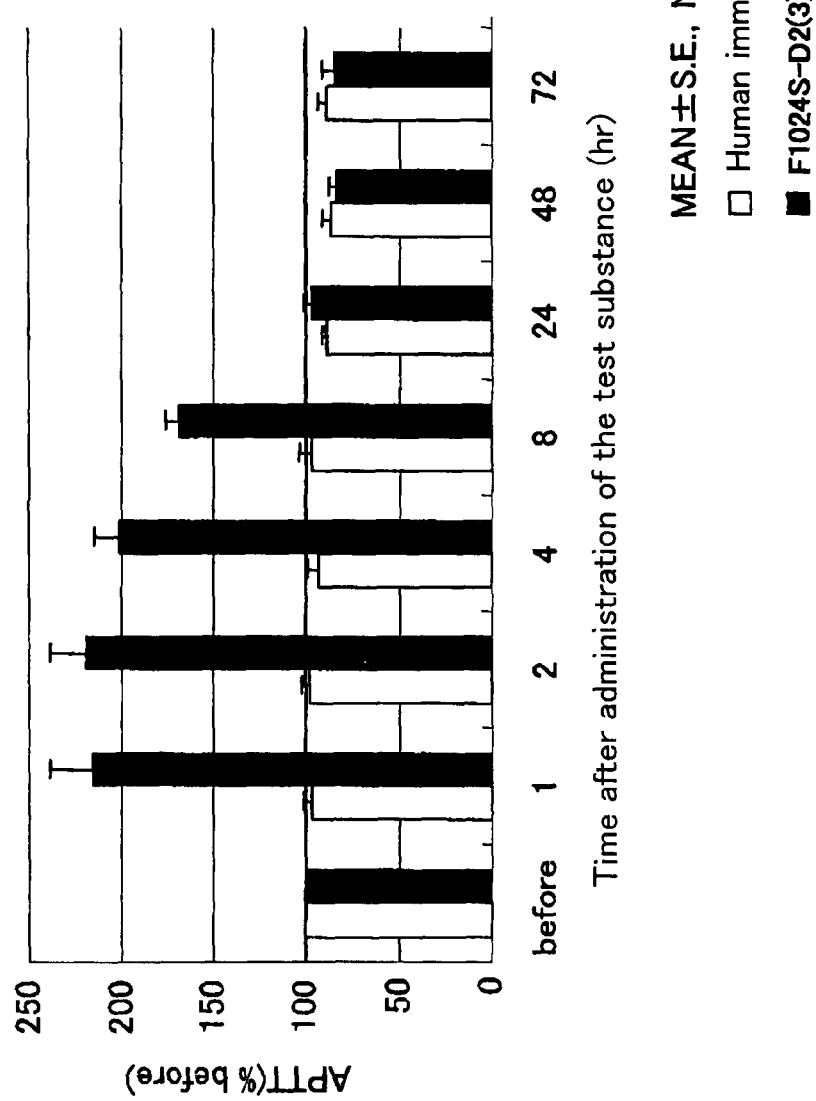
FIG. 55 is a view showing time course of APTT after administration of F1024S-D2(3) to the rabbit.

The plasma obtained by centrifugation immediately after the blood collection in Example 13-1) was used for the measurement of activated partial thromboplastin time (APTT). The measurement of the APTT was conducted by repeating the procedure of Example 3-3). Extension of APTT was found until 8 hours after the administration of the F1024S-D2(3) (FIG. 55).

Example 14

Evaluation of In Vivo Effectiveness 14-1) Rabbit CLP (Cecal Ligation and Puncture) Model Rabbit CLP (cecal ligation and puncture) peritonitis model was produced, and improvement in the survival rate and coagulation parameter after the administration of the F1024S-D2(3) was confirmed.

The rabbit peritonitis model by cecal ligation and puncture was produced by the method of Keith, A. et al. (Journal of Surgical Research, 29: 189, 1980) by puncturing cecum of a rabbit (New Zealand white, 1.8 to 2.6 kg, Kitayama Labes Co., Ltd.) under anesthesia, and sprinkling the content of the cecum in the abdominal cavity. After 2 hours, 10 mg/kg of F1024S-D2(3) was administered to auricular vein, and after this, F1024S-D2(3) was administered twice a day for 3 days. The control group was administered with human immunoglobulin (hIg) instead of the F1024S-D2(3). The survival was monitored and recorded for 72 hours to depict Kaplan-Meier survival curve. At 8 hours after the cecal ligation and puncture, blood was collected with addition of citric acid, and D dimer was measured as coagulation parameter of the plasma. It was then found that both the survival rate (FIG. 56) and the D dimer (FIG. 57) were improved in the group administered with the F1024S-D2(3) compared to the control group.

Figure 56:
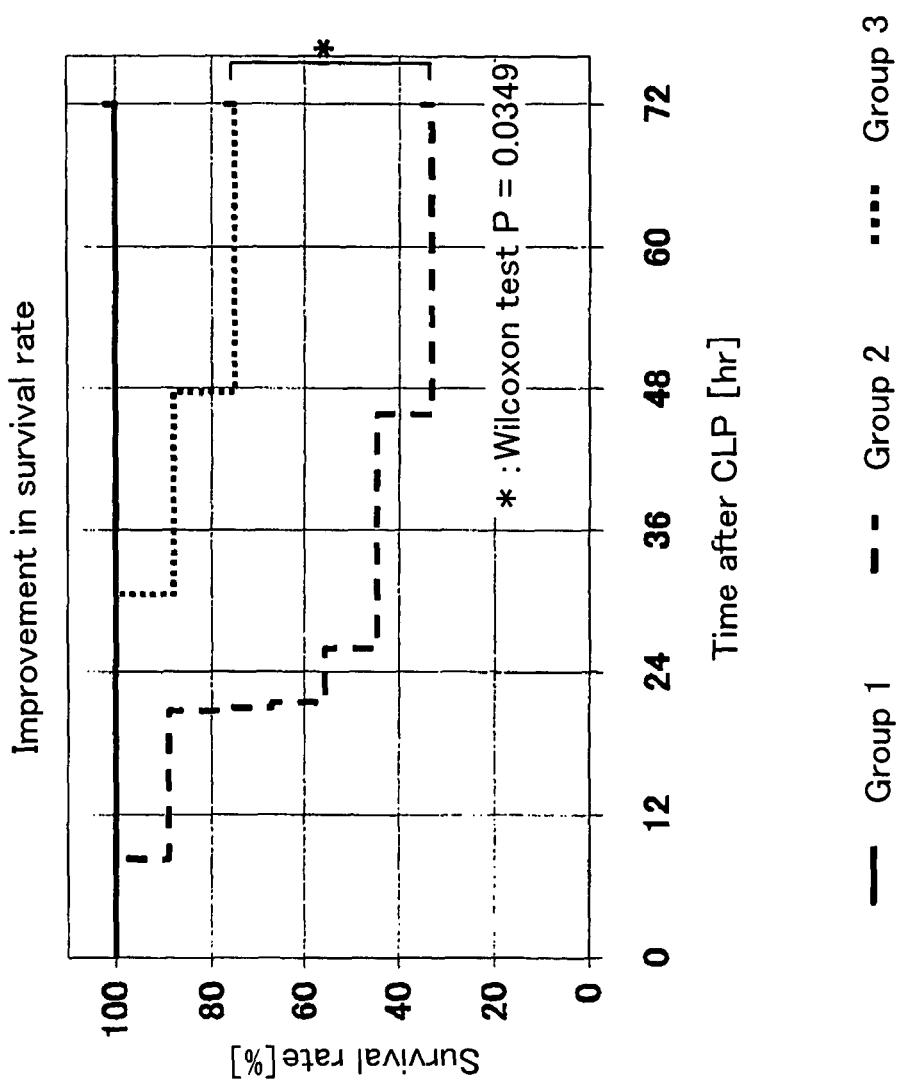
FIG. 56 is a view showing time course of survival rate after administration of F1024S-D2(3) to rabbit cecal ligation and puncture (CLP) model.
Figure 57:
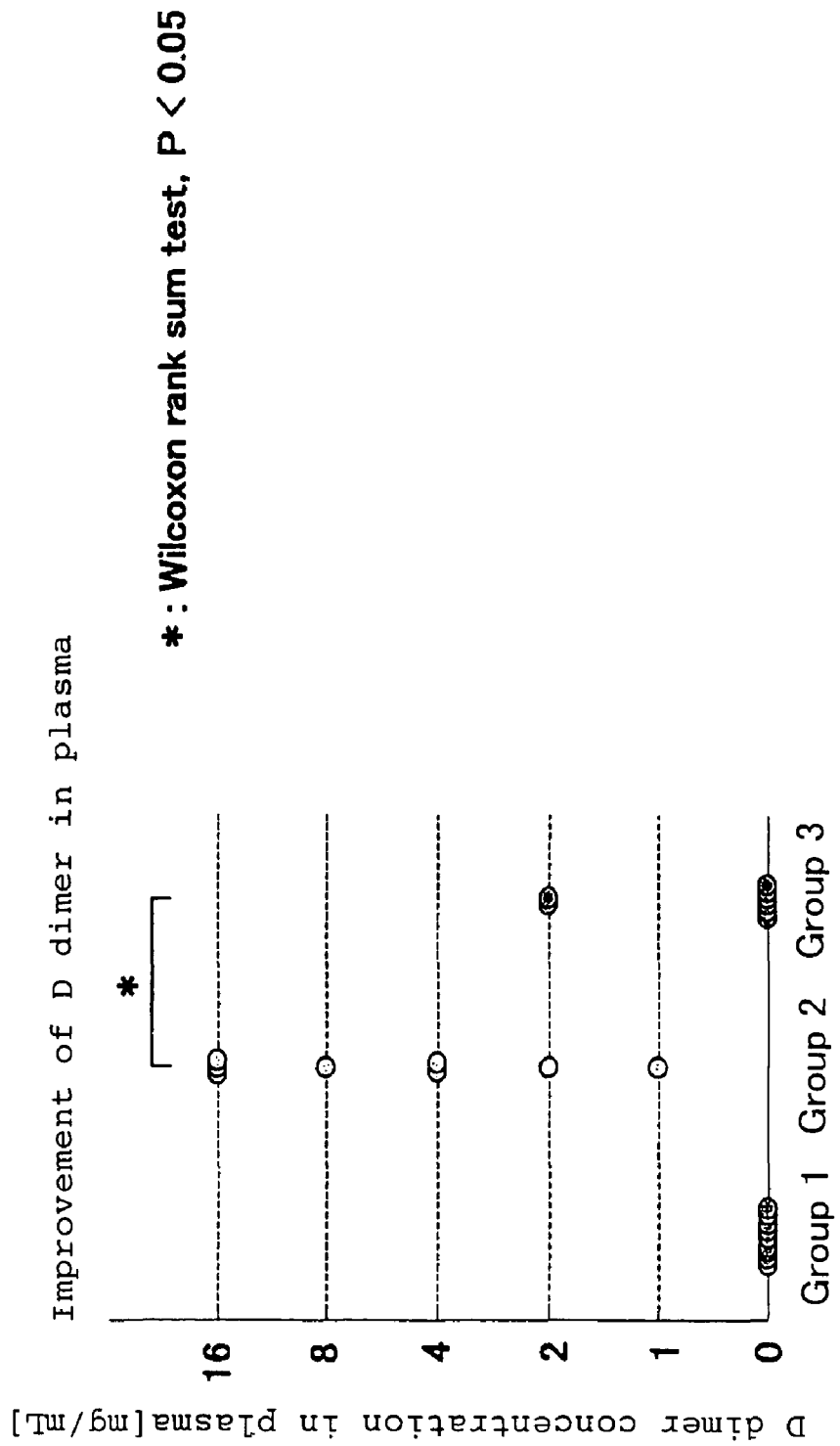
FIG. 57 is a view showing D dimer levels in plasma after administration of F1024S-D2(3) to rabbit cecal ligation and puncture (CLP) model.

The overview of the control group of FIGS. 56 and 57 is shown in Table 15.

TABLE 15

| Group | Treatment | Antibiotic | Test substance | Dose | Number of cases |
|---|---|---|---|---|---|
| 1 | Sham | 60 mg/kg | Human Immuno-globulin preparation | 10 mg/kg, twice, 3 days | 9 |
| 2 | Cecal ligation and puncture peritonitis | | | | 9 |
| 3 | | | FR1024S-D2(3) | | 8 |

Example 15

A polypeptide, Y46E, having an amino acid sequence derived from the formula 1 amino acid sequence by substituting Glu for the position 42 Tyr of the formula 1 sequence, counting from its N-terminus, was prepared as described in Example 2 of JP 6-25289 A to Morishita et al.

```
Formula 1 (amino acids 478-528) of SEQ ID NO: 10

Cys Asn Leu Pro Ile Val Arg Gly Pro Cys

Arg Ala Phe Ile Gln Leu Trp Ala Phe Asp

Ala Val Lys Gly Lys Cys Val Leu Phe Pro

Tyr Gly Gly Cys Gln Gly Asn Gly Asn Lys

Phe Tyr Ser Glu Lys Glu Cys Arg Glu Tyr

Cys
```

It was confirmed that the purified polypeptide sample obtained was the polypeptide of interest Y46E (amino acids 1-70 of SEQ ID NO: 234).

A polypeptide, Q19K, having an amino acid sequence derived from the aforementioned formula 1 amino acid sequence by substituting Lys for the position 15 Gln of the formula 1 sequence, counting from its N-terminus, was prepared as described in Example 3 of JP 6-25289 A to Morishita et al.

It was confirmed that the purified polypeptide sample obtained was the polypeptide Q19K of the present invention (amino acids 1-70 of SEQ ID NO: 235).

A polypeptide, Q19R, having an amino acid sequence derived from the aforementioned formula 1 amino acid sequence by substituting Arg for the position 15 Gln of the formula 1 sequence, counting from its N-terminus, was prepared as described in Example 4 of JP 6-25289 A to Morishita et al.

It was thus confirmed that the purified polypeptide sample obtained is the polypeptide Q19R of the present invention (amino acids 1-68 of SEQ ID NO: 236).

A polypeptide, Q19K/Y46E, having an amino acid sequence derived from the aforementioned formula 1 amino acid sequence by substituting Lys for the position 15 Gln, as well as Glu for position 42 Tyr, of the formula 1 sequence, counting from its N-terminus, was prepared as described in Example 5 of JP 6-25289 A to Morishita et al.

It was confirmed that the purified polypeptide sample obtained is the polypeptide Q19K/Y46E of the present invention (amino acids 1-68 of SEQ ID NO: 237).

A polypeptide, R11E/Y46E, having an amino acid sequence derived from the aforementioned formula 1 amino acid sequence by substituting Glu for the position 7 Arg, as well as Glu for the position 42 Tyr, of the formula 1 sequence, counting from its N-terminus, was prepared as described in Example 6 of JP 6-25289 A to Morishita et al.

It was confirmed that the purified polypeptide sample obtained is the desired polypeptide R11E/Y46E of the present invention (amino acids 1-68 of SEQ ID NO: 238).

A polypeptide, Y46E-AN, having an amino acid sequence derived from the aforementioned formula 1 amino acid sequence by substituting Glu for the position 42 Tyr of the formula 1 sequence, counting from its N-terminus, was prepared as described in Example 7 of JP 6-25289 A to Morishita et al.

It was confirmed that the purified polypeptide sample obtained is the desired polypeptide Y46E-AN of the present invention (amino acids 1-68 of SEQ ID NO: 250).

A polypeptide, Q19K-AN, having an amino acid sequence derived from the aforementioned formula 1 amino acid sequence by substituting Lys for the position 15 Gln of the formula 1 sequence, counting from its N-terminus, was prepared as described in Example 8 of JP 6-25289 A to Morishita et al.

It was confirmed that the purified polypeptide sample obtained is the polypeptide Q19K-AN of the present invention (amino acids 1-68 of SEQ ID NO: 251).

A polypeptide, Q19R/Y46E, having an amino acid sequence derived from the aforementioned formula 1 amino acid sequence by substituting Arg for the position 15 Gln, as well as Glu for the position 42 Tyr, of the formula 1 sequence, counting from its N-terminus, was prepared as described in Example 9 of JP 6-25289 A to Morishita et al.

It was confirmed that the purified polypeptide sample is the polypeptide Q19R/Y46E (amino acids 1-68 of SEQ ID NO: 239).

A polypeptide, Q19K/Y46D, having an amino acid sequence derived from the aforementioned formula 1 amino acid sequence by substituting Lys for the position 15 Gln, as well as Asp for the position 42 Tyr, of the formula 1 sequence, counting from its N-terminus, was prepared as described in Example 10 of JP 6-25289 A to Morishita et al.

It was confirmed that the purified sample is the polypeptide Q19K/Y46D of the present invention (amino acids 1-68 of SEQ ID NO: 240).

A polypeptide, Q19R/Y46D, having an amino acid sequence derived from the aforementioned formula 1 amino acid sequence by substituting Arg for the position 15 Gln, as well as Asp for the position 42 Tyr, of the formula 1 sequence, counting from its N-terminus, was prepared as described in Example 11 of JP 6-25289 A to Morishita et al.

It was confirmed that the purified polypeptide sample obtained is the polypeptide Q19R/Y46D of the present invention (amino acids 1-68 of SEQ ID NO: 241).

A polypeptide, R11Q/Q19K/Y46D, having an amino acid sequence derived from the aforementioned formula 1 amino acid sequence by substituting Gln for the position 7 Arg, Lys for the position 15 Gln, as well as Asp for the position 42 Tyr, of the formula 1 sequence, counting from its N-terminus, was prepared as described in Example 12 of JP 6-25289 A to Morishita et al.

It was confirmed that the purified polypeptide sample obtained is the polypeptide R11Q/Q19K/Y46D of the present invention (amino acids 1-68 of SEQ ID NO: 242).

A polypeptide, R11D/Q19K/Y46D, having an amino acid sequence derived from the aforementioned formula 1 amino acid sequence by substituting Asp for the position 7 Arg, Lys for the position 15 Gln, as well as Asp for the position 42 Tyr, of the formula 1 sequence, counting from its N-terminus, side was prepared as described in Example 13 of JP 6-25289 A to Morishita et al.

It was confirmed that the purified polypeptide sample obtained is the polypeptide R11D/Q19K/Y46D of the present invention (amino acids 1-68 of SEQ ID NO: 243).

A polypeptide, R11L/Q19K/Y46D, having an amino acid sequence derived from the aforementioned formula 1 amino acid sequence by substituting Leu for the position 7 Arg, Lys for the position 15 Gln, as well as Asp for the position 42 Tyr, of the formula 1 sequence, counting from its N-terminus, was prepared as described in Example 14 of JP 6-25289 A to Morishita et al.

It was confirmed that the purified polypeptide sample obtained is the polypeptide R11L/Q19K/Y46D of the present invention (amino acids 1-68 of SEQ ID NO: 244).

A polypeptide, R11E/Q19K/Y46E, having an amino acid sequence derived from the aforementioned formula 1 amino acid sequence by substituting Glu for the 7 position Arg, Lys for the position 15 Gln, as well as Glu for the position 42 Tyr, of the formula 1 sequence, counting from its N-terminus, was prepared as described in Example 15 of JP 6-25289 A to Morishita et al.

It was confirmed that the purified polypeptide sample is the desired polypeptide R11E/Q19K/Y46E of the present invention (amino acids 1-68 of SEQ ID NO: 245).

Polypeptides R11N/Q19K/Y46D (SEQ ID NO: 248), R11S/Q19K/Y46D (SEQ ID NO: 246) and R11A/Q19K/Y46D (SEQ ID NO: 249) having an amino acid sequence derived from the aforementioned formula 1 amino acid sequence by substituting Asn, Ser and Ala for the position 7 Arg, respectively, in addition to substituting Lys for the position 15 Gln and Asp for the position 42 Tyr of the formula 1 sequence, counting from its N-terminus, were prepared as described in Example 16 of JP 6-25289 A to Morishita et al.

FXa-inhibiting activities of the polypeptide of the present invention were measured in the following manner, using polypeptide samples Y46E, Q19K, Q19R, Q19K/Y46E, R11E/Y46E, Y46E-AN, Q19K-AN, Q19R/Y46E, Q19K/Y46D, Q19R/Y46D, R11Q/Q19K/Y46D, R11D/Q19K/Y46D, R11L/Q19K/Y46D, R11E/Q19K/Y46E, R11N/Q19K/Y46D, R11S/Q19K/Y46D and R11A/Q19K/Y46D.

The purified polypeptide of the present invention was dissolved in 100 μl of distilled water. Polypeptide concentration of this solution was determined based on its bovine trypsin-inhibiting activity using the aforementioned UTI as a standard as described in Example 17(1) of JP 6-25289 A to Morishita et al. The thus prepared solution was then diluted to various concentration levels with 0.1% BSA/150 mM NaCl/5 mM CaCl$_2$/50 mM Tris-HCl buffer (pH 8.3) for use in the activity measurement. On the other hand, the purified polypeptide TN70 and AN68 were diluted to various concentration levels to be used as a control solution. In this case a polypeptide TN70 (cf. Japanese Patent Application No. 3-325220) was purified respectively in accordance with the procedure of Example 2(4) in JP 6-25289 A to Morishita et al. from a culture supernatant of E. coli JE5505(pM552) (deposit No., FERM BP-3561) and polypeptide AN68 was purified in accordance with the procedure of Example 2(4) in JP 6-25289 A to Morishita et al. from a culture supernatant of E. coli JE5505(pM594) obtained by transforming E. coli JE5505 with the aforementioned plasmid pM594 obtained as described in Example 4 of JP 6-25289 A to Morishita et al. AN68 were diluted to various concentration levels to be used as control solutions.

The amino acid sequence of polypeptide TN 70 and AN68 are represented below.

```
Polypeptide TN70

(amino acids 474-543 of SEQ ID NO: 10)

Thr Val Ala Ala Cys Asn Leu Pro Ile Val

Arg Gly Pro Cys Arg Ala Phe Ile Gln Leu

Trp Ala Phe Asp Ala Val Lys Gly Lys Cys

Val Leu Phe Pro Tyr Gly Gly Cys Gln Gly

Asn Gly Asn Lys Phe Tyr Ser Glu Lys Glu

Cys Arg Glu Tyr Cys Gly Val Pro Gly Asp

Gly Asp Glu Glu Leu Leu Arg Phe Ser Asn

Polypeptide An68

(amino acids 476-543 of SEQ ID NO: 10)

Ala Ala Cys Asn Leu Pro Ile Val Arg Gly

Pro Cys Arg Ala Phe Ile Gln Leu Trp Ala

Phe Asp Ala Val Lys Gly Lys Cys Val Leu

Phe Pro Tyr Gly Gly Cys Gln Gly Asn Gly

Asn Lys Phe Tyr Ser Glu Lys Glu Cys Arg

Glu Tyr Cys Gly Val Pro Gly Asp Gly Asp

Glu Glu Leu Leu Arg Phe Ser Asn
```

Using a synthetic compound S-2222 (Daiichi Pure Chemicals Co., Ltd.) as a substrate, FXa-inhibiting activities in the thus prepared test sample solution and control solution were measured in accordance with the method of Ohno et al. (Ohno H. et al., Thromb. Res., vol.19, pp.579-588, 1980) as follows. First, human FXa (American Diagnostica Inc.) was dissolved in distilled water to a final concentration of 10 PEU/ml and the solution was further diluted with the aforementioned 0.1% BSA/150 mM NaCl/5 mM CaCl$_2$/50 mM Tris-HCl buffer (pH 8.3) to prepare 0.1 PEU/ml of FXa solution. Separately from this, a 4 mM solution of S-2222 was prepared by dissolving it in distilled water and the solution was further diluted with the 0.1% BSA/150 mM NaCl/5 mM CaCl$_2$/50 mM Tris-HCl buffer (pH 8.3) to obtain a 2 mM solution of S-2222.

Next, 25 μl of the test sample or control solution was mixed with 100 μl of the 0.1% BSA/150 mM NaCl/5 mM CaCl$_2$/50 mM Tris-HCl buffer (pH 8.3) and 25 μl of the FXa solution. After incubating statically at 37° C. for 10 minutes, 100 μl of the S-2222 solution was added to start the reaction. The reaction was carried out at 37° C. for 30 minutes and then stopped by adding 50 μl of 50% acetic acid solution to the reaction mixture. Thereafter, absorbance at a wavelength of 405 nm was measured using a spectrophotometer. In this instance, in order to eliminate absorbancy of various contents in the reaction mixture other than the reaction product, a blank solution was prepared by mixing 25 μl of the FXa solution with 50 μl of 50% acetic acid and then with 25 μl of each test sample or the control solution, 100 μl of the 0.1% BSA/150 mM NaCl/5 mM CaCl 2/50 mM Tris-HCl buffer (pH 8.3) and with 100 μl of the S-2222 solution.

The results are shown in FIG. 58-66. In these figures, polypeptide concentration in the reaction solution was expressed as its bovine trypsin-inhibiting activity. Also, residual human FXa activity was expressed by percentage based on the absorbance of a control reaction mixture in which 25 μl of the 0.1% BSA/150 mM NaCl/5 mM CaCl 2/50 mM Tris-HCl buffer (pH 8.3) was used instead of the test sample.

Figure 58:
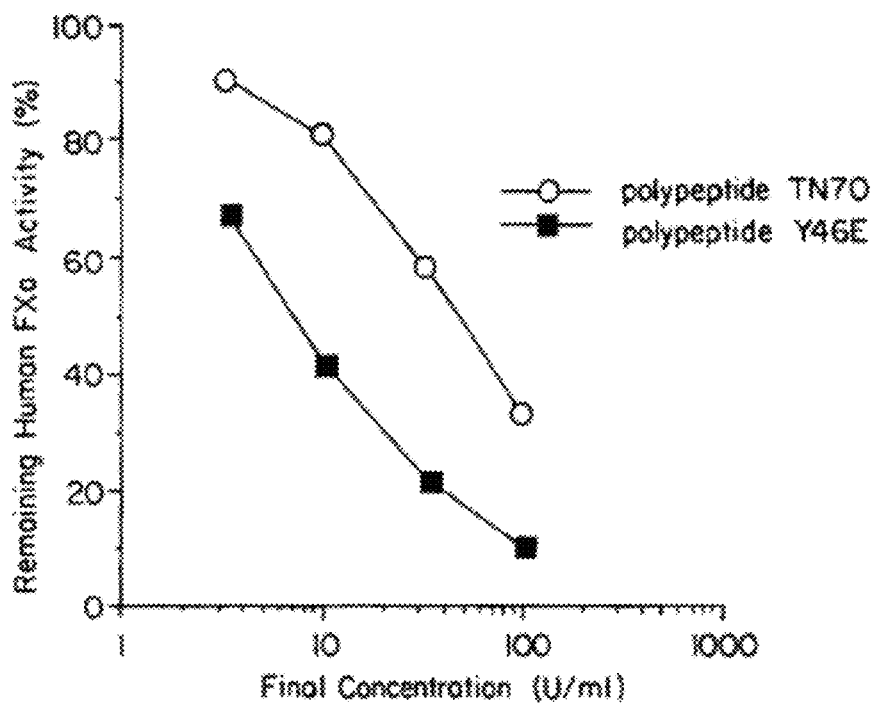
FIG. 58 is a graph showing FXa-inhibiting activity of polypeptide Y46E of the present invention.

FIG. 58 shows the polypeptide Y46E of the present invention has significantly high FXa-inhibiting activity in comparison with the polypeptide TN70 used as a control. In other words, it has an FXa-inhibiting activity which is about seven times higher than that of the polypeptide TN70.

Figure 59:
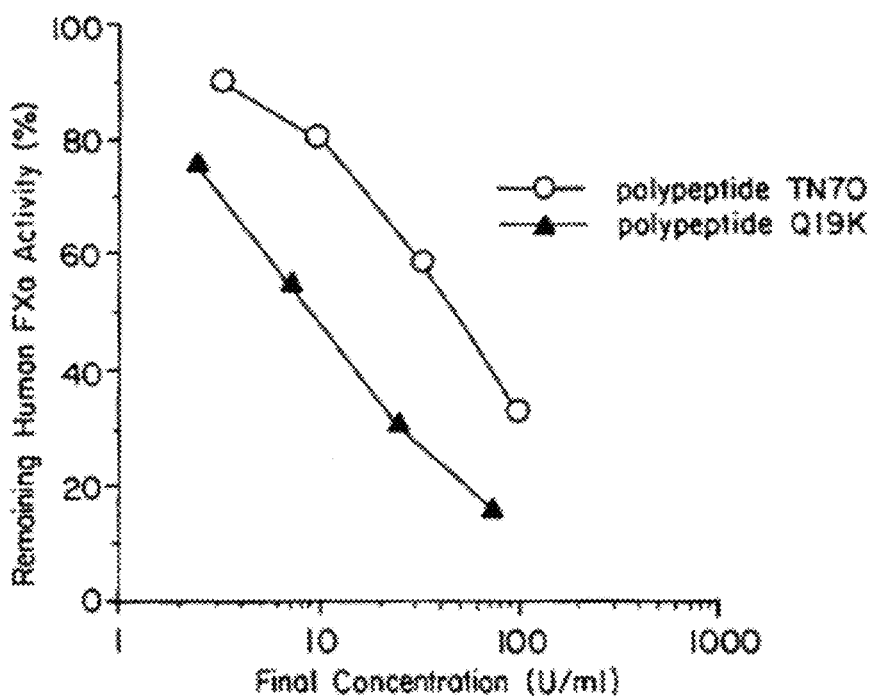
FIG. 59 is a graph showing FXa-inhibiting activity of polypeptide Q19K of the present invention.

FIG. 59 shows the polypeptide Q19K of the present invention has significantly high FXa-inhibiting activity in comparison with the polypeptide TN70 used as a control. In other words, it has an FXa-inhibiting activity which is about five times higher than that of the polypeptide TN70.

Figure 60:
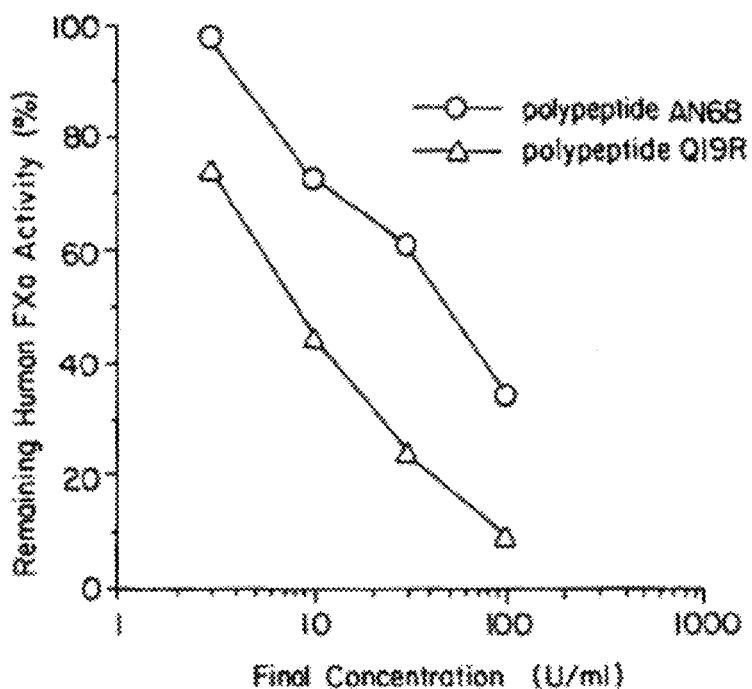
FIG. 60 is a graph showing FXa-inhibiting activity of polypeptide Q19R of the present invention.

FIG. 60 shows the polypeptide Q19R of the present invention has significantly high FXa-inhibiting activity in comparison with the polypeptide AN68 used as a control. In other words, it has an FXa-inhibiting activity which is about six times higher than that of the polypeptide AN68.

Figure 61:
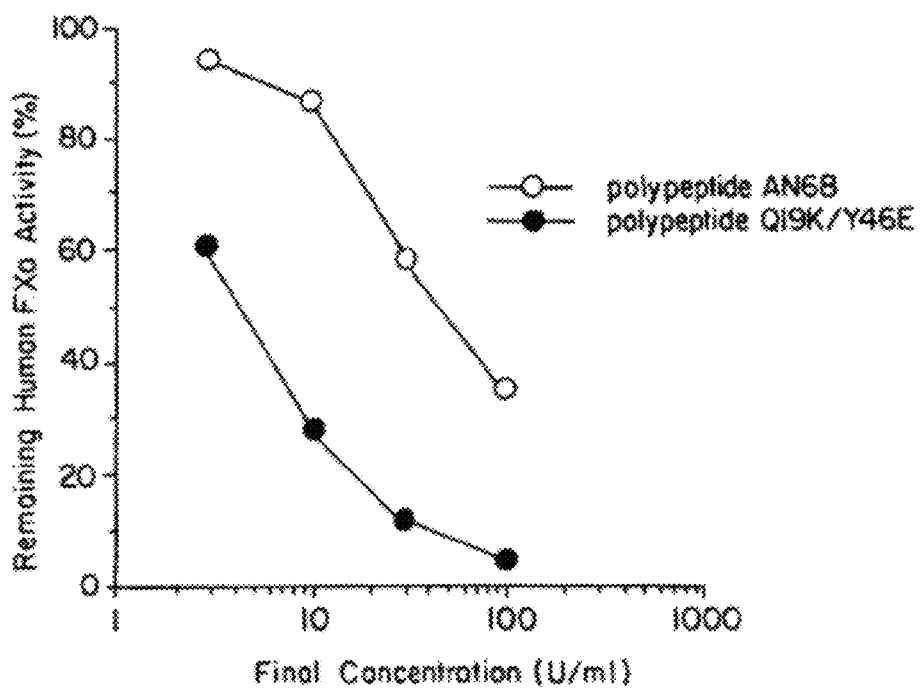
FIG. 61 is a graph showing FXa-inhibiting activity of polypeptide Q19K/Y46E of the present invention.

FIG. 61 shows the polypeptide Q19K/Y46E of the present invention has significantly high FXa-inhibiting activity in comparison with the polypeptide AN68 used as a control. In other words, it has an FXa-inhibiting activity which is about ten times higher than that of the polypeptide AN68.

Figure 62:
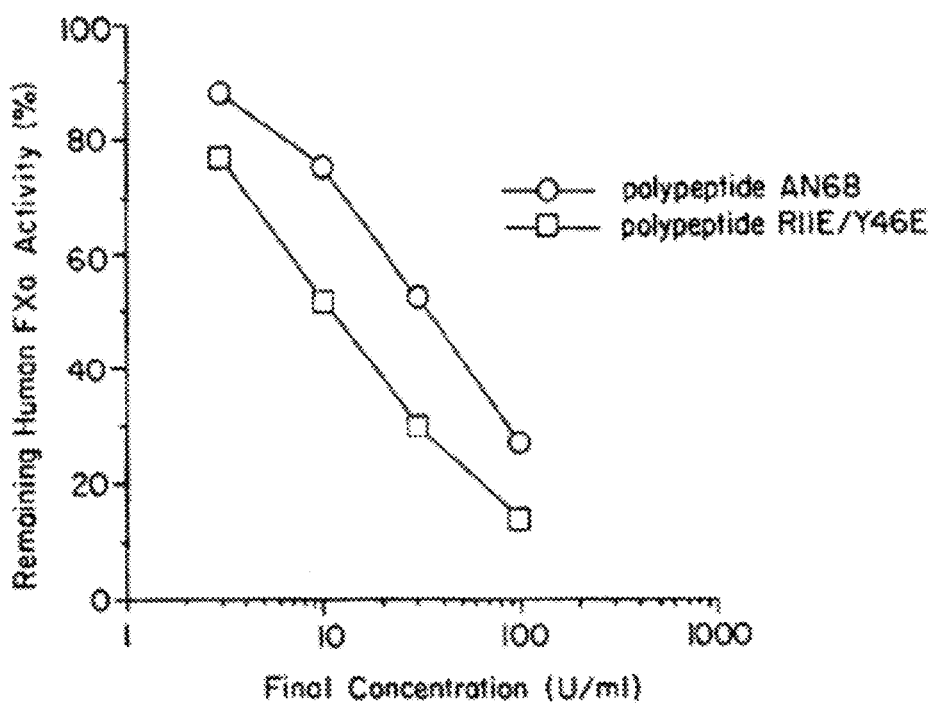
FIG. 62 is a graph showing FXa-inhibiting activity of polypeptide R11E/Y46E of the present invention.

FIG. 62 shows the polypeptide R11E/Y46E of the present invention has significantly high FXa-inhibiting activity in comparison with the polypeptide AN68 used as a control. In other words, it has an FXa-inhibiting activity which is about three times higher than that of the polypeptide AN68.

Figure 63:
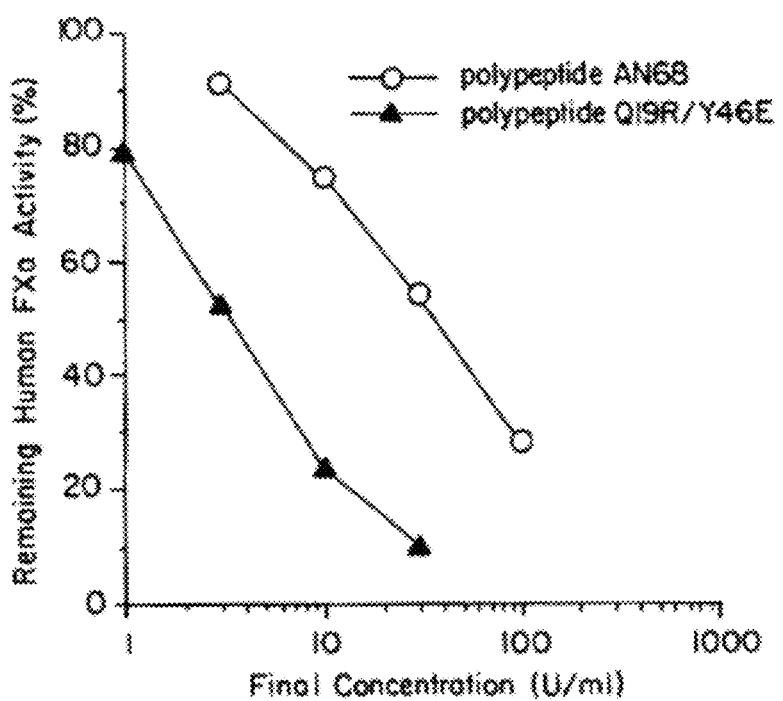
FIG. 63 is a graph showing FXa-inhibiting activity of polypeptide Q19R/Y46E of the present invention.

FIG. 63 shows the polypeptide Q19/Y46E of the present invention has an FXa-inhibiting activity which is about ten times higher than that of the polypeptide AN68.

Figure 64:
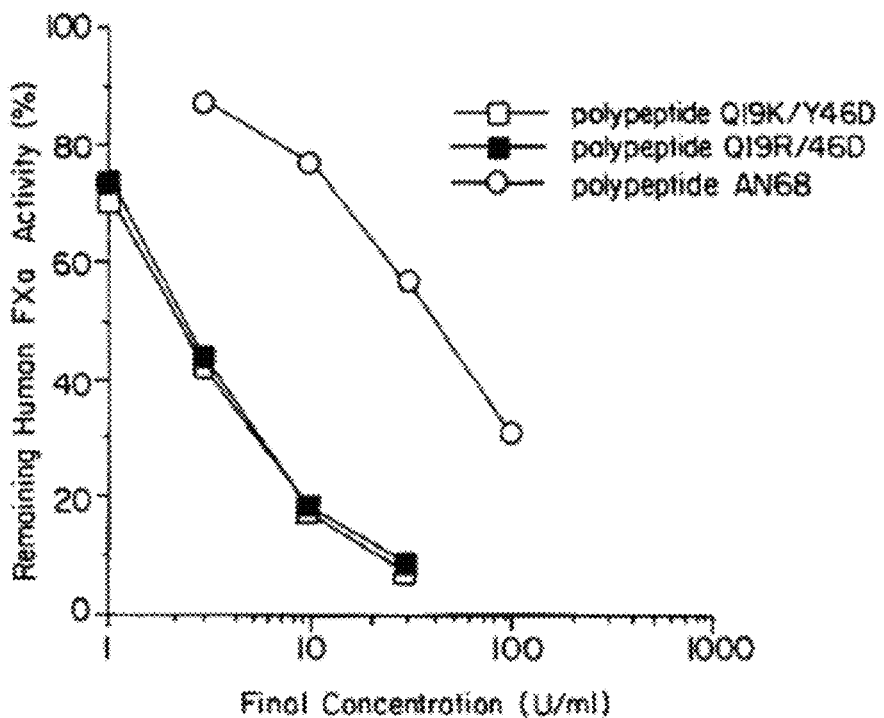
FIG. 64 is a graph showing FXa-inhibiting activity of polypeptides Q19K/Y46D and Q19R/Y46D of the present invention.

FIG. 64 shows the polypeptides Q19K/Y46D and Q19R/Y46D of the present invention have significantly high FXa-inhibiting activity in comparison with the polypeptide AN68 used as a control. In other words, polypeptide Q19K/Y46D has an FXa-inhibiting activity which is about twenty times higher than that of the polypeptide AN68. Polypeptide Q19R/Y46D has an FXa-inhibiting activity which is about 18 times higher than that of the polypeptide AN68.

Figure 65:
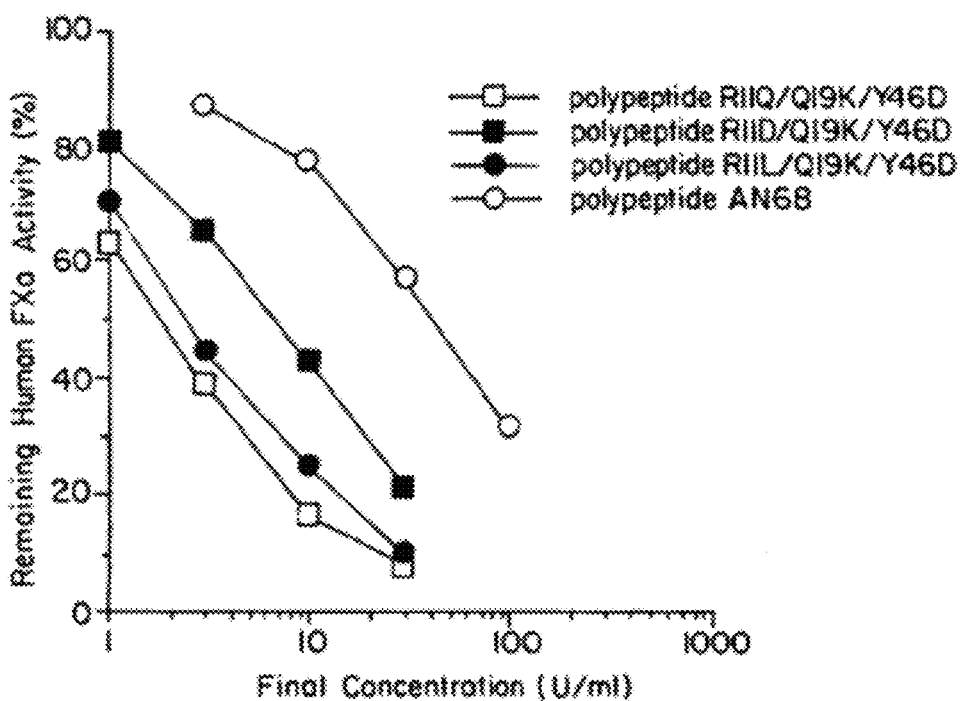
FIG. 65 is a graph showing FXa-inhibiting activity of polypeptides R11Q/Q19K/Y46D, R11D/Q19K/Y46D and R11L/Q19K/Y46D of the present invention.

FIG. 65 shows the polypeptides R11Q/Q19K/Y46D, R11L/Q19K/Y46D, R11D/Q19K/Y46D of the present invention have significantly high FXa-inhibiting activity in comparison with the polypeptide AN68 used as a control. In other words, polypeptide R11Q/Q19K/Y46D of the present invention has an FXa-inhibiting activity which is about twenty times higher than that of the polypeptide AN68. The polypeptide R11D/Q19K/Y46D has an FXa-inhibiting activity which is about 5 times higher than that of the polypeptide AN68. The polypeptide R11L/Q19K/Y46D has an FXa-inhibiting activity which is about 16 times higher than that of the polypeptide AN68.

FIG. 66 shows the polypeptides R11E/Q19K/Y46E of the present invention has significantly high FXa-inhibiting activity in comparison with the polypeptide AN68 used as a control. In other words, polypeptide R11E/Q19K/Y46E has an FXa-inhibiting activity which is about 13 times higher than that of the polypeptide AN68.

The invention claimed is:

1. A fusion protein comprising (I) an anti-CD14 antibody or its CD14 binding fragment, wherein said antibody or the fragment has an antigen binding activity and an inhibitory activity for LPS-induced IL-6 production in a TLR expressing cell, and (II) an inhibitor for a protease recited in 1) or 2) below;
   1) a polypeptide consisting of any one of amino acid sequences selected from the group consisting of a human UTI domain 2 (hereinafter referred to "UTI-D2") represented by from 474th to 543rd amino acid residues of SEQ ID NO 10 and a mutant of human UTI domain 2 with 3 amino acid substitutions (R11S/Q19K/Y46D) (hereinafter referred to "UTI-D2(3)") represented by from 474th to 543rd amino acid residues of SEQ ID NO 12,
   2) a mutant of UTI-D2, wherein the mutant has one or more mutations, and wherein the one or more mutations are selected from the group consisting of:
   a deletion of the $474^{th}$ amino acid of SEQ ID NO: 10,
   a deletion of the $475^{th}$ amino acid of SEQ ID NO: 10,
   a substitution of the $484^{th}$ amino acid of SEQ ID NO: 10,
   a substitution of the $492^{nd}$ amino acid of SEQ ID NO: 10, and
   a substitution of the $519^{th}$ amino acid of SEQ ID NO: 10
   to the amino acid sequence recited in 1) above, wherein said mutant has an anticoagulant action, or an inhibitory action for a blood coagulation factor.

2. A fusion protein according to (A) or (B) recited below;
   (A) a fusion protein which is obtained by binding (I) an anti-CD14 antibody or its CD-14 binding fragment, wherein said antibody or the fragment has an antigen binding activity and an inhibitory activity for LPS-induced IL-6 production in a TLR expressing cell, with (II) an inhibitor for a protease, recited in 1) or 2) below,
   1) a polypeptide consisting of any one of amino acid sequences selected from the group consisting of UTI-D2 and UTI-D2(3),
   2) a mutant of UTI-D2, wherein the mutant has one or more mutations, and wherein the one or more mutations are selected from the group consisting of:
   a deletion of the $474^{th}$ amino acid of SEQ ID NO: 10,
   a deletion of the $475^{th}$ amino acid of SEQ ID NO: 10,
   a substitution of the $484^{th}$ amino acid of SEQ ID NO: 10,
   a substitution of the $492^{nd}$ amino acid of SEQ ID NO: 10, and
   a substitution of the $519^{th}$ amino acid of SEQ ID NO: 10 to the amino acid sequence recited in 1) above, wherein said mutant has an anticoagulant action, or an inhibitory action for a blood coagulation factor,
   (B) a fusion protein which is obtained by binding (I) an anti-CD14 antibody or its CD-14 binding fragment, wherein said antibody or the fragment has an antigen binding activity and an inhibitory activity for LPS-induced IL-6 production in a TLR expressing cell, with (II) an inhibitor for a protease recited in 1) or 2) below by using a linker;
   1) a polypeptide consisting of any one of amino acids sequences selected from the group consisting of UTI-D2 and UTI-D2 (3),
   2) a mutant of UTI-D2, wherein the mutant has one or more mutations, and wherein the one or more mutations are selected from the group consisting of:
   a deletion of the $474^{th}$ amino acid of SEQ ID NO: 10,
   a deletion of the $475^{th}$ amino acid of SEQ ID NO: 10,
   a substitution of the $484^{th}$ amino acid of SEQ ID NO: 10,
   a substitution of the $492^{nd}$ amino acid of SEQ ID NO: 10, and
   a substitution of the $519^{th}$ amino acid of SEQ ID NO: 10
   to the amino acid sequence recited in 1) above, wherein said mutant has an anticoagulant action, or an inhibitory action for a blood coagulation factor.

3. The fusion protein according to claim 1 wherein the fusion protein has an inhibitory activity for LPS-induced IL-6 production in a TLR expressing cell; and; an anticoagulant action, or an inhibitory action for a blood coagulation factor.

4. The fusion protein according to claim 1 wherein the fusion protein has an inhibitory activity for FXa or FXIa; or an APTT extending action.

5. The fusion protein according to claim 1 wherein the fusion protein has an inhibitory activity for FXIa, or an APTT extending action.

6. The fusion protein according to claim 1 wherein said fusion protein has the action of inhibiting the binding between CD14 and the TLR.

7. The fusion protein according to claim 1 wherein said anti-CD 14 antibody or its CD14 binding fragment in (I) has the action of inhibiting the binding between CD14 and the TLR.

8. A fusion protein which is obtained by binding (I) an anti-CD14 antibody or its CD14 binding fragment wherein said antibody or the fragment has an antigen binding activity and an action of inhibiting the binding between CD14 and TLR, with (II) a polypeptide consisting of any one of amino acid sequences selected from the group consisting of UTI-D2 and UTI-D2(3), by using a linker.

9. The fusion protein according to claim 1 wherein the anti-CD14 antibody or its CD14 binding fragment in (I) recognizes at least a part of the region represented by from 269th to 315th amino acid residues of the amino acid sequence of human CD14.

10. The fusion protein according to claim 1 wherein the anti-CD14 antibody or its CD14 binding fragment in (I) recognizes at least a part of the region represented by from 294th to 296th amino acid residues of an amino acid sequence of human CD14.

11. The fusion protein according to claim 1 wherein the anti-CD14 antibody or its CD14 binding fragment in (I) comprises CDR1 consisting of SEQ ID NO 173, CDR2 consisting of SEQ ID NO 174, and CDR3 consisting of SEQ ID NO 175 of the heavy chain as the CDR1, CDR2, and CDR3 in the heavy chain variable region; and CDR1 consisting of SEQ ID NO 176, CDR2 consisting of SEQ ID NO 177, and CDR3 consisting of SEQ ID NO 178 of the light chain as the CDR1, CDR2, and CDR3 of the light chain variable region.

12. A fusion protein which is obtained by binding (I) an anti-CD14 antibody or its CD14 binding fragment comprising CDR1 consisting of SEQ ID NO 173, CDR2 consisting of SEQ ID NO 174, and CDR3 consisting of SEQ ID NO 175 of the heavy chain as the CDR1, CDR2, and CDR3 in the heavy chain variable region, and CDR1 consisting of SEQ ID NO 176, CDR2 consisting of SEQ ID NO 177, and CDR3 consisting of SEQ ID NO 178 of the light chain as the CDR1, CDR2, and CDR3 of the light chain variable region, wherein said fragment or derivative has an antigen binding activity, with (II) a polypeptide consisting of any one of amino acid sequences selected from the group consisting of UTI-D2 and UTI-D2 (3), by using a linker.

13. The fusion protein according to claim 1 wherein the anti-CD14 antibody or its CD14 binding fragment in (I) is a chimeric antibody.

14. The fusion protein according to claim 1 wherein the anti-CD14 antibody or its CD14 binding fragment in (I) is a humanized antibody.

15. The fusion protein according to claim 1 wherein the anti-CD14 antibody or its CD14 binding fragment in (I) is monovalent.

16. The fusion protein according to claim 1 wherein the anti-CD14 antibody or its CD14 binding fragment in (I) is divalent.

17. The fusion protein according to claim 1 wherein the protease inhibitor in (II) is fused to the C terminal side of the heavy chain of an anti-CD14 antibody or its CD14 binding fragment in (I).

18. A therapeutic agent comprising the fusion protein of claim 1 for sepsis, severe sepsis, septic ARDS, septic shock, SIRS related disease, or endotoxin shock.

19. The fusion protein according to claim 7 wherein the fusion protein has an inhibitory activity for LPS-induced IL-6 production in a TLR expressing cell; and an anticoagulant action, or an inhibitory action for a blood coagulation factor.

20. The fusion protein according to claim 9 wherein the fusion protein has an inhibitory activity for LPS-induced IL-6 production in a TLR expressing cell; and an anticoagulant action, or an inhibitory action for a blood coagulation factor.

21. The fusion protein according to claim 7 wherein the fusion protein has an inhibitory activity for FXa or FXIa; or an APTT extending action.

22. The fusion protein according to claim 9 wherein the fusion protein has an inhibitory activity for FXa or FXIa; or an APTT extending action.

23. The fusion protein according to claim 7 wherein the fusion protein has the action of inhibiting the binding between CD14 and the TLR.

24. The fusion protein according to claim 9 wherein the fusion protein has the action of inhibiting the binding between CD14 and the TLR.

25. The fusion protein according to claim 7 wherein the anti-CD14 antibody or its CD14 binding fragment in (I) recognizes at least a part of the region represented by from 269th to 315th amino acid residues of the amino acid sequence of human CD14.

26. The fusion protein according to claim 7 wherein the anti-CD14 antibody or its CD14 binding fragment in (I) recognizes at least a part of the region represented by from 294th to 296th amino acid residues of an amino acid sequence of human CD14.

27. The fusion protein according to claim 7 wherein the anti-CD14 antibody or its CD14 binding fragment in (I) comprises CDR1 consisting of SEQ ID NO 173, CDR2 consisting of SEQ ID NO 174, and CDR3 consisting of SEQ ID NO 175 of the heavy chain as the CDR1, CDR2, and CDR3 in the heavy chain variable region; and CDR1 consisting of SEQ ID NO 176, CDR2 consisting of SEQ ID NO 177, and CDR3 consisting of SEQ ID NO 178 of the light chain as the CDR1, CDR2, and CDR3 of the light chain variable region.

28. The fusion protein according to claim 9 wherein the anti-CD14 antibody or its CD14 binding fragment in (I) comprises CDR1 consisting of SEQ ID NO 173, CDR2 consisting of SEQ ID NO 174, and CDR3 consisting of SEQ ID NO 175 of the heavy chain as the CDR1, CDR2, and CDR3 in the heavy chain variable region; and CDR1 consisting of SEQ ID NO 176, CDR2 consisting of SEQ ID NO 177, and CDR3 consisting of SEQ ID NO 178 of the light chain as the CDR1, CDR2, and CDR3 of the light chain variable region.

29. The fusion protein according to claim 7 wherein the anti-CD14 antibody or its CD14 binding fragment in (I) is a chimeric antibody.

30. The fusion protein according to claim 9 wherein the anti-CD14 antibody or its CD14 binding fragment in (I) is a chimeric antibody.

31. The fusion protein according to claim 12 wherein the anti-CD14 antibody or its CD14 binding fragment in (I) is a chimeric antibody.

32. The fusion protein according to claim 7 wherein the anti-CD14 antibody or its CD14 binding fragment in (I) is a humanized antibody.

33. The fusion protein according to claim 9 wherein the anti-CD14 antibody or its CD14 binding fragment in (I) is a humanized antibody.

34. The fusion protein according to claim 12 wherein the anti-CD14 antibody or its CD14 binding fragment in (I) is a humanized antibody.

35. The fusion protein according to claim 7 wherein the anti-CD14 antibody or its CD14 binding fragment in (I) is monovalent.

36. The fusion protein according to claim 9 wherein the anti-CD14 antibody or its CD14 binding fragment in (I) is monovalent.

37. The fusion protein according to claim 12 wherein the anti-CD14 antibody or its CD14 binding fragment in (I) is monovalent.

38. The fusion protein according to claim 7 wherein the anti-CD14 antibody or its CD14 binding fragment in (I) is divalent.

39. The fusion protein according to claim 9 wherein the anti-CD14 antibody or its CD14 binding fragment in (I) is divalent.

40. The fusion protein according to claim 12 wherein the anti-CD14 antibody or its CD14 binding fragment in (I) is divalent.

41. The fusion protein according to claim 7 wherein the protease inhibitor in (II) is fused to the C terminal side of the heavy chain of an anti-CD14 antibody or its CD14 binding fragment in (I).

42. The fusion protein according to claim 9 wherein the protease inhibitor in (II) is fused to the C terminal side of the heavy chain of an anti-CD14 antibody or its CD14 binding fragment in (I).

43. The fusion protein according to claim 12 wherein the protease inhibitor in (II) is fused to the C terminal side of the heavy chain of an anti-CD14 antibody or its CD14 binding fragment in (I).

44. A pharmaceutical composition comprising the fusion protein of claim 1 as an active ingredient and a pharmaceutically acceptable additive.

45. The pharmaceutical composition according to claim 44 for sepsis, severe sepsis, septic ARDS, septic shock, SIRS related disease, or endotoxin shock.

46. The fusion protein according to claim 1 wherein the CD14 binding fragment in (I) is selected from the group consisting of Fab, F(ab')$_2$, single chain Fv, disulfide stabilized Fv, diabody and single domain antibody.

47. The fusion protein according to claim 7 wherein the CD14 binding fragment in (I) is selected from the group consisting of Fab, F(ab')$_2$, single chain Fv, disulfide stabilized Fv, diabody and single domain antibody.

48. The fusion protein according to claim 9 wherein the CD14 binding fragment in (I) is selected from the group consisting of Fab, F(ab')$_2$, single chain Fv, disulfide stabilized Fv, diabody and single domain antibody.

49. The fusion protein according to claim 12 wherein the CD14 binding fragment in (I) is selected from the group consisting of Fab, F(ab')$_2$, single chain Fv, disulfide stabilized Fv, diabody and single domain antibody.

50. The fusion protein according to claim 1, wherein the mutant of UTI-D2 of part 2) has one or more mutations, and wherein the one or more mutations are selected from the group consisting of:
- a deletion of the 474$^{th}$ amino acid of SEQ ID NO: 10,
- a deletion of the 475$^{th}$ amino acid of SEQ ID NO: 10,
- a substitution of the 484$^{th}$ amino acid of SEQ ID NO: 10 by an amino acid selected from the group consisting of Ala, Asp, Asn, Gln, Leu, Glu and Ser,
- a substitution of the 492$^{nd}$ amino acid of SEQ ID NO: 10 by Arg or Lys, and
- a substitution of the 519$^{th}$ amino acid of SEQ ID NO: 10 by Asp or Glu, to the amino acid sequence recited in 1).

51. The fusion protein according to claim 2, wherein the mutant of UTI-D2 of part (A) 2) or part (B) 2) has one or more mutations, and wherein the one or more mutations are selected from the group consisting of:
- a deletion of the 474$^{th}$ amino acid of SEQ ID NO: 10,
- a deletion of the 475$^{th}$ amino acid of SEQ ID NO: 10,
- a substitution of the 484$^{th}$ amino acid of SEQ ID NO: 10 by an amino acid selected from the group consisting of Ala, Asp, Asn, Gln, Leu, Glu and Ser,
- a substitution of the 492$^{nd}$ amino acid of SEQ ID NO: 10 by Arg or Lys, and
- a substitution of the 519$^{th}$ amino acid of SEQ ID NO: 10 by Asp or Glu, to the amino acid sequence recited in 1).

52. The fusion protein according to claim 1, wherein the mutant of UTI-D2 of part 2) has one or more mutations, and wherein the one or more mutations are selected from the group consisting of:
- a deletion of the 474$^{th}$ amino acid of SEQ ID NO: 10,
- a deletion of the 475$^{th}$ amino acid of SEQ ID NO: 10,
- a substitution of the 484$^{th}$ amino acid of SEQ ID NO: 10 by Ser,
- a substitution of the 492$^{nd}$ amino acid of SEQ ID NO: 10 by Lys, and
- a substitution of the 519$^{th}$ amino acid of SEQ ID NO: 10 by Asp, to the amino acid sequence recited in 1).

53. The fusion protein according to claim 2, wherein the mutant of UTI-D2 of part (A) 2) or part (B) 2) has one or more mutations, and wherein the one or more mutations are selected from the group consisting of:
- a deletion of the 474$^{th}$ amino acid of SEQ ID NO: 10,
- a deletion of the 475$^{th}$ amino acid of SEQ ID NO: 10,
- a substitution of the 484$^{th}$ amino acid of SEQ ID NO: 10 by Ser,
- a substitution of the 492$^{nd}$ amino acid of SEQ ID NO: 10 by Lys, and
- a substitution of the 519$^{th}$ amino acid of SEQ ID NO: 10 by Asp, to the amino acid sequence recited in 1).

* * * * *

SEQUENCE LISTING

```
<160> NUMBER OF SEQ ID NOS: 251

<210> SEQ ID NO 1
<211> LENGTH: 1860
<212> TYPE: DNA
<213> ORGANISM: Artificial Sequence
<220> FEATURE:
<223> OTHER INFORMATION: Synthetic Antibody fusion protein F1024D-D1D2
<220> FEATURE:
<221> NAME/KEY: CDS
<222> LOCATION: (1)..(1860)

<400> SEQUENCE: 1 atg gat tgg ttg tgg aac ttg cta ttc ctg atg gta gtt gcc caa agt        48
Met Asp Trp Leu Trp Asn Leu Leu Phe Leu Met Val Val Ala Gln Ser
1               5                   10                  15 gct caa gca cag atc cag ttg gta cag tct gga cct gaa ctg aag aag        96
Ala Gln Ala Gln Ile Gln Leu Val Gln Ser Gly Pro Glu Leu Lys Lys
                20                  25                  30 cct gga gag tca gtg aag atc tcc tgc aag gct tct ggg tat acc ttc       144
Pro Gly Glu Ser Val Lys Ile Ser Cys Lys Ala Ser Gly Tyr Thr Phe
            35                  40                  45 aca gac tat gca atg aac tgg gtg aaa cag gct cca gga aat ggc ttg       192
Thr Asp Tyr Ala Met Asn Trp Val Lys Gln Ala Pro Gly Asn Gly Leu
        50                  55                  60 aag tgg atg ggc tgg atc aac acc caa act gga aag cca aca tat gcg       240
Lys Trp Met Gly Trp Ile Asn Thr Gln Thr Gly Lys Pro Thr Tyr Ala
65                  70                  75                  80
```

| | | |
|---|---|---|
| gat gat ttc aaa caa cgg ttt gtc ttc tct ttg gaa act tct gcc agc<br>Asp Asp Phe Lys Gln Arg Phe Val Phe Ser Leu Glu Thr Ser Ala Ser<br>85 90 95 | | 288 |
| act gca tac ttg cag atc aac aac ctc aat att gag gac aca gct aca<br>Thr Ala Tyr Leu Gln Ile Asn Asn Leu Asn Ile Glu Asp Thr Ala Thr<br>100 105 110 | | 336 |
| tat ttc tgt aca aga tcc act ttt tac tat agc agc tat atc tac ggg<br>Tyr Phe Cys Thr Arg Ser Thr Phe Tyr Tyr Ser Ser Tyr Ile Tyr Gly<br>115 120 125 | | 384 |
| tgg tac ttt gac ttc tgg ggc cca gga acc atg gtc acc gtc tcc agc<br>Trp Tyr Phe Asp Phe Trp Gly Pro Gly Thr Met Val Thr Val Ser Ser<br>130 135 140 | | 432 |
| gct agc acc aag ggc cca tcc gtc ttc ccc ctg gcg ccc tgc tcc agg<br>Ala Ser Thr Lys Gly Pro Ser Val Phe Pro Leu Ala Pro Cys Ser Arg<br>145 150 155 160 | | 480 |
| agc acc tcc gag agc aca gcc gcc ctg ggc tgc ctg gtc aag gac tat<br>Ser Thr Ser Glu Ser Thr Ala Ala Leu Gly Cys Leu Val Lys Asp Tyr<br>165 170 175 | | 528 |
| ttc ccc gaa ccg gtg acg gtg tcg tgg aac tca ggt gcc ctg acc agc<br>Phe Pro Glu Pro Val Thr Val Ser Trp Asn Ser Gly Ala Leu Thr Ser<br>180 185 190 | | 576 |
| ggc gtg cac acc ttc ccg gct gtc cta cag tcc tca gga ctc tac tcc<br>Gly Val His Thr Phe Pro Ala Val Leu Gln Ser Ser Gly Leu Tyr Ser<br>195 200 205 | | 624 |
| ctc agc agc gtg gtg acc gtg ccc tcc agc agc ttg ggc acg aag acc<br>Leu Ser Ser Val Val Thr Val Pro Ser Ser Ser Leu Gly Thr Lys Thr<br>210 215 220 | | 672 |
| tac acc tgc aac gta gat cac aag ccc agc aac acc aag gtg gac aag<br>Tyr Thr Cys Asn Val Asp His Lys Pro Ser Asn Thr Lys Val Asp Lys<br>225 230 235 240 | | 720 |
| aga gtt gag tcc aaa tat ggt ccc cca tgc cca tca tgc cca gca cct<br>Arg Val Glu Ser Lys Tyr Gly Pro Pro Cys Pro Ser Cys Pro Ala Pro<br>245 250 255 | | 768 |
| gag ttc ctg ggg gga cca tca gtc ttc ctg ttc ccc cca aaa ccc aag<br>Glu Phe Leu Gly Gly Pro Ser Val Phe Leu Phe Pro Pro Lys Pro Lys<br>260 265 270 | | 816 |
| gac act ctc atg atc tcc cgg acc cct gag gtc acg tgc gtg gtg gtg<br>Asp Thr Leu Met Ile Ser Arg Thr Pro Glu Val Thr Cys Val Val Val<br>275 280 285 | | 864 |
| gac gtg agc cag gaa gac ccc gag gtc cag ttc aac tgg tac gtg gat<br>Asp Val Ser Gln Glu Asp Pro Glu Val Gln Phe Asn Trp Tyr Val Asp<br>290 295 300 | | 912 |
| ggc gtg gag gtg cat aat gcc aag aca aag ccg cgg gag gag cag ttc<br>Gly Val Glu Val His Asn Ala Lys Thr Lys Pro Arg Glu Glu Gln Phe<br>305 310 315 320 | | 960 |
| aac agc acg tac cgt gtg gtc agc gtc ctc acc gtc ctg cac cag gac<br>Asn Ser Thr Tyr Arg Val Val Ser Val Leu Thr Val Leu His Gln Asp<br>325 330 335 | | 1008 |
| tgg ctg aac ggc aag gag tac aag tgc aag gtc tcc aac aaa ggc ctc<br>Trp Leu Asn Gly Lys Glu Tyr Lys Cys Lys Val Ser Asn Lys Gly Leu<br>340 345 350 | | 1056 |
| ccg tcc tcc atc gag aaa acc atc tcc aaa gcc aaa ggg cag ccc cga<br>Pro Ser Ser Ile Glu Lys Thr Ile Ser Lys Ala Lys Gly Gln Pro Arg<br>355 360 365 | | 1104 |
| gag cca cag gtg tac acc ctg ccc cca tcc cag gag gag atg acc aag<br>Glu Pro Gln Val Tyr Thr Leu Pro Pro Ser Gln Glu Glu Met Thr Lys<br>370 375 380 | | 1152 |
| aac cag gtc agc ctg acc tgc ctg gtc aaa ggc ttc tac ccc agc gac<br>Asn Gln Val Ser Leu Thr Cys Leu Val Lys Gly Phe Tyr Pro Ser Asp<br>385 390 395 400 | | 1200 |

-continued

```
atc gcc gtg gag tgg gag agc aat ggg cag ccg gag aac aac tac aag    1248
Ile Ala Val Glu Trp Glu Ser Asn Gly Gln Pro Glu Asn Asn Tyr Lys
            405                 410                 415 acc acg cct ccc gtg ctg gac tcc gac ggc tcc ttc ttc ctc tac agc    1296
Thr Thr Pro Pro Val Leu Asp Ser Asp Gly Ser Phe Phe Leu Tyr Ser
        420                 425                 430 agg cta acc gtg gac aag agc agg tgg cag gag ggg aat gtc ttc tca    1344
Arg Leu Thr Val Asp Lys Ser Arg Trp Gln Glu Gly Asn Val Phe Ser
    435                 440                 445 tgc tcc gtg atg cat gag gct ctg cac aac cac tac aca cag aag agc    1392
Cys Ser Val Met His Glu Ala Leu His Asn His Tyr Thr Gln Lys Ser
450                 455                 460 ctc tcc ctg tct ctg ggt aaa gga tcc gct gtg cta ccc caa gaa gag    1440
Leu Ser Leu Ser Leu Gly Lys Gly Ser Ala Val Leu Pro Gln Glu Glu
465                 470                 475                 480 gaa gga tca ggg ggt ggg caa ctg gta act gaa gtc acc aag aaa gaa    1488
Glu Gly Ser Gly Gly Gly Gln Leu Val Thr Glu Val Thr Lys Lys Glu
                485                 490                 495 gat tcc tgc cag ctg ggc tac tcg gcc ggt ccc tgc atg gga atg acc    1536
Asp Ser Cys Gln Leu Gly Tyr Ser Ala Gly Pro Cys Met Gly Met Thr
            500                 505                 510 agc agg tat ttc tat aat ggt aca tcc atg gcc tgt gag act ttc cag    1584
Ser Arg Tyr Phe Tyr Asn Gly Thr Ser Met Ala Cys Glu Thr Phe Gln
        515                 520                 525 tac ggc ggc tgc atg ggc aac ggt aac aac ttc gtc aca gaa aag gag    1632
Tyr Gly Gly Cys Met Gly Asn Gly Asn Asn Phe Val Thr Glu Lys Glu
    530                 535                 540 tgt ctg cag acc tgc cga act gtg gcg gcc tgc aat ctc ccc ata gtc    1680
Cys Leu Gln Thr Cys Arg Thr Val Ala Ala Cys Asn Leu Pro Ile Val
545                 550                 555                 560 cgg ggc ccc tgc cga gcc ttc atc cag ctc tgg gca ttt gat gct gtc    1728
Arg Gly Pro Cys Arg Ala Phe Ile Gln Leu Trp Ala Phe Asp Ala Val
                565                 570                 575 aag ggg aag tgc gtc ctc ttc ccc tac ggg ggc tgc cag ggc aac ggg    1776
Lys Gly Lys Cys Val Leu Phe Pro Tyr Gly Gly Cys Gln Gly Asn Gly
            580                 585                 590 aac aag ttc tac tca gag aag gag tgc aga gag tac tgc ggt gtc cct    1824
Asn Lys Phe Tyr Ser Glu Lys Glu Cys Arg Glu Tyr Cys Gly Val Pro
        595                 600                 605 ggt gat ggt gat gag gag ctg ctg cgc ttc tcc aac                    1860
Gly Asp Gly Asp Glu Glu Leu Leu Arg Phe Ser Asn
    610                 615                 620

<210> SEQ ID NO 2
<211> LENGTH: 620
<212> TYPE: PRT
<213> ORGANISM: Artificial Sequence
<220> FEATURE:
<223> OTHER INFORMATION: Synthetic Antibody fusion protein F1024D-D1D2

<400> SEQUENCE: 2

Met Asp Trp Leu Trp Asn Leu Leu Phe Leu Met Val Val Ala Gln Ser
1               5                   10                  15

Ala Gln Ala Gln Ile Gln Leu Val Gln Ser Gly Pro Glu Leu Lys Lys
            20                  25                  30

Pro Gly Glu Ser Val Lys Ile Ser Cys Lys Ala

-continued

```
Asp Asp Phe Lys Gln Arg Phe Val Phe Ser Leu Glu Thr Ser Ala Ser
                 85                  90                  95
Thr Ala Tyr Leu Gln Ile Asn Asn Leu Asn Ile Glu Asp Thr Ala Thr
            100                 105                 110
Tyr Phe Cys Thr Arg Ser Thr Phe Tyr Tyr Ser Ser Tyr Ile Tyr Gly
        115                 120                 125
Trp Tyr Phe Asp Phe Trp Gly Pro Gly Thr Met Val Thr Val Ser Ser
130                 135                 140
Ala Ser Thr Lys Gly Pro Ser Val Phe Pro Leu Ala Pro Cys Ser Arg
145                 150                 155                 160
Ser Thr Ser Glu Ser Thr Ala Ala Leu Gly Cys Leu Val Lys Asp Tyr
                165                 170                 175
Phe Pro Glu Pro Val Thr Val Ser Trp Asn Ser Gly Ala Leu Thr Ser
            180                 185                 190
Gly Val His Thr Phe Pro Ala Val Leu Gln Ser Ser Gly Leu Tyr Ser
        195                 200                 205
Leu Ser Ser Val Val Thr Val Pro Ser Ser Ser Leu Gly Thr Lys Thr
210                 215                 220
Tyr Thr Cys Asn Val Asp His Lys Pro Ser Asn Thr Lys Val Asp Lys
225                 230                 235                 240
Arg Val Glu Ser Lys Tyr Gly Pro Pro Cys Pro Ser Cys Pro Ala Pro
                245                 250                 255
Glu Phe Leu Gly Gly Pro Ser Val Phe Leu Phe Pro Pro Lys Pro Lys
            260                 265                 270
Asp Thr Leu Met Ile Ser Arg Thr Pro Glu Val Thr Cys Val Val Val
        275                 280                 285
Asp Val Ser Gln Glu Asp Pro Glu Val Gln Phe Asn Trp Tyr Val Asp
290                 295                 300
Gly Val Glu Val His Asn Ala Lys Thr Lys Pro Arg Glu Glu Gln Phe
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Gly Leu
            340                 345                 350
Pro Ser Ser Ile Glu Lys Thr Ile Ser Lys Ala Lys Gly Gln Pro Arg
        355                 360                 365
Glu Pro Gln Val Tyr Thr Leu Pro Pro Ser Gln Glu Glu Met Thr Lys
370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Arg Leu Thr Val Asp Lys Ser Arg Trp Gln Glu Gly Asn Val Phe Ser
        435                 440                 445
Cys Ser Val Met His Glu Ala Leu His Asn His Tyr Thr Gln Lys Ser
450                 455                 460
Leu Ser Leu Ser Leu Gly Lys Gly Ser Ala Val Leu Pro Gln Glu Glu
465                 470                 475                 480
Glu Gly Ser Gly Gly Gly Gln Leu Val Thr Glu Val Thr Lys Lys Glu
                485                 490                 495
Asp Ser Cys Gln Leu Gly Tyr Ser Ala Gly Pro Cys Met Gly Met Thr
```

```
                        500                 505                 510
Ser Arg Tyr Phe Tyr Asn Gly Thr Ser Met Ala Cys Glu Thr Phe Gln
                515                 520                 525

Tyr Gly Gly Cys Met Gly Asn Gly Asn Asn Phe Val Thr Glu Lys Glu
        530                 535                 540

Cys Leu Gln Thr Cys Arg Thr Val Ala Ala Cys Asn Leu Pro Ile Val
545                 550                 555                 560

Arg Gly Pro Cys Arg Ala Phe Ile Gln Leu Trp Ala Phe Asp Ala Val
                565                 570                 575

Lys Gly Lys Cys Val Leu Phe Pro Tyr Gly Gly Cys Gln Gly Asn Gly
        580                 585                 590

Asn Lys Phe Tyr Ser Glu Lys Glu Cys Arg Glu Tyr Cys Gly Val Pro
            595                 600                 605

Gly Asp Gly Asp Glu Glu Leu Leu Arg Phe Ser Asn
        610                 615                 620

<210> SEQ ID NO 3
<211> LENGTH: 1629
<212> TYPE: DNA
<213> ORGANISM: Artificial Sequence
<220> FEATURE:
<223> OTHER INFORMATION: Synthetic Antibody fusion protein F1024D-D2
<220> FEATURE:
<221> NAME/KEY: CDS
<222> LOCATION: (1)..(1629)

<400> SEQUENCE: 3 atg gat tgg ttg tgg aac ttg cta ttc ctg atg gta gtt gcc caa agt        48
Met Asp Trp Leu Trp Asn Leu Leu Phe Leu Met Val Val Ala Gln Ser
1               5                   10                  15 gct caa gca cag atc cag ttg gta cag tct gga cct gaa ctg aag aag        96
Ala Gln Ala Gln Ile Gln Leu Val Gln Ser Gly Pro Glu Leu Lys Lys
                20                  25                  30 cct gga gag tca gtg aag atc tcc tgc aag gct tct ggg tat acc ttc       144
Pro Gly Glu Ser Val Lys Ile Ser Cys Lys Ala Ser Gly Tyr Thr Phe
            35                  40                  45 aca gac tat gca atg aac tgg gtg aaa cag gct cca gga aat ggc ttg       192
Thr Asp Tyr Ala Met Asn Trp Val Lys Gln Ala Pro Gly Asn Gly Leu
        50                  55                  60 aag tgg atg ggc tgg atc aac acc caa act gga aag cca aca tat gcg       240
Lys Trp Met Gly Trp Ile Asn Thr Gln Thr Gly Lys Pro Thr Tyr Ala
65                  70                  75                  80 gat gat ttc aaa caa cgg ttt gtc ttc tct ttg gaa act tct gcc agc       288
Asp Asp Phe Lys Gln Arg Phe Val Phe Ser Leu Glu Thr Ser Ala Ser
                85                  90                  95 act gca tac ttg cag atc aac aac ctc aat att gag gac aca gct aca       336
Thr Ala Tyr Leu Gln Ile Asn Asn Leu Asn Ile Glu Asp Thr Ala Thr
                100                 105                 110 tat ttc tgt aca aga tcc act ttt tac tat agc agc tat atc tac ggg       384
Tyr Phe Cys Thr Arg Ser Thr Phe Tyr Tyr Ser Ser Tyr Ile Tyr Gly
            115                 120                 125 tgg tac ttt gac ttc tgg ggc cca gga acc atg gtc acc gtc tcc agc       432
Trp Tyr Phe Asp Phe Trp Gly Pro Gly Thr Met Val Thr Val Ser Ser
        130                 135                 140 gct agc acc aag ggc cca tcc gtc ttc ccc ctg gcg ccc tgc tcc agg       480
Ala Ser Thr Lys Gly Pro Ser Val Phe Pro Leu Ala Pro Cys Ser Arg
145                 150                 155                 160 agc acc tcc gag agc aca gcc gcc ctg ggc tgc ctg gtc aag gac tat       528
Ser Thr Ser Glu Ser Thr Ala Ala Leu Gly Cys Leu Val Lys Asp Tyr
                165                 170                 175
```

| | | |
|---|---|---|
| ttc ccc gaa ccg gtg acg gtg tcg tgg aac tca ggt gcc ctg acc agc<br>Phe Pro Glu Pro Val Thr Val Ser Trp Asn Ser Gly Ala Leu Thr Ser<br>          180                          185                    190 | | 576 |
| ggc gtg cac acc ttc ccg gct gtc cta cag tcc tca gga ctc tac tcc<br>Gly Val His Thr Phe Pro Ala Val Leu Gln Ser Ser Gly Leu Tyr Ser<br>        195                        200                    205 | | 624 |
| ctc agc agc gtg gtg acc gtg ccc tcc agc agc ttg ggc acg aag acc<br>Leu Ser Ser Val Val Thr Val Pro Ser Ser Ser Leu Gly Thr Lys Thr<br>210                        215                        220 | | 672 |
| tac acc tgc aac gta gat cac aag ccc agc aac acc aag gtg gac aag<br>Tyr Thr Cys Asn Val Asp His Lys Pro Ser Asn Thr Lys Val Asp Lys<br>225                      230                    235                    240 | | 720 |
| aga gtt gag tcc aaa tat ggt ccc cca tgc cca tca tgc cca gca cct<br>Arg Val Glu Ser Lys Tyr Gly Pro Pro Cys Pro Ser Cys Pro Ala Pro<br>                    245                    250                    255 | | 768 |
| gag ttc ctg ggg gga cca tca gtc ttc ctg ttc ccc cca aaa ccc aag<br>Glu Phe Leu Gly Gly Pro Ser Val Phe Leu Phe Pro Pro Lys Pro Lys<br>                260                    265                    270 | | 816 |
| gac act ctc atg atc tcc cgg acc cct gag gtc acg tgc gtg gtg gtg<br>Asp Thr Leu Met Ile Ser Arg Thr Pro Glu Val Thr Cys Val Val Val<br>        275                        280                    285 | | 864 |
| gac gtg agc cag gaa gac ccc gag gtc cag ttc aac tgg tac gtg gat<br>Asp Val Ser Gln Glu Asp Pro Glu Val Gln Phe Asn Trp Tyr Val Asp<br>        290                        295                    300 | | 912 |
| ggc gtg gag gtg cat aat gcc aag aca aag ccg cgg gag gag cag ttc<br>Gly Val Glu Val His Asn Ala Lys Thr Lys Pro Arg Glu Glu Gln Phe<br>305                      310                    315                    320 | | 960 |
| aac agc acg tac cgt gtg gtc agc gtc ctc acc gtc ctg cac cag gac<br>Asn Ser Thr Tyr Arg Val Val Ser Val Leu Thr Val Leu His Gln Asp<br>                    325                    330                    335 | | 1008 |
| tgg ctg aac ggc aag gag tac aag tgc aag gtc tcc aac aaa ggc ctc<br>Trp Leu Asn Gly Lys Glu Tyr Lys Cys Lys Val Ser Asn Lys Gly Leu<br>                340                    345                    350 | | 1056 |
| ccg tcc tcc atc gag aaa acc atc tcc aaa gcc aaa ggg cag ccc cga<br>Pro Ser Ser Ile Glu Lys Thr Ile Ser Lys Ala Lys Gly Gln Pro Arg<br>            355                        360                    365 | | 1104 |
| gag cca cag gtg tac acc ctg ccc cca tcc cag gag gag atg acc aag<br>Glu Pro Gln Val Tyr Thr Leu Pro Pro Ser Gln Glu Glu Met Thr Lys<br>370                        375                    380 | | 1152 |
| aac cag gtc agc ctg acc tgc ctg gtc aaa ggc ttc tac ccc agc gac<br>Asn Gln Val Ser Leu Thr Cys Leu Val Lys Gly Phe Tyr Pro Ser Asp<br>385                      390                    395                    400 | | 1200 |
| atc gcc gtg gag tgg gag agc aat ggg cag ccg gag aac aac tac aag<br>Ile Ala Val Glu Trp Glu Ser Asn Gly Gln Pro Glu Asn Asn Tyr Lys<br>                    405                    410                    415 | | 1248 |
| acc acg cct ccc gtg ctg gac tcc gac ggc tcc ttc ttc ctc tac agc<br>Thr Thr Pro Pro Val Leu Asp Ser Asp Gly Ser Phe Phe Leu Tyr Ser<br>                420                        425                    430 | | 1296 |
| agg cta acc gtg gac aag agc agg tgg cag gag ggg aat gtc ttc tca<br>Arg Leu Thr Val Asp Lys Ser Arg Trp Gln Glu Gly Asn Val Phe Ser<br>                    435                    440                    445 | | 1344 |
| tgc tcc gtg atg cat gag gct ctg cac aac cac tac aca cag aag agc<br>Cys Ser Val Met His Glu Ala Leu His Asn His Tyr Thr Gln Lys Ser<br>450                        455                    460 | | 1392 |
| ctc tcc ctg tct ctg ggt aaa gga tcc act gtg gcg gcc tgc aat ctc<br>Leu Ser Leu Ser Leu Gly Lys Gly Ser Thr Val Ala Ala Cys Asn Leu<br>465                      470                    475                    480 | | 1440 |
| ccc ata gtc cgg ggc ccc tgc cga gcc ttc atc cag ctc tgg gca ttt<br>Pro Ile Val Arg Gly Pro Cys Arg Ala Phe Ile Gln Leu Trp Ala Phe<br>                    485                    490                    495 | | 1488 |

```
gat gct gtc aag ggg aag tgc gtc ctc ttc ccc tac ggg ggc tgc cag    1536
Asp Ala Val Lys Gly Lys Cys Val Leu Phe Pro Tyr Gly Gly Cys Gln
        500                 505                 510 ggc aac ggg aac aag ttc tac tca gag aag gag tgc aga gag tac tgc    1584
Gly Asn Gly Asn Lys Phe Tyr Ser Glu Lys Glu Cys Arg Glu Tyr Cys
        515                 520                 525 ggt gtc cct ggt gat ggt gat gag gag ctg ctg cgc ttc tcc aac        1629
Gly Val Pro Gly Asp Gly Asp Glu Glu Leu Leu Arg Phe Ser Asn
        530                 535                 540

<210> SEQ ID NO 4
<211> LENGTH: 543
<212> TYPE: PRT
<213> ORGANISM: Artificial Sequence
<220> FEATURE:
<223> OTHER INFORMATION: Synthetic Antibody fusion protein F1024D-D2

<400> SEQUENCE: 4

Met Asp Trp Leu Trp Asn Leu Leu Phe Leu Met Val Val Ala Gln Ser
1               5                   10                  15

Ala Gln Ala Gln Ile Gln Leu Val Gln Ser Gly Pro Glu Leu Lys Lys
            20                  25                  30

Pro Gly Glu Ser Val Lys Ile Ser Cys Lys Ala Ser Gly Tyr Thr Phe
        35                  40                  45

Thr Asp Tyr Ala Met Asn Trp Val Lys Gln Ala Pro Gly Asn Gly Leu
    50                  55                  60

Lys Trp Met Gly Trp Ile Asn Thr Gln Thr Gly Lys Pro Thr Tyr Ala
65                  70                  75                  80

Asp Asp Phe Lys Gln Arg Phe Val Phe Ser Leu Glu Thr Ser Ala Ser
                85                  90                  95

Thr Ala Tyr Leu Gln Ile Asn Asn Leu Asn Ile Glu Asp Thr Ala Thr
            100                 105                 110

Tyr Phe Cys Thr Arg Ser Thr Phe Tyr Ser Ser Tyr Ile Tyr Gly
        115                 120                 125

Trp Tyr Phe Asp Phe Trp Gly Pro Gly Thr Met Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Lys Thr
    210                 215                 220

Tyr Thr Cys Asn Val Asp His Lys Pro Ser Asn Thr Lys Val Asp Lys
225                 230                 235                 240

Arg Val Glu Ser Lys Tyr Gly Pro Pro Cys Pro Ser Cys Pro Ala Pro
                245                 250                 255

Glu Phe Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser Gln Glu Asp Pro Glu Val Gln Phe Asn Trp Tyr Val Asp
    290                 295                 300

Gly Val Glu Val His Asn Ala Lys Thr Lys Pro Arg Glu Glu Gln Phe
```

```
                305                 310                 315                 320
Asn Ser Thr Tyr Arg Val Val Ser Val Leu Thr Val Leu His Gln Asp
                    325                 330                 335

Trp Leu Asn Gly Lys Glu Tyr Lys Cys Lys Val Ser Asn Lys Gly Leu
                340                 345                 350

Pro Ser Ser Ile Glu Lys Thr Ile Ser Lys Ala Lys Gly Gln Pro Arg
                355                 360                 365

Glu Pro Gln Val Tyr Thr Leu Pro Pro Ser Gln Glu Glu Met Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Arg Leu Thr Val Asp Lys Ser Arg Trp Gln Glu Gly Asn Val Phe Ser
                435                 440                 445

Cys Ser Val Met His Glu Ala Leu His Asn His Tyr Thr Gln Lys Ser
                450                 455                 460

Leu Ser Leu Ser Leu Gly Lys Gly Ser Thr Val Ala Ala Cys Asn Leu
465                 470                 475                 480

Pro Ile Val Arg Gly Pro Cys Arg Ala Phe Ile Gln Leu Trp Ala Phe
                485                 490                 495

Asp Ala Val Lys Gly Lys Cys Val Leu Phe Pro Tyr Gly Gly Cys Gln
                500                 505                 510

Gly Asn Gly Asn Lys Phe Tyr Ser Glu Lys Glu Cys Arg Glu Tyr Cys
                515                 520                 525

Gly Val Pro Gly Asp Gly Asp Glu Glu Leu Leu Arg Phe Ser Asn
            530                 535                 540

<210> SEQ ID NO 5
<211> LENGTH: 1629
<212> TYPE: DNA
<213> ORGANISM: Artificial Sequence
<220> FEATURE:
<223> OTHER INFORMATION: Synthetic Antibody fusion protein F1024D-D2(3)
<220> FEATURE:
<221> NAME/KEY: CDS
<222> LOCATION: (1)..(1629)

<400> SEQUENCE: 5 atg gat tgg ttg tgg aac ttg cta ttc ctg atg gta gtt gcc caa agt     48
Met Asp Trp Leu Trp Asn Leu Leu Phe Leu Met Val Val Ala Gln Ser
1               5                   10                  15 gct caa gca cag atc cag ttg gta cag tct gga cct gaa ctg aag aag     96
Ala Gln Ala Gln Ile Gln Leu Val Gln Ser Gly Pro Glu Leu Lys Lys
                20                  25                  30 cct gga gag tca gtg aag atc tcc tgc aag gct tct ggg tat acc ttc    144
Pro Gly Glu Ser Val Lys Ile Ser Cys Lys Ala Ser Gly Tyr Thr Phe
            35                  40                  45 aca gac tat gca atg aac tgg gtg aaa cag gct cca gga aat ggc ttg    192
Thr Asp Tyr Ala Met Asn Trp Val Lys Gln Ala Pro Gly Asn Gly Leu
        50                  55                  60 aag tgg atg ggc tgg atc aac acc caa act gga aag cca aca tat gcg    240
Lys Trp Met Gly Trp Ile Asn Thr Gln Thr Gly Lys Pro Thr Tyr Ala
65                  70                  75                  80 gat gat ttc aaa caa cgg ttt gtc ttc tct ttg gaa act tct gcc agc    288
Asp Asp Phe Lys Gln Arg Phe Val Phe Ser Leu Glu Thr Ser Ala Ser
                85                  90                  95
```

-continued

| | | |
|---|---|---|
| act gca tac ttg cag atc aac aac ctc aat att gag gac aca gct aca<br>Thr Ala Tyr Leu Gln Ile Asn Asn Leu Asn Ile Glu Asp Thr Ala Thr<br>                  100                            105                            110 | 336 | |
| tat ttc tgt aca aga tcc act ttt tac tat agc agc tat atc tac ggg<br>Tyr Phe Cys Thr Arg Ser Thr Phe Tyr Tyr Ser Ser Tyr Ile Tyr Gly<br>                115                            120                            125 | 384 | |
| tgg tac ttt gac ttc tgg ggc cca gga acc atg gtc acc gtc tcc agc<br>Trp Tyr Phe Asp Phe Trp Gly Pro Gly Thr Met Val Thr Val Ser Ser<br>130                              135                            140 | 432 | |
| gct agc acc aag ggc cca tcc gtc ttc ccc ctg gcg ccc tgc tcc agg<br>Ala Ser Thr Lys Gly Pro Ser Val Phe Pro Leu Ala Pro Cys Ser Arg<br>145                              150                          155                        160 | 480 | |
| agc acc tcc gag agc aca gcc gcc ctg ggc tgc ctg gtc aag gac tat<br>Ser Thr Ser Glu Ser Thr Ala Ala Leu Gly Cys Leu Val Lys Asp Tyr<br>                            165                            170                            175 | 528 | |
| ttc ccc gaa ccg gtg acg gtg tcg tgg aac tca ggt gcc ctg acc agc<br>Phe Pro Glu Pro Val Thr Val Ser Trp Asn Ser Gly Ala Leu Thr Ser<br>                180                            185                            190 | 576 | |
| ggc gtg cac acc ttc ccg gct gtc cta cag tcc tca gga ctc tac tcc<br>Gly Val His Thr Phe Pro Ala Val Leu Gln Ser Ser Gly Leu Tyr Ser<br>                          195                            200                            205 | 624 | |
| ctc agc agc gtg gtg acc gtg ccc tcc agc agc ttg ggc acg aag acc<br>Leu Ser Ser Val Val Thr Val Pro Ser Ser Ser Leu Gly Thr Lys Thr<br>210                              215                            220 | 672 | |
| tac acc tgc aac gta gat cac aag ccc agc aac acc aag gtg gac aag<br>Tyr Thr Cys Asn Val Asp His Lys Pro Ser Asn Thr Lys Val Asp Lys<br>225                              230                          235                        240 | 720 | |
| aga gtt gag tcc aaa tat ggt ccc cca tgc cca tca tgc cca gca cct<br>Arg Val Glu Ser Lys Tyr Gly Pro Pro Cys Pro Ser Cys Pro Ala Pro<br>                            245                            250                            255 | 768 | |
| gag ttc ctg ggg gga cca tca gtc ttc ctg ttc ccc cca aaa ccc aag<br>Glu Phe Leu Gly Gly Pro Ser Val Phe Leu Phe Pro Pro Lys Pro Lys<br>                260                            265                            270 | 816 | |
| gac act ctc atg atc tcc cgg acc cct gag gtc acg tgc gtg gtg gtg<br>Asp Thr Leu Met Ile Ser Arg Thr Pro Glu Val Thr Cys Val Val Val<br>                          275                            280                            285 | 864 | |
| gac gtg agc cag gaa gac ccc gag gtc cag ttc aac tgg tac gtg gat<br>Asp Val Ser Gln Glu Asp Pro Glu Val Gln Phe Asn Trp Tyr Val Asp<br>290                              295                            300 | 912 | |
| ggc gtg gag gtg cat aat gcc aag aca aag ccg cgg gag gag cag ttc<br>Gly Val Glu Val His Asn Ala Lys Thr Lys Pro Arg Glu Glu Gln Phe<br>305                              310                          315                        320 | 960 | |
| aac agc acg tac cgt gtg gtc agc gtc ctc acc gtc ctg cac cag gac<br>Asn Ser Thr Tyr Arg Val Val Ser Val Leu Thr Val Leu His Gln Asp<br>                          325                            330                            335 | 1008 | |
| tgg ctg aac ggc aag gag tac aag tgc aag gtc tcc aac aaa ggc ctc<br>Trp Leu Asn Gly Lys Glu Tyr Lys Cys Lys Val Ser Asn Lys Gly Leu<br>                            340                            345                            350 | 1056 | |
| ccg tcc tcc atc gag aaa acc atc tcc aaa gcc aaa ggg cag ccc cga<br>Pro Ser Ser Ile Glu Lys Thr Ile Ser Lys Ala Lys Gly Gln Pro Arg<br>                355                            360                            365 | 1104 | |
| gag cca cag gtg tac acc ctg ccc cca tcc cag gag gag atg acc aag<br>Glu Pro Gln Val Tyr Thr Leu Pro Pro Ser Gln Glu Glu Met Thr Lys<br>370                              375                          380 | 1152 | |
| aac cag gtc agc ctg acc tgc ctg gtc aaa ggc ttc tac ccc agc gac<br>Asn Gln Val Ser Leu Thr Cys Leu Val Lys Gly Phe Tyr Pro Ser Asp<br>385                              390                          395                        400 | 1200 | |
| atc gcc gtg gag tgg gag agc aat ggg cag ccg gag aac aac tac aag<br>Ile Ala Val Glu Trp Glu Ser Asn Gly Gln Pro Glu Asn Asn Tyr Lys<br>                            405                            410                        415 | 1248 | |

```
acc acg cct ccc gtg ctg gac tcc gac ggc tcc ttc ttc ctc tac agc    1296
Thr Thr Pro Pro Val Leu Asp Ser Asp Gly Ser Phe Phe Leu Tyr Ser
            420                 425                 430 agg cta acc gtg gac aag agc agg tgg cag gag ggg aat gtc ttc tca    1344
Arg Leu Thr Val Asp Lys Ser Arg Trp Gln Glu Gly Asn Val Phe Ser
    435                 440                 445 tgc tcc gtg atg cat gag gct ctg cac aac cac tac aca cag aag agc    1392
Cys Ser Val Met His Glu Ala Leu His Asn His Tyr Thr Gln Lys Ser
450                 455                 460 ctc tcc ctg tct ctg ggt aaa gga tcc act gtg gcg gcc tgc aat cta    1440
Leu Ser Leu Ser Leu Gly Lys Gly Ser Thr Val Ala Ala Cys Asn Leu
465                 470                 475                 480 cca ata gtc agc ggc ccc tgc cga gcc ttc atc aag ctc tgg gca ttt    1488
Pro Ile Val Ser Gly Pro Cys Arg Ala Phe Ile Lys Leu Trp Ala Phe
            485                 490                 495 gat gct gtc aag ggg aag tgc gtc ctc ttc ccc tac ggg ggc tgc cag    1536
Asp Ala Val Lys Gly Lys Cys Val Leu Phe Pro Tyr Gly Gly Cys Gln
            500                 505                 510 ggc aac ggg aac aag ttc gac tca gag aag gag tgc aga gag tac tgc    1584
Gly Asn Gly Asn Lys Phe Asp Ser Glu Lys Glu Cys Arg Glu Tyr Cys
    515                 520                 525 ggt gtc cct ggt gat ggt gat gag gag ctg ctg cgc ttc tcc aac        1629
Gly Val Pro Gly Asp Gly Asp Glu Glu Leu Leu Arg Phe Ser Asn
530                 535                 540

<210> SEQ ID NO 6
<211> LENGTH: 543
<212> TYPE: PRT
<213> ORGANISM: Artificial Sequence
<220> FEATURE:
<223> OTHER INFORMATION: Synthetic Antibody fusion protein F1024D-D2(3)

<400> SEQUENCE: 6

Met Asp Trp Leu Trp Asn Leu Leu Phe Leu Met Val Val Ala Gln Ser
1               5                   10                  15

Ala Gln Ala Gln Ile Gln Leu Val Gln Ser Gly Pro Glu Leu Lys Lys
            20                  25                  30

Pro Gly Glu Ser Val Lys Ile Ser Cys Lys Ala Ser Gly Tyr Thr Phe
        35                  40                  45

Thr Asp Tyr Ala Met Asn Trp Val Lys Gln Ala Pro Gly Asn Gly Leu
    50                  55                  60

Lys Trp Met Gly Trp Ile Asn Thr Gln Thr Gly Lys Pro Thr Tyr Ala
65                  70                  75                  80

Asp Asp Phe Lys Gln Arg Phe Val Phe Ser Leu Glu Thr Ser Ala Ser
                85                  90                  95

Thr Ala Tyr Leu Gln Ile Asn Asn Leu Asn Ile Glu Asp Thr Ala Thr
            100                 105                 110

Tyr Phe Cys Thr Arg Ser Thr Phe Tyr Ser Ser Tyr Ile Tyr Gly
        115                 120                 125

Trp Tyr Phe Asp Phe Trp Gly Pro Gly Thr Met Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
```

|   |   |   |   | 195 |   |   |   | 200 |   |   |   | 205 |   |   |
|---|---|---|---|---|---|---|---|---|---|---|---|---|---|---|---|

Leu Ser Ser Val Val Thr Val Pro Ser Ser Leu Gly Thr Lys Thr
210                     215                 220

Tyr Thr Cys Asn Val Asp His Lys Pro Ser Asn Thr Lys Val Asp Lys
225                 230                 235                 240

Arg Val Glu Ser Lys Tyr Gly Pro Pro Cys Pro Ser Cys Pro Ala Pro
                245                 250                 255

Glu Phe Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser Gln Glu Asp Pro Glu Val Gln Phe Asn Trp Tyr Val Asp
    290                 295                 300

Gly Val Glu Val His Asn Ala Lys Thr Lys Pro Arg Glu Glu Gln Phe
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
            340                 345                 350

Pro Ser Ser Ile Glu Lys Thr Ile Ser Lys Ala Lys Gly Gln Pro Arg
        355                 360                 365

Glu Pro Gln Val Tyr Thr Leu Pro Pro Ser Gln Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Arg Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
450                 455                 460

Leu Ser Leu Ser Leu Gly Lys Gly Ser Thr Val Ala Ala Cys Asn Leu
465                 470                 475                 480

Pro Ile Val Ser Gly Pro Cys Arg Ala Phe Ile Lys Leu Trp Ala Phe
                485                 490                 495

Asp Ala Val Lys Gly Lys Cys Val Leu Phe Pro Tyr Gly Gly Cys Gln
            500                 505                 510

Gly Asn Gly Asn Lys Phe Asp Ser Glu Lys Glu Cys Arg Glu Tyr Cys
        515                 520                 525

Gly Val Pro Gly Asp Gly Asp Glu Glu Leu Leu Arg Phe Ser Asn
    530                 535                 540

```
<210> SEQ ID NO 7
<211> LENGTH: 1860
<212> TYPE: DNA
<213> ORGANISM: Artificial Sequence
<220> FEATURE:
<223> OTHER INFORMATION: Synthetic Antibody fusion protein F1024S-D1D2
<220> FEATURE:
<221> NAME/KEY: CDS
<222> LOCATION: (1)..(1860)

<400> SEQUENCE: 7
``` atg gat tgg ttg tgg aac ttg cta ttc ctg atg gta gtt gcc caa agt    48
Met Asp Trp Leu Trp Asn Leu Leu Phe Leu Met Val Val Ala Gln Ser

```
1               5                   10                  15
gct caa gca cag atc cag ttg gta cag tct gga cct gaa ctg aag aag         96
Ala Gln Ala Gln Ile Gln Leu Val Gln Ser Gly Pro Glu Leu Lys Lys
             20                  25                  30 cct gga gag tca gtg aag atc tcc tgc aag gct tct ggg tat acc ttc        144
Pro Gly Glu Ser Val Lys Ile Ser Cys Lys Ala Ser Gly Tyr Thr Phe
         35                  40                  45 aca gac tat gca atg aac tgg gtg aaa cag gct cca gga aat ggc ttg        192
Thr Asp Tyr Ala Met Asn Trp Val Lys Gln Ala Pro Gly Asn Gly Leu
 50                  55                  60 aag tgg atg ggc tgg atc aac acc caa act gga aag cca aca tat gcg        240
Lys Trp Met Gly Trp Ile Asn Thr Gln Thr Gly Lys Pro Thr Tyr Ala
65                  70                  75                  80 gat gat ttc aaa caa cgg ttt gtc ttc tct ttg gaa act tct gcc agc        288
Asp Asp Phe Lys Gln Arg Phe Val Phe Ser Leu Glu Thr Ser Ala Ser
                 85                  90                  95 act gca tac ttg cag atc aac aac ctc aat att gag gac aca gct aca        336
Thr Ala Tyr Leu Gln Ile Asn Asn Leu Asn Ile Glu Asp Thr Ala Thr
             100                 105                 110 tat ttc tgt aca aga tcc act ttt tac tat agc agc tat atc tac ggg        384
Tyr Phe Cys Thr Arg Ser Thr Phe Tyr Tyr Ser Ser Tyr Ile Tyr Gly
         115                 120                 125 tgg tac ttt gac ttc tgg ggc cca gga acc atg gtc acc gtc tcc agc        432
Trp Tyr Phe Asp Phe Trp Gly Pro Gly Thr Met Val Thr Val Ser Ser
 130                 135                 140 gct agc acc aag ggc cca tcc gtc ttc ccc ctg gcg ccc tgc tcc agg        480
Ala Ser Thr Lys Gly Pro Ser Val Phe Pro Leu Ala Pro Cys Ser Arg
145                 150                 155                 160 agc acc tcc gag agc aca gcc gcc ctg ggc tgc ctg gtc aag gac tat        528
Ser Thr Ser Glu Ser Thr Ala Ala Leu Gly Cys Leu Val Lys Asp Tyr
                 165                 170                 175 ttc ccc gaa ccg gtg acg gtg tcg tgg aac tca ggt gcc ctg acc agc        576
Phe Pro Glu Pro Val Thr Val Ser Trp Asn Ser Gly Ala Leu Thr Ser
             180                 185                 190 ggc gtg cac acc ttc ccg gct gtc cta cag tcc tca gga ctc tac tcc        624
Gly Val His Thr Phe Pro Ala Val Leu Gln Ser Ser Gly Leu Tyr Ser
         195                 200                 205 ctc agc agc gtg gtg acc gtg ccc tcc agc agc ttg ggc acg aag acc        672
Leu Ser Ser Val Val Thr Val Pro Ser Ser Ser Leu Gly Thr Lys Thr
 210                 215                 220 tac acc tgc aac gta gat cac aag ccc agc aac acc aag gtg gac aag        720
Tyr Thr Cys Asn Val Asp His Lys Pro Ser Asn Thr Lys Val Asp Lys
225                 230                 235                 240 aga gtt gag tcc aaa tat ggt ccc cca ggc cca tca ggc cca gca cct        768
Arg Val Glu Ser Lys Tyr Gly Pro Pro Gly Pro Ser Gly Pro Ala Pro
                 245                 250                 255 gag ttc ctg ggg gga cca tca gtc ttc ctg ttc ccc cca aaa ccc aag        816
Glu Phe Leu Gly Gly Pro Ser Val Phe Leu Phe Pro Pro Lys Pro Lys
             260                 265                 270 gac act ctc atg atc tcc cgg acc cct gag gtc acg tgc gtg gtg gtg        864
Asp Thr Leu Met Ile Ser Arg Thr Pro Glu Val Thr Cys Val Val Val
         275                 280                 285 gac gtg agc cag gaa gac ccc gag gtc cag ttc aac tgg tac gtg gat        912
Asp Val Ser Gln Glu Asp Pro Glu Val Gln Phe Asn Trp Tyr Val Asp
 290                 295                 300 ggc gtg gag gtg cat aat gcc aag aca aag ccg cgg gag gag cag ttc        960
Gly Val Glu Val His Asn Ala Lys Thr Lys Pro Arg Glu Glu Gln Phe
305                 310                 315                 320 aac agc acg tac cgt gtg gtc agc gtc ctc acc gtc ctg cac cag gac       1008
Asn Ser Thr Tyr Arg Val Val Ser Val Leu Thr Val Leu His Gln Asp
```

```
                      325                 330                 335
tgg ctg aac ggc aag gag tac aag tgc aag gtc tcc aac aaa ggc ctc         1056
Trp Leu Asn Gly Lys Glu Tyr Lys Cys Lys Val Ser Asn Lys Gly Leu
            340                 345                 350 ccg tcc tcc atc gag aaa acc atc tcc aaa gcc aaa ggg cag ccc cga         1104
Pro Ser Ser Ile Glu Lys Thr Ile Ser Lys Ala Lys Gly Gln Pro Arg
        355                 360                 365 gag cca cag gtg tac acc ctg ccc cca tcc cag gag gag atg acc aag         1152
Glu Pro Gln Val Tyr Thr Leu Pro Pro Ser Gln Glu Glu Met Thr Lys
370                 375                 380 aac cag gtc agc ctg acc tgc ctg gtc aaa ggc ttc tac ccc agc gac         1200
Asn Gln Val Ser Leu Thr Cys Leu Val Lys Gly Phe Tyr Pro Ser Asp
385                 390                 395                 400 atc gcc gtg gag tgg gag agc aat ggg cag ccg gag aac aac tac aag         1248
Ile Ala Val Glu Trp Glu Ser Asn Gly Gln Pro Glu Asn Asn Tyr Lys
                405                 410                 415 acc acg cct ccc gtg ctg gac tcc gac ggc tcc ttc ttc ctc tac agc         1296
Thr Thr Pro Pro Val Leu Asp Ser Asp Gly Ser Phe Phe Leu Tyr Ser
            420                 425                 430 agg cta acc gtg gac aag agc agg tgg cag gag ggg aat gtc ttc tca         1344
Arg Leu Thr Val Asp Lys Ser Arg Trp Gln Glu Gly Asn Val Phe Ser
        435                 440                 445 tgc tcc gtg atg cat gag gct ctg cac aac cac tac aca cag aag agc         1392
Cys Ser Val Met His Glu Ala Leu His Asn His Tyr Thr Gln Lys Ser
450                 455                 460 ctc tcc ctg tct ctg ggt aaa gga tcc gct gtg cta ccc caa gaa gag         1440
Leu Ser Leu Ser Leu Gly Lys Gly Ser Ala Val Leu Pro Gln Glu Glu
465                 470                 475                 480 gaa gga tca ggg ggt ggg caa ctg gta act gaa gtc acc aag aaa gaa         1488
Glu Gly Ser Gly Gly Gly Gln Leu Val Thr Glu Val Thr Lys Lys Glu
                485                 490                 495 gat tcc tgc cag ctg ggc tac tcg gcc ggt ccc tgc atg gga atg acc         1536
Asp Ser Cys Gln Leu Gly Tyr Ser Ala Gly Pro Cys Met Gly Met Thr
            500                 505                 510 agc agg tat ttc tat aat ggt aca tcc atg gcc tgt gag act ttc cag         1584
Ser Arg Tyr Phe Tyr Asn Gly Thr Ser Met Ala Cys Glu Thr Phe Gln
        515                 520                 525 tac ggc ggc tgc atg ggc aac ggt aac aac ttc gtc aca gaa aag gag         1632
Tyr Gly Gly Cys Met Gly Asn Gly Asn Asn Phe Val Thr Glu Lys Glu
530                 535                 540 tgt ctg cag acc tgc cga act gtg gcg gcc tgc aat ctc ccc ata gtc         1680
Cys Leu Gln Thr Cys Arg Thr Val Ala Ala Cys Asn Leu Pro Ile Val
545                 550                 555                 560 cgg ggc ccc tgc cga gcc ttc atc cag ctc tgg gca ttt gat gct gtc         1728
Arg Gly Pro Cys Arg Ala Phe Ile Gln Leu Trp Ala Phe Asp Ala Val
                565                 570                 575 aag ggg aag tgc gtc ctc ttc ccc tac ggg ggc tgc cag ggc aac ggg         1776
Lys Gly Lys Cys Val Leu Phe Pro Tyr Gly Gly Cys Gln Gly Asn Gly
            580                 585                 590 aac aag ttc tac tca gag aag gag tgc aga gag tac tgc ggt gtc cct         1824
Asn Lys Phe Tyr Ser Glu Lys Glu Cys Arg Glu Tyr Cys Gly Val Pro
        595                 600                 605 ggt gat ggt gat gag gag ctg ctg cgc ttc tcc aac                         1860
Gly Asp Gly Asp Glu Glu Leu Leu Arg Phe Ser Asn
610                 615                 620

<210> SEQ ID NO 8
<211> LENGTH: 620
<212> TYPE: PRT
<213> ORGANISM: Artificial Sequence
<220> FEATURE:
```

<223> OTHER INFORMATION: Synthetic Antibody fusion protein F1024S-D1D2

<400> SEQUENCE: 8

```
Met Asp Trp Leu Trp Asn Leu Leu Phe Leu Met Val Val Ala Gln Ser
1               5                   10                  15

Ala Gln Ala Gln Ile Gln Leu Val Gln Ser Gly Pro Glu Leu Lys Lys
            20                  25                  30

Pro Gly Glu Ser Val Lys Ile Ser Cys Lys Ala Ser Gly Tyr Thr Phe
        35                  40                  45

Thr Asp Tyr Ala Met Asn Trp Val Lys Gln Ala Pro Gly Asn Gly Leu
    50                  55                  60

Lys Trp Met Gly Trp Ile Asn Thr Gln Thr Gly Lys Pro Thr Tyr Ala
65                  70                  75                  80

Asp Asp Phe Lys Gln Arg Phe Val Phe Ser Leu Glu Thr Ser Ala Ser
                85                  90                  95

Thr Ala Tyr Leu Gln Ile Asn Asn Leu Asn Ile Glu Asp Thr Ala Thr
            100                 105                 110

Tyr Phe Cys Thr Arg Ser Thr Phe Tyr Tyr Ser Ser Tyr Ile Tyr Gly
        115                 120                 125

Trp Tyr Phe Asp Phe Trp Gly Pro Gly Thr Met Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Lys Thr
    210                 215                 220

Tyr Thr Cys Asn Val Asp His Lys Pro Ser Asn Thr Lys Val Asp Lys
225                 230                 235                 240

Arg Val Glu Ser Lys Tyr Gly Pro Pro Gly Pro Ser Gly Pro Ala Pro
                245                 250                 255

Glu Phe Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser Gln Glu Asp Pro Glu Val Gln Phe Asn Trp Tyr Val Asp
    290                 295                 300

Gly Val Glu Val His Asn Ala Lys Thr Lys Pro Arg Glu Glu Gln Phe
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
            340                 345                 350

Pro Ser Ser Ile Glu Lys Thr Ile Ser Lys Ala Lys Gly Gln Pro Arg
        355                 360                 365

Glu Pro Gln Val Tyr Thr Leu Pro Pro Ser Gln Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
```

```
                405                 410                 415
Thr Thr Pro Pro Val Leu Asp Ser Asp Gly Ser Phe Phe Leu Tyr Ser
            420                 425                 430

Arg Leu Thr Val Asp Lys Ser Arg Trp Gln Glu Gly Asn Val Phe Ser
            435                 440                 445

Cys Ser Val Met His Glu Ala Leu His Asn His Tyr Thr Gln Lys Ser
        450                 455                 460

Leu Ser Leu Ser Leu Gly Lys Gly Ser Ala Val Leu Pro Gln Glu Glu
465                 470                 475                 480

Glu Gly Ser Gly Gly Gln Leu Val Thr Glu Val Thr Lys Lys Glu
                485                 490                 495

Asp Ser Cys Gln Leu Gly Tyr Ser Ala Gly Pro Cys Met Gly Met Thr
            500                 505                 510

Ser Arg Tyr Phe Tyr Asn Gly Thr Ser Met Ala Cys Glu Thr Phe Gln
            515                 520                 525

Tyr Gly Gly Cys Met Gly Asn Gly Asn Asn Phe Val Thr Glu Lys Glu
            530                 535                 540

Cys Leu Gln Thr Cys Arg Thr Val Ala Ala Cys Asn Leu Pro Ile Val
545                 550                 555                 560

Arg Gly Pro Cys Arg Ala Phe Ile Gln Leu Trp Ala Phe Asp Ala Val
                565                 570                 575

Lys Gly Lys Cys Val Leu Phe Pro Tyr Gly Gly Cys Gln Gly Asn Gly
            580                 585                 590

Asn Lys Phe Tyr Ser Glu Lys Glu Cys Arg Glu Tyr Cys Gly Val Pro
            595                 600                 605

Gly Asp Gly Asp Glu Glu Leu Leu Arg Phe Ser Asn
    610                 615                 620

<210> SEQ ID NO 9
<211> LENGTH: 1629
<212> TYPE: DNA
<213> ORGANISM: Artificial Sequence
<220> FEATURE:
<223> OTHER INFORMATION: Synthetic Antibody fusion protein F1024S-D2
<220> FEATURE:
<221> NAME/KEY: CDS
<222> LOCATION: (1)..(1629)

<400> SEQUENCE: 9 atg gat tgg ttg tgg aac ttg cta ttc ctg atg gta gtt gcc caa agt     48
Met Asp Trp Leu Trp Asn Leu Leu Phe Leu Met Val Val Ala Gln Ser
1               5                   10                  15 gct caa gca cag atc cag ttg gta cag tct gga cct gaa ctg aag aag     96
Ala Gln Ala Gln Ile Gln Leu Val Gln Ser Gly Pro Glu Leu Lys Lys
                20                  25                  30 cct gga gag tca gtg aag atc tcc tgc aag gct tct ggg tat acc ttc    144
Pro Gly Glu Ser Val Lys Ile Ser Cys Lys Ala Ser Gly Tyr Thr Phe
            35                  40                  45 aca gac tat gca atg aac tgg gtg aaa cag gct cca gga aat ggc ttg    192
Thr Asp Tyr Ala Met Asn Trp Val Lys Gln Ala Pro Gly Asn Gly Leu
        50                  55                  60 aag tgg atg ggc tgg atc aac acc caa act gga aag cca aca tat gcg    240
Lys Trp Met Gly Trp Ile Asn Thr Gln Thr Gly Lys Pro Thr Tyr Ala
65                  70                  75                  80 gat gat ttc aaa caa cgg ttt gtc ttc tct ttg gaa act tct gcc agc    288
Asp Asp Phe Lys Gln Arg Phe Val Phe Ser Leu Glu Thr Ser Ala Ser
                85                  90                  95 act gca tac ttg cag atc aac aac ctc aat att gag gac aca gct aca    336
Thr Ala Tyr Leu Gln Ile Asn Asn Leu Asn Ile Glu Asp Thr Ala Thr
```

-continued

```
            100                 105                 110
tat ttc tgt aca aga tcc act ttt tac tat agc agc tat atc tac ggg      384
Tyr Phe Cys Thr Arg Ser Thr Phe Tyr Tyr Ser Ser Tyr Ile Tyr Gly
            115                 120                 125 tgg tac ttt gac ttc tgg ggc cca gga acc atg gtc acc gtc tcc agc      432
Trp Tyr Phe Asp Phe Trp Gly Pro Gly Thr Met Val Thr Val Ser Ser
130                 135                 140 gct agc acc aag ggc cca tcc gtc ttc ccc ctg gcg ccc tgc tcc agg      480
Ala Ser Thr Lys Gly Pro Ser Val Phe Pro Leu Ala Pro Cys Ser Arg
145                 150                 155                 160 agc acc tcc gag agc aca gcc gcc ctg ggc tgc ctg gtc aag gac tat      528
Ser Thr Ser Glu Ser Thr Ala Ala Leu Gly Cys Leu Val Lys Asp Tyr
                165                 170                 175 ttc ccc gaa ccg gtg acg gtg tcg tgg aac tca ggt gcc ctg acc agc      576
Phe Pro Glu Pro Val Thr Val Ser Trp Asn Ser Gly Ala Leu Thr Ser
            180                 185                 190 ggc gtg cac acc ttc ccg gct gtc cta cag tcc tca gga ctc tac tcc      624
Gly Val His Thr Phe Pro Ala Val Leu Gln Ser Ser Gly Leu Tyr Ser
            195                 200                 205 ctc agc agc gtg gtg acc gtg ccc tcc agc agc ttg ggc acg aag acc      672
Leu Ser Ser Val Val Thr Val Pro Ser Ser Ser Leu Gly Thr Lys Thr
210                 215                 220 tac acc tgc aac gta gat cac aag ccc agc aac acc aag gtg gac aag      720
Tyr Thr Cys Asn Val Asp His Lys Pro Ser Asn Thr Lys Val Asp Lys
225                 230                 235                 240 aga gtt gag tcc aaa tat ggt ccc cca ggc cca tca ggc cca gca cct      768
Arg Val Glu Ser Lys Tyr Gly Pro Pro Gly Pro Ser Gly Pro Ala Pro
                245                 250                 255 gag ttc ctg ggg gga cca tca gtc ttc ctg ttc ccc cca aaa ccc aag      816
Glu Phe Leu Gly Gly Pro Ser Val Phe Leu Phe Pro Pro Lys Pro Lys
            260                 265                 270 gac act ctc atg atc tcc cgg acc cct gag gtc acg tgc gtg gtg gtg      864
Asp Thr Leu Met Ile Ser Arg Thr Pro Glu Val Thr Cys Val Val Val
            275                 280                 285 gac gtg agc cag gaa gac ccc gag gtc cag ttc aac tgg tac gtg gat      912
Asp Val Ser Gln Glu Asp Pro Glu Val Gln Phe Asn Trp Tyr Val Asp
            290                 295                 300 ggc gtg gag gtg cat aat gcc aag aca aag ccg cgg gag gag cag ttc      960
Gly Val Glu Val His Asn Ala Lys Thr Lys Pro Arg Glu Glu Gln Phe
305                 310                 315                 320 aac agc acg tac cgt gtg gtc agc gtc ctc acc gtc ctg cac cag gac     1008
Asn Ser Thr Tyr Arg Val Val Ser Val Leu Thr Val Leu His Gln Asp
                325                 330                 335 tgg ctg aac ggc aag gag tac aag tgc aag gtc tcc aac aaa ggc ctc     1056
Trp Leu Asn Gly Lys Glu Tyr Lys Cys Lys Val Ser Asn Lys Gly Leu
            340                 345                 350 ccg tcc tcc atc gag aaa acc atc tcc aaa gcc aaa ggg cag ccc cga     1104
Pro Ser Ser Ile Glu Lys Thr Ile Ser Lys Ala Lys Gly Gln Pro Arg
            355                 360                 365 gag cca cag gtg tac acc ctg ccc cca tcc cag gag gag atg acc aag     1152
Glu Pro Gln Val Tyr Thr Leu Pro Pro Ser Gln Glu Glu Met Thr Lys
            370                 375                 380 aac cag gtc agc ctg acc tgc ctg gtc aaa ggc ttc tac ccc agc gac     1200
Asn Gln Val Ser Leu Thr Cys Leu Val Lys Gly Phe Tyr Pro Ser Asp
385                 390                 395                 400 atc gcc gtg gag tgg gag agc aat ggg cag ccg gag aac aac tac aag     1248
Ile Ala Val Glu Trp Glu Ser Asn Gly Gln Pro Glu Asn Asn Tyr Lys
                405                 410                 415 acc acg cct ccc gtg ctg gac tcc gac ggc tcc ttc ttc ctc tac agc     1296
Thr Thr Pro Pro Val Leu Asp Ser Asp Gly Ser Phe Phe Leu Tyr Ser
```

```
                     420                 425                 430
agg cta acc gtg gac aag agc agg tgg cag gag ggg aat gtc ttc tca      1344
Arg Leu Thr Val Asp Lys Ser Arg Trp Gln Glu Gly Asn Val Phe Ser
        435                 440                 445 tgc tcc gtg atg cat gag gct ctg cac aac cac tac aca cag aag agc      1392
Cys Ser Val Met His Glu Ala Leu His Asn His Tyr Thr Gln Lys Ser
450                 455                 460 ctc tcc ctg tct ctg ggt aaa gga tcc act gtg gcg gcc tgc aat ctc      1440
Leu Ser Leu Ser Leu Gly Lys Gly Ser Thr Val Ala Ala Cys Asn Leu
465                 470                 475                 480 ccc ata gtc cgg ggc ccc tgc cga gcc ttc atc cag ctc tgg gca ttt      1488
Pro Ile Val Arg Gly Pro Cys Arg Ala Phe Ile Gln Leu Trp Ala Phe
            485                 490                 495 gat gct gtc aag ggg aag tgc gtc ctc ttc ccc tac ggg ggc tgc cag      1536
Asp Ala Val Lys Gly Lys Cys Val Leu Phe Pro Tyr Gly Gly Cys Gln
                500                 505                 510 ggc aac ggg aac aag ttc tac tca gag aag gag tgc aga gag tac tgc      1584
Gly Asn Gly Asn Lys Phe Tyr Ser Glu Lys Glu Cys Arg Glu Tyr Cys
            515                 520                 525 ggt gtc cct ggt gat ggt gat gag gag ctg ctg cgc ttc tcc aac          1629
Gly Val Pro Gly Asp Gly Asp Glu Glu Leu Leu Arg Phe Ser Asn
    530                 535                 540

<210> SEQ ID NO 10
<211> LENGTH: 543
<212> TYPE: PRT
<213> ORGANISM: Artificial Sequence
<220> FEATURE:
<223> OTHER INFORMATION: Synthetic Antibody fusion protein F1024S-D2

<400> SEQUENCE: 10

Met Asp Trp Leu Trp Asn Leu Leu Phe Leu Met Val Val Ala Gln Ser
1               5                   10                  15

Ala Gln Ala Gln Ile Gln Leu Val Gln Ser Gly Pro Glu Leu Lys Lys
            20                  25                  30

Pro Gly Glu Ser Val Lys Ile Ser Cys Lys Ala Ser Gly Tyr Thr Phe
        35                  40                  45

Thr Asp Tyr Ala Met Asn Trp Val Lys Gln Ala Pro Gly Asn Gly Leu
    50                  55                  60

Lys Trp Met Gly Trp Ile Asn Thr Gln Thr Gly Lys Pro Thr Tyr Ala
65                  70                  75                  80

Asp Asp Phe Lys Gln Arg Phe Val Phe Ser Leu Glu Thr Ser Ala Ser
                85                  90                  95

Thr Ala Tyr Leu Gln Ile Asn Asn Leu Asn Ile Glu Asp Thr Ala Thr
            100                 105                 110

Tyr Phe Cys Thr Arg Ser Thr Tyr Tyr Ser Ser Tyr Ile Tyr Gly
        115                 120                 125

Trp Tyr Phe Asp Phe Trp Gly Pro Gly Thr Met Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Lys Thr
```

```
                210                 215                 220
Tyr Thr Cys Asn Val Asp His Lys Pro Ser Asn Thr Lys Val Asp Lys
225                 230                 235                 240

Arg Val Glu Ser Lys Tyr Gly Pro Pro Gly Pro Ser Gly Pro Ala Pro
                245                 250                 255

Glu Phe Leu Gly Gly Pro Ser Val Phe Leu Phe Pro Pro Lys Pro Lys
        260                 265                 270

Asp Thr Leu Met Ile Ser Arg Thr Pro Glu Val Thr Cys Val Val Val
            275                 280                 285

Asp Val Ser Gln Glu Asp Pro Glu Val Gln Phe Asn Trp Tyr Val Asp
290                 295                 300

Gly Val Glu Val His Asn Ala Lys Thr Lys Pro Arg Glu Glu Gln Phe
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
            340                 345                 350

Pro Ser Ser Ile Glu Lys Thr Ile Ser Lys Ala Lys Gly Gln Pro Arg
        355                 360                 365

Glu Pro Gln Val Tyr Thr Leu Pro Pro Ser Gln Glu Glu Met Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Arg Leu Thr Val Asp Lys Ser Arg Trp Gln Glu Gly Asn Val Phe Ser
        435                 440                 445

Cys Ser Val Met His Glu Ala Leu His Asn His Tyr Thr Gln Lys Ser
450                 455                 460

Leu Ser Leu Ser Leu Gly Lys Gly Ser Thr Val Ala Ala Cys Asn Leu
465                 470                 475                 480

Pro Ile Val Arg Gly Pro Cys Arg Ala Phe Ile Gln Leu Trp Ala Phe
                485                 490                 495

Asp Ala Val Lys Gly Lys Cys Val Leu Phe Pro Tyr Gly Gly Cys Gln
            500                 505                 510

Gly Asn Gly Asn Lys Phe Tyr Ser Glu Lys Glu Cys Arg Glu Tyr Cys
        515                 520                 525

Gly Val Pro Gly Asp Gly Asp Glu Glu Leu Leu Arg Phe Ser Asn
530                 535                 540

<210> SEQ ID NO 11
<211> LENGTH: 1629
<212> TYPE: DNA
<213> ORGANISM: Artificial Sequence
<220> FEATURE:
<223> OTHER INFORMATION: Synthetic Antibody fusion protein F1024S-D2(3)
<220> FEATURE:
<221> NAME/KEY: CDS
<222> LOCATION: (1)..(1629)

<400> SEQUENCE: 11 atg gat tgg ttg tgg aac ttg cta ttc ctg atg gta gtt gcc caa agt    48
Met Asp Trp Leu Trp Asn Leu Leu Phe Leu Met Val Val Ala Gln Ser
1               5                   10                  15 gct caa gca cag atc cag ttg gta cag tct gga cct gaa ctg aag aag    96
```

```
                Ala Gln Ala Gln Ile Gln Leu Val Gln Ser Gly Pro Glu Leu Lys Lys
                         20                  25                  30 cct gga gag tca gtg aag atc tcc tgc aag gct tct ggg tat acc ttc          144
Pro Gly Glu Ser Val Lys Ile Ser Cys Lys Ala Ser Gly Tyr Thr Phe
         35                  40                  45 aca gac tat gca atg aac tgg gtg aaa cag gct cca gga aat ggc ttg          192
Thr Asp Tyr Ala Met Asn Trp Val Lys Gln Ala Pro Gly Asn Gly Leu
 50                  55                  60 aag tgg atg ggc tgg atc aac acc caa act gga aag cca aca tat gcg          240
Lys Trp Met Gly Trp Ile Asn Thr Gln Thr Gly Lys Pro Thr Tyr Ala
 65                  70                  75                  80 gat gat ttc aaa caa cgg ttt gtc ttc tct ttg gaa act tct gcc agc          288
Asp Asp Phe Lys Gln Arg Phe Val Phe Ser Leu Glu Thr Ser Ala Ser
                 85                  90                  95 act gca tac ttg cag atc aac aac ctc aat att gag gac aca gct aca          336
Thr Ala Tyr Leu Gln Ile Asn Asn Leu Asn Ile Glu Asp Thr Ala Thr
            100                 105                 110 tat ttc tgt aca aga tcc act ttt tac tat agc agc tat atc tac ggg          384
Tyr Phe Cys Thr Arg Ser Thr Phe Tyr Tyr Ser Ser Tyr Ile Tyr Gly
            115                 120                 125 tgg tac ttt gac ttc tgg ggc cca gga acc atg gtc acc gtc tcc agc          432
Trp Tyr Phe Asp Phe Trp Gly Pro Gly Thr Met Val Thr Val Ser Ser
130                 135                 140 gct agc acc aag ggc cca tcc gtc ttc ccc ctg gcg ccc tgc tcc agg          480
Ala Ser Thr Lys Gly Pro Ser Val Phe Pro Leu Ala Pro Cys Ser Arg
145                 150                 155                 160 agc acc tcc gag agc aca gcc gcc ctg ggc tgc ctg gtc aag gac tat          528
Ser Thr Ser Glu Ser Thr Ala Ala Leu Gly Cys Leu Val Lys Asp Tyr
                165                 170                 175 ttc ccc gaa ccg gtg acg gtg tcg tgg aac tca ggt gcc ctg acc agc          576
Phe Pro Glu Pro Val Thr Val Ser Trp Asn Ser Gly Ala Leu Thr Ser
            180                 185                 190 ggc gtg cac acc ttc ccg gct gtc cta cag tcc tca gga ctc tac tcc          624
Gly Val His Thr Phe Pro Ala Val Leu Gln Ser Ser Gly Leu Tyr Ser
            195                 200                 205 ctc agc agc gtg gtg acc gtg ccc tcc agc agc ttg ggc acg aag acc          672
Leu Ser Ser Val Val Thr Val Pro Ser Ser Ser Leu Gly Thr Lys Thr
            210                 215                 220 tac acc tgc aac gta gat cac aag ccc agc aac acc aag gtg gac aag          720
Tyr Thr Cys Asn Val Asp His Lys Pro Ser Asn Thr Lys Val Asp Lys
225                 230                 235                 240 aga gtt gag tcc aaa tat ggt ccc cca ggc cca tca ggc cca gca cct          768
Arg Val Glu Ser Lys Tyr Gly Pro Pro Gly Pro Ser Gly Pro Ala Pro
                245                 250                 255 gag ttc ctg ggg gga cca tca gtc ttc ctg ttc ccc cca aaa ccc aag          816
Glu Phe Leu Gly Gly Pro Ser Val Phe Leu Phe Pro Pro Lys Pro Lys
            260                 265                 270 gac act ctc atg atc tcc cgg acc cct gag gtc acg tgc gtg gtg gtg          864
Asp Thr Leu Met Ile Ser Arg Thr Pro Glu Val Thr Cys Val Val Val
            275                 280                 285 gac gtg agc cag gaa gac ccc gag gtc cag ttc aac tgg tac gtg gat          912
Asp Val Ser Gln Glu Asp Pro Glu Val Gln Phe Asn Trp Tyr Val Asp
            290                 295                 300 ggc gtg gag gtg cat aat gcc aag aca aag ccg cgg gag gag cag ttc          960
Gly Val Glu Val His Asn Ala Lys Thr Lys Pro Arg Glu Glu Gln Phe
305                 310                 315                 320 aac agc acg tac cgt gtg gtc agc gtc ctc acc gtc ctg cac cag gac         1008
Asn Ser Thr Tyr Arg Val Val Ser Val Leu Thr Val Leu His Gln Asp
                325                 330                 335 tgg ctg aac ggc aag gag tac aag tgc aag gtc tcc aac aaa ggc ctc         1056
```

```
Trp Leu Asn Gly Lys Glu Tyr Lys Cys Lys Val Ser Asn Lys Gly Leu
                340                 345                 350 ccg tcc tcc atc gag aaa acc atc tcc aaa gcc aaa ggg cag ccc cga      1104
Pro Ser Ser Ile Glu Lys Thr Ile Ser Lys Ala Lys Gly Gln Pro Arg
            355                 360                 365 gag cca cag gtg tac acc ctg ccc cca tcc cag gag gag atg acc aag      1152
Glu Pro Gln Val Tyr Thr Leu Pro Pro Ser Gln Glu Glu Met Thr Lys
        370                 375                 380 aac cag gtc agc ctg acc tgc ctg gtc aaa ggc ttc tac ccc agc gac      1200
Asn Gln Val Ser Leu Thr Cys Leu Val Lys Gly Phe Tyr Pro Ser Asp
385                 390                 395                 400 atc gcc gtg gag tgg gag agc aat ggg cag ccg gag aac aac tac aag      1248
Ile Ala Val Glu Trp Glu Ser Asn Gly Gln Pro Glu Asn Asn Tyr Lys
                405                 410                 415 acc acg cct ccc gtg ctg gac tcc gac ggc tcc ttc ttc ctc tac agc      1296
Thr Thr Pro Pro Val Leu Asp Ser Asp Gly Ser Phe Phe Leu Tyr Ser
            420                 425                 430 agg cta acc gtg gac aag agc agg tgg cag gag ggg aat gtc ttc tca      1344
Arg Leu Thr Val Asp Lys Ser Arg Trp Gln Glu Gly Asn Val Phe Ser
        435                 440                 445 tgc tcc gtg atg cat gag gct ctg cac aac cac tac aca cag aag agc      1392
Cys Ser Val Met His Glu Ala Leu His Asn His Tyr Thr Gln Lys Ser
450                 455                 460 ctc tcc ctg tct ctg ggt aaa gga tcc act gtg gcg gcc tgc aat cta      1440
Leu Ser Leu Ser Leu Gly Lys Gly Ser Thr Val Ala Ala Cys Asn Leu
465                 470                 475                 480 cca ata gtc agc ggc ccc tgc cga gcc ttc atc aag ctc tgg gca ttt      1488
Pro Ile Val Ser Gly Pro Cys Arg Ala Phe Ile Lys Leu Trp Ala Phe
                485                 490                 495 gat gct gtc aag ggg aag tgc gtc ctc ttc ccc tac ggg ggc tgc cag      1536
Asp Ala Val Lys Gly Lys Cys Val Leu Phe Pro Tyr Gly Gly Cys Gln
            500                 505                 510 ggc aac ggg aac aag ttc gac tca gag aag gag tgc aga gag tac tgc      1584
Gly Asn Gly Asn Lys Phe Asp Ser Glu Lys Glu Cys Arg Glu Tyr Cys
        515                 520                 525 ggt gtc cct ggt gat ggt gat gag gag ctg ctg cgc ttc tcc aac          1629
Gly Val Pro Gly Asp Gly Asp Glu Glu Leu Leu Arg Phe Ser Asn
530                 535                 540

<210> SEQ ID NO 12
<211> LENGTH: 543
<212> TYPE: PRT
<213> ORGANISM: Artificial Sequence
<220> FEATURE:
<223> OTHER INFORMATION: Synthetic Antibody fusion protein F1024S-D2(3)

<400> SEQUENCE: 12

Met Asp Trp Leu Trp Asn Leu Leu Phe Leu Met Val Val Ala Gln Ser
1               5                   10                  15

Ala Gln Ala Gln Ile Gln Leu Val Gln Ser Gly Pro Glu Leu Lys Lys
            20                  25                  30

Pro Gly Glu Ser Val Lys Ile Ser Cys Lys Ala Ser Gly Tyr Thr Phe
        35                  40                  45

Thr Asp Tyr Ala Met Asn Trp Val Lys Gln Ala Pro Gly Asn Gly Leu
    50                  55                  60

Lys Trp Met Gly Trp Ile Asn Thr Gln Thr Gly Lys Pro Thr Tyr Ala
65                  70                  75                  80

Asp Asp Phe Lys Gln Arg Phe Val Phe Ser Leu Glu Thr Ser Ala Ser
                85                  90                  95

Thr Ala Tyr Leu Gln Ile Asn Asn Leu Asn Ile Glu Asp Thr Ala Thr
```

-continued

```
                100                 105                 110
Tyr Phe Cys Thr Arg Ser Thr Phe Tyr Ser Ser Tyr Ile Tyr Gly
            115                 120                 125
Trp Tyr Phe Asp Phe Trp Gly Pro Gly Thr Met Val Thr Val Ser Ser
        130                 135                 140
Ala Ser Thr Lys Gly Pro Ser Val Phe Pro Leu Ala Pro Cys Ser Arg
145                 150                 155                 160
Ser Thr Ser Glu Ser Thr Ala Ala Leu Gly Cys Leu Val Lys Asp Tyr
                165                 170                 175
Phe Pro Glu Pro Val Thr Val Ser Trp Asn Ser Gly Ala Leu Thr Ser
                180                 185                 190
Gly Val His Thr Phe Pro Ala Val Leu Gln Ser Ser Gly Leu Tyr Ser
            195                 200                 205
Leu Ser Ser Val Val Thr Val Pro Ser Ser Ser Leu Gly Thr Lys Thr
            210                 215                 220
Tyr Thr Cys Asn Val Asp His Lys Pro Ser Asn Thr Lys Val Asp Lys
225                 230                 235                 240
Arg Val Glu Ser Lys Tyr Gly Pro Pro Gly Pro Ser Gly Pro Ala Pro
                245                 250                 255
Glu Phe Leu Gly Gly Pro Ser Val Phe Leu Phe Pro Pro Lys Pro Lys
                260                 265                 270
Asp Thr Leu Met Ile Ser Arg Thr Pro Glu Val Thr Cys Val Val Val
            275                 280                 285
Asp Val Ser Gln Glu Asp Pro Glu Val Gln Phe Asn Trp Tyr Val Asp
            290                 295                 300
Gly Val Glu Val His Asn Ala Lys Thr Lys Pro Arg Glu Glu Gln Phe
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Gly Leu
            340                 345                 350
Pro Ser Ser Ile Glu Lys Thr Ile Ser Lys Ala Lys Gly Gln Pro Arg
            355                 360                 365
Glu Pro Gln Val Tyr Thr Leu Pro Pro Ser Gln Glu Glu Met Thr Lys
        370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
                420                 425                 430
Arg Leu Thr Val Asp Lys Ser Arg Trp Gln Glu Gly Asn Val Phe Ser
            435                 440                 445
Cys Ser Val Met His Glu Ala Leu His Asn His Tyr Thr Gln Lys Ser
            450                 455                 460
Leu Ser Leu Ser Leu Gly Lys Gly Ser Thr Val Ala Ala Cys Asn Leu
465                 470                 475                 480
Pro Ile Val Ser Gly Pro Cys Arg Ala Phe Ile Lys Leu Trp Ala Phe
                485                 490                 495
Asp Ala Val Lys Gly Lys Cys Val Leu Phe Pro Tyr Gly Gly Cys Gln
                500                 505                 510
Gly Asn Gly Asn Lys Phe Asp Ser Glu Lys Glu Cys Arg Glu Tyr Cys
            515                 520                 525
```

```
                                      Gly Val Pro Gly Asp Gly Asp Glu Leu Leu Arg Phe Ser Asn
                                          530             535                 540

<210> SEQ ID NO 13
<211> LENGTH: 1737
<212> TYPE: DNA
<213> ORGANISM: Artificial Sequence
<220> FEATURE:
<223> OTHER INFORMATION: Synthetic Antibody fusion protein
      F1024D-SLPI(D1D2)
<220> FEATURE:
<221> NAME/KEY: CDS
<222> LOCATION: (1)..(1737)

<400> SEQUENCE: 13 atg gat tgg ttg tgg aac ttg cta ttc ctg atg gta gtt gcc caa agt        48
Met Asp Trp Leu Trp Asn Leu Leu Phe Leu Met Val Val Ala Gln Ser
1               5                   10                  15 gct caa gca cag atc cag ttg gta cag tct gga cct gaa ctg aag aag        96
Ala Gln Ala Gln Ile Gln Leu Val Gln Ser Gly Pro Glu Leu Lys Lys
            20                  25                  30 cct gga gag tca gtg aag atc tcc tgc aag gct tct ggg tat acc ttc       144
Pro Gly Glu Ser Val Lys Ile Ser Cys Lys Ala Ser Gly Tyr Thr Phe
        35                  40                  45 aca gac tat gca atg aac tgg gtg aaa cag gct cca gga aat ggc ttg       192
Thr Asp Tyr Ala Met Asn Trp Val Lys Gln Ala Pro Gly Asn Gly Leu
    50                  55                  60 aag tgg atg ggc tgg atc aac acc caa act gga aag cca aca tat gcg       240
Lys Trp Met Gly Trp Ile Asn Thr Gln Thr Gly Lys Pro Thr Tyr Ala
65                  70                  75                  80 gat gat ttc aaa caa cgg ttt gtc ttc tct ttg gaa act tct gcc agc       288
Asp Asp Phe Lys Gln Arg Phe Val Phe Ser Leu Glu Thr Ser Ala Ser
                85                  90                  95 act gca tac ttg cag atc aac aac ctc aat att gag gac aca gct aca       336
Thr Ala Tyr Leu Gln Ile Asn Asn Leu Asn Ile Glu Asp Thr Ala Thr
            100                 105                 110 tat ttc tgt aca aga tcc act ttt tac tat agc agc tat atc tac ggg       384
Tyr Phe Cys Thr Arg Ser Thr Phe Tyr Tyr Ser Ser Tyr Ile Tyr Gly
        115                 120                 125 tgg tac ttt gac ttc tgg ggc cca gga acc atg gtc acc gtc tcc agc       432
Trp Tyr Phe Asp Phe Trp Gly Pro Gly Thr Met Val Thr Val Ser Ser
    130                 135                 140 gct agc acc aag ggc cca tcc gtc ttc ccc ctg gcg ccc tgc tcc agg       480
Ala Ser Thr Lys Gly Pro Ser Val Phe Pro Leu Ala Pro Cys Ser Arg
145                 150                 155                 160 agc acc tcc gag agc aca gcc gcc ctg ggc tgc ctg gtc aag gac tat       528
Ser Thr Ser Glu Ser Thr Ala Ala Leu Gly Cys Leu Val Lys Asp Tyr
                165                 170                 175 ttc ccc gaa ccg gtg acg gtg tcg tgg aac tca ggt gcc ctg acc agc       576
Phe Pro Glu Pro Val Thr Val Ser Trp Asn Ser Gly Ala Leu Thr Ser
            180                 185                 190 ggc gtg cac acc ttc ccg gct gtc cta cag tcc tca gga ctc tac tcc       624
Gly Val His Thr Phe Pro Ala Val Leu Gln Ser Ser Gly Leu Tyr Ser
        195                 200                 205 ctc agc agc gtg gtg acc gtg ccc tcc agc agc ttg ggc acg aag acc       672
Leu Ser Ser Val Val Thr Val Pro Ser Ser Ser Leu Gly Thr Lys Thr
    210                 215                 220 tac acc tgc aac gta gat cac aag ccc agc aac acc aag gtg gac aag       720
Tyr Thr Cys Asn Val Asp His Lys Pro Ser Asn Thr Lys Val Asp Lys
225                 230                 235                 240 aga gtt gag tcc aaa tat ggt ccc cca tgc cca tca tgc cca gca cct       768
Arg Val Glu Ser Lys Tyr Gly Pro Pro Cys Pro Ser Cys Pro Ala Pro
                245                 250                 255
```

```
gag ttc ctg ggg gga cca tca gtc ttc ctg ttc ccc cca aaa ccc aag      816
Glu Phe Leu Gly Gly Pro Ser Val Phe Leu Phe Pro Pro Lys Pro Lys
            260                 265                 270 gac act ctc atg atc tcc cgg acc cct gag gtc acg tgc gtg gtg gtg      864
Asp Thr Leu Met Ile Ser Arg Thr Pro Glu Val Thr Cys Val Val Val
        275                 280                 285 gac gtg agc cag gaa gac ccc gag gtc cag ttc aac tgg tac gtg gat      912
Asp Val Ser Gln Glu Asp Pro Glu Val Gln Phe Asn Trp Tyr Val Asp
    290                 295                 300 ggc gtg gag gtg cat aat gcc aag aca aag ccg cgg gag gag cag ttc      960
Gly Val Glu Val His Asn Ala Lys Thr Lys Pro Arg Glu Glu Gln Phe
305                 310                 315                 320 aac agc acg tac cgt gtg gtc agc gtc ctc acc gtc ctg cac cag gac     1008
Asn Ser Thr Tyr Arg Val Val Ser Val Leu Thr Val Leu His Gln Asp
                325                 330                 335 tgg ctg aac ggc aag gag tac aag tgc aag gtc tcc aac aaa ggc ctc     1056
Trp Leu Asn Gly Lys Glu Tyr Lys Cys Lys Val Ser Asn Lys Gly Leu
            340                 345                 350 ccg tcc tcc atc gag aaa acc atc tcc aaa gcc aaa ggg cag ccc cga     1104
Pro Ser Ser Ile Glu Lys Thr Ile Ser Lys Ala Lys Gly Gln Pro Arg
        355                 360                 365 gag cca cag gtg tac acc ctg ccc cca tcc cag gag gag atg acc aag     1152
Glu Pro Gln Val Tyr Thr Leu Pro Pro Ser Gln Glu Glu Met Thr Lys
    370                 375                 380 aac cag gtc agc ctg acc tgc ctg gtc aaa ggc ttc tac ccc agc gac     1200
Asn Gln Val Ser Leu Thr Cys Leu Val Lys Gly Phe Tyr Pro Ser Asp
385                 390                 395                 400 atc gcc gtg gag tgg gag agc aat ggg cag ccg gag aac aac tac aag     1248
Ile Ala Val Glu Trp Glu Ser Asn Gly Gln Pro Glu Asn Asn Tyr Lys
                405                 410                 415 acc acg cct ccc gtg ctg gac tcc gac ggc tcc ttc ttc ctc tac agc     1296
Thr Thr Pro Pro Val Leu Asp Ser Asp Gly Ser Phe Phe Leu Tyr Ser
            420                 425                 430 agg cta acc gtg gac aag agc agg tgg cag gag ggg aat gtc ttc tca     1344
Arg Leu Thr Val Asp Lys Ser Arg Trp Gln Glu Gly Asn Val Phe Ser
        435                 440                 445 tgc tcc gtg atg cat gag gct ctg cac aac cac tac aca cag aag agc     1392
Cys Ser Val Met His Glu Ala Leu His Asn His Tyr Thr Gln Lys Ser
    450                 455                 460 ctc tcc ctg tct ctg ggt aaa gga tct gga aag tcc ttc aaa gct gga     1440
Leu Ser Leu Ser Leu Gly Lys Gly Ser Gly Lys Ser Phe Lys Ala Gly
465                 470                 475                 480 gtc tgt cct cct aag aaa tct gcc cag tgc ctt aga tac aag aaa cct     1488
Val Cys Pro Pro Lys Lys Ser Ala Gln Cys Leu Arg Tyr Lys Lys Pro
                485                 490                 495 gag tgc cag agt gac tgg cag tgt cca ggg aag aag aga tgt tgt cct     1536
Glu Cys Gln Ser Asp Trp Gln Cys Pro Gly Lys Lys Arg Cys Cys Pro
            500                 505                 510 gac act tgt ggc atc aaa tgc ctg gat cct gtt gac acc cca aac cca     1584
Asp Thr Cys Gly Ile Lys Cys Leu Asp Pro Val Asp Thr Pro Asn Pro
        515                 520                 525 aca agg agg aag cct ggg aag tgc cca gtg act tat ggc caa tgt ttg     1632
Thr Arg Arg Lys Pro Gly Lys Cys Pro Val Thr Tyr Gly Gln Cys Leu
    530                 535                 540 atg ctt aac ccc ccc aat ttc tgt gag atg gat ggc cag tgc aag cgt     1680
Met Leu Asn Pro Pro Asn Phe Cys Glu Met Asp Gly Gln Cys Lys Arg
545                 550                 555                 560 gac ttg aag tgt tgc atg ggc atg tgt ggg aaa tcc tgc gtt tcc cct     1728
Asp Leu Lys Cys Cys Met Gly Met Cys Gly Lys Ser Cys Val Ser Pro
                565                 570                 575
```

```
gtg aaa gct                                                      1737
Val Lys Ala <210> SEQ ID NO 14
<211> LENGTH: 579
<212> TYPE: PRT
<213> ORGANISM: Artificial Sequence
<220> FEATURE:
<223> OTHER INFORMATION: Synthetic Antibody fusion protein
      F1024D-SLPI(D1D2)

<400> SEQUENCE: 14

Met Asp Trp Leu Trp Asn Leu Leu Phe Leu Met Val Val Ala Gln Ser
1               5                   10                  15

Ala Gln Ala Gln Ile Gln Leu Val Gln Ser Gly Pro Glu Leu Lys Lys
            20                  25                  30

Pro Gly Glu Ser Val Lys Ile Ser Cys Lys Ala Ser Gly Tyr Thr Phe
        35                  40                  45

Thr Asp Tyr Ala Met Asn Trp Val Lys Gln Ala Pro Gly Asn Gly Leu
    50                  55                  60

Lys Trp Met Gly Trp Ile Asn Thr Gln Thr Gly Lys Pro Thr Tyr Ala
65                  70                  75                  80

Asp Asp Phe Lys Gln Arg Phe Val Phe Ser Leu Glu Thr Ser Ala Ser
                85                  90                  95

Thr Ala Tyr Leu Gln Ile Asn Asn Leu Asn Ile Glu Asp Thr Ala Thr
            100                 105                 110

Tyr Phe Cys Thr Arg Ser Thr Phe Tyr Tyr Ser Ser Tyr Ile Tyr Gly
        115                 120                 125

Trp Tyr Phe Asp Phe Trp Gly Pro Gly Thr Met Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Lys Thr
    210                 215                 220

Tyr Thr Cys Asn Val Asp His Lys Pro Ser Asn Thr Lys Val Asp Lys
225                 230                 235                 240

Arg Val Glu Ser Lys Tyr Gly Pro Pro Cys Pro Ser Cys Pro Ala Pro
                245                 250                 255

Glu Phe Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser Gln Glu Asp Pro Glu Val Gln Phe Asn Trp Tyr Val Asp
    290                 295                 300

Gly Val Glu Val His Asn Ala Lys Thr Lys Pro Arg Glu Glu Gln Phe
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
            340                 345                 350
```

```
Pro Ser Ser Ile Glu Lys Thr Ile Ser Lys Ala Lys Gly Gln Pro Arg
            355                 360                 365

Glu Pro Gln Val Tyr Thr Leu Pro Pro Ser Gln Glu Glu Met Thr Lys
        370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Arg Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Leu Gly Lys Gly Ser Gly Lys Ser Phe Lys Ala Gly
465                 470                 475                 480

Val Cys Pro Pro Lys Lys Ser Ala Gln Cys Leu Arg Tyr Lys Lys Pro
                485                 490                 495

Glu Cys Gln Ser Asp Trp Gln Cys Pro Gly Lys Lys Arg Cys Cys Pro
            500                 505                 510

Asp Thr Cys Gly Ile Lys Cys Leu Asp Pro Val Asp Thr Pro Asn Pro
        515                 520                 525

Thr Arg Arg Lys Pro Gly Lys Cys Pro Val Thr Tyr Gly Gln Cys Leu
    530                 535                 540

Met Leu Asn Pro Pro Asn Phe Cys Glu Met Asp Gly Gln Cys Lys Arg
545                 550                 555                 560

Asp Leu Lys Cys Cys Met Gly Met Cys Gly Lys Ser Cys Val Ser Pro
                565                 570                 575

Val Lys Ala

<210> SEQ ID NO 15
<211> LENGTH: 1569
<212> TYPE: DNA
<213> ORGANISM: Artificial Sequence
<220> FEATURE:
<223> OTHER INFORMATION: Synthetic Antibody fusion protein
      F1024D-SLPI(D2)
<220> FEATURE:
<221> NAME/KEY: CDS
<222> LOCATION: (1)..(1569)

<400> SEQUENCE: 15 atg gat tgg ttg tgg aac ttg cta ttc ctg atg gta gtt gcc caa agt      48
Met Asp Trp Leu Trp Asn Leu Leu Phe Leu Met Val Val Ala Gln Ser
1               5                   10                  15 gct caa gca cag atc cag ttg gta cag tct gga cct gaa ctg aag aag      96
Ala Gln Ala Gln Ile Gln Leu Val Gln Ser Gly Pro Glu Leu Lys Lys
            20                  25                  30 cct gga gag tca gtg aag atc tcc tgc aag gct tct ggg tat acc ttc     144
Pro Gly Glu Ser Val Lys Ile Ser Cys Lys Ala Ser Gly Tyr Thr Phe
        35                  40                  45 aca gac tat gca atg aac tgg gtg aaa cag gct cca gga aat ggc ttg     192
Thr Asp Tyr Ala Met Asn Trp Val Lys Gln Ala Pro Gly Asn Gly Leu
    50                  55                  60 aag tgg atg ggc tgg atc aac acc caa act gga aag cca aca tat gcg     240
Lys Trp Met Gly Trp Ile Asn Thr Gln Thr Gly Lys Pro Thr Tyr Ala
65                  70                  75                  80 gat gat ttc aaa caa cgg ttt gtc ttc tct ttg gaa act tct gcc agc     288
```

-continued

```
Asp Asp Phe Lys Gln Arg Phe Val Phe Ser Leu Glu Thr Ser Ala Ser
             85                  90                  95 act gca tac ttg cag atc aac aac ctc aat att gag gac aca gct aca      336
Thr Ala Tyr Leu Gln Ile Asn Asn Leu Asn Ile Glu Asp Thr Ala Thr
                100                 105                 110 tat ttc tgt aca aga tcc act ttt tac tat agc agc tat atc tac ggg      384
Tyr Phe Cys Thr Arg Ser Thr Phe Tyr Tyr Ser Ser Tyr Ile Tyr Gly
            115                 120                 125 tgg tac ttt gac ttc tgg ggc cca gga acc atg gtc acc gtc tcc agc      432
Trp Tyr Phe Asp Phe Trp Gly Pro Gly Thr Met Val Thr Val Ser Ser
        130                 135                 140 gct agc acc aag ggc cca tcc gtc ttc ccc ctg gcg ccc tgc tcc agg      480
Ala Ser Thr Lys Gly Pro Ser Val Phe Pro Leu Ala Pro Cys Ser Arg
145                 150                 155                 160 agc acc tcc gag agc aca gcc gcc ctg ggc tgc ctg gtc aag gac tat      528
Ser Thr Ser Glu Ser Thr Ala Ala Leu Gly Cys Leu Val Lys Asp Tyr
                165                 170                 175 ttc ccc gaa ccg gtg acg gtg tcg tgg aac tca ggt gcc ctg acc agc      576
Phe Pro Glu Pro Val Thr Val Ser Trp Asn Ser Gly Ala Leu Thr Ser
            180                 185                 190 ggc gtg cac acc ttc ccg gct gtc cta cag tcc tca gga ctc tac tcc      624
Gly Val His Thr Phe Pro Ala Val Leu Gln Ser Ser Gly Leu Tyr Ser
        195                 200                 205 ctc agc agc gtg gtg acc gtg ccc tcc agc agc ttg ggc acg aag acc      672
Leu Ser Ser Val Val Thr Val Pro Ser Ser Ser Leu Gly Thr Lys Thr
    210                 215                 220 tac acc tgc aac gta gat cac aag ccc agc aac acc aag gtg gac aag      720
Tyr Thr Cys Asn Val Asp His Lys Pro Ser Asn Thr Lys Val Asp Lys
225                 230                 235                 240 aga gtt gag tcc aaa tat ggt ccc cca tgc cca tca tgc cca gca cct      768
Arg Val Glu Ser Lys Tyr Gly Pro Pro Cys Pro Ser Cys Pro Ala Pro
                245                 250                 255 gag ttc ctg ggg gga cca tca gtc ttc ctg ttc ccc cca aaa ccc aag      816
Glu Phe Leu Gly Gly Pro Ser Val Phe Leu Phe Pro Pro Lys Pro Lys
            260                 265                 270 gac act ctc atg atc tcc cgg acc cct gag gtc acg tgc gtg gtg gtg      864
Asp Thr Leu Met Ile Ser Arg Thr Pro Glu Val Thr Cys Val Val Val
        275                 280                 285 gac gtg agc cag gaa gac ccc gag gtc cag ttc aac tgg tac gtg gat      912
Asp Val Ser Gln Glu Asp Pro Glu Val Gln Phe Asn Trp Tyr Val Asp
    290                 295                 300 ggc gtg gag gtg cat aat gcc aag aca aag ccg cgg gag gag cag ttc      960
Gly Val Glu Val His Asn Ala Lys Thr Lys Pro Arg Glu Glu Gln Phe
305                 310                 315                 320 aac agc acg tac cgt gtg gtc agc gtc ctc acc gtc ctg cac cag gac     1008
Asn Ser Thr Tyr Arg Val Val Ser Val Leu Thr Val Leu His Gln Asp
                325                 330                 335 tgg ctg aac ggc aag gag tac aag tgc aag gtc tcc aac aaa ggc ctc     1056
Trp Leu Asn Gly Lys Glu Tyr Lys Cys Lys Val Ser Asn Lys Gly Leu
            340                 345                 350 ccg tcc tcc atc gag aaa acc atc tcc aaa gcc aaa ggg cag ccc cga     1104
Pro Ser Ser Ile Glu Lys Thr Ile Ser Lys Ala Lys Gly Gln Pro Arg
        355                 360                 365 gag cca cag gtg tac acc ctg ccc cca tcc cag gag gag atg acc aag     1152
Glu Pro Gln Val Tyr Thr Leu Pro Pro Ser Gln Glu Glu Met Thr Lys
    370                 375                 380 aac cag gtc agc ctg acc tgc ctg gtc aaa ggc ttc tac ccc agc gac     1200
Asn Gln Val Ser Leu Thr Cys Leu Val Lys Gly Phe Tyr Pro Ser Asp
385                 390                 395                 400 atc gcc gtg gag tgg gag agc aat ggg cag ccg gag aac aac tac aag     1248
```

```
Ile Ala Val Glu Trp Glu Ser Asn Gly Gln Pro Glu Asn Asn Tyr Lys
            405                 410                 415 acc acg cct ccc gtg ctg gac tcc gac ggc tcc ttc ttc ctc tac agc    1296
Thr Thr Pro Pro Val Leu Asp Ser Asp Gly Ser Phe Phe Leu Tyr Ser
            420                 425                 430 agg cta acc gtg gac aag agc agg tgg cag gag ggg aat gtc ttc tca    1344
Arg Leu Thr Val Asp Lys Ser Arg Trp Gln Glu Gly Asn Val Phe Ser
            435                 440                 445 tgc tcc gtg atg cat gag gct ctg cac aac cac tac aca cag aag agc    1392
Cys Ser Val Met His Glu Ala Leu His Asn His Tyr Thr Gln Lys Ser
        450                 455                 460 ctc tcc ctg tct ctg ggt aaa gga tct agg agg aag cct ggg aag tgc    1440
Leu Ser Leu Ser Leu Gly Lys Gly Ser Arg Arg Lys Pro Gly Lys Cys
465                 470                 475                 480 cca gtg act tat ggc caa tgt ttg atg ctt aac ccc ccc aat ttc tgc    1488
Pro Val Thr Tyr Gly Gln Cys Leu Met Leu Asn Pro Pro Asn Phe Cys
                485                 490                 495 gag atg gat ggc cag tgc aag cgt gac ttg aag tgt tgc atg ggc atg    1536
Glu Met Asp Gly Gln Cys Lys Arg Asp Leu Lys Cys Cys Met Gly Met
            500                 505                 510 tgt ggg aaa tcc tgc gtt tcc cct gtg aaa gct                        1569
Cys Gly Lys Ser Cys Val Ser Pro Val Lys Ala
        515                 520

<210> SEQ ID NO 16
<211> LENGTH: 523
<212> TYPE: PRT
<213> ORGANISM: Artificial Sequence
<220> FEATURE:
<223> OTHER INFORMATION: Synthetic Antibody fusion protein
      F1024D-SLPI(D2)

<400> SEQUENCE: 16

Met Asp Trp Leu Trp Asn Leu Leu Phe Leu Met Val Val Ala Gln Ser
1               5                   10                  15

Ala Gln Ala Gln Ile Gln Leu Val Gln Ser Gly Pro Glu Leu Lys Lys
            20                  25                  30

Pro Gly Glu Ser Val Lys Ile Ser Cys Lys Ala Ser Tyr Thr Phe
        35                  40                  45

Thr Asp Tyr Ala Met Asn Trp Val Lys Gln Ala Pro Gly Asn Gly Leu
    50                  55                  60

Lys Trp Met Gly Trp Ile Asn Thr Gln Thr Gly Lys Pro Thr Tyr Ala
65                  70                  75                  80

Asp Asp Phe Lys Gln Arg Phe Val Phe Ser Leu Glu Thr Ser Ala Ser
                85                  90                  95

Thr Ala Tyr Leu Gln Ile Asn Asn Leu Asn Ile Glu Asp Thr Ala Thr
            100                 105                 110

Tyr Phe Cys Thr Arg Ser Thr Phe Tyr Tyr Ser Ser Tyr Ile Tyr Gly
        115                 120                 125

Trp Tyr Phe Asp Phe Trp Gly Pro Gly Thr Met Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205
```

Leu Ser Ser Val Val Thr Val Pro Ser Ser Leu Gly Thr Lys Thr
    210                 215                 220

Tyr Thr Cys Asn Val Asp His Lys Pro Ser Asn Thr Lys Val Asp Lys
225                 230                 235                 240

Arg Val Glu Ser Lys Tyr Gly Pro Pro Cys Pro Ser Cys Pro Ala Pro
                245                 250                 255

Glu Phe Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
            275                 280                 285

Asp Val Ser Gln Glu Asp Pro Glu Val Gln Phe Asn Trp Tyr Val Asp
        290                 295                 300

Gly Val Glu Val His Asn Ala Lys Thr Lys Pro Arg Glu Glu Gln Phe
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
            340                 345                 350

Pro Ser Ser Ile Glu Lys Thr Ile Ser Lys Ala Lys Gly Gln Pro Arg
        355                 360                 365

Glu Pro Gln Val Tyr Thr Leu Pro Pro Ser Gln Glu Glu Met Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Arg Leu Thr Val Asp Lys Ser Arg Trp Gln Glu Gly Asn Val Phe Ser
        435                 440                 445

Cys Ser Val Met His Glu Ala Leu His Asn His Tyr Thr Gln Lys Ser
450                 455                 460

Leu Ser Leu Ser Leu Gly Lys Gly Ser Arg Arg Lys Pro Gly Lys Cys
465                 470                 475                 480

Pro Val Thr Tyr Gly Gln Cys Leu Met Leu Asn Pro Pro Asn Phe Cys
                485                 490                 495

Glu Met Asp Gly Gln Cys Lys Arg Asp Leu Lys Cys Cys Met Gly Met
            500                 505                 510

Cys Gly Lys Ser Cys Val Ser Pro Val Lys Ala
        515                 520

<210> SEQ ID NO 17
<211> LENGTH: 1737
<212> TYPE: DNA
<213> ORGANISM: Artificial Sequence
<220> FEATURE:
<223> OTHER INFORMATION: Synthetic Antibody fusion protein
      F1024S-SLPI(D1D2)
<220> FEATURE:
<221> NAME/KEY: CDS
<222> LOCATION: (1)..(1737)

<400> SEQUENCE: 17 atg gat tgg ttg tgg aac ttg cta ttc ctg atg gta gtt gcc caa agt     48
Met Asp Trp Leu Trp Asn Leu Leu Phe Leu Met Val Val Ala Gln Ser
1               5                   10                  15 gct caa gca cag atc cag ttg gta cag tct gga cct gaa ctg aag aag     96

-continued

| | | | | | | | | | | | | | | |
|---|---|---|---|---|---|---|---|---|---|---|---|---|---|---|
| Ala | Gln | Ala | Gln | Ile | Gln | Leu | Val | Gln | Ser | Gly | Pro | Glu | Leu | Lys | Lys |
| | | 20 | | | | | 25 | | | | | 30 | | | |

```
cct gga gag tca gtg aag atc tcc tgc aag gct tct ggg tat acc ttc      144
Pro Gly Glu Ser Val Lys Ile Ser Cys Lys Ala Ser Gly Tyr Thr Phe
        35                  40                  45 aca gac tat gca atg aac tgg gtg aaa cag gct cca gga aat ggc ttg      192
Thr Asp Tyr Ala Met Asn Trp Val Lys Gln Ala Pro Gly Asn Gly Leu
 50                  55                  60 aag tgg atg ggc tgg atc aac acc caa act gga aag cca aca tat gcg      240
Lys Trp Met Gly Trp Ile Asn Thr Gln Thr Gly Lys Pro Thr Tyr Ala
 65                  70                  75                  80 gat gat ttc aaa caa cgg ttt gtc ttc tct ttg gaa act tct gcc agc      288
Asp Asp Phe Lys Gln Arg Phe Val Phe Ser Leu Glu Thr Ser Ala Ser
             85                  90                  95 act gca tac ttg cag atc aac aac ctc aat att gag gac aca gct aca      336
Thr Ala Tyr Leu Gln Ile Asn Asn Leu Asn Ile Glu Asp Thr Ala Thr
        100                 105                 110 tat ttc tgt aca aga tcc act ttt tac tat agc agc tat atc tac ggg      384
Tyr Phe Cys Thr Arg Ser Thr Phe Tyr Tyr Ser Ser Tyr Ile Tyr Gly
        115                 120                 125 tgg tac ttt gac ttc tgg ggc cca gga acc atg gtc acc gtc tcc agc      432
Trp Tyr Phe Asp Phe Trp Gly Pro Gly Thr Met Val Thr Val Ser Ser
130                 135                 140 gct agc acc aag ggc cca tcc gtc ttc ccc ctg gcg ccc tgc tcc agg      480
Ala Ser Thr Lys Gly Pro Ser Val Phe Pro Leu Ala Pro Cys Ser Arg
145                 150                 155                 160 agc acc tcc gag agc aca gcc gcc ctg ggc tgc ctg gtc aag gac tat      528
Ser Thr Ser Glu Ser Thr Ala Ala Leu Gly Cys Leu Val Lys Asp Tyr
             165                 170                 175 ttc ccc gaa ccg gtg acg gtg tcg tgg aac tca ggt gcc ctg acc agc      576
Phe Pro Glu Pro Val Thr Val Ser Trp Asn Ser Gly Ala Leu Thr Ser
        180                 185                 190 ggc gtg cac acc ttc ccg gct gtc cta cag tcc tca gga ctc tac tcc      624
Gly Val His Thr Phe Pro Ala Val Leu Gln Ser Ser Gly Leu Tyr Ser
        195                 200                 205 ctc agc agc gtg gtg acc gtg ccc tcc agc agc ttg ggc acg aag acc      672
Leu Ser Ser Val Val Thr Val Pro Ser Ser Ser Leu Gly Thr Lys Thr
210                 215                 220 tac acc tgc aac gta gat cac aag ccc agc aac acc aag gtg gac aag      720
Tyr Thr Cys Asn Val Asp His Lys Pro Ser Asn Thr Lys Val Asp Lys
225                 230                 235                 240 aga gtt gag tcc aaa tat ggt ccc cca ggc cca tca ggc cca gca cct      768
Arg Val Glu Ser Lys Tyr Gly Pro Pro Gly Pro Ser Gly Pro Ala Pro
             245                 250                 255 gag ttc ctg ggg gga cca tca gtc ttc ctg ttc ccc cca aaa ccc aag      816
Glu Phe Leu Gly Gly Pro Ser Val Phe Leu Phe Pro Pro Lys Pro Lys
        260                 265                 270 gac act ctc atg atc tcc cgg acc cct gag gtc acg tgc gtg gtg gtg      864
Asp Thr Leu Met Ile Ser Arg Thr Pro Glu Val Thr Cys Val Val Val
        275                 280                 285 gac gtg agc cag gaa gac ccc gag gtc cag ttc aac tgg tac gtg gat      912
Asp Val Ser Gln Glu Asp Pro Glu Val Gln Phe Asn Trp Tyr Val Asp
290                 295                 300 ggc gtg gag gtg cat aat gcc aag aca aag ccg cgg gag gag cag ttc      960
Gly Val Glu Val His Asn Ala Lys Thr Lys Pro Arg Glu Glu Gln Phe
305                 310                 315                 320 aac agc acg tac cgt gtg gtc agc gtc ctc acc gtc ctg cac cag gac     1008
Asn Ser Thr Tyr Arg Val Val Ser Val Leu Thr Val Leu His Gln Asp
             325                 330                 335 tgg ctg aac ggc aag gag tac aag tgc aag gtc tcc aac aaa ggc ctc     1056
```

```
                                                                        1104
ccg tcc tcc atc gag aaa acc atc tcc aaa gcc aaa ggg cag ccc cga
Pro Ser Ser Ile Glu Lys Thr Ile Ser Lys Ala Lys Gly Gln Pro Arg
        355                 360                 365

1152
gag cca cag gtg tac acc ctg ccc cca tcc cag gag gag atg acc aag
Glu Pro Gln Val Tyr Thr Leu Pro Pro Ser Gln Glu Glu Met Thr Lys
    370                 375                 380

1200
aac cag gtc agc ctg acc tgc ctg gtc aaa ggc ttc tac ccc agc gac
Asn Gln Val Ser Leu Thr Cys Leu Val Lys Gly Phe Tyr Pro Ser Asp
385                 390                 395                 400

1248
atc gcc gtg gag tgg gag agc aat ggg cag ccg gag aac aac tac aag
Ile Ala Val Glu Trp Glu Ser Asn Gly Gln Pro Glu Asn Asn Tyr Lys
                405                 410                 415

1296
acc acg cct ccc gtg ctg gac tcc gac ggc tcc ttc ttc ctc tac agc
Thr Thr Pro Pro Val Leu Asp Ser Asp Gly Ser Phe Phe Leu Tyr Ser
        420                 425                 430

1344
agg cta acc gtg gac aag agc agg tgg cag gag ggg aat gtc ttc tca
Arg Leu Thr Val Asp Lys Ser Arg Trp Gln Glu Gly Asn Val Phe Ser
    435                 440                 445

1392
tgc tcc gtg atg cat gag gct ctg cac aac cac tac aca cag aag agc
Cys Ser Val Met His Glu Ala Leu His Asn His Tyr Thr Gln Lys Ser
450                 455                 460

1440
ctc tcc ctg tct ctg ggt aaa gga tct gga aag tcc ttc aaa gct gga
Leu Ser Leu Ser Leu Gly Lys Gly Ser Gly Lys Ser Phe Lys Ala Gly
465                 470                 475                 480

1488
gtc tgt cct cct aag aaa tct gcc cag tgc ctt aga tac aag aaa cct
Val Cys Pro Pro Lys Lys Ser Ala Gln Cys Leu Arg Tyr Lys Lys Pro
                485                 490                 495

1536
gag tgc cag agt gac tgg cag tgt cca ggg aag aag aga tgt tgt cct
Glu Cys Gln Ser Asp Trp Gln Cys Pro Gly Lys Lys Arg Cys Cys Pro
        500                 505                 510

1584
gac act tgt ggc atc aaa tgc ctg gat cct gtt gac acc cca aac cca
Asp Thr Cys Gly Ile Lys Cys Leu Asp Pro Val Asp Thr Pro Asn Pro
    515                 520                 525

1632
aca agg agg aag cct ggg aag tgc cca gtg act tat ggc caa tgt ttg
Thr Arg Arg Lys Pro Gly Lys Cys Pro Val Thr Tyr Gly Gln Cys Leu
530                 535                 540

1680
atg ctt aac ccc ccc aat ttc tgt gag atg gat ggc cag tgc aag cgt
Met Leu Asn Pro Pro Asn Phe Cys Glu Met Asp Gly Gln Cys Lys Arg
545                 550                 555                 560

1728
gac ttg aag tgt tgc atg ggc atg tgt ggg aaa tcc tgc gtt tcc cct
Asp Leu Lys Cys Cys Met Gly Met Cys Gly Lys Ser Cys Val Ser Pro
                565                 570                 575

1737
gtg aaa gct
Val Lys Ala

<210> SEQ ID NO 18
<211> LENGTH: 579
<212> TYPE: PRT
<213> ORGANISM: Artificial Sequence
<220> FEATURE:
<223> OTHER INFORMATION: Synthetic Antibody fusion protein
      F1024S-SLPI(D1D2)

<400> SEQUENCE: 18

Met Asp Trp Leu Trp Asn Leu Leu Phe Leu Met Val Val Ala Gln Ser
1               5                   10                  15

Ala Gln Ala Gln Ile Gln Leu Val Gln Ser Gly Pro Glu Leu Lys Lys
            20                  25                  30

Pro Gly Glu Ser Val Lys Ile Ser Cys Lys Ala Ser Gly Tyr Thr Phe
```

-continued

```
              35                  40                  45
Thr Asp Tyr Ala Met Asn Trp Val Lys Gln Ala Pro Gly Asn Gly Leu
 50                  55                  60

Lys Trp Met Gly Trp Ile Asn Thr Gln Thr Gly Lys Pro Thr Tyr Ala
 65                  70                  75                  80

Asp Asp Phe Lys Gln Arg Phe Val Phe Ser Leu Glu Thr Ser Ala Ser
                 85                  90                  95

Thr Ala Tyr Leu Gln Ile Asn Asn Leu Asn Ile Glu Asp Thr Ala Thr
                100                 105                 110

Tyr Phe Cys Thr Arg Ser Thr Phe Tyr Ser Ser Tyr Ile Tyr Gly
            115                 120                 125

Trp Tyr Phe Asp Phe Trp Gly Pro Gly Thr Met Val Thr Val Ser Ser
130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
                180                 185                 190

Gly Val His Thr Phe Pro Ala Val Leu Gln Ser Ser Gly Leu Tyr Ser
            195                 200                 205

Leu Ser Ser Val Val Thr Val Pro Ser Ser Ser Leu Gly Thr Lys Thr
            210                 215                 220

Tyr Thr Cys Asn Val Asp His Lys Pro Ser Asn Thr Lys Val Asp Lys
225                 230                 235                 240

Arg Val Glu Ser Lys Tyr Gly Pro Pro Gly Pro Ser Gly Pro Ala Pro
                245                 250                 255

Glu Phe Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
            275                 280                 285

Asp Val Ser Gln Glu Asp Pro Glu Val Gln Phe Asn Trp Tyr Val Asp
290                 295                 300

Gly Val Glu Val His Asn Ala Lys Thr Lys Pro Arg Glu Glu Gln Phe
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
            340                 345                 350

Pro Ser Ser Ile Glu Lys Thr Ile Ser Lys Ala Lys Gly Gln Pro Arg
            355                 360                 365

Glu Pro Gln Val Tyr Thr Leu Pro Pro Ser Gln Glu Glu Met Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Arg Leu Thr Val Asp Lys Ser Arg Trp Gln Glu Gly Asn Val Phe Ser
            435                 440                 445

Cys Ser Val Met His Glu Ala Leu His Asn His Tyr Thr Gln Lys Ser
450                 455                 460
```

```
Leu Ser Leu Ser Leu Gly Lys Gly Ser Gly Lys Ser Phe Lys Ala Gly
465                 470                 475                 480

Val Cys Pro Pro Lys Ser Ala Gln Cys Leu Arg Tyr Lys Lys Pro
                485                 490                 495

Glu Cys Gln Ser Asp Trp Gln Cys Pro Gly Lys Lys Arg Cys Cys Pro
            500                 505                 510

Asp Thr Cys Gly Ile Lys Cys Leu Asp Pro Val Asp Thr Pro Asn Pro
            515                 520                 525

Thr Arg Arg Lys Pro Gly Lys Cys Pro Val Thr Tyr Gly Gln Cys Leu
            530                 535                 540

Met Leu Asn Pro Pro Asn Phe Cys Glu Met Asp Gly Gln Cys Lys Arg
545                 550                 555                 560

Asp Leu Lys Cys Cys Met Gly Met Cys Gly Lys Ser Cys Val Ser Pro
                565                 570                 575

Val Lys Ala

<210> SEQ ID NO 19
<211> LENGTH: 1569
<212> TYPE: DNA
<213> ORGANISM: Artificial Sequence
<220> FEATURE:
<223> OTHER INFORMATION: Synthetic Antibody fusion protein
      F1024S-SLPI(D2)
<220> FEATURE:
<221> NAME/KEY: CDS
<222> LOCATION: (1)..(1569)

<400> SEQUENCE: 19 atg gat tgg ttg tgg aac ttg cta ttc ctg atg gta gtt gcc caa agt     48
Met Asp Trp Leu Trp Asn Leu Leu Phe Leu Met Val Val Ala Gln Ser
1               5                   10                  15 gct caa gca cag atc cag ttg gta cag tct gga cct gaa ctg aag aag     96
Ala Gln Ala Gln Ile Gln Leu Val Gln Ser Gly Pro Glu Leu Lys Lys
                20                  25                  30 cct gga gag tca gtg aag atc tcc tgc aag gct tct ggg tat acc ttc    144
Pro Gly Glu Ser Val Lys Ile Ser Cys Lys Ala Ser Gly Tyr Thr Phe
            35                  40                  45 aca gac tat gca atg aac tgg gtg aaa cag gct cca gga aat ggc ttg    192
Thr Asp Tyr Ala Met Asn Trp Val Lys Gln Ala Pro Gly Asn Gly Leu
 50                  55                  60 aag tgg atg ggc tgg atc aac acc caa act gga aag cca aca tat gcg    240
Lys Trp Met Gly Trp Ile Asn Thr Gln Thr Gly Lys Pro Thr Tyr Ala
 65                  70                  75                  80 gat gat ttc aaa caa cgg ttt gtc ttc tct ttg gaa act tct gcc agc    288
Asp Asp Phe Lys Gln Arg Phe Val Phe Ser Leu Glu Thr Ser Ala Ser
                85                  90                  95 act gca tac ttg cag atc aac aac ctc aat att gag gac aca gct aca    336
Thr Ala Tyr Leu Gln Ile Asn Asn Leu Asn Ile Glu Asp Thr Ala Thr
            100                 105                 110 tat ttc tgt aca aga tcc act ttt tac tat agc agc tat atc tac ggg    384
Tyr Phe Cys Thr Arg Ser Thr Phe Tyr Tyr Ser Ser Tyr Ile Tyr Gly
        115                 120                 125 tgg tac ttt gac ttc tgg ggc cca gga acc atg gtc acc gtc tcc agc    432
Trp Tyr Phe Asp Phe Trp Gly Pro Gly Thr Met Val Thr Val Ser Ser
    130                 135                 140 gct agc acc aag ggc cca tcc gtc ttc ccc ctg gcg ccc tgc tcc agg    480
Ala Ser Thr Lys Gly Pro Ser Val Phe Pro Leu Ala Pro Cys Ser Arg
145                 150                 155                 160 agc acc tcc gag agc aca gcc gcc ctg ggc tgc ctg gtc aag gac tat    528
Ser Thr Ser Glu Ser Thr Ala Ala Leu Gly Cys Leu Val Lys Asp Tyr
                165                 170                 175
```

| | | |
|---|---|---|
| ttc ccc gaa ccg gtg acg gtg tcg tgg aac tca ggt gcc ctg acc agc<br>Phe Pro Glu Pro Val Thr Val Ser Trp Asn Ser Gly Ala Leu Thr Ser<br>180 185 190 | 576 | |
| ggc gtg cac acc ttc ccg gct gtc cta cag tcc tca gga ctc tac tcc<br>Gly Val His Thr Phe Pro Ala Val Leu Gln Ser Ser Gly Leu Tyr Ser<br>195 200 205 | 624 | |
| ctc agc agc gtg gtg acc gtg ccc tcc agc agc ttg ggc acg aag acc<br>Leu Ser Ser Val Val Thr Val Pro Ser Ser Ser Leu Gly Thr Lys Thr<br>210 215 220 | 672 | |
| tac acc tgc aac gta gat cac aag ccc agc aac acc aag gtg gac aag<br>Tyr Thr Cys Asn Val Asp His Lys Pro Ser Asn Thr Lys Val Asp Lys<br>225 230 235 240 | 720 | |
| aga gtt gag tcc aaa tat ggt ccc cca ggc cca tca ggc cca gca cct<br>Arg Val Glu Ser Lys Tyr Gly Pro Pro Gly Pro Ser Gly Pro Ala Pro<br>245 250 255 | 768 | |
| gag ttc ctg ggg gga cca tca gtc ttc ctg ttc ccc cca aaa ccc aag<br>Glu Phe Leu Gly Gly Pro Ser Val Phe Leu Phe Pro Pro Lys Pro Lys<br>260 265 270 | 816 | |
| gac act ctc atg atc tcc cgg acc cct gag gtc acg tgc gtg gtg gtg<br>Asp Thr Leu Met Ile Ser Arg Thr Pro Glu Val Thr Cys Val Val Val<br>275 280 285 | 864 | |
| gac gtg agc cag gaa gac ccc gag gtc cag ttc aac tgg tac gtg gat<br>Asp Val Ser Gln Glu Asp Pro Glu Val Gln Phe Asn Trp Tyr Val Asp<br>290 295 300 | 912 | |
| ggc gtg gag gtg cat aat gcc aag aca aag ccg cgg gag gag cag ttc<br>Gly Val Glu Val His Asn Ala Lys Thr Lys Pro Arg Glu Glu Gln Phe<br>305 310 315 320 | 960 | |
| aac agc acg tac cgt gtg gtc agc gtc ctc acc gtc ctg cac cag gac<br>Asn Ser Thr Tyr Arg Val Val Ser Val Leu Thr Val Leu His Gln Asp<br>325 330 335 | 1008 | |
| tgg ctg aac ggc aag gag tac aag tgc aag gtc tcc aac aaa ggc ctc<br>Trp Leu Asn Gly Lys Glu Tyr Lys Cys Lys Val Ser Asn Lys Gly Leu<br>340 345 350 | 1056 | |
| ccg tcc tcc atc gag aaa acc atc tcc aaa gcc aaa ggg cag ccc cga<br>Pro Ser Ser Ile Glu Lys Thr Ile Ser Lys Ala Lys Gly Gln Pro Arg<br>355 360 365 | 1104 | |
| gag cca cag gtg tac acc ctg ccc cca tcc cag gag gag atg acc aag<br>Glu Pro Gln Val Tyr Thr Leu Pro Pro Ser Gln Glu Glu Met Thr Lys<br>370 375 380 | 1152 | |
| aac cag gtc agc ctg acc tgc ctg gtc aaa ggc ttc tac ccc agc gac<br>Asn Gln Val Ser Leu Thr Cys Leu Val Lys Gly Phe Tyr Pro Ser Asp<br>385 390 395 400 | 1200 | |
| atc gcc gtg gag tgg gag agc aat ggg cag ccg gag aac aac tac aag<br>Ile Ala Val Glu Trp Glu Ser Asn Gly Gln Pro Glu Asn Asn Tyr Lys<br>405 410 415 | 1248 | |
| acc acg cct ccc gtg ctg gac tcc gac ggc tcc ttc ttc ctc tac agc<br>Thr Thr Pro Pro Val Leu Asp Ser Asp Gly Ser Phe Phe Leu Tyr Ser<br>420 425 430 | 1296 | |
| agg cta acc gtg gac aag agc agg tgg cag gag ggg aat gtc ttc tca<br>Arg Leu Thr Val Asp Lys Ser Arg Trp Gln Glu Gly Asn Val Phe Ser<br>435 440 445 | 1344 | |
| tgc tcc gtg atg cat gag gct ctg cac aac cac tac aca cag aag agc<br>Cys Ser Val Met His Glu Ala Leu His Asn His Tyr Thr Gln Lys Ser<br>450 455 460 | 1392 | |
| ctc tcc ctg tct ctg ggt aaa gga tct agg agg aag cct ggg aag tgc<br>Leu Ser Leu Ser Leu Gly Lys Gly Ser Arg Arg Lys Pro Gly Lys Cys<br>465 470 475 480 | 1440 | |
| cca gtg act tat ggc caa tgt ttg atg ctt aac ccc ccc aat ttc tgt<br>Pro Val Thr Tyr Gly Gln Cys Leu Met Leu Asn Pro Pro Asn Phe Cys<br>485 490 495 | 1488 | |

```
gag atg gat ggc cag tgc aag cgt gac ttg aag tgt tgc atg ggc atg         1536
Glu Met Asp Gly Gln Cys Lys Arg Asp Leu Lys Cys Cys Met Gly Met
            500                 505                 510 tgt ggg aaa tcc tgc gtt tcc cct gtg aaa gct                             1569
Cys Gly Lys Ser Cys Val Ser Pro Val Lys Ala
        515                 520
```

<210> SEQ ID NO 20
<211> LENGTH: 523
<212> TYPE: PRT
<213> ORGANISM: Artificial Sequence
<220> FEATURE:
<223> OTHER INFORMATION: Synthetic Antibody fusion protein
      F1024S-SLPI(D2)

<400> SEQUENCE: 20

```
Met Asp Trp Leu Trp Asn Leu Leu Phe Leu Met Val Val Ala Gln Ser
1               5                   10                  15

Ala Gln Ala Gln Ile Gln Leu Val Gln Ser Gly Pro Glu Leu Lys Lys
            20                  25                  30

Pro Gly Glu Ser Val Lys Ile Ser Cys Lys Ala Ser Gly Tyr Thr Phe
        35                  40                  45

Thr Asp Tyr Ala Met Asn Trp Val Lys Gln Ala Pro Gly Asn Gly Leu
    50                  55                  60

Lys Trp Met Gly Trp Ile Asn Thr Gln Thr Gly Lys Pro Thr Tyr Ala
65                  70                  75                  80

Asp Asp Phe Lys Gln Arg Phe Val Phe Ser Leu Glu Thr Ser Ala Ser
                85                  90                  95

Thr Ala Tyr Leu Gln Ile Asn Asn Leu Asn Ile Glu Asp Thr Ala Thr
            100                 105                 110

Tyr Phe Cys Thr Arg Ser Thr Phe Tyr Tyr Ser Ser Tyr Ile Tyr Gly
        115                 120                 125

Trp Tyr Phe Asp Phe Trp Gly Pro Gly Thr Met Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Lys Thr
    210                 215                 220

Tyr Thr Cys Asn Val Asp His Lys Pro Ser Asn Thr Lys Val Asp Lys
225                 230                 235                 240

Arg Val Glu Ser Lys Tyr Gly Pro Pro Gly Pro Ser Gly Pro Ala Pro
                245                 250                 255

Glu Phe Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser Gln Glu Asp Pro Glu Val Gln Phe Asn Trp Tyr Val Asp
    290                 295                 300

Gly Val Glu Val His Asn Ala Lys Thr Lys Pro Arg Glu Glu Gln Phe
305                 310                 315                 320
```

```
Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
            340                 345                 350

Pro Ser Ser Ile Glu Lys Thr Ile Ser Lys Ala Lys Gly Gln Pro Arg
        355                 360                 365

Glu Pro Gln Val Tyr Thr Leu Pro Pro Ser Gln Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Arg Leu Thr Val Asp Lys Ser Arg Trp Gln Glu Gly Asn Val Phe Ser
        435                 440                 445

Cys Ser Val Met His Glu Ala Leu His Asn His Tyr Thr Gln Lys Ser
    450                 455                 460

Leu Ser Leu Ser Leu Gly Lys Gly Ser Arg Arg Lys Pro Gly Lys Cys
465                 470                 475                 480

Pro Val Thr Tyr Gly Gln Cys Leu Met Leu Asn Pro Asn Phe Cys
                485                 490                 495

Glu Met Asp Gly Gln Cys Lys Arg Asp Leu Lys Cys Cys Met Gly Met
            500                 505                 510

Cys Gly Lys Ser Cys Val Ser Pro Val Lys Ala
        515                 520

<210> SEQ ID NO 21
<211> LENGTH: 705
<212> TYPE: DNA
<213> ORGANISM: Artificial Sequence
<220> FEATURE:
<223> OTHER INFORMATION: Synthetic Antibody fusion protein, F1024
      chimeric antibody light chain
<220> FEATURE:
<221> NAME/KEY: CDS
<222> LOCATION: (1)..(705)

<400> SEQUENCE: 21 atg gag tca cat act agg gtc ttc ata ttc ctg ctg ctc tgg ttg tct        48
Met Glu Ser His Thr Arg Val Phe Ile Phe Leu Leu Leu Trp Leu Ser
1               5                   10                  15 ggt gct gat ggg gac att gtg atg act cag tct ccc aca tcc att tcc        96
Gly Ala Asp Gly Asp Ile Val Met Thr Gln Ser Pro Thr Ser Ile Ser
            20                  25                  30 ata tca gta gga gag agg gtc acc atg aac tgc aag gcc agt cag aat       144
Ile Ser Val Gly Glu Arg Val Thr Met Asn Cys Lys Ala Ser Gln Asn
        35                  40                  45 gtg ggt tct aat gta gac tgg tac caa cag aaa aca ggg cag tct cct       192
Val Gly Ser Asn Val Asp Trp Tyr Gln Gln Lys Thr Gly Gln Ser Pro
    50                  55                  60 aaa ctg ctt atc tac aag gca tcc aac cgg tac act ggc gtc cct gat       240
Lys Leu Leu Ile Tyr Lys Ala Ser Asn Arg Tyr Thr Gly Val Pro Asp
65                  70                  75                  80 cgc ttc aca ggc agt gga tct gga aca gat ttc act ttc acc atc agc       288
Arg Phe Thr Gly Ser Gly Ser Gly Thr Asp Phe Thr Phe Thr Ile Ser
                85                  90                  95 aac atg cag gct gtg gac ctg gct gtt tat tac tgt atg cag tct aac       336
Asn Met Gln Ala Val Asp Leu Ala Val Tyr Tyr Cys Met Gln Ser Asn
            100                 105                 110
```

```
acc aat cct ccg tgg acg ttc ggt gga ggc acc aag ctg gaa ttg aaa      384
Thr Asn Pro Pro Trp Thr Phe Gly Gly Gly Thr Lys Leu Glu Leu Lys
        115                 120                 125 cgt acg gtg gct gca cca tct gtc ttc atc ttc ccg cca tct gat gag      432
Arg Thr Val Ala Ala Pro Ser Val Phe Ile Phe Pro Pro Ser Asp Glu
    130                 135                 140 cag ttg aaa tct gga act gcc tct gtt gtg tgc ctg ctg aat aac ttc      480
Gln Leu Lys Ser Gly Thr Ala Ser Val Val Cys Leu Leu Asn Asn Phe
145                 150                 155                 160 tat ccc aga gag gcc aaa gta cag tgg aag gtg gat aac gcc ctc caa      528
Tyr Pro Arg Glu Ala Lys Val Gln Trp Lys Val Asp Asn Ala Leu Gln
            165                 170                 175 tcg ggt aac tcc cag gag agt gtc aca gag cag gac agc aag gac agc      576
Ser Gly Asn Ser Gln Glu Ser Val Thr Glu Gln Asp Ser Lys Asp Ser
        180                 185                 190 acc tac agc ctc agc agc acc ctg acg ctg agc aaa gca gac tac gag      624
Thr Tyr Ser Leu Ser Ser Thr Leu Thr Leu Ser Lys Ala Asp Tyr Glu
    195                 200                 205 aaa cac aaa gtc tac gcc tgc gaa gtc acc cat cag ggc ctg agc tcg      672
Lys His Lys Val Tyr Ala Cys Glu Val Thr His Gln Gly Leu Ser Ser
210                 215                 220 ccc gtc aca aag agc ttc aac agg gga gag tgt                          705
Pro Val Thr Lys Ser Phe Asn Arg Gly Glu Cys
225                 230                 235

<210> SEQ ID NO 22
<211> LENGTH: 235
<212> TYPE: PRT
<213> ORGANISM: Artificial Sequence
<220> FEATURE:
<223> OTHER INFORMATION: Synthetic Antibody fusion protein, F1024
      chimeric antibody light chain

<400> SEQUENCE: 22

Met Glu Ser His Thr Arg Val Phe Ile Phe Leu Leu Leu Trp Leu Ser
1               5                   10                  15

Gly Ala Asp Gly Asp Ile Val Met Thr Gln Ser Pro Thr Ser Ile Ser
            20                  25                  30

Ile Ser Val Gly Glu Arg Val Thr Met Asn Cys Lys Ala Ser Gln Asn
        35                  40                  45

Val Gly Ser Asn Val Asp Trp Tyr Gln Gln Lys Thr Gly Gln Ser Pro
    50                  55                  60

Lys Leu Leu Ile Tyr Lys Ala Ser Asn Arg Tyr Thr Gly Val Pro Asp
65                  70                  75                  80

Arg Phe Thr Gly Ser Gly Ser Gly Thr Asp Phe Thr Phe Thr Ile Ser
                85                  90                  95

Asn Met Gln Ala Val Asp Leu Ala Val Tyr Tyr Cys Met Gln Ser Asn
            100                 105                 110

Thr Asn Pro Pro Trp Thr Phe Gly Gly Gly Thr Lys Leu Glu Leu Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
            165                 170                 175

Ser Gly Asn Ser Gln Glu Ser Val Thr Glu Gln Asp Ser Lys Asp Ser
        180                 185                 190
```

```
                    Thr Tyr Ser Leu Ser Ser Thr Leu Thr Leu Ser Lys Ala Asp Tyr Glu
                            195                 200                 205

Lys His Lys Val Tyr Ala Cys Glu Val Thr His Gln Gly Leu Ser Ser
                        210                 215                 220

Pro Val Thr Lys Ser Phe Asn Arg Gly Glu Cys
                    225                 230                 235

<210> SEQ ID NO 23
<211> LENGTH: 1614
<212> TYPE: DNA
<213> ORGANISM: Artificial Sequence
<220> FEATURE:
<223> OTHER INFORMATION: Synthetic Antibody fusion protein
      F1031-13S-D2(3)
<220> FEATURE:
<221> NAME/KEY: CDS
<222> LOCATION: (1)..(1614)

<400> SEQUENCE: 23 atg gaa tgt aac tgg ata ctt cct ttt att ctg tcg gta att tca gga      48
Met Glu Cys Asn Trp Ile Leu Pro Phe Ile Leu Ser Val Ile Ser Gly
1               5                   10                  15 gtc tac tca gag gtt cag ctc cag cag tct ggg act gtg ctg gca agg      96
Val Tyr Ser Glu Val Gln Leu Gln Gln Ser Gly Thr Val Leu Ala Arg
                20                  25                  30 cct ggg gct tcc gtg aag atg tcc tgc aag gct tct ggc tac agg tat     144
Pro Gly Ala Ser Val Lys Met Ser Cys Lys Ala Ser Gly Tyr Arg Tyr
            35                  40                  45 acc aac tac tgg ttg cac tgg gta aaa cag agg cct gga cag ggt cta     192
Thr Asn Tyr Trp Leu His Trp Val Lys Gln Arg Pro Gly Gln Gly Leu
        50                  55                  60 gag tgg att ggt gct att tat cct gga aat agt gat tct agc tac aac     240
Glu Trp Ile Gly Ala Ile Tyr Pro Gly Asn Ser Asp Ser Ser Tyr Asn
65                  70                  75                  80 cag aac ttc aag ggc aag gcc aaa ctg act gca gtc aca tcc gcc agc     288
Gln Asn Phe Lys Gly Lys Ala Lys Leu Thr Ala Val Thr Ser Ala Ser
                85                  90                  95 act gcc tac atg gag ctc agc agc ctg aca aat gag gac tct gcg gtc     336
Thr Ala Tyr Met Glu Leu Ser Ser Leu Thr Asn Glu Asp Ser Ala Val
            100                 105                 110 tat tac tgt aca aga tgg ggc cct tat ggc atc tat gct atg gac tac     384
Tyr Tyr Cys Thr Arg Trp Gly Pro Tyr Gly Ile Tyr Ala Met Asp Tyr
        115                 120                 125 tgg ggt caa gga acc tca gtc acc gtc tcc agc gct agc acc aag ggc     432
Trp Gly Gln Gly Thr Ser Val Thr Val Ser Ser Ala Ser Thr Lys Gly
130                 135                 140 cca tcc gtc ttc ccc ctg gcg ccc tgc tcc agg agc acc tcc gag agc     480
Pro Ser Val Phe Pro Leu Ala Pro Cys Ser Arg Ser Thr Ser Glu Ser
145                 150                 155                 160 aca gcc gcc ctg ggc tgc ctg gtc aag gac tat ttc ccc gaa ccg gtg     528
Thr Ala Ala Leu Gly Cys Leu Val Lys Asp Tyr Phe Pro Glu Pro Val
                165                 170                 175 acg gtg tcg tgg aac tca ggt gcc ctg acc agc ggc gtg cac acc ttc     576
Thr Val Ser Trp Asn Ser Gly Ala Leu Thr Ser Gly Val His Thr Phe
            180                 185                 190 ccg gct gtc cta cag tcc tca gga ctc tac tcc ctc agc agc gtg gtg     624
Pro Ala Val Leu Gln Ser Ser Gly Leu Tyr Ser Leu Ser Ser Val Val
        195                 200                 205 acc gtg ccc tcc agc agc ttg ggc acg aag acc tac acc tgc aac gta     672
Thr Val Pro Ser Ser Ser Leu Gly Thr Lys Thr Tyr Thr Cys Asn Val
210                 215                 220 gat cac aag ccc agc aac acc aag gtg gac aag aga gtt gag tcc aaa     720
```

```
Asp His Lys Pro Ser Asn Thr Lys Val Asp Lys Arg Val Glu Ser Lys
225                 230                 235                 240 tat ggt ccc cca ggc cca tca ggc cca gca cct gag ttc ctg ggg gga    768
Tyr Gly Pro Pro Gly Pro Ser Gly Pro Ala Pro Glu Phe Leu Gly Gly
                    245                 250                 255 cca tca gtc ttc ctg ttc ccc cca aaa ccc aag gac act ctc atg atc    816
Pro Ser Val Phe Leu Phe Pro Pro Lys Pro Lys Asp Thr Leu Met Ile
            260                 265                 270 tcc cgg acc cct gag gtc acg tgc gtg gtg gtg gac gtg agc cag gaa    864
Ser Arg Thr Pro Glu Val Thr Cys Val Val Val Asp Val Ser Gln Glu
        275                 280                 285 gac ccc gag gtc cag ttc aac tgg tac gtg gat ggc gtg gag gtg cat    912
Asp Pro Glu Val Gln Phe Asn Trp Tyr Val Asp Gly Val Glu Val His
    290                 295                 300 aat gcc aag aca aag ccg cgg gag gag cag ttc aac agc acg tac cgt    960
Asn Ala Lys Thr Lys Pro Arg Glu Glu Gln Phe Asn Ser Thr Tyr Arg
305                 310                 315                 320 gtg gtc agc gtc ctc acc gtc ctg cac cag gac tgg ctg aac ggc aag   1008
Val Val Ser Val Leu Thr Val Leu His Gln Asp Trp Leu Asn Gly Lys
                    325                 330                 335 gag tac aag tgc aag gtc tcc aac aaa ggc ctc ccg tcc tcc atc gag   1056
Glu Tyr Lys Cys Lys Val Ser Asn Lys Gly Leu Pro Ser Ser Ile Glu
            340                 345                 350 aaa acc atc tcc aaa gcc aaa ggg cag ccc cga gag cca cag gtg tac   1104
Lys Thr Ile Ser Lys Ala Lys Gly Gln Pro Arg Glu Pro Gln Val Tyr
        355                 360                 365 acc ctg ccc cca tcc cag gag gag atg acc aag aac cag gtc agc ctg   1152
Thr Leu Pro Pro Ser Gln Glu Glu Met Thr Lys Asn Gln Val Ser Leu
    370                 375                 380 acc tgc ctg gtc aaa ggc ttc tac ccc agc gac atc gcc gtg gag tgg   1200
Thr Cys Leu Val Lys Gly Phe Tyr Pro Ser Asp Ile Ala Val Glu Trp
385                 390                 395                 400 gag agc aat ggg cag ccg gag aac aac tac aag acc acg cct ccc gtg   1248
Glu Ser Asn Gly Gln Pro Glu Asn Asn Tyr Lys Thr Thr Pro Pro Val
                    405                 410                 415 ctg gac tcc gac ggc tcc ttc ttc ctc tac agc agg cta acc gtg gac   1296
Leu Asp Ser Asp Gly Ser Phe Phe Leu Tyr Ser Arg Leu Thr Val Asp
            420                 425                 430 aag agc agg tgg cag gag ggg aat gtc ttc tca tgc tcc gtg atg cat   1344
Lys Ser Arg Trp Gln Glu Gly Asn Val Phe Ser Cys Ser Val Met His
        435                 440                 445 gag gct ctg cac aac cac tac aca cag aag agc ctc tcc ctg tct ctg   1392
Glu Ala Leu His Asn His Tyr Thr Gln Lys Ser Leu Ser Leu Ser Leu
    450                 455                 460 ggt aaa gga tcc act gtg gcg gcc tgc aat cta cca ata gtc agc ggc   1440
Gly Lys Gly Ser Thr Val Ala Ala Cys Asn Leu Pro Ile Val Ser Gly
465                 470                 475                 480 ccc tgc cga gcc ttc atc aag ctc tgg gca ttt gat gct gtc aag ggg   1488
Pro Cys Arg Ala Phe Ile Lys Leu Trp Ala Phe Asp Ala Val Lys Gly
                    485                 490                 495 aag tgc gtc ctc ttc ccc tac ggg ggc tgc cag ggc aac ggg aac aag   1536
Lys Cys Val Leu Phe Pro Tyr Gly Gly Cys Gln Gly Asn Gly Asn Lys
            500                 505                 510 ttc gac tca gag aag gag tgc aga gag tac tgc ggt gtc cct ggt gat   1584
Phe Asp Ser Glu Lys Glu Cys Arg Glu Tyr Cys Gly Val Pro Gly Asp
        515                 520                 525 ggt gat gag gag ctg ctg cgc ttc tcc aac                           1614
Gly Asp Glu Glu Leu Leu Arg Phe Ser Asn
    530                 535
```

<210> SEQ ID NO 24
<211> LENGTH: 538
<212> TYPE: PRT
<213> ORGANISM: Artificial Sequence
<220> FEATURE:
<223> OTHER INFORMATION: Synthetic Antibody fusion protein
      F1031-13S-D2(3)

<400> SEQUENCE: 24

```
Met Glu Cys Asn Trp Ile Leu Pro Phe Ile Leu Ser Val Ile Ser Gly
1               5                   10                  15

Val Tyr Ser Glu Val Gln Leu Gln Gln Ser Gly Thr Val Leu Ala Arg
            20                  25                  30

Pro Gly Ala Ser Val Lys Met Ser Cys Lys Ala Ser Gly Tyr Arg Tyr
        35                  40                  45

Thr Asn Tyr Trp Leu His Trp Val Lys Gln Arg Pro Gly Gln Gly Leu
    50                  55                  60

Glu Trp Ile Gly Ala Ile Tyr Pro Gly Asn Ser Asp Ser Ser Tyr Asn
65                  70                  75                  80

Gln Asn Phe Lys Gly Lys Ala Lys Leu Thr Ala Val Thr Ser Ala Ser
                85                  90                  95

Thr Ala Tyr Met Glu Leu Ser Ser Leu Thr Asn Glu Asp Ser Ala Val
            100                 105                 110

Tyr Tyr Cys Thr Arg Trp Gly Pro Tyr Gly Ile Tyr Ala Met Asp Tyr
        115                 120                 125

Trp Gly Gln Gly Thr Ser Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Gly Pro Ser Gly Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
```

|  |  |  |  |  |  |  |  |  |  |  |  |
|---|---|---|---|---|---|---|---|---|---|---|---|
| | | 370 | | | | 375 | | | | 380 | |
| Thr | Cys | Leu | Val | Lys | Gly | Phe | Tyr | Pro | Ser | Asp | Ile | Ala | Val | Glu | Trp |
| 385 | | | | | 390 | | | | | 395 | | | | | 400 |

Thr Cys Leu Val Lys Gly Phe Tyr Pro Ser Asp Ile Ala Val Glu Trp
385               390               395               400

Glu Ser Asn Gly Gln Pro Glu Asn Asn Tyr Lys Thr Thr Pro Pro Val
               405               410               415

Leu Asp Ser Asp Gly Ser Phe Phe Leu Tyr Ser Arg Leu Thr Val Asp
               420               425               430

Lys Ser Arg Trp Gln Glu Gly Asn Val Phe Ser Cys Ser Val Met His
               435               440               445

Glu Ala Leu His Asn His Tyr Thr Gln Lys Ser Leu Ser Leu Ser Leu
    450               455               460

Gly Lys Gly Ser Thr Val Ala Ala Cys Asn Leu Pro Ile Val Ser Gly
465               470               475               480

Pro Cys Arg Ala Phe Ile Lys Leu Trp Ala Phe Asp Ala Val Lys Gly
               485               490               495

Lys Cys Val Leu Phe Pro Tyr Gly Gly Cys Gln Gly Asn Gly Asn Lys
           500               505               510

Phe Asp Ser Glu Lys Glu Cys Arg Glu Tyr Cys Gly Val Pro Gly Asp
               515               520               525

Gly Asp Glu Glu Leu Leu Arg Phe Ser Asn
530               535

<210> SEQ ID NO 25
<211> LENGTH: 714
<212> TYPE: DNA
<213> ORGANISM: Artificial Sequence
<220> FEATURE:
<223> OTHER INFORMATION: Synthetic Antibody fusion protein, F1031-13
     chimeric antibody light chain
<220> FEATURE:
<221> NAME/KEY: CDS
<222> LOCATION: (1)..(714)

<400> SEQUENCE: 25

```
atg gag aca gac aca ctc ctg cta tgg gtc ctg ctt ctc tgg gtt cca      48
Met Glu Thr Asp Thr Leu Leu Leu Trp Val Leu Leu Leu Trp Val Pro
1               5                  10                  15 ggt tcc aca ggt gac att gtg ctg acc caa tct cca gct tct ttg gct      96
Gly Ser Thr Gly Asp Ile Val Leu Thr Gln Ser Pro Ala Ser Leu Ala
            20                  25                  30 gtg tct ctg ggg cag agg gcc acc atc tcc tgc aga gcc agc gaa agt     144
Val Ser Leu Gly Gln Arg Ala Thr Ile Ser Cys Arg Ala Ser Glu Ser
        35                  40                  45 gtt gat tat tct ggc att agt ttt atg aac tgg ttc caa cag aaa cca     192
Val Asp Tyr Ser Gly Ile Ser Phe Met Asn Trp Phe Gln Gln Lys Pro
    50                  55                  60 gga cag cca ccc aaa ctc ctc atc tat gct gca tcc aac caa gga tcc     240
Gly Gln Pro Pro Lys Leu Leu Ile Tyr Ala Ala Ser Asn Gln Gly Ser
65                  70                  75                  80 ggg gtc cct gcc agg ttt agt ggc agt ggg tct ggg aca gac ttc agc     288
Gly Val Pro Ala Arg Phe Ser Gly Ser Gly Ser Gly Thr Asp Phe Ser
                85                  90                  95 ctc aac atc cat cct atg gag gag gat gat act gca atg tat ttc tgt     336
Leu Asn Ile His Pro Met Glu Glu Asp Asp Thr Ala Met Tyr Phe Cys
            100                 105                 110 cag cac agt aag gag ctt ccg tac acg ttc gga ggg ggg acc aag ctg     384
Gln His Ser Lys Glu Leu Pro Tyr Thr Phe Gly Gly Gly Thr Lys Leu
        115                 120                 125 gaa atc aaa cgt acg gtg gct gca cca tct gtc ttc atc ttc ccg cca     432
Glu Ile Lys Arg Thr Val Ala Ala Pro Ser Val Phe Ile Phe Pro Pro
```

```
                130               135              140
tct gat gag cag ttg aaa tct gga act gcc tct gtt gtg tgc ctg ctg     480
Ser Asp Glu Gln Leu Lys Ser Gly Thr Ala Ser Val Val Cys Leu Leu
145                 150              155                  160 aat aac ttc tat ccc aga gag gcc aaa gta cag tgg aag gtg gat aac     528
Asn Asn Phe Tyr Pro Arg Glu Ala Lys Val Gln Trp Lys Val Asp Asn
                165              170                  175 gcc ctc caa tcg ggt aac tcc cag gag agt gtc aca gag cag gac agc     576
Ala Leu Gln Ser Gly Asn Ser Gln Glu Ser Val Thr Glu Gln Asp Ser
            180              185                  190 aag gac agc acc tac agc ctc agc agc acc ctg acg ctg agc aaa gca     624
Lys Asp Ser Thr Tyr Ser Leu Ser Ser Thr Leu Thr Leu Ser Lys Ala
        195              200                  205 gac tac gag aaa cac aaa gtc tac gcc tgc gaa gtc acc cat cag ggc     672
Asp Tyr Glu Lys His Lys Val Tyr Ala Cys Glu Val Thr His Gln Gly
    210              215                  220 ctg agc tcg ccc gtc aca aag agc ttc aac agg gga gag tgt             714
Leu Ser Ser Pro Val Thr Lys Ser Phe Asn Arg Gly Glu Cys
225                 230              235
```

<210> SEQ ID NO 26
<211> LENGTH: 238
<212> TYPE: PRT
<213> ORGANISM: Artificial Sequence
<220> FEATURE:
<223> OTHER INFORMATION: Synthetic Antibody fusion protein, F1031-13
      chimeric antibody light chain

<400> SEQUENCE: 26

```
Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Asp Tyr Ser Gly Ile Ser Phe Met Asn Trp Phe Gln Gln Lys Pro
    50                  55                  60

Gly Gln Pro Pro Lys Leu Leu Ile Tyr Ala Ala Ser Asn Gln Gly Ser
65                  70                  75                  80

Gly Val Pro Ala Arg Phe Ser Gly Ser Gly Ser Gly Thr Asp Phe Ser
                85                  90                  95

Leu Asn Ile His Pro Met Glu Glu Asp Asp Thr Ala Met Tyr Phe Cys
            100                 105                 110

Gln His Ser Lys Glu Leu Pro Tyr Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
```

225   230   235

<210> SEQ ID NO 27
<211> LENGTH: 70
<212> TYPE: PRT
<213> ORGANISM: Artificial Sequence
<220> FEATURE:
<223> OTHER INFORMATION: Synthetic peptide F1024S-D2 (R15A)

<400> SEQUENCE: 27

Thr Val Ala Ala Cys Asn Leu Pro Ile Val Arg Gly Pro Cys Ala Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Tyr Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 28
<211> LENGTH: 70
<212> TYPE: PRT
<213> ORGANISM: Artificial Sequence
<220> FEATURE:
<223> OTHER INFORMATION: Synthetic peptide F1024S-D2(R15C)

<400> SEQUENCE: 28

Thr Val Ala Ala Cys Asn Leu Pro Ile Val Arg Gly Pro Cys Cys Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Tyr Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 29
<211> LENGTH: 70
<212> TYPE: PRT
<213> ORGANISM: Artificial Sequence
<220> FEATURE:
<223> OTHER INFORMATION: Synthetic peptide F1024S-D2 (R15D)

<400> SEQUENCE: 29

Thr Val Ala Ala Cys Asn Leu Pro Ile Val Arg Gly Pro Cys Asp Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Tyr Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 30
<211> LENGTH: 70

```
<212> TYPE: PRT
<213> ORGANISM: Artificial Sequence
<220> FEATURE:
<223> OTHER INFORMATION: Synthetic peptide F1024S-D2(R15E)

<400> SEQUENCE: 30

Thr Val Ala Ala Cys Asn Leu Pro Ile Val Arg Gly Pro Cys Glu Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Tyr Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 31
<211> LENGTH: 70
<212> TYPE: PRT
<213> ORGANISM: Artificial Sequence
<220> FEATURE:
<223> OTHER INFORMATION: Synthetic peptide F1024S-D2(R15F)

<400> SEQUENCE: 31

Thr Val Ala Ala Cys Asn Leu Pro Ile Val Arg Gly Pro Cys Phe Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Tyr Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 32
<211> LENGTH: 70
<212> TYPE: PRT
<213> ORGANISM: Artificial Sequence
<220> FEATURE:
<223> OTHER INFORMATION: Synthetic peptide F1024F-D2(R15G)

<400> SEQUENCE: 32

Thr Val Ala Ala Cys Asn Leu Pro Ile Val Arg Gly Pro Cys Gly Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Tyr Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 33
<211> LENGTH: 70
<212> TYPE: PRT
<213> ORGANISM: Artificial Sequence
<220> FEATURE:
<223> OTHER INFORMATION: Synthetic peptide F1024-D2(R15H)
```

```
<400> SEQUENCE: 33

Thr Val Ala Ala Cys Asn Leu Pro Ile Val Arg Gly Pro Cys His Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Tyr Ser Glu
            35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 34
<211> LENGTH: 70
<212> TYPE: PRT
<213> ORGANISM: Artificial Sequence
<220> FEATURE:
<223> OTHER INFORMATION: Synthetic peptide F1024-D2(R15I)

<400> SEQUENCE: 34

Thr Val Ala Ala Cys Asn Leu Pro Ile Val Arg Gly Pro Cys Ile Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Tyr Ser Glu
            35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 35
<211> LENGTH: 70
<212> TYPE: PRT
<213> ORGANISM: Artificial Sequence
<220> FEATURE:
<223> OTHER INFORMATION: Synthetic peptide F1024S-D2 (R15K)

<400> SEQUENCE: 35

Thr Val Ala Ala Cys Asn Leu Pro Ile Val Arg Gly Pro Cys Lys Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Tyr Ser Glu
            35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 36
<211> LENGTH: 70
<212> TYPE: PRT
<213> ORGANISM: Artificial Sequence
<220> FEATURE:
<223> OTHER INFORMATION: Synthetic peptide F1024S-D2(R15L)

<400> SEQUENCE: 36

Thr Val Ala Ala Cys Asn Leu Pro Ile Val Arg Gly Pro Cys Leu Ala
1               5                   10                  15
```

Phe Ile Gln Leu Trp Ala Phe Asp Ala Val Lys Gly Lys Cys Val Leu
                20                  25                  30

Phe Pro Tyr Gly Gly Cys Gln Gly Asn Gly Asn Lys Phe Tyr Ser Glu
            35                  40                  45

Lys Glu Cys Arg Glu Tyr Cys Gly Val Pro Gly Asp Gly Asp Glu Glu
50                  55                  60

Leu Leu Arg Phe Ser Asn
65                  70

<210> SEQ ID NO 37
<211> LENGTH: 70
<212> TYPE: PRT
<213> ORGANISM: Artificial Sequence
<220> FEATURE:
<223> OTHER INFORMATION: Synthetic peptide F1024S-D2(R15M)

<400> SEQUENCE: 37

Thr Val Ala Ala Cys Asn Leu Pro Ile Val Arg Gly Pro Cys Met Ala
1               5                   10                  15

Phe Ile Gln Leu Trp Ala Phe Asp Ala Val Lys Gly Lys Cys Val Leu
                20                  25                  30

Phe Pro Tyr Gly Gly Cys Gln Gly Asn Gly Asn Lys Phe Tyr Ser Glu
            35                  40                  45

Lys Glu Cys Arg Glu Tyr Cys Gly Val Pro Gly Asp Gly Asp Glu Glu
50                  55                  60

Leu Leu Arg Phe Ser Asn
65                  70

<210> SEQ ID NO 38
<211> LENGTH: 70
<212> TYPE: PRT
<213> ORGANISM: Artificial Sequence
<220> FEATURE:
<223> OTHER INFORMATION: Synthetic peptide F1024S-D2(R15N)

<400> SEQUENCE: 38

Thr Val Ala Ala Cys Asn Leu Pro Ile Val Arg Gly Pro Cys Asn Ala
1               5                   10                  15

Phe Ile Gln Leu Trp Ala Phe Asp Ala Val Lys Gly Lys Cys Val Leu
                20                  25                  30

Phe Pro Tyr Gly Gly Cys Gln Gly Asn Gly Asn Lys Phe Tyr Ser Glu
            35                  40                  45

Lys Glu Cys Arg Glu Tyr Cys Gly Val Pro Gly Asp Gly Asp Glu Glu
50                  55                  60

Leu Leu Arg Phe Ser Asn
65                  70

<210> SEQ ID NO 39
<211> LENGTH: 70
<212> TYPE: PRT
<213> ORGANISM: Artificial Sequence
<220> FEATURE:
<223> OTHER INFORMATION: Synthetic peptide F1024S-D2 (R15P)

<400> SEQUENCE: 39

Thr Val Ala Ala Cys Asn Leu Pro Ile Val Arg Gly Pro Cys Pro Ala
1               5                   10                  15

Phe Ile Gln Leu Trp Ala Phe Asp Ala Val Lys Gly Lys Cys Val Leu
                20                  25                  30

Phe Pro Tyr Gly Gly Cys Gln Gly Asn Gly Asn Lys Phe Tyr Ser Glu
            35                  40                  45

```
Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 40
<211> LENGTH: 70
<212> TYPE: PRT
<213> ORGANISM: Artificial Sequence
<220> FEATURE:
<223> OTHER INFORMATION: Synthetic peptide F1024S-D2(R15Q)

<400> SEQUENCE: 40

Thr Val Ala Ala Cys Asn Leu Pro Ile Val Arg Gly Pro Cys Gln Ala
1               5                   10                  15

Phe Ile Gln Leu Trp Ala Phe Asp Ala Val Lys Gly Lys Cys Val Leu
                20                  25                  30

Phe Pro Tyr Gly Gly Cys Gln Gly Asn Gly Asn Lys Phe Tyr Ser Glu
            35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 41
<211> LENGTH: 70
<212> TYPE: PRT
<213> ORGANISM: Artificial Sequence
<220> FEATURE:
<223> OTHER INFORMATION: Synthetic peptide F1024S-D2 (R15S)

<400> SEQUENCE: 41

Thr Val Ala Ala Cys Asn Leu Pro Ile Val Arg Gly Pro Cys Ser Ala
1               5                   10                  15

Phe Ile Gln Leu Trp Ala Phe Asp Ala Val Lys Gly Lys Cys Val Leu
                20                  25                  30

Phe Pro Tyr Gly Gly Cys Gln Gly Asn Gly Asn Lys Phe Tyr Ser Glu
            35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 42
<211> LENGTH: 70
<212> TYPE: PRT
<213> ORGANISM: Artificial Sequence
<220> FEATURE:
<223> OTHER INFORMATION: Synthetic peptide F1024S-D2 (R15T)

<400> SEQUENCE: 42

Thr Val Ala Ala Cys Asn Leu Pro Ile Val Arg Gly Pro Cys Thr Ala
1               5                   10                  15

Phe Ile Gln Leu Trp Ala Phe Asp Ala Val Lys Gly Lys Cys Val Leu
                20                  25                  30

Phe Pro Tyr Gly Gly Cys Gln Gly Asn Gly Asn Lys Phe Tyr Ser Glu
            35                  40                  45

Lys Glu Cys Arg Glu Tyr Cys Gly Val Pro Gly Asp Gly Asp Glu Glu
    50                  55                  60

Leu Leu Arg Phe Ser Asn
```

<210> SEQ ID NO 43
<211> LENGTH: 70
<212> TYPE: PRT
<213> ORGANISM: Artificial Sequence
<220> FEATURE:
<223> OTHER INFORMATION: Synthetic peptide F1024S-D2 (R15V)

<400> SEQUENCE: 43

Thr Val Ala Ala Cys Asn Leu Pro Ile Val Arg Gly Pro Cys Val Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Tyr Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 44
<211> LENGTH: 70
<212> TYPE: PRT
<213> ORGANISM: Artificial Sequence
<220> FEATURE:
<223> OTHER INFORMATION: Synthetic peptide F1024S-D2 (R15W)

<400> SEQUENCE: 44

Thr Val Ala Ala Cys Asn Leu Pro Ile Val Arg Gly Pro Cys Trp Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Tyr Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 45
<211> LENGTH: 70
<212> TYPE: PRT
<213> ORGANISM: Artificial Sequence
<220> FEATURE:
<223> OTHER INFORMATION: Synthetic peptide F1024S-D2 (R15Y)

<400> SEQUENCE: 45

Thr Val Ala Ala Cys Asn Leu Pro Ile Val Arg Gly Pro Cys Tyr Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Tyr Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 46
<211> LENGTH: 70

```
<212> TYPE: PRT
<213> ORGANISM: Artificial Sequence
<220> FEATURE:
<223> OTHER INFORMATION: Synthetic peptide
      F1024S-D2(R11S/R15I/Q19K/Y46D)

<400> SEQUENCE: 46

Thr Val Ala Ala Cys Asn Leu Pro Ile Val Ser Gly Pro Cys Ile Ala
1               5                   10                  15

Phe Ile Lys Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 47
<211> LENGTH: 70
<212> TYPE: PRT
<213> ORGANISM: Artificial Sequence
<220> FEATURE:
<223> OTHER INFORMATION: Synthetic peptide F1024S-D2
      (R11S/R15L/Q19K/Y46D)

<400> SEQUENCE: 47

Thr Val Ala Ala Cys Asn Leu Pro Ile Val Ser Gly Pro Cys Leu Ala
1               5                   10                  15

Phe Ile Lys Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 48
<211> LENGTH: 70
<212> TYPE: PRT
<213> ORGANISM: Artificial Sequence
<220> FEATURE:
<223> OTHER INFORMATION: Synthetic peptide
      F1024S-D2(R11S/R15T/Q19K/Y46D)

<400> SEQUENCE: 48

Thr Val Ala Ala Cys Asn Leu Pro Ile Val Ser Gly Pro Cys Thr Ala
1               5                   10                  15

Phe Ile Lys Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 49
<211> LENGTH: 70
<212> TYPE: PRT
<213> ORGANISM: Artificial Sequence
```

<220> FEATURE:
<223> OTHER INFORMATION: Synthetic peptide
F1024S-D2(R11S/R15V/Q19K/Y46D)

<400> SEQUENCE: 49

Thr Val Ala Ala Cys Asn Leu Pro Ile Val Ser Gly Pro Cys Val Ala
1               5                   10                  15

Phe Ile Lys Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 50
<211> LENGTH: 70
<212> TYPE: PRT
<213> ORGANISM: Artificial Sequence
<220> FEATURE:
<223> OTHER INFORMATION: Synthetic peptide
F1024S-D2(R11S/R15T/Q19A/Y46D)

<400> SEQUENCE: 50

Thr Val Ala Ala Cys Asn Leu Pro Ile Val Ser Gly Pro Cys Thr Ala
1               5                   10                  15

Phe Ile Ala Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 51
<211> LENGTH: 70
<212> TYPE: PRT
<213> ORGANISM: Artificial Sequence
<220> FEATURE:
<223> OTHER INFORMATION: Synthetic peptide F1024S-D2
(R11S/R15T/Q19C/Y46D)

<400> SEQUENCE: 51

Thr Val Ala Ala Cys Asn Leu Pro Ile Val Ser Gly Pro Cys Thr Ala
1               5                   10                  15

Phe Ile Cys Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 52
<211> LENGTH: 70
<212> TYPE: PRT
<213> ORGANISM: Artificial Sequence
<220> FEATURE:
<223> OTHER INFORMATION: Synthetic peptide F1024S-D2

(R11S/R15T/Q19D/Y46D)

<400> SEQUENCE: 52

Thr Val Ala Ala Cys Asn Leu Pro Ile Val Ser Gly Pro Cys Thr Ala
1               5                   10                  15

Phe Ile Asp Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 53
<211> LENGTH: 70
<212> TYPE: PRT
<213> ORGANISM: Artificial Sequence
<220> FEATURE:
<223> OTHER INFORMATION: Synthetic peptide
      F1024S-D2(R11S/R15T/Q19E/Y46D)

<400> SEQUENCE: 53

Thr Val Ala Ala Cys Asn Leu Pro Ile Val Ser Gly Pro Cys Thr Ala
1               5                   10                  15

Phe Ile Glu Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 54
<211> LENGTH: 70
<212> TYPE: PRT
<213> ORGANISM: Artificial Sequence
<220> FEATURE:
<223> OTHER INFORMATION: Synthetic peptide F1024S-D2
      (R11S/R15T/Q19F/Y46D)

<400> SEQUENCE: 54

Thr Val Ala Ala Cys Asn Leu Pro Ile Val Ser Gly Pro Cys Thr Ala
1               5                   10                  15

Phe Ile Phe Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 55
<211> LENGTH: 70
<212> TYPE: PRT
<213> ORGANISM: Artificial Sequence
<220> FEATURE:
<223> OTHER INFORMATION: Synthetic peptide F1024S-D2
      (R11S/R15T/Q19G/Y46D)

<400> SEQUENCE: 55

Thr Val Ala Ala Cys Asn Leu Pro Ile Val Ser Gly Pro Cys Thr Ala
1               5                   10                  15

Phe Ile Gly Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 56
<211> LENGTH: 70
<212> TYPE: PRT
<213> ORGANISM: Artificial Sequence
<220> FEATURE:
<223> OTHER INFORMATION: Synthetic peptide
      F1024S-D2(R11S/R15T/Q19H/Y46D)

<400> SEQUENCE: 56

Thr Val Ala Ala Cys Asn Leu Pro Ile Val Ser Gly Pro Cys Thr Ala
1               5                   10                  15

Phe Ile His Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 57
<211> LENGTH: 70
<212> TYPE: PRT
<213> ORGANISM: Artificial Sequence
<220> FEATURE:
<223> OTHER INFORMATION: Synthetic peptide F1024S-D2
      (R11S/R15T/Q19I/Y46D)

<400> SEQUENCE: 57

Thr Val Ala Ala Cys Asn Leu Pro Ile Val Ser Gly Pro Cys Thr Ala
1               5                   10                  15

Phe Ile Ile Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 58
<211> LENGTH: 70
<212> TYPE: PRT
<213> ORGANISM: Artificial Sequence
<220> FEATURE:
<223> OTHER INFORMATION: Synthetic peptide
      F1024S-D2(R11S/R15T/Q19L/Y46D)

<400> SEQUENCE: 58

Thr Val Ala Ala Cys Asn Leu Pro Ile Val Ser Gly Pro Cys Thr Ala
1               5                   10                  15

Phe Ile Leu Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
            35                  40                  45

Lys Glu Cys Arg Glu Tyr Cys Gly Val Pro Gly Asp Gly Asp Glu Glu
        50                  55                  60

Leu Leu Arg Phe Ser Asn
65                  70

<210> SEQ ID NO 59
<211> LENGTH: 70
<212> TYPE: PRT
<213> ORGANISM: Artificial Sequence
<220> FEATURE:
<223> OTHER INFORMATION: Synthetic peptide F1024S-D2
      (R11S/R15T/Q19M/Y46D)

<400> SEQUENCE: 59

Thr Val Ala Ala Cys Asn Leu Pro Ile Val Ser Gly Pro Cys Thr Ala
1               5                   10                  15

Phe Ile Met Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
            35                  40                  45

Lys Glu Cys Arg Glu Tyr Cys Gly Val Pro Gly Asp Gly Asp Glu Glu
        50                  55                  60

Leu Leu Arg Phe Ser Asn
65                  70

<210> SEQ ID NO 60
<211> LENGTH: 70
<212> TYPE: PRT
<213> ORGANISM: Artificial Sequence
<220> FEATURE:
<223> OTHER INFORMATION: Synthetic peptide F1024S-D2
      (R11S/R15T/Q19N/Y46D)

<400> SEQUENCE: 60

Thr Val Ala Ala Cys Asn Leu Pro Ile Val Ser Gly Pro Cys Thr Ala
1               5                   10                  15

Phe Ile Asn Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
            35                  40                  45

Lys Glu Cys Arg Glu Tyr Cys Gly Val Pro Gly Asp Gly Asp Glu Glu
        50                  55                  60

Leu Leu Arg Phe Ser Asn
65                  70

<210> SEQ ID NO 61
<211> LENGTH: 70
<212> TYPE: PRT
<213> ORGANISM: Artificial Sequence
<220> FEATURE:
<223> OTHER INFORMATION: Synthetic peptide
      F1024S-D2(R11S/R15T/Q19P/Y46D)

<400> SEQUENCE: 61

Thr Val Ala Ala Cys Asn Leu Pro Ile Val Ser Gly Pro Cys Thr Ala
1               5                   10                  15

Phe Ile Pro Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
            35                  40                  45

Lys Glu Cys Arg Glu Tyr Cys Gly Val Pro Gly Asp Gly Asp Glu Glu
        50                  55                  60

Leu Leu Arg Phe Ser Asn
65                  70

<210> SEQ ID NO 62
<211> LENGTH: 70
<212> TYPE: PRT
<213> ORGANISM: Artificial Sequence
<220> FEATURE:
<223> OTHER INFORMATION: Synthetic peptide F1024S-D2(R11S/R15T/Y46D)

<400> SEQUENCE: 62

Thr Val Ala Ala Cys Asn Leu Pro Ile Val Ser Gly Pro Cys Thr Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
            35                  40                  45

Lys Glu Cys Arg Glu Tyr Cys Gly Val Pro Gly Asp Gly Asp Glu Glu
        50                  55                  60

Leu Leu Arg Phe Ser Asn
65                  70

<210> SEQ ID NO 63
<211> LENGTH: 70
<212> TYPE: PRT
<213> ORGANISM: Artificial Sequence
<220> FEATURE:
<223> OTHER INFORMATION: Synthetic peptide F1024S-D2
      (R11S/R15T/Q19R/Y46D)

<400> SEQUENCE: 63

Thr Val Ala Ala Cys Asn Leu Pro Ile Val Ser Gly Pro Cys Thr Ala
1               5                   10                  15

Phe Ile Arg Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
            35                  40                  45

Lys Glu Cys Arg Glu Tyr Cys Gly Val Pro Gly Asp Gly Asp Glu Glu
        50                  55                  60

Leu Leu Arg Phe Ser Asn
65                  70

<210> SEQ ID NO 64
<211> LENGTH: 70
<212> TYPE: PRT
<213> ORGANISM: Artificial Sequence
<220> FEATURE:
<223> OTHER INFORMATION: Synthetic peptide F1024S-D2
      (R11S/R15T/Q19S/Y46D)

<400> SEQUENCE: 64

Thr Val Ala Ala Cys Asn Leu Pro Ile Val Ser Gly Pro Cys Thr Ala
1               5                   10                  15

Phe Ile Ser Leu Trp Ala Phe Asp Ala Val Lys Gly Lys Cys Val Leu
            20                  25                  30

```
Phe Pro Tyr Gly Gly Cys Gln Gly Asn Gly Asn Lys Phe Asp Ser Glu
            35                  40                  45

Lys Glu Cys Arg Glu Tyr Cys Gly Val Pro Gly Asp Gly Asp Glu Glu
        50                  55                  60

Leu Leu Arg Phe Ser Asn
65                  70

<210> SEQ ID NO 65
<211> LENGTH: 70
<212> TYPE: PRT
<213> ORGANISM: Artificial Sequence
<220> FEATURE:
<223> OTHER INFORMATION: Synthetic peptide F1024S-D2
      (R11S/R15T/Q19T/Y46D)

<400> SEQUENCE: 65

Thr Val Ala Ala Cys Asn Leu Pro Ile Val Ser Gly Pro Cys Thr Ala
1               5                   10                  15

Phe Ile Thr Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
            35                  40                  45

Lys Glu Cys Arg Glu Tyr Cys Gly Val Pro Gly Asp Gly Asp Glu Glu
        50                  55                  60

Leu Leu Arg Phe Ser Asn
65                  70

<210> SEQ ID NO 66
<211> LENGTH: 70
<212> TYPE: PRT
<213> ORGANISM: Artificial Sequence
<220> FEATURE:
<223> OTHER INFORMATION: Synthetic peptide F1024S-D2
      (R11S/R15T/Q19V/Y46D)

<400> SEQUENCE: 66

Thr Val Ala Ala Cys Asn Leu Pro Ile Val Ser Gly Pro Cys Thr Ala
1               5                   10                  15

Phe Ile Val Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
            35                  40                  45

Lys Glu Cys Arg Glu Tyr Cys Gly Val Pro Gly Asp Gly Asp Glu Glu
        50                  55                  60

Leu Leu Arg Phe Ser Asn
65                  70

<210> SEQ ID NO 67
<211> LENGTH: 70
<212> TYPE: PRT
<213> ORGANISM: Artificial Sequence
<220> FEATURE:
<223> OTHER INFORMATION: Synthetic peptide
      F1024S-D2(R11S/R15T/Q19W/Y46D)

<400> SEQUENCE: 67

Thr Val Ala Ala Cys Asn Leu Pro Ile Val Ser Gly Pro Cys Thr Ala
1               5                   10                  15

Phe Ile Trp Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
```

```
            35                  40                  45
Lys Glu Cys Arg Glu Tyr Cys Gly Val Pro Gly Asp Gly Glu Glu
 50                  55                  60

Leu Leu Arg Phe Ser Asn
 65                  70

<210> SEQ ID NO 68
<211> LENGTH: 70
<212> TYPE: PRT
<213> ORGANISM: Artificial Sequence
<220> FEATURE:
<223> OTHER INFORMATION: Synthetic peptide F1024S-D2
      (R11S/R15T/Q19Y/Y46D)

<400> SEQUENCE: 68

Thr Val Ala Ala Cys Asn Leu Pro Ile Val Ser Gly Pro Cys Thr Ala
 1               5                  10                  15

Phe Ile Tyr Leu Trp Ala Phe Asp Ala Val Lys Gly Lys Cys Val Leu
                20                  25                  30

Phe Pro Tyr Gly Gly Cys Gln Gly Asn Gly Asn Lys Phe Asp Ser Glu
            35                  40                  45

Lys Glu Cys Arg Glu Tyr Cys Gly Val Pro Gly Asp Gly Asp Glu Glu
 50                  55                  60

Leu Leu Arg Phe Ser Asn
 65                  70

<210> SEQ ID NO 69
<211> LENGTH: 70
<212> TYPE: PRT
<213> ORGANISM: Artificial Sequence
<220> FEATURE:
<223> OTHER INFORMATION: Synthetic peptide F1024S-D2
      (R11S/R15T/F17A/Y46D)

<400> SEQUENCE: 69

Thr Val Ala Ala Cys Asn Leu Pro Ile Val Ser Gly Pro Cys Thr Ala
 1               5                  10                  15

Ala Ile Gln Leu Trp Ala Phe Asp Ala Val Lys Gly Lys Cys Val Leu
                20                  25                  30

Phe Pro Tyr Gly Gly Cys Gln Gly Asn Gly Asn Lys Phe Asp Ser Glu
            35                  40                  45

Lys Glu Cys Arg Glu Tyr Cys Gly Val Pro Gly Asp Gly Asp Glu Glu
 50                  55                  60

Leu Leu Arg Phe Ser Asn
 65                  70

<210> SEQ ID NO 70
<211> LENGTH: 70
<212> TYPE: PRT
<213> ORGANISM: Artificial Sequence
<220> FEATURE:
<223> OTHER INFORMATION: Synthetic peptide F1024S-D2
      (R11S/R15T/F17C/Y46D)

<400> SEQUENCE: 70

Thr Val Ala Ala Cys Asn Leu Pro Ile Val Ser Gly Pro Cys Thr Ala
 1               5                  10                  15

Cys Ile Gln Leu Trp Ala Phe Asp Ala Val Lys Gly Lys Cys Val Leu
                20                  25                  30

Phe Pro Tyr Gly Gly Cys Gln Gly Asn Gly Asn Lys Phe Asp Ser Glu
            35                  40                  45
```

```
Lys Glu Cys Arg Glu Tyr Cys Gly Val Pro Gly Asp Gly Asp Glu Glu
 50                  55                  60

Leu Leu Arg Phe Ser Asn
 65                  70

<210> SEQ ID NO 71
<211> LENGTH: 70
<212> TYPE: PRT
<213> ORGANISM: Artificial Sequence
<220> FEATURE:
<223> OTHER INFORMATION: Synthetic peptide F1024S-D2
      (R11S/R15T/F17D/Y46D)

<400> SEQUENCE: 71

Thr Val Ala Ala Cys Asn Leu Pro Ile Val Ser Gly Pro Cys Thr Ala
 1               5                  10                  15

Asp Ile Gln Leu Trp Ala Phe Asp Ala Val Lys Gly Lys Cys Val Leu
                20                  25                  30

Phe Pro Tyr Gly Gly Cys Gln Gly Asn Gly Asn Lys Phe Asp Ser Glu
            35                  40                  45

Lys Glu Cys Arg Glu Tyr Cys G

Leu Leu Arg Phe Ser Asn
65                  70

<210> SEQ ID NO 74
<211> LENGTH: 70
<212> TYPE: PRT
<213> ORGANISM: Artificial Sequence
<220> FEATURE:
<223> OTHER INFORMATION: Synthetic peptide
      F1024S-D2(R11S/R15T/F17H/Y46D)

<400> SEQUENCE: 74

Thr Val Ala Ala Cys Asn Leu Pro Ile Val Ser Gly Pro Cys Thr Ala
1               5                   10                  15

His Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
            35                  40                  45

Lys Glu Cys Arg Glu Tyr Cys Gly Val Pro Gly Asp Gly Asp Glu Glu
        50                  55                  60

Leu Leu Arg Phe Ser Asn
65                  70

<210> SEQ ID NO 75
<211> LENGTH: 70
<212> TYPE: PRT
<213> ORGANISM: Artificial Sequence
<220> FEATURE:
<223> OTHER INFORMATION: Synthetic peptide
      F1024S-D2(R11S/R15T/F17I/Y46D)

<400> SEQUENCE: 75

Thr Val Ala Ala Cys Asn Leu Pro Ile Val Ser Gly Pro Cys Thr Ala
1               5                   10                  15

Ile Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
            35                  40                  45

Lys Glu Cys Arg Glu Tyr Cys Gly Val Pro Gly Asp Gly Asp Glu Glu
        50                  55                  60

Leu Leu Arg Phe Ser Asn
65                  70

<210> SEQ ID NO 76
<211> LENGTH: 70
<212> TYPE: PRT
<213> ORGANISM: Artificial Sequence
<220> FEATURE:
<223> OTHER INFORMATION: Synthetic peptide
      F1024S-D2(R11S/R15T/F17K/Y46D)

<400> SEQUENCE: 76

Thr Val Ala Ala Cys Asn Leu Pro Ile Val Ser Gly Pro Cys Thr Ala
1               5                   10                  15

Lys Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
            35                  40                  45

Lys Glu Cys Arg Glu Tyr Cys Gly Val Pro Gly Asp Gly Asp Glu Glu
        50                  55                  60

Leu Leu Arg Phe Ser Asn

<210> SEQ ID NO 77
<211> LENGTH: 70
<212> TYPE: PRT
<213> ORGANISM: Artificial Sequence
<220> FEATURE:
<223> OTHER INFORMATION: Synthetic peptide F1024S-D2
(R11S/R15T/F17L/Y46D)

<400> SEQUENCE: 77

Thr Val Ala Ala Cys Asn Leu Pro Ile Val Ser Gly Pro Cys Thr Ala
1               5                   10                  15

Leu Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Ar

-continued

<210> SEQ ID NO 80
<211> LENGTH: 70
<212> TYPE: PRT
<213> ORGANISM: Artificial Sequence
<220> FEATURE:
<223> OTHER INFORMATION: Synthetic peptide
      F1024S-D2(R11S/R15T/F17P/Y46D)

<400> SEQUENCE: 80

Thr Val Ala Ala Cys Asn Leu Pro Ile Val Ser Gly Pro Cys Thr Ala
1               5                   10                  15

Pro Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 81
<211> LENGTH: 70
<212> TYPE: PRT
<213> ORGANISM: Artificial Sequence
<220> FEATURE:
<223> OTHER INFORMATION: Synthetic peptide F1024S-D2
      (R11S/R15T/F17Q/Y46D)

<400> SEQUENCE: 81

Thr Val Ala Ala Cys Asn Leu Pro Ile Val Ser Gly Pro Cys Thr Ala
1               5                   10                  15

Gln Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 82
<211> LENGTH: 70
<212> TYPE: PRT
<213> ORGANISM: Artificial Sequence
<220> FEATURE:
<223> OTHER INFORMATION: Synthetic peptide F1024S-D2
      (R11S/R15T/F17R/Y46D)

<400> SEQUENCE: 82

Thr Val Ala Ala Cys Asn Leu Pro Ile Val Ser Gly Pro Cys Thr Ala
1               5                   10                  15

Arg Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 83

```
<211> LENGTH: 70
<212> TYPE: PRT
<213> ORGANISM: Artificial Sequence
<220> FEATURE:
<223> OTHER INFORMATION: Synthetic peptide
      F1024S-D2(R11S/R15T/F17S/Y46D)

<400> SEQUENCE: 83

Thr Val Ala Ala Cys Asn Leu Pro Ile Val Ser Gly Pro Cys Thr Ala
1               5                   10                  15

Ser Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 84
<211> LENGTH: 70
<212> TYPE: PRT
<213> ORGANISM: Artificial Sequence
<220> FEATURE:
<223> OTHER INFORMATION: Synthetic peptide
      F1024S-D2(R11S/R15T/F17T/Y46D)

<400> SEQUENCE: 84

Thr Val Ala Ala Cys Asn Leu Pro Ile Val Ser Gly Pro Cys Thr Ala
1               5                   10                  15

Thr Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 85
<211> LENGTH: 70
<212> TYPE: PRT
<213> ORGANISM: Artificial Sequence
<220> FEATURE:
<223> OTHER INFORMATION: Synthetic peptide F1024S-D2
      (R11S/R15T/F17V/Y46D)

<400> SEQUENCE: 85

Thr Val Ala Ala Cys Asn Leu Pro Ile Val Ser Gly Pro Cys Thr Ala
1               5                   10                  15

Val Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 86
<211> LENGTH: 70
<212> TYPE: PRT
```

<213> ORGANISM: Artificial Sequence
<220> FEATURE:
<223> OTHER INFORMATION: Synthetic peptide F1024S-D2
      (R11S/R15T/F17W/Y46D)

<400> SEQUENCE: 86

Thr Val Ala Ala Cys Asn Leu Pro Ile Val Ser Gly Pro Cys Thr Ala
1               5                   10                  15

Trp Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 87
<211> LENGTH: 70
<212> TYPE: PRT
<213> ORGANISM: Artificial Sequence
<220> FEATURE:
<223> OTHER INFORMATION: Synthetic peptide
      F1024S-D2(R11S/R15T/F17Y/Y46D)

<400> SEQUENCE: 87

Thr Val Ala Ala Cys Asn Leu Pro Ile Val Ser Gly Pro Cys Thr Ala
1               5                   10                  15

Tyr Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 88
<211> LENGTH: 70
<212> TYPE: PRT
<213> ORGANISM: Artificial Sequence
<220> FEATURE:
<223> OTHER INFORMATION: Synthetic peptide F1024S-D2(R11A/R15T/Y46D)

<400> SEQUENCE: 88

Thr Val Ala Ala Cys Asn Leu Pro Ile Val Ala Gly Pro Cys Thr Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 89
<211> LENGTH: 70
<212> TYPE: PRT
<213> ORGANISM: Artificial Sequence
<220> FEATURE:
<223> OTHER INFORMATION: Synthetic peptide F1024S-D2 (R11C/R15T/Y46D)

<400> SEQUENCE: 89

Thr Val Ala Ala Cys Asn Leu Pro Ile Val Cys Gly Pro Cys Thr Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 90
<211> LENGTH: 70
<212> TYPE: PRT
<213> ORGANISM: Artificial Sequence
<220> FEATURE:
<223> OTHER INFORMATION: Synthetic peptide F1024S-D2(R11D/R15T/Y46D)

<400> SEQUENCE: 90

Thr Val Ala Ala Cys Asn Leu Pro Ile Val Asp Gly Pro Cys Thr Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 91
<211> LENGTH: 70
<212> TYPE: PRT
<213> ORGANISM: Artificial Sequence
<220> FEATURE:
<223> OTHER INFORMATION: Synthetic peptide F1024S-D2 (R11E/R15T/Y46D)

<400> SEQUENCE: 91

Thr Val Ala Ala Cys Asn Leu Pro Ile Val Glu Gly Pro Cys Thr Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 92
<211> LENGTH: 70
<212> TYPE: PRT
<213> ORGANISM: Artificial Sequence
<220> FEATURE:
<223> OTHER INFORMATION: Synthetic peptide F1024S-D2(R11F/R15T/Y46D)

<400> SEQUENCE: 92

Thr Val Ala Ala Cys Asn Leu Pro Ile Val Phe Gly Pro Cys Thr Ala
1               5                   10                  15

```
Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
50                  55                  60

Leu Leu Arg Phe Ser Asn
65                  70

<210> SEQ ID NO 93
<211> LENGTH: 70
<212> TYPE: PRT
<213> ORGANISM: Artificial Sequence
<220> FEATURE:
<223> OTHER INFORMATION: Synthetic peptide F1024S-D2 (R11G/R15T/Y46D)

<400> SEQUENCE: 93

Thr Val Ala Ala Cys Asn Leu Pro Ile Val Gly Gly Pro Cys Thr Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
50                  55                  60

Leu Leu Arg Phe Ser Asn
65                  70

<210> SEQ ID NO 94
<211> LENGTH: 70
<212> TYPE: PRT
<213> ORGANISM: Artificial Sequence
<220> FEATURE:
<223> OTHER INFORMATION: Synthetic peptide F1024S-D2(R11H/R15T/Y46D)

<400> SEQUENCE: 94

Thr Val Ala Ala Cys Asn Leu Pro Ile Val His Gly Pro Cys Thr Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
50                  55                  60

Leu Leu Arg Phe Ser Asn
65                  70

<210> SEQ ID NO 95
<211> LENGTH: 70
<212> TYPE: PRT
<213> ORGANISM: Artificial Sequence
<220> FEATURE:
<223> OTHER INFORMATION: Synthetic peptide F1024S-D2 (R11I/R15T/Y46D)

<400> SEQUENCE: 95

Thr Val Ala Ala Cys Asn Leu Pro Ile Val Ile Gly Pro Cys Thr Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
```

```
              35                  40                  45

Lys Glu Cys Arg Glu Tyr Cys Gly Val Pro Gly Asp Gly Asp Glu Glu
 50                  55                  60

Leu Leu Arg Phe Ser Asn
 65                  70

<210> SEQ ID NO 96
<211> LENGTH: 70
<212> TYPE: PRT
<213> ORGANISM: Artificial Sequence
<220> FEATURE:
<223> OTHER INFORMATION: Synthetic peptide F1024S-D2 (R11K/R15T/Y46D)

<400> SEQUENCE: 96

Thr Val Ala Ala Cys Asn Leu Pro Ile Val Lys Gly Pro Cys Thr Ala
 1               5                  10                  15

Phe Ile Gln Leu Trp Ala Phe Asp Ala Val Lys Gly Lys Cys Val Leu
                20                  25                  30

Phe Pro Tyr Gly Gly Cys Gln Gly Asn Gly Asn Lys Phe Asp Ser Glu
              35                  40                  45

Lys Glu Cys Arg Glu Tyr Cys Gly Val Pro Gly Asp Gly Asp Glu Glu
 50                  55                  60

Leu Leu Arg Phe Ser Asn
 65                  70

<210> SEQ ID NO 97
<211> LENGTH: 70
<212> TYPE: PRT
<213> ORGANISM: Artificial Sequence
<220> FEATURE:
<223> OTHER INFORMATION: Synthetic peptide F1024S-D2 (R11L/R15T/Y46D)

<400> SEQUENCE: 97

Thr Val Ala Ala Cys Asn Leu Pro Ile Val Leu Gly Pro Cys Thr Ala
 1               5                  10                  15

Phe Ile Gln Leu Trp Ala Phe Asp Ala Val Lys Gly Lys Cys Val Leu
                20                  25                  30

Phe Pro Tyr Gly Gly Cys Gln Gly Asn Gly Asn Lys Phe Asp Ser Glu
              35                  40                  45

Lys Glu Cys Arg Glu Tyr Cys Gly Val Pro Gly Asp Gly Asp Glu Glu
 50                  55                  60

Leu Leu Arg Phe Ser Asn
 65                  70

<210> SEQ ID NO 98
<211> LENGTH: 70
<212> TYPE: PRT
<213> ORGANISM: Artificial Sequence
<220> FEATURE:
<223> OTHER INFORMATION: Synthetic peptide F1024S-D2(R11M/R15T/Y46D)

<400> SEQUENCE: 98

Thr Val Ala Ala Cys Asn Leu Pro Ile Val Met Gly Pro Cys Thr Ala
 1               5                  10                  15

Phe Ile Gln Leu Trp Ala Phe Asp Ala Val Lys Gly Lys Cys Val Leu
                20                  25                  30

Phe Pro Tyr Gly Gly Cys Gln Gly Asn Gly Asn Lys Phe Asp Ser Glu
              35                  40                  45

Lys Glu Cys Arg Glu Tyr Cys Gly Val Pro Gly Asp Gly Asp Glu Glu
 50                  55                  60
```

```
Leu Leu Arg Phe Ser Asn
 65                  70

<210> SEQ ID NO 99
<211> LENGTH: 70
<212> TYPE: PRT
<213> ORGANISM: Artificial Sequence
<220> FEATURE:
<223> OTHER INFORMATION: Synthetic peptide F1024S-D2 (R11N/R15T/Y46D)

<400> SEQUENCE: 99

Thr Val Ala Ala Cys Asn Leu Pro Ile Val Asn Gly Pro Cys Thr Ala
  1               5                  10                  15

Phe Ile Gln Leu Trp Ala Phe Asp Ala Val Lys Gly Lys Cys Val Leu
                 20                  25                  30

Phe Pro Tyr Gly Gly Cys Gln Gly Asn Gly Asn Lys Phe Asp Ser Glu
             35                  40                  45

Lys Glu Cys Arg Glu Tyr Cys Gly Val Pro Gly Asp Gly Asp Glu Glu
         50                  55                  60

Leu Leu Arg Phe Ser Asn
 65                  70

<210> SEQ ID NO 100
<211> LENGTH: 70
<212> TYPE: PRT
<213> ORGANISM: Artificial Sequence
<220> FEATURE:
<223> OTHER INFORMATION: Synthetic peptide F1024S-D2(R11P/R15T/Y46D)

<400> SEQUENCE: 100

Thr Val Ala Ala Cys Asn Leu Pro Ile Val Pro Gly Pro Cys Thr Ala
  1               5                  10                  15

Phe Ile Gln Leu Trp Ala Phe Asp Ala Val Lys Gly Lys Cys Val Leu
                 20                  25                  30

Phe Pro Tyr Gly Gly Cys Gln Gly Asn Gly Asn Lys Phe Asp Ser Glu
             35                  40                  45

Lys Glu Cys Arg Glu Tyr Cys Gly Val Pro Gly Asp Gly Asp Glu Glu
         50                  55                  60

Leu Leu Arg Phe Ser Asn
 65                  70

<210> SEQ ID NO 101
<211> LENGTH: 70
<212> TYPE: PRT
<213> ORGANISM: Artificial Sequence
<220> FEATURE:
<223> OTHER INFORMATION: Synthetic peptide F1024S-D2 (R11Q/R15T/Y46D)

<400> SEQUENCE: 101

Thr Val Ala Ala Cys Asn Leu Pro Ile Val Gln Gly Pro Cys Thr Ala
  1               5                  10                  15

Phe Ile Gln Leu Trp Ala Phe Asp Ala Val Lys Gly Lys Cys Val Leu
                 20                  25                  30

Phe Pro Tyr Gly Gly Cys Gln Gly Asn Gly Asn Lys Phe Asp Ser Glu
             35                  40                  45

Lys Glu Cys Arg Glu Tyr Cys Gly Val Pro Gly Asp Gly Asp Glu Glu
         50                  55                  60

Leu Leu Arg Phe Ser Asn
 65                  70

<210> SEQ ID NO 102
```

```
<211> LENGTH: 70
<212> TYPE: PRT
<213> ORGANISM: Artificial Sequence
<220> FEATURE:
<223> OTHER INFORMATION: Synthetic peptide F1024S-D2(R15T/Y46D)

<400> SEQUENCE: 102

Thr Val Ala Ala Cys Asn Leu Pro Ile Val Arg Gly Pro Cys Thr Ala
1               5                   10                  15

Phe Ile Gln Leu Trp Ala Phe Asp Ala Val Lys Gly Lys Cys Val Leu
                20                  25                  30

Phe Pro Tyr Gly Gly Cys Gln Gly Asn Gly Asn Lys Phe Asp Ser Glu
            35                  40                  45

Lys Glu Cys Arg Glu Tyr Cys Gly Val Pro Gly Asp Gly Asp Glu Glu
        50                  55                  60

Leu Leu Arg Phe Ser Asn
65                  70

<210> SEQ ID NO 103
<211> LENGTH: 70
<212> TYPE: PRT
<213> ORGANISM: Artificial Sequence
<220> FEATURE:
<223> OTHER INFORMATION: Synthetic peptide F1024S-D2 (R11T/R15T/Y46D)

<400> SEQUENCE: 103

Thr Val Ala Ala Cys Asn Leu Pro Ile Val Thr Gly Pro Cys Thr Ala
1               5                   10                  15

Phe Ile Gln Leu Trp Ala Phe Asp Ala Val Lys Gly Lys Cys Val Leu
                20                  25                  30

Phe Pro Tyr Gly Gly Cys Gln Gly Asn Gly Asn Lys Phe Asp Ser Glu
            35                  40                  45

Lys Glu Cys Arg Glu Tyr Cys Gly Val Pro Gly Asp Gly Asp Glu Glu
        50                  55                  60

Leu Leu Arg Phe Ser Asn
65                  70

<210> SEQ ID NO 104
<211> LENGTH: 70
<212> TYPE: PRT
<213> ORGANISM: Artificial Sequence
<220> FEATURE:
<223> OTHER INFORMATION: Synthetic peptide F1024S-D2(R11V/R15T/Y46D)

<400> SEQUENCE: 104

Thr Val Ala Ala Cys Asn Leu Pro Ile Val Val Gly Pro Cys Thr Ala
1               5                   10                  15

Phe Ile Gln Leu Trp Ala Phe Asp Ala Val Lys Gly Lys Cys Val Leu
                20                  25                  30

Phe Pro Tyr Gly Gly Cys Gln Gly Asn Gly Asn Lys Phe Asp Ser Glu
            35                  40                  45

Lys Glu Cys Arg Glu Tyr Cys Gly Val Pro Gly Asp Gly Asp Glu Glu
        50                  55                  60

Leu Leu Arg Phe Ser Asn
65                  70

<210> SEQ ID NO 105
<211> LENGTH: 70
<212> TYPE: PRT
<213> ORGANISM: Artificial Sequence
<220> FEATURE:
<223> OTHER INFORMATION: Synthetic peptide F1024S-D2 (R11W/R15T/Y46D)
```

<400> SEQUENCE: 105

Thr Val Ala Ala Cys Asn Leu Pro Ile Val Trp Gly Pro Cys Thr Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 106
<211> LENGTH: 70
<212> TYPE: PRT
<213> ORGANISM: Artificial Sequence
<220> FEATURE:
<223> OTHER INFORMATION: Synthetic peptide F1024S-D2 (R11Y/R15T/Y46D)

<400> SEQUENCE: 106

Thr Val Ala Ala Cys Asn Leu Pro Ile Val Tyr Gly Pro Cys Thr Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Asp Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70

<210> SEQ ID NO 107
<211> LENGTH: 236
<212> TYPE: PRT
<213> ORGANISM: Artificial
<220> FEATURE:
<223> OTHER INFORMATION: Synthetic peptide F1024S-TM123456M

<400> SEQUENCE: 107

Cys Ser Val Glu Asn Gly Gly Cys Glu His Ala Cys Asn Ala Ile Pro
1               5                   10                  15

Gly Ala Pro Arg Cys Gln Cys Pro Ala Gly Ala Ala Leu Gln Ala Asp
            20                  25                  30

Gly Arg Ser Cys Thr Ala Ser Ala Thr Gln Ser Cys Asn Asp Leu Cys
        35                  40                  45

Glu His Phe Cys Val Pro Asn Pro Asp Gln Pro Gly Ser Tyr Ser Cys
    50                  55                  60

Met Cys Glu Thr Gly Tyr Arg Leu Ala Ala Asp Gln His Arg Cys Glu
65                  70                  75                  80

Asp Val Asp Asp Cys Ile Leu Glu Pro Ser Pro Cys Pro Gln Arg Cys
                85                  90                  95

Val Asn Thr Gln Gly Gly Phe Glu Cys His Cys Tyr Pro Asn Tyr Asp
            100                 105                 110

Leu Val Asp Gly Glu Cys Val Glu Pro Val Asp Pro Cys Phe Arg Ala
        115                 120                 125

Asn Cys Glu Tyr Gln Cys Gln Pro Leu Asn Gln Thr Ser Tyr Leu Cys
    130                 135                 140

```
Val Cys Ala Glu Gly Phe Ala Pro Ile Pro His Glu Pro His Arg Cys
145                 150                 155                 160

Gln Met Phe Cys Asn Gln Thr Ala Cys Pro Ala Asp Cys Asp Pro Asn
                165                 170                 175

Thr Gln Ala Ser Cys Glu Cys Pro Glu Gly Tyr Ile Leu Asp Asp Gly
            180                 185                 190

Phe Ile Cys Thr Asp Ile Asp Glu Cys Glu Asn Gly Gly Phe Cys Ser
        195                 200                 205

Gly Val Cys His Asn Leu Pro Gly Thr Phe Glu Cys Ile Cys Gly Pro
    210                 215                 220

Asp Ser Ala Leu Ala Arg His Ile Gly Thr Asp Cys
225                 230                 235

<210> SEQ ID NO 108
<211> LENGTH: 236
<212> TYPE: PRT
<213> ORGANISM: Artificial Sequence
<220> FEATURE:
<223> OTHER INFORMATION: Synthetic peptide F1024S-TM123456L

<400> SEQUENCE: 108

Cys Ser Val Glu Asn Gly Gly Cys Glu His Ala Cys Asn Ala Ile Pro
1               5                   10                  15

Gly Ala Pro Arg Cys Gln Cys Pro Ala Gly Ala Leu Gln Ala Asp
            20                  25                  30

Gly Arg Ser Cys Thr Ala Ser Ala Thr Gln Ser Cys Asn Asp Leu Cys
            35                  40                  45

Glu His Phe Cys Val Pro Asn Pro Asp Gln Pro Gly Ser Tyr Ser Cys
50                  55                  60

Met Cys Glu Thr Gly Tyr Arg Leu Ala Ala Asp Gln His Arg Cys Glu
65                  70                  75                  80

Asp Val Asp Asp Cys Ile Leu Glu Pro Ser Pro Cys Pro Gln Arg Cys
                85                  90                  95

Val Asn Thr Gln Gly Gly Phe Glu Cys His Cys Tyr Pro Asn Tyr Asp
            100                 105                 110

Leu Val Asp Gly Glu Cys Val Glu Pro Val Asp Pro Cys Phe Arg Ala
        115                 120                 125

Asn Cys Glu Tyr Gln Cys Gln Pro Leu Asn Gln Thr Ser Tyr Leu Cys
    130                 135                 140

Val Cys Ala Glu Gly Phe Ala Pro Ile Pro His Glu Pro His Arg Cys
145                 150                 155                 160

Gln Leu Phe Cys Asn Gln Thr Ala Cys Pro Ala Asp Cys Asp Pro Asn
                165                 170                 175

Thr Gln Ala Ser Cys Glu Cys Pro Glu Gly Tyr Ile Leu Asp Asp Gly
            180                 185                 190

Phe Ile Cys Thr Asp Ile Asp Glu Cys Glu Asn Gly Gly Phe Cys Ser
        195                 200                 205

Gly Val Cys His Asn Leu Pro Gly Thr Phe Glu Cys Ile Cys Gly Pro
    210                 215                 220

Asp Ser Ala Leu Ala Arg His Ile Gly Thr Asp Cys
225                 230                 235

<210> SEQ ID NO 109
<211> LENGTH: 271
<212> TYPE: PRT
<213> ORGANISM: Artificial Sequence
<220> FEATURE:
<223> OTHER INFORMATION: Synthetic peptide F1024S-TM1234567M
```

```
<400> SEQUENCE: 109

Cys Ser Val Glu Asn Gly Gly Cys Glu His Ala Cys Asn Ala Ile Pro
 1               5                  10                  15
Gly Ala Pro Arg Cys Gln Cys Pro Ala Gly Ala Ala Leu Gln Ala Asp
            20                  25                  30
Gly Arg Ser Cys Thr Ala Ser Ala Thr Gln Ser Cys Asn Asp Leu Cys
        35                  40                  45
Glu His Phe Cys Val Pro Asn Pro Asp Gln Pro Gly Ser Tyr Ser Cys
    50                  55                  60
Met Cys Glu Thr Gly Tyr Arg Leu Ala Ala Asp Gln His Arg Cys Glu
 65                  70                  75                  80
Asp Val Asp Asp Cys Ile Leu Glu Pro Ser Pro Cys Pro Gln Arg Cys
                85                  90                  95
Val Asn Thr Gln Gly Gly Phe Glu Cys His Cys Tyr Pro Asn Tyr Asp
            100                 105                 110
Leu Val Asp Gly Glu Cys Val Glu Pro Val Asp Pro Cys Phe Arg Ala
        115                 120                 125
Asn Cys Glu Tyr Gln Cys Gln Pro Leu Asn Gln Thr Ser Tyr Leu Cys
    130                 135                 140
Val Cys Ala Glu Gly Phe Ala Pro Ile Pro His Glu Pro His Arg Cys
145                 150                 155                 160
Gln Met Phe Cys Asn Gln Thr Ala Cys Pro Ala Asp Cys Asp Pro Asn
                165                 170                 175
Thr Gln Ala Ser Cys Glu Cys Pro Glu Gly Tyr Ile Leu Asp Asp Gly
            180                 185                 190
Phe Ile Cys Thr Asp Ile Asp Glu Cys Glu Asn Gly Gly Phe Cys Ser
        195                 200                 205
Gly Val Cys His Asn Leu Pro Gly Thr Phe Glu Cys Ile Cys Gly Pro
    210                 215                 220
Asp Ser Ala Leu Ala Arg His Ile Gly Thr Asp Cys Asp Ser Gly Lys
225                 230                 235                 240
Val Asp Gly Gly Asp Ser Gly Ser Gly Glu Pro Pro Pro Ser Pro Thr
                245                 250                 255
Pro Gly Ser Thr Leu Thr Pro Pro Ala Val Gly Leu Val His Ser
            260                 265                 270

<210> SEQ ID NO 110
<211> LENGTH: 271
<212> TYPE: PRT
<213> ORGANISM: Artificial Sequence
<220> FEATURE:
<223> OTHER INFORMATION: Synthetic peptide F1024S-TM1234567L

<400> SEQUENCE: 110

Cys Ser Val Glu Asn Gly Gly Cys Glu His Ala Cys Asn Ala Ile Pro
 1               5                  10                  15
Gly Ala Pro Arg Cys Gln Cys Pro Ala Gly Ala Ala Leu Gln Ala Asp
            20                  25                  30
Gly Arg Ser Cys Thr Ala Ser Ala Thr Gln Ser Cys Asn Asp Leu Cys
        35                  40                  45
Glu His Phe Cys Val Pro Asn Pro Asp Gln Pro Gly Ser Tyr Ser Cys
    50                  55                  60
Met Cys Glu Thr Gly Tyr Arg Leu Ala Ala Asp Gln His Arg Cys Glu
 65                  70                  75                  80
Asp Val Asp Asp Cys Ile Leu Glu Pro Ser Pro Cys Pro Gln Arg Cys
```

| | | | | 85 | | | | 90 | | | | 95 | |
|---|---|---|---|---|---|---|---|---|---|---|---|---|---|

Val Asn Thr Gln Gly Gly Phe Glu Cys His Cys Tyr Pro Asn Tyr Asp
           100                    105                 110

Leu Val Asp Gly Glu Cys Val Glu Pro Val Asp Pro Cys Phe Arg Ala
        115                    120                   125

Asn Cys Glu Tyr Gln Cys Gln Pro Leu Asn Gln Thr Ser Tyr Leu Cys
        130                    135                 140

Val Cys Ala Glu Gly Phe Ala Pro Ile Pro His Glu Pro His Arg Cys
145                 150                    155                 160

Gln Leu Phe Cys Asn Gln Thr Ala Cys Pro Ala Asp Cys Asp Pro Asn
        165                    170                 175

Thr Gln Ala Ser Cys Glu Cys Pro Glu Gly Tyr Ile Leu Asp Asp Gly
        180                    185                 190

Phe Ile Cys Thr Asp Ile Asp Glu Cys Glu Asn Gly Gly Phe Cys Ser
        195                    200                 205

Gly Val Cys His Asn Leu Pro Gly Thr Phe Glu Cys Ile Cys Gly Pro
        210                    215                 220

Asp Ser Ala Leu Ala Arg His Ile Gly Thr Asp Cys Asp Ser Gly Lys
225                 230                    235                 240

Val Asp Gly Gly Asp Ser Gly Ser Gly Glu Pro Pro Ser Pro Pro Thr
        245                    250                 255

Pro Gly Ser Thr Leu Thr Pro Pro Ala Val Gly Leu Val His Ser
        260                    265                 270

<210> SEQ ID NO 111
<211> LENGTH: 200
<212> TYPE: PRT
<213> ORGANISM: Artificial Sequence
<220> FEATURE:
<223> OTHER INFORMATION: Synthetic peptide F1024S-TM23456M

<400> SEQUENCE: 111

Thr Ala Ser Ala Thr Gln Ser Cys Asn Asp Leu Cys Glu His Phe Cys
1               5                    10                 15

Val Pro Asn Pro Asp Gln Pro Gly Ser Tyr Ser Cys Met Cys Glu Thr
         20                   25                 30

Gly Tyr Arg Leu Ala Ala Asp Gln His Arg Cys Glu Asp Val Asp Asp
         35                   40                 45

Cys Ile Leu Glu Pro Ser Pro Cys Pro Gln Arg Cys Val Asn Thr Gln
        50                    55                 60

Gly Gly Phe Glu Cys His Cys Tyr Pro Asn Tyr Asp Leu Val Asp Gly
65                 70                    75                 80

Glu Cys Val Glu Pro Val Asp Pro Cys Phe Arg Ala Asn Cys Glu Tyr
                 85                   90                 95

Gln Cys Gln Pro Leu Asn Gln Thr Ser Tyr Leu Cys Val Cys Ala Glu
        100                    105                 110

Gly Phe Ala Pro Ile Pro His Glu Pro His Arg Cys Gln Met Phe Cys
        115                    120                 125

Asn Gln Thr Ala Cys Pro Ala Asp Cys Asp Pro Asn Thr Gln Ala Ser
        130                    135                 140

Cys Glu Cys Pro Glu Gly Tyr Ile Leu Asp Asp Gly Phe Ile Cys Thr
145                 150                    155                 160

Asp Ile Asp Glu Cys Glu Asn Gly Gly Phe Cys Ser Gly Val Cys His
        165                    170                 175

Asn Leu Pro Gly Thr Phe Glu Cys Ile Cys Gly Pro Asp Ser Ala Leu
        180                    185                 190

Ala Arg His Ile Gly Thr Asp Cys
        195                 200

<210> SEQ ID NO 112
<211> LENGTH: 200
<212> TYPE: PRT
<213> ORGANISM: Artificial Sequence
<220> FEATURE:
<223> OTHER INFORMATION: Synthetic peptide F1024S-TM23456L

<400> SEQUENCE: 112

Thr Ala Ser Ala Thr Gln Ser Cys Asn Asp Leu Cys Glu His Phe Cys
1               5                   10                  15

Val Pro Asn Pro Asp Gln Pro Gly Ser Tyr Ser Cys Met Cys Glu Thr
            20                  25                  30

Gly Tyr Arg Leu Ala Ala Asp Gln His Arg Cys Glu Asp Val Asp Asp
        35                  40                  45

Cys Ile Leu Glu Pro Ser Pro Cys Pro Gln Arg Cys Val Asn Thr Gln
    50                  55                  60

Gly Gly Phe Glu Cys His Cys Tyr Pro Asn Tyr Asp Leu Val Asp Gly
65                  70                  75                  80

Glu Cys Val Glu Pro Val Asp Pro Cys Phe Arg Ala Asn Cys Glu Tyr
                85                  90                  95

Gln Cys Gln Pro Leu Asn Gln Thr Ser Tyr Leu Cys Val Cys Ala Glu
            100                 105                 110

Gly Phe Ala Pro Ile Pro His Glu Pro His Arg Cys Gln Leu Phe Cys
        115                 120                 125

Asn Gln Thr Ala Cys Pro Ala Asp Cys Asp Pro Asn Thr Gln Ala Ser
    130                 135                 140

Cys Glu Cys Pro Glu Gly Tyr Ile Leu Asp Asp Gly Phe Ile Cys Thr
145                 150                 155                 160

Asp Ile Asp Glu Cys Glu Asn Gly Gly Phe Cys Ser Gly Val Cys His
                165                 170                 175

Asn Leu Pro Gly Thr Phe Glu Cys Ile Cys Gly Pro Asp Ser Ala Leu
            180                 185                 190

Ala Arg His Ile Gly Thr Asp Cys
        195                 200

<210> SEQ ID NO 113
<211> LENGTH: 235
<212> TYPE: PRT
<213> ORGANISM: Artificial Sequence
<220> FEATURE:
<223> OTHER INFORMATION: Synthetic peptide F1024S-TM234567M

<400> SEQUENCE: 113

Thr Ala Ser Ala Thr Gln Ser Cys Asn Asp Leu Cys Glu His Phe Cys
1               5                   10                  15

Val Pro Asn Pro Asp Gln Pro Gly Ser Tyr Ser Cys Met Cys Glu Thr
            20                  25                  30

Gly Tyr Arg Leu Ala Ala Asp Gln His Arg Cys Glu Asp Val Asp Asp
        35                  40                  45

Cys Ile Leu Glu Pro Ser Pro Cys Pro Gln Arg Cys Val Asn Thr Gln
    50                  55                  60

Gly Gly Phe Glu Cys His Cys Tyr Pro Asn Tyr Asp Leu Val Asp Gly
65                  70                  75                  80

Glu Cys Val Glu Pro Val Asp Pro Cys Phe Arg Ala Asn Cys Glu Tyr
                85                  90                  95

```
Gln Cys Gln Pro Leu Asn Gln Thr Ser Tyr Leu Cys Val Cys Ala Glu
                100                 105                 110

Gly Phe Ala Pro Ile Pro His Glu Pro His Arg Cys Gln Met Phe Cys
                115                 120                 125

Asn Gln Thr Ala Cys Pro Ala Asp Cys Asp Pro Asn Thr Gln Ala Ser
            130                 135                 140

Cys Glu Cys Pro Glu Gly Tyr Ile Leu Asp Asp Gly Phe Ile Cys Thr
145                 150                 155                 160

Asp Ile Asp Glu Cys Glu Asn Gly Gly Phe Cys Ser Gly Val Cys His
                165                 170                 175

Asn Leu Pro Gly Thr Phe Glu Cys Ile Cys Gly Pro Asp Ser Ala Leu
            180                 185                 190

Ala Arg His Ile Gly Thr Asp Cys Asp Ser Gly Lys Val Asp Gly Gly
                195                 200                 205

Asp Ser Gly Ser Gly Glu Pro Pro Ser Pro Thr Pro Gly Ser Thr
            210                 215                 220

Leu Thr Pro Pro Ala Val Gly Leu Val His Ser
225                 230                 235

<210> SEQ ID NO 114
<211> LENGTH: 235
<212> TYPE: PRT
<213> ORGANISM: Artificial Sequence
<220> FEATURE:
<223> OTHER INFORMATION: Synthetic peptide F1024S-TM234567L

<400> SEQUENCE: 114

Thr Ala Ser Ala Thr Gln Ser Cys Asn Asp Leu Cys Glu His Phe Cys
1               5                   10                  15

Val Pro Asn Pro Asp Gln Pro Gly Ser Tyr Ser Cys Met Cys Glu Thr
                20                  25                  30

Gly Tyr Arg Leu Ala Ala Asp Gln His Arg Cys Glu Asp Val Asp Asp
                35                  40                  45

Cys Ile Leu Glu Pro Ser Pro Cys Pro Gln Arg Cys Val Asn Thr Gln
50                  55                  60

Gly Gly Phe Glu Cys His Cys Tyr Pro Asn Tyr Asp Leu Val Asp Gly
65                  70                  75                  80

Glu Cys Val Glu Pro Val Asp Pro Cys Phe Arg Ala Asn Cys Glu Tyr
                85                  90                  95

Gln Cys Gln Pro Leu Asn Gln Thr Ser Tyr Leu Cys Val Cys Ala Glu
                100                 105                 110

Gly Phe Ala Pro Ile Pro His Glu Pro His Arg Cys Gln Leu Phe Cys
                115                 120                 125

Asn Gln Thr Ala Cys Pro Ala Asp Cys Asp Pro Asn Thr Gln Ala Ser
            130                 135                 140

Cys Glu Cys Pro Glu Gly Tyr Ile Leu Asp Asp Gly Phe Ile Cys Thr
145                 150                 155                 160

Asp Ile Asp Glu Cys Glu Asn Gly Gly Phe Cys Ser Gly Val Cys His
                165                 170                 175

Asn Leu Pro Gly Thr Phe Glu Cys Ile Cys Gly Pro Asp Ser Ala Leu
            180                 185                 190

Ala Arg His Ile Gly Thr Asp Cys Asp Ser Gly Lys Val Asp Gly Gly
                195                 200                 205

Asp Ser Gly Ser Gly Glu Pro Pro Ser Pro Thr Pro Gly Ser Thr
            210                 215                 220
```

```
Leu Thr Pro Pro Ala Val Gly Leu Val His Ser
225                 230                 235

<210> SEQ ID NO 115
<211> LENGTH: 157
<212> TYPE: PRT
<213> ORGANISM: Artificial Sequence
<220> FEATURE:
<223> OTHER INFORMATION: Synthetic peptide F1024S-TM3456M

<400> SEQUENCE: 115

Glu Asp Val Asp Asp Cys Ile Leu Glu Pro Ser Pro Cys Pro Gln Arg
1               5                   10                  15

Cys Val Asn Thr Gln Gly Gly Phe Glu Cys His Cys Tyr Pro Asn Tyr
                20                  25                  30

Asp Leu Val Asp Gly Glu Cys Val Glu Pro Val Asp Pro Cys Phe Arg
            35                  40                  45

Ala Asn Cys Glu Tyr Gln Cys Gln Pro Leu Asn Gln Thr Ser Tyr Leu
        50                  55                  60

Cys Val Cys Ala Glu Gly Phe Ala Pro Ile Pro His Glu Pro His Arg
65                  70                  75                  80

Cys Gln Met Phe Cys Asn Gln Thr Ala Cys Pro Ala Asp Cys Asp Pro
                85                  90                  95

Asn Thr Gln Ala Ser Cys Glu Cys Pro Glu Gly Tyr Ile Leu Asp Asp
            100                 105                 110

Gly Phe Ile Cys Thr Asp Ile Asp Glu Cys Glu Asn Gly Gly Phe Cys
        115                 120                 125

Ser Gly Val Cys His Asn Leu Pro Gly Thr Phe Glu Cys Ile Cys Gly
    130                 135                 140

Pro Asp Ser Ala Leu Ala Arg His Ile Gly Thr Asp Cys
145                 150                 155

<210> SEQ ID NO 116
<211> LENGTH: 157
<212> TYPE: PRT
<213> ORGANISM: Artificial Sequence
<220> FEATURE:
<223> OTHER INFORMATION: Synthetic peptide F1024S-TM3456L

<400> SEQUENCE: 116

Glu Asp Val Asp Asp Cys Ile Leu Glu Pro Ser Pro Cys Pro Gln Arg
1               5                   10                  15

Cys Val Asn Thr Gln Gly Gly Phe Glu Cys His Cys Tyr Pro Asn Tyr
                20                  25                  30

Asp Leu Val Asp Gly Glu Cys Val Glu Pro Val Asp Pro Cys Phe Arg
            35                  40                  45

Ala Asn Cys Glu Tyr Gln Cys Gln Pro Leu Asn Gln Thr Ser Tyr Leu
        50                  55                  60

Cys Val Cys Ala Glu Gly Phe Ala Pro Ile Pro His Glu Pro His Arg
65                  70                  75                  80

Cys Gln Leu Phe Cys Asn Gln Thr Ala Cys Pro Ala Asp Cys Asp Pro
                85                  90                  95

Asn Thr Gln Ala Ser Cys Glu Cys Pro Glu Gly Tyr Ile Leu Asp Asp
            100                 105                 110

Gly Phe Ile Cys Thr Asp Ile Asp Glu Cys Glu Asn Gly Gly Phe Cys
        115                 120                 125

Ser Gly Val Cys His Asn Leu Pro Gly Thr Phe Glu Cys Ile Cys Gly
    130                 135                 140
```

Pro Asp Ser Ala Leu Ala Arg His Ile Gly Thr Asp Cys
145                 150                 155

<210> SEQ ID NO 117
<211> LENGTH: 192
<212> TYPE: PRT
<213> ORGANISM: Artificial Sequence
<220> FEATURE:
<223> OTHER INFORMATION: Synthetic peptide F1024S-TM34567M

<400> SEQUENCE: 117

Glu Asp Val Asp Cys Ile Leu Glu Pro Ser Pro Cys Pro Gln Arg
1               5                   10                  15

Cys Val Asn Thr Gln Gly Gly Phe Glu Cys His Cys Tyr Pro Asn Tyr
                20                  25                  30

Asp Leu Val Asp Gly Glu Cys Val Glu Pro Val Asp Pro Cys Phe Arg
            35                  40                  45

Ala Asn Cys Glu Tyr Gln Cys Gln Pro Leu Asn Gln Thr Ser Tyr Leu
50                  55                  60

Cys Val Cys Ala Glu Gly Phe Ala Pro Ile Pro His Glu Pro His Arg
65                  70                  75                  80

Cys Gln Met Phe Cys Asn Gln Thr Ala Cys Pro Ala Asp Cys Asp Pro
                85                  90                  95

Asn Thr Gln Ala Ser Cys Glu Cys Pro Glu Gly Tyr Ile Leu Asp Asp
            100                 105                 110

Gly Phe Ile Cys Thr Asp Ile Asp Glu Cys Glu Asn Gly Gly Phe Cys
        115                 120                 125

Ser Gly Val Cys His Asn Leu Pro Gly Thr Phe Glu Cys Ile Cys Gly
    130                 135                 140

Pro Asp Ser Ala Leu Ala Arg His Ile Gly Thr Asp Cys Asp Ser Gly
145                 150                 155                 160

Lys Val Asp Gly Gly Asp Ser Gly Ser Gly Glu Pro Pro Pro Ser Pro
                165                 170                 175

Thr Pro Gly Ser Thr Leu Thr Pro Pro Ala Val Gly Leu Val His Ser
            180                 185                 190

<210> SEQ ID NO 118
<211> LENGTH: 192
<212> TYPE: PRT
<213> ORGANISM: Artificial Sequence
<220> FEATURE:
<223> OTHER INFORMATION: Synthetic peptide F1024S-TM34567L

<400> SEQUENCE: 118

Glu Asp Val Asp Cys Ile Leu Glu Pro Ser Pro Cys Pro Gln Arg
1               5                   10                  15

Cys Val Asn Thr Gln Gly Gly Phe Glu Cys His Cys Tyr Pro Asn Tyr
                20                  25                  30

Asp Leu Val Asp Gly Glu Cys Val Glu Pro Val Asp Pro Cys Phe Arg
            35                  40                  45

Ala Asn Cys Glu Tyr Gln Cys Gln Pro Leu Asn Gln Thr Ser Tyr Leu
50                  55                  60

Cys Val Cys Ala Glu Gly Phe Ala Pro Ile Pro His Glu Pro His Arg
65                  70                  75                  80

Cys Gln Leu Phe Cys Asn Gln Thr Ala Cys Pro Ala Asp Cys Asp Pro
                85                  90                  95

Asn Thr Gln Ala Ser Cys Glu Cys Pro Glu Gly Tyr Ile Leu Asp Asp
            100                 105                 110

```
Gly Phe Ile Cys Thr Asp Ile Asp Glu Cys Glu Asn Gly Gly Phe Cys
        115                 120                 125

Ser Gly Val Cys His Asn Leu Pro Gly Thr Phe Glu Cys Ile Cys Gly
        130                 135                 140

Pro Asp Ser Ala Leu Ala Arg His Ile Gly Thr Asp Cys Asp Ser Gly
145                 150                 155                 160

Lys Val Asp Gly Gly Asp Ser Gly Ser Gly Glu Pro Pro Ser Pro
                165                 170                 175

Thr Pro Gly Ser Thr Leu Thr Pro Pro Ala Val Gly Leu Val His Ser
                180                 185                 190
```

<210> SEQ ID NO 119
<211> LENGTH: 118
<212> TYPE: PRT
<213> ORGANISM: Artificial Sequence
<220> FEATURE:
<223> OTHER INFORMATION: Synthetic peptide F1024S-TM456M

<400> SEQUENCE: 119

```
Val Glu Pro Val Asp Pro Cys Phe Arg Ala Asn Cys Glu Tyr Gln Cys
1               5                   10                  15

Gln Pro Leu Asn Gln Thr Ser Tyr Leu Cys Val Cys Ala Glu Gly Phe
            20                  25                  30

Ala Pro Ile Pro His Glu Pro His Arg Cys Gln Met Phe Cys Asn Gln
        35                  40                  45

Thr Ala Cys Pro Ala Asp Cys Asp Pro Asn Thr Gln Ala Ser Cys Glu
    50                  55                  60

Cys Pro Glu Gly Tyr Ile Leu Asp Asp Gly Phe Ile Cys Thr Asp Ile
65                  70                  75                  80

Asp Glu Cys Glu Asn Gly Gly Phe Cys Ser Gly Val Cys His Asn Leu
                85                  90                  95

Pro Gly Thr Phe Glu Cys Ile Cys Gly Pro Asp Ser Ala Leu Ala Arg
            100                 105                 110

His Ile Gly Thr Asp Cys
        115
```

<210> SEQ ID NO 120
<211> LENGTH: 118
<212> TYPE: PRT
<213> ORGANISM: Artificial Sequence
<220> FEATURE:
<223> OTHER INFORMATION: Synthetic peptide F1024S-TM456L

<400> SEQUENCE: 120

```
Val Glu Pro Val Asp Pro Cys Phe Arg Ala Asn Cys Glu Tyr Gln Cys
1               5                   10                  15

Gln Pro Leu Asn Gln Thr Ser Tyr Leu Cys Val Cys Ala Glu Gly Phe
            20                  25                  30

Ala Pro Ile Pro His Glu Pro His Arg Cys Gln Leu Phe Cys Asn Gln
        35                  40                  45

Thr Ala Cys Pro Ala Asp Cys Asp Pro Asn Thr Gln Ala Ser Cys Glu
    50                  55                  60

Cys Pro Glu Gly Tyr Ile Leu Asp Asp Gly Phe Ile Cys Thr Asp Ile
65                  70                  75                  80

Asp Glu Cys Glu Asn Gly Gly Phe Cys Ser Gly Val Cys His Asn Leu
                85                  90                  95

Pro Gly Thr Phe Glu Cys Ile Cys Gly Pro Asp Ser Ala Leu Ala Arg
            100                 105                 110
```

```
His Ile Gly Thr Asp Cys
            115

<210> SEQ ID NO 121
<211> LENGTH: 153
<212> TYPE: PRT
<213> ORGANISM: Artificial Sequence
<220> FEATURE:
<223> OTHER INFORMATION: Synthetic peptide F1024S-TM4567M

<400> SEQUENCE: 121

Val Glu Pro Val Asp Pro Cys Phe Arg Ala Asn Cys Glu Tyr Gln Cys
1               5                   10                  15

Gln Pro Leu Asn Gln Thr Ser Tyr Leu Cys Val Cys Ala Glu Gly Phe
            20                  25                  30

Ala Pro Ile Pro His Glu Pro His Arg Cys Gln Met Phe Cys Asn Gln
        35                  40                  45

Thr Ala Cys Pro Ala Asp Cys Asp Pro Asn Thr Gln Ala Ser Cys Glu
    50                  55                  60

Cys Pro Glu Gly Tyr Ile Leu Asp Asp Gly Phe Ile Cys Thr Asp Ile
65                  70                  75                  80

Asp Glu Cys Glu Asn Gly Gly Phe Cys Ser Gly Val Cys His Asn Leu
                85                  90                  95

Pro Gly Thr Phe Glu Cys Ile Cys Gly Pro Asp Ser Ala Leu Ala Arg
            100                 105                 110

His Ile Gly Thr Asp Cys Asp Ser Gly Lys Val Asp Gly Gly Asp Ser
        115                 120                 125

Gly Ser Gly Glu Pro Pro Ser Pro Thr Pro Gly Ser Thr Leu Thr
    130                 135                 140

Pro Pro Ala Val Gly Leu Val His Ser
145                 150

<210> SEQ ID NO 122
<211> LENGTH: 153
<212> TYPE: PRT
<213> ORGANISM: Artificial Sequence
<220> FEATURE:
<223> OTHER INFORMATION: Synthetic peptide F1024S-TM4567L

<400> SEQUENCE: 122

Val Glu Pro Val Asp Pro Cys Phe Arg Ala Asn Cys Glu Tyr Gln Cys
1               5                   10                  15

Gln Pro Leu Asn Gln Thr Ser Tyr Leu Cys Val Cys Ala Glu Gly Phe
            20                  25                  30

Ala Pro Ile Pro His Glu Pro His Arg Cys Gln Leu Phe Cys Asn Gln
        35                  40                  45

Thr Ala Cys Pro Ala Asp Cys Asp Pro Asn Thr Gln Ala Ser Cys Glu
    50                  55                  60

Cys Pro Glu Gly Tyr Ile Leu Asp Asp Gly Phe Ile Cys Thr Asp Ile
65                  70                  75                  80

Asp Glu Cys Glu Asn Gly Gly Phe Cys Ser Gly Val Cys His Asn Leu
                85                  90                  95

Pro Gly Thr Phe Glu Cys Ile Cys Gly Pro Asp Ser Ala Leu Ala Arg
            100                 105                 110

His Ile Gly Thr Asp Cys Asp Ser Gly Lys Val Asp Gly Gly Asp Ser
        115                 120                 125

Gly Ser Gly Glu Pro Pro Ser Pro Thr Pro Gly Ser Thr Leu Thr
    130                 135                 140
```

<210> SEQ ID NO 123
<211> LENGTH: 444
<212> TYPE: DNA
<213> ORGANISM: Artificial Sequence
<220> FEATURE:
<223> OTHER INFORMATION: Synthetic F1024 Antibody Heavy Chain variable region
<220> FEATURE:
<221> NAME/KEY: CDS
<222> LOCATION: (1)..(444)

<400> SEQUENCE: 123

```
atg gat tgg ttg tgg aac ttg cta ttc ctg atg gta gtt gcc caa agt        48
Met Asp Trp Leu Trp Asn Leu Leu Phe Leu Met Val Val Ala Gln Ser
1               5                   10                  15 gct caa gca cag atc cag ttg gta cag tct gga cct gaa ctg aag aag        96
Ala Gln Ala Gln Ile Gln Leu Val Gln Ser Gly Pro Glu Leu Lys Lys
            20                  25                  30 cct gga gag tca gtg aag atc tcc tgc aag gct tct ggg tat acc ttc       144
Pro Gly Glu Ser Val Lys Ile Ser Cys Lys Ala Ser Gly Tyr Thr Phe
        35                  40                  45 aca gac tat gca atg aac tgg gtg aaa cag gct cca gga aat ggc ttg       192
Thr Asp Tyr Ala Met Asn Trp Val Lys Gln Ala Pro Gly Asn Gly Leu
    50                  55                  60 aag tgg atg ggc tgg atc aac acc caa act gga aag cca aca tat gcg       240
Lys Trp Met Gly Trp Ile Asn Thr Gln Thr Gly Lys Pro Thr Tyr Ala
65                  70                  75                  80 gat gat ttc aaa caa cgg ttt gtc ttc tct ttg gaa act tct gcc agc       288
Asp Asp Phe Lys Gln Arg Phe Val Phe Ser Leu Glu Thr Ser Ala Ser
                85                  90                  95 act gca tac ttg cag atc aac aac ctc aat att gag gac aca gct aca       336
Thr Ala Tyr Leu Gln Ile Asn Asn Leu Asn Ile Glu Asp Thr Ala Thr
            100                 105                 110 tat ttc tgt aca aga tcc act ttt tac tat agc agc tat atc tac ggg       384
Tyr Phe Cys Thr Arg Ser Thr Phe Tyr Tyr Ser Ser Tyr Ile Tyr Gly
        115                 120                 125 tgg tac ttt gac ttc tgg ggc cca gga acc atg gtc acc gtg tcc tca       432
Trp Tyr Phe Asp Phe Trp Gly Pro Gly Thr Met Val Thr Val Ser Ser
    130                 135                 140 gct gaa aca aca                                                       444
Ala Glu Thr Thr
145
```

<210> SEQ ID NO 124
<211> LENGTH: 148
<212> TYPE: PRT
<213> ORGANISM: Artificial Sequence
<220> FEATURE:
<223> OTHER INFORMATION: Synthetic F1024 Antibody Heavy Chain variable region

<400> SEQUENCE: 124

```
Met Asp Trp Leu Trp Asn Leu Leu Phe Leu Met Val Val Ala Gln Ser
1               5                   10                  15

Ala Gln Ala Gln Ile Gln Leu Val Gln Ser Gly Pro Glu Leu Lys Lys
            20                  25                  30

Pro Gly Glu Ser Val Lys Ile Ser Cys Lys Ala Ser Gly Tyr Thr Phe
        35                  40                  45

Thr Asp Tyr Ala Met Asn Trp Val Lys Gln Ala Pro Gly Asn Gly Leu
    50                  55                  60
```

```
Lys Trp Met Gly Trp Ile Asn Thr Gln Thr Gly Lys Pro Thr Tyr Ala
 65                  70                  75                  80

Asp Asp Phe Lys Gln Arg Phe Val Phe Ser Leu Glu Thr Ser Ala Ser
             85                  90                  95

Thr Ala Tyr Leu Gln Ile Asn Asn Leu Asn Ile Glu Asp Thr Ala Thr
        100                 105                 110

Tyr Phe Cys Thr Arg Ser Thr Phe Tyr Tyr Ser Ser Tyr Ile Tyr Gly
    115                 120                 125

Trp Tyr Phe Asp Phe Trp Gly Pro Gly Thr Met Val Thr Val Ser Ser
130                 135                 140

Ala Glu Thr Thr
145

<210> SEQ ID NO 125
<211> LENGTH: 411
<212> TYPE: DNA
<213> ORGANISM: Artificial Sequence
<220> FEATURE:
<223> OTHER INFORMATION: Synthetic F1024 Antibody Light Chain variable
      region
<220> FEATURE:
<221> NAME/KEY: CDS
<222> LOCATION: (1)..(411)

<400> SEQUENCE: 125 atg gag tca cat act agg gtc ttc ata ttc ctg ctg ctc tgg ttg tct    48
Met Glu Ser His Thr Arg Val Phe Ile Phe Leu Leu Leu Trp Leu Ser
  1               5                  10                  15 ggt gct gat ggg gac att gtg atg act cag tct ccc aca tcc att tcc    96
Gly Ala Asp Gly Asp Ile Val Met Thr Gln Ser Pro Thr Ser Ile Ser
             20                  25                  30 ata tca gta gga gag agg gtc acc atg aac tgc aag gcc agt cag aat   144
Ile Ser Val Gly Glu Arg Val Thr Met Asn Cys Lys Ala Ser Gln Asn
        35                  40                  45 gtg ggt tct aat gta gac tgg tac caa cag aaa aca ggg cag tct cct   192
Val Gly Ser Asn Val Asp Trp Tyr Gln Gln Lys Thr Gly Gln Ser Pro
    50                  55                  60 aaa ctg ctt atc tac aag gca tcc aac cgg tac act ggc gtc cct gat   240
Lys Leu Leu Ile Tyr Lys Ala Ser Asn Arg Tyr Thr Gly Val Pro Asp
 65                  70                  75                  80 cgc ttc aca ggc agt gga tct gga aca gat ttc act ttc acc atc agc   288
Arg Phe Thr Gly Ser Gly Ser Gly Thr Asp Phe Thr Phe Thr Ile Ser
             85                  90                  95 aac atg cag gct gtg gac ctg gct gtt tat tac tgt atg cag tct aac   336
Asn Met Gln Ala Val Asp Leu Ala Val Tyr Tyr Cys Met Gln Ser Asn
        100                 105                 110 acc aat cct ccg tgg acg ttc ggt gga ggc acc aag ctg gaa ttg aaa   384
Thr Asn Pro Pro Trp Thr Phe Gly Gly Gly Thr Lys Leu Glu Leu Lys
    115                 120                 125 cgg gct gat gct gca cca act gta tct                               411
Arg Ala Asp Ala Ala Pro Thr Val Ser
    130                 135

<210> SEQ ID NO 126
<211> LENGTH: 137
<212> TYPE: PRT
<213> ORGANISM: Artificial Sequence
<220> FEATURE:
<223> OTHER INFORMATION: Synthetic F1024 Antibody Light Chain variable
      region

<400> SEQUENCE: 126

Met Glu Ser His Thr Arg Val Phe Ile Phe Leu Leu Leu Trp Leu Ser
```

```
            1               5                  10                 15
Gly Ala Asp Gly Asp Ile Val Met Thr Gln Ser Pro Thr Ser Ile Ser
            20                  25                  30

Ile Ser Val Gly Glu Arg Val Thr Met Asn Cys Lys Ala Ser Gln Asn
            35                  40                  45

Val Gly Ser Asn Val Asp Trp Tyr Gln Gln Lys Thr Gly Gln Ser Pro
    50                  55                  60

Lys Leu Leu Ile Tyr Lys Ala Ser Asn Arg Tyr Thr Gly Val Pro Asp
65                  70                  75                  80

Arg Phe Thr Gly Ser Gly Ser Gly Thr Asp Phe Thr Phe Thr Ile Ser
                85                  90                  95

Asn Met Gln Ala Val Asp Leu Ala Val Tyr Tyr Cys Met Gln Ser Asn
            100                 105                 110

Thr Asn Pro Pro Trp Thr Phe Gly Gly Gly Thr Lys Leu Glu Leu Lys
            115                 120                 125

Arg Ala Asp Ala Ala Pro Thr Val Ser
            130                 135

<210> SEQ ID NO 127
<211> LENGTH: 473
<212> TYPE: DNA
<213> ORGANISM: Artificial Sequence
<220> FEATURE:
<223> OTHER INFORMATION: Synthetic F1031-13-2 heavy chain variable
      region
<220> FEATURE:
<221> NAME/KEY: CDS
<222> LOCATION: (20)..(472)

<400> SEQUENCE: 127
tgaacacaga ccactcacc atg gaa tgt aac tgg ata ctt cct ttt att ctg      52
                    Met Glu Cys Asn Trp Ile Leu Pro Phe Ile Leu
                     1               5                  10 tcg gta att tca gga gtc tac tca gag gtt cag ctc cag cag tct ggg     100
Ser Val Ile Ser Gly Val Tyr Ser Glu Val Gln Leu Gln Gln Ser Gly
            15                  20                  25 act gtg ctg gca agg cct ggg gct tcc gtg aag atg tcc tgc aag gct     148
Thr Val Leu Ala Arg Pro Gly Ala Ser Val Lys Met Ser Cys Lys Ala
        30                  35                  40 tct ggc tac agg tat acc aac tac tgg ttg cac tgg gta aaa cag agg     196
Ser Gly Tyr Arg Tyr Thr Asn Tyr Trp Leu His Trp Val Lys Gln Arg
    45                  50                  55 cct gga cag ggt cta gag tgg att ggt gct att tat cct gga aat agt     244
Pro Gly Gln Gly Leu Glu Trp Ile Gly Ala Ile Tyr Pro Gly Asn Ser
60                  65                  70                  75 gat tct agc tac aac cag aac ttc aag ggc aag gcc aaa ctg act gca     292
Asp Ser Ser Tyr Asn Gln Asn Phe Lys Gly Lys Ala Lys Leu Thr Ala
                80                  85                  90 gtc aca tcc gcc agc act gcc tac atg gag ctc agc agc ctg aca aat     340
Val Thr Ser Ala Ser Thr Ala Tyr Met Glu Leu Ser Ser Leu Thr Asn
            95                  100                 105 gag gac tct gcg gtc tat tac tgt aca aga tgg ggc cct tat ggc atc     388
Glu Asp Ser Ala Val Tyr Tyr Cys Thr Arg Trp Gly Pro Tyr Gly Ile
        110                 115                 120 tat gct atg gac tac tgg ggt caa gga acc tca gtc acc gtc tcc tca     436
Tyr Ala Met Asp Tyr Trp Gly Gln Gly Thr Ser Val Thr Val Ser Ser
    125                 130                 135 gcc aaa aca aca ccc cca tca gtc tat cca ctg gcc c                   473
Ala Lys Thr Thr Pro Pro Ser Val Tyr Pro Leu Ala
140                 145                 150
```

<210> SEQ ID NO 128
<211> LENGTH: 151
<212> TYPE: PRT
<213> ORGANISM: Artificial Sequence
<220> FEATURE:
<223> OTHER INFORMATION: Synthetic F1031-13-2 heavy chain variable
      region

<400> SEQUENCE: 128

```
Met Glu Cys Asn Trp Ile Leu Pro Phe Ile Leu Ser Val Ile Ser Gly
1               5                   10                  15

Val Tyr Ser Glu Val Gln Leu Gln Gln Ser Gly Thr Val Leu Ala Arg
            20                  25                  30

Pro Gly Ala Ser Val Lys Met Ser Cys Lys Ala Ser Gly Tyr Arg Tyr
        35                  40                  45

Thr Asn Tyr Trp Leu His Trp Val Lys Gln Arg Pro Gly Gln Gly Leu
    50                  55                  60

Glu Trp Ile Gly Ala Ile Tyr Pro Gly Asn Ser Asp Ser Ser Tyr Asn
65                  70                  75                  80

Gln Asn Phe Lys Gly Lys Ala Lys Leu Thr Ala Val Thr Ser Ala Ser
                85                  90                  95

Thr Ala Tyr Met Glu Leu Ser Ser Leu Thr Asn Glu Asp Ser Ala Val
            100                 105                 110

Tyr Tyr Cys Thr Arg Trp Gly Pro Tyr Gly Ile Tyr Ala Met Asp Tyr
        115                 120                 125

Trp Gly Gln Gly Thr Ser Val Thr Val Ser Ser Ala Lys Thr Thr Pro
    130                 135                 140

Pro Ser Val Tyr Pro Leu Ala
145                 150
```

<210> SEQ ID NO 129
<211> LENGTH: 328
<212> TYPE: DNA
<213> ORGANISM: Artificial Sequence
<220> FEATURE:
<223> OTHER INFORMATION: Synthetic F1031-13-2 light chain variable
      region
<220> FEATURE:
<221> NAME/KEY: CDS
<222> LOCATION: (1)..(327)

<400> SEQUENCE: 129

```
gac atc gtg atg acc cag tct cca gct tct ttg gct gtg tct ctg ggg      48
Asp Ile Val Met Thr Gln Ser Pro Ala Ser Leu Ala Val Ser Leu Gly
1               5                   10                  15 cag agg gcc acc atc tcc tgc aga gcc agc gaa agt gtt gat tat tct      96
Gln Arg Ala Thr Ile Ser Cys Arg Ala Ser Glu Ser Val Asp Tyr Ser
            20                  25                  30 ggc att agt ttt atg aac tgg ttc caa cag aaa cca gga cag cca ccc     144
Gly Ile Ser Phe Met Asn Trp Phe Gln Gln Lys Pro Gly Gln Pro Pro
        35                  40                  45 aaa ctc ctc atc tat gct gca tcc aac caa gga tcc ggg gtc cct gcc     192
Lys Leu Leu Ile Tyr Ala Ala Ser Asn Gln Gly Ser Gly Val Pro Ala
    50                  55                  60 agg ttt agt ggc agt ggg tct ggg aca gac ttc agc ctc aac atc cat     240
Arg Phe Ser Gly Ser Gly Ser Gly Thr Asp Phe Ser Leu Asn Ile His
65                  70                  75                  80 cct atg gag gag gat gat act gca atg tat ttc tgt cag cac agt aag     288
Pro Met Glu Glu Asp Asp Thr Ala Met Tyr Phe Cys Gln His Ser Lys
                85                  90                  95 gag ctt ccg tac acg ttc gga ggg ggg acc aag ctg gaa a                328
Glu Leu Pro Tyr Thr Phe Gly Gly Gly Thr Lys Leu Glu
```

```
Glu Leu Pro Tyr Thr Phe Gly Gly Gly Thr Lys Leu Glu
                100                 105
```

<210> SEQ ID NO 130
<211> LENGTH: 109
<212> TYPE: PRT
<213> ORGANISM: Artificial Sequence
<220> FEATURE:
<223> OTHER INFORMATION: Synthetic F1031-13-2 light chain variable
      region

<400> SEQUENCE: 130

```
Asp Ile Val Met Thr Gln Ser Pro Ala Ser Leu Ala Val Ser Leu Gly
1               5                   10                  15

Gln Arg Ala Thr Ile Ser Cys Arg Ala Ser Glu Ser Val Asp Tyr Ser
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln His Ser Lys
                85                  90                  95

Glu Leu Pro Tyr Thr Phe Gly Gly Gly Thr Lys Leu Glu
                100                 105
```

<210> SEQ ID NO 131
<211> LENGTH: 430
<212> TYPE: DNA
<213> ORGANISM: Artificial Sequence
<220> FEATURE:
<223> OTHER INFORMATION: Synthetic F1031-13-2 heavy chain variable
      region
<220> FEATURE:
<221> NAME/KEY: CDS
<222> LOCATION: (8)..(430)

<400> SEQUENCE: 131

```
gaattcc atg gaa tgt aac tgg ata ctt cct ttt att ctg tcg gta att        49
        Met Glu Cys Asn Trp Ile Leu Pro Phe Ile Leu Ser Val Ile
        1               5                   10 tca gga gtc tac tca gag gtt cag ctc cag cag tct ggg act gtg ctg        97
Ser Gly Val Tyr Ser Glu Val Gln Leu Gln Gln Ser Gly Thr Val Leu
15                  20                  25                  30 gca agg cct ggg gct tcc gtg aag atg tcc tgc aag gct tct ggc tac       145
Ala Arg Pro Gly Ala Ser Val Lys Met Ser Cys Lys Ala Ser Gly Tyr
                35                  40                  45 agg tat acc aac tac tgg ttg cac tgg gta aaa cag agg cct gga cag       193
Arg Tyr Thr Asn Tyr Trp Leu His Trp Val Lys Gln Arg Pro Gly Gln
            50                  55                  60 ggt cta gag tgg att ggt gct att tat cct gga aat agt gat tct agc       241
Gly Leu Glu Trp Ile Gly Ala Ile Tyr Pro Gly Asn Ser Asp Ser Ser
        65                  70                  75 tac aac cag aac ttc aag ggc aag gcc aaa ctg act gca gtc aca tcc       289
Tyr Asn Gln Asn Phe Lys Gly Lys Ala Lys Leu Thr Ala Val Thr Ser
    80                  85                  90 gcc agc act gcc tac atg gag ctc agc agc ctg aca aat gag gac tct       337
Ala Ser Thr Ala Tyr Met Glu Leu Ser Ser Leu Thr Asn Glu Asp Ser
95                  100                 105                 110 gcg gtc tat tac tgt aca aga tgg ggc cct tat ggc atc tat gct atg       385
Ala Val Tyr Tyr Cys Thr Arg Trp Gly Pro Tyr Gly Ile Tyr Ala Met
                115                 120                 125
```

```
gac tac tgg ggt caa gga acc tca gtc acc gtc tcc agc gct agc          430
Asp Tyr Trp Gly Gln Gly Thr Ser Val Thr Val Ser Ser Ala Ser
            130                 135                 140

<210> SEQ ID NO 132
<211> LENGTH: 141
<212> TYPE: PRT
<213> ORGANISM: Artificial Sequence
<220> FEATURE:
<223> OTHER INFORMATION: Synthetic F1031-13-2 heavy chain variable
      region

<400> SEQUENCE: 132

Met Glu Cys Asn Trp Ile Leu Pro Phe Ile Leu Ser Val Ile Ser Gly
1               5                   10                  15

Val Tyr Ser Glu Val Gln Leu Gln Gln Ser Gly Thr Val Leu Ala Arg
            20                  25                  30

Pro Gly Ala Ser Val Lys Met Ser Cys Lys Ala Ser Gly Tyr Arg Tyr
        35                  40                  45

Thr Asn Tyr Trp Leu His Trp Val Lys Gln Arg Pro Gly Gln Gly Leu
    50                  55                  60

Glu Trp Ile Gly Ala Ile Tyr Pro Gly Asn Ser Asp Ser Ser Tyr Asn
65                  70                  75                  80

Gln Asn Phe Lys Gly Lys Ala Lys Leu Thr Ala Val Thr Ser Ala Ser
                85                  90                  95

Thr Ala Tyr Met Glu Leu Ser Ser Leu Thr Asn Glu Asp Ser Ala Val
            100                 105                 110

Tyr Tyr Cys Thr Arg Trp Gly Pro Tyr Gly Ile Tyr Ala Met Asp Tyr
        115                 120                 125

Trp Gly Gln Gly Thr Ser Val Thr Val Ser Ser Ala Ser
    130                 135                 140

<210> SEQ ID NO 133
<211> LENGTH: 406
<212> TYPE: DNA
<213> ORGANISM: Artificial Sequence
<220> FEATURE:
<223> OTHER INFORMATION: Synthetic F1031-13-2 light chain variable
      region
<220> FEATURE:
<221> NAME/KEY: CDS
<222> LOCATION: (8)..(406)

<400> SEQUENCE: 133 gaattcc atg gag aca gac aca ctc ctg cta tgg gtc ctg ctt ctc tgg    49
        Met Glu Thr Asp Thr Leu Leu Leu Trp Val Leu Leu Leu Trp
        1               5                   10 gtt cca ggt tcc aca ggt gac att gtg ctg acc caa tct cca gct tct    97
Val Pro Gly Ser Thr Gly Asp Ile Val Leu Thr Gln Ser Pro Ala Ser
15                  20                  25                  30 ttg gct gtg tct ctg ggg cag agg gcc acc atc tcc tgc aga gcc agc    145
Leu Ala Val Ser Leu Gly Gln Arg Ala Thr Ile Ser Cys Arg Ala Ser
                35                  40                  45 gaa agt gtt gat tat tct ggc att agt ttt atg aac tgg ttc caa cag    193
Glu Ser Val Asp Tyr Ser Gly Ile Ser Phe Met Asn Trp Phe Gln Gln
            50                  55                  60 aaa cca gga cag cca ccc aaa ctc ctc atc tat gct gca tcc aac caa    241
Lys Pro Gly Gln Pro Pro Lys Leu Leu Ile Tyr Ala Ala Ser Asn Gln
        65                  70                  75 gga tcc ggg gtc cct gcc agg ttt agt ggc agt ggg tct ggg aca gac    289
Gly Ser Gly Val Pro Ala Arg Phe Ser Gly Ser Gly Ser Gly Thr Asp
    80                  85                  90
```

```
ttc agc ctc aac atc cat cct atg gag gag gat gat act gca atg tat      337
Phe Ser Leu Asn Ile His Pro Met Glu Glu Asp Asp Thr Ala Met Tyr
 95                 100                 105                 110 ttc tgt cag cac agt aag gag ctt ccg tac acg ttc gga ggg ggg acc      385
Phe Cys Gln His Ser Lys Glu Leu Pro Tyr Thr Phe Gly Gly Gly Thr
            115                 120                 125 aag ctg gaa atc aaa cgt acg                                          406
Lys Leu Glu Ile Lys Arg Thr
        130

<210> SEQ ID NO 134
<211> LENGTH: 133
<212> TYPE: PRT
<213> ORGANISM: Artificial Sequence
<220> FEATURE:
<223> OTHER INFORMATION: Synthetic F1031-13-2 light chain variable
      region

<400> SEQUENCE: 134

Met Glu Thr Asp Thr Leu Leu Leu Trp Val Leu Leu Leu Trp Val Pro
 1               5                  10                  15

Gly Ser Thr Gly Asp Ile Val Leu Thr Gln Ser Pro Ala Ser Leu Ala
             20                  25                  30

Val Ser Leu Gly Gln Arg Ala Thr Ile Ser Cys Arg Ala Ser Glu Ser
         35                  40                  45

Val Asp Tyr Ser Gly Ile Ser Phe Met Asn Trp Phe Gln Gln Lys Pro
     50                  55                  60

Gly Gln Pro Pro Lys Leu Leu Ile Tyr Ala Ala Ser Asn Gln Gly Ser
 65                  70                  75                  80

Gly Val Pro Ala Arg Phe Ser Gly Ser Gly Ser Gly Thr Asp Phe Ser
                 85                  90                  95

Leu Asn Ile His Pro Met Glu Glu Asp Asp Thr Ala Met Tyr Phe Cys
            100                 105                 110

Gln His Ser Lys Glu Leu Pro Tyr Thr Phe Gly Gly Gly Thr Lys Leu
        115                 120                 125

Glu Ile Lys Arg Thr
    130

<210> SEQ ID NO 135
<211> LENGTH: 18
<212> TYPE: DNA
<213> ORGANISM: Artificial Sequence
<220> FEATURE:
<223> OTHER INFORMATION: M4 synthetic primer

<400> SEQUENCE: 135
gttttcccag tcacgacg                                                   18

<210> SEQ ID NO 136
<211> LENGTH: 22
<212> TYPE: DNA
<213> ORGANISM: Artificial Sequence
<220> FEATURE:
<223> OTHER INFORMATION: T7 synthetic primer

<400> SEQUENCE: 136
ctgttgtttc agctgaggac ac                                              22

<210> SEQ ID NO 137
<211> LENGTH: 22
<212> TYPE: DNA
<213> ORGANISM: Artificial Sequence
```

```
<220> FEATURE:
<223> OTHER INFORMATION: rIgH-b synthetic primer

<400> SEQUENCE: 137
ctgttgtttc agctgaggac ac                                          22

<210> SEQ ID NO 138
<211> LENGTH: 21
<212> TYPE: DNA
<213> ORGANISM: Artificial Sequence
<220> FEATURE:
<223> OTHER INFORMATION: rIgH-c synthetic primer

<400> SEQUENCE: 138
agggtcacca tggagttact t                                           21

<210> SEQ ID NO 139
<211> LENGTH: 24
<212> TYPE: DNA
<213> ORGANISM: Artificial Sequence
<220> FEATURE:
<223> OTHER INFORMATION: rIgK-a synthetic primer

<400> SEQUENCE: 139
agatacagtt ggtgcagcat cagc                                        24

<210> SEQ ID NO 140
<211> LENGTH: 23
<212> TYPE: DNA
<213> ORGANISM: Artificial Sequence
<220> FEATURE:
<223> OTHER INFORMATION: rIgK-b synthetic primer

<400> SEQUENCE: 140
gacactgatg tctctgggat aga                                         23

<210> SEQ ID NO 141
<211> LENGTH: 27
<212> TYPE: DNA
<213> ORGANISM: Artificial Sequence
<220> FEATURE:
<223> OTHER INFORMATION: 1024H-a synthetic primer

<400> SEQUENCE: 141
gaattccatg gattggttgt ggaactt                                     27

<210> SEQ ID NO 142
<211> LENGTH: 24
<212> TYPE: DNA
<213> ORGANISM: Artificial Sequence
<220> FEATURE:
<223> OTHER INFORMATION: 1024K-a synthetic primer

<400> SEQUENCE: 142
gaattccatg gagtcacata ctag                                        24

<210> SEQ ID NO 143
<211> LENGTH: 27
<212> TYPE: DNA
<213> ORGANISM: Artificial Sequence
<220> FEATURE:
<223> OTHER INFORMATION: HchainEco47NheI synthetic primer

<400> SEQUENCE: 143
cccccgctag cgctggagac ggtgacc                                     27
```

```
<210> SEQ ID NO 144
<211> LENGTH: 24
<212> TYPE: DNA
<213> ORGANISM: Artificial Sequence
<220> FEATURE:
<223> OTHER INFORMATION: rIgK-BsiWI synthetic primer

<400> SEQUENCE: 144
cgtacgtttc aattccagct tggt                                      24

<210> SEQ ID NO 145
<211> LENGTH: 30
<212> TYPE: DNA
<213> ORGANISM: Artificial Sequence
<220> FEATURE:
<223> OTHER INFORMATION: IgG4-m synthetic primer

<400> SEQUENCE: 145
agcgctagca ccaagggccc atccgtcttc                                30

<210> SEQ ID NO 146
<211> LENGTH: 24
<212> TYPE: DNA
<213> ORGANISM: Artificial Sequence
<220> FEATURE:
<223> OTHER INFORMATION: IgG4-v synthetic primer

<400> SEQUENCE: 146
ggatccttta cccagagaca ggga                                      24

<210> SEQ ID NO 147
<211> LENGTH: 30
<212> TYPE: DNA
<213> ORGANISM: Artificial Sequence
<220> FEATURE:
<223> OTHER INFORMATION: IgG4-s synthetic primer

<400> SEQUENCE: 147
ttacctgggc ctgatgggcc tgggggacca                                30

<210> SEQ ID NO 148
<211> LENGTH: 30
<212> TYPE: DNA
<213> ORGANISM: Artificial Sequence
<220> FEATURE:
<223> OTHER INFORMATION: IgG4-r synthetic primer

<400> SEQUENCE: 148
tggtccccca ggcccatcag gcccaggtaa                                30

<210> SEQ ID NO 149
<211> LENGTH: 20
<212> TYPE: DNA
<213> ORGANISM: Artificial Sequence
<220> FEATURE:
<223> OTHER INFORMATION: IgK-e synthetic primer

<400> SEQUENCE: 149
gcacttctcc ctctaacact                                           20

<210> SEQ ID NO 150
<211> LENGTH: 24
<212> TYPE: DNA
<213> ORGANISM: Artificial Sequence
<220> FEATURE:
<223> OTHER INFORMATION: BsiWI-hIgK synthetic primer

<400> SEQUENCE: 150
```

```
cgtacggtgg ctgcaccatc tgtc                                          24

<210> SEQ ID NO 151
<211> LENGTH: 24
<212> TYPE: DNA
<213> ORGANISM: Artificial Sequence
<220> FEATURE:
<223> OTHER INFORMATION: UTI-a synthetic primer

<400> SEQUENCE: 151
ggatccgctg tgctacccca agaa                                          24

<210> SEQ ID NO 152
<211> LENGTH: 24
<212> TYPE: DNA
<213> ORGANISM: Artificial Sequence
<220> FEATURE:
<223> OTHER INFORMATION: UTI-b synthetic primer

<400> SEQUENCE: 152
ggatccactg tggcggcctg caat                                          24

<210> SEQ ID NO 153
<211> LENGTH: 29
<212> TYPE: DNA
<213> ORGANISM: Artificial Sequence
<220> FEATURE:
<223> OTHER INFORMATION: UTI-c synthetic primer

<400> SEQUENCE: 153
gcggccgctc agttggagaa gcgcagcag                                     29

<210> SEQ ID NO 154
<211> LENGTH: 35
<212> TYPE: DNA
<213> ORGANISM: Artificial Sequence
<220> FEATURE:
<223> OTHER INFORMATION: UTI-f synthetic primer

<400> SEQUENCE: 154
gatatcacca ccaccaccgt tggagaagcg cagca                              35

<210> SEQ ID NO 155
<211> LENGTH: 35
<212> TYPE: DNA
<213> ORGANISM: Artificial Sequence
<220> FEATURE:
<223> OTHER INFORMATION: UTI-g synthetic primer

<400> SEQUENCE: 155
aggcctacca ccaccaccgt tggagaagcg cagca                              35

<210> SEQ ID NO 156
<211> LENGTH: 35
<212> TYPE: DNA
<213> ORGANISM: Artificial Sequence
<220> FEATURE:
<223> OTHER INFORMATION: UTI-h synthetic primer

<400> SEQUENCE: 156
gatatcggag gaggaggagc tgtgctaccc caaga                              35

<210> SEQ ID NO 157
<211> LENGTH: 35
<212> TYPE: DNA
<213> ORGANISM: Artificial Sequence
```

```
<220> FEATURE:
<223> OTHER INFORMATION: UTI-i synthetic primer

<400> SEQUENCE: 157
gatatcggag gaggaggaac tgtggcggcc tgcaa                              35

<210> SEQ ID NO 158
<211> LENGTH: 20
<212> TYPE: DNA
<213> ORGANISM: Artificial Sequence
<220> FEATURE:
<223> OTHER INFORMATION: SLPI-a synthetic primer

<400> SEQUENCE: 158
cagagtcact cctgccttca                                              20

<210> SEQ ID NO 159
<211> LENGTH: 30
<212> TYPE: DNA
<213> ORGANISM: Artificial Sequence
<220> FEATURE:
<223> OTHER INFORMATION: SLPI-c synthetic primer

<400> SEQUENCE: 159
agatctggaa agtccttcaa agctggagtc                                   30

<210> SEQ ID NO 160
<211> LENGTH: 30
<212> TYPE: DNA
<213> ORGANISM: Artificial Sequence
<220> FEATURE:
<223> OTHER INFORMATION: SLPI-d synthetic primer

<400> SEQUENCE: 160
acaccccaaa cccaacaagg aggaagcctg                                   30

<210> SEQ ID NO 161
<211> LENGTH: 30
<212> TYPE: DNA
<213> ORGANISM: Artificial Sequence
<220> FEATURE:
<223> OTHER INFORMATION: SLPI-e synthetic primer

<400> SEQUENCE: 161
caggcttcct ccttgttggg tttggggtgt                                   30

<210> SEQ ID NO 162
<211> LENGTH: 30
<212> TYPE: DNA
<213> ORGANISM: Artificial Sequence
<220> FEATURE:
<223> OTHER INFORMATION: SLPI-g synthetic primer

<400> SEQUENCE: 162
gcggccgctc aagctttcac aggggaaacg                                   30

<210> SEQ ID NO 163
<211> LENGTH: 28
<212> TYPE: DNA
<213> ORGANISM: Artificial Sequence
<220> FEATURE:
<223> OTHER INFORMATION: 1031H-a synthetic primer

<400> SEQUENCE: 163
ggggaattcc atgggatgga gccggatc                                     28
```

```
<210> SEQ ID NO 164
<211> LENGTH: 22
<212> TYPE: DNA
<213> ORGANISM: Artificial Sequence
<220> FEATURE:
<223> OTHER INFORMATION: mIgG2b-c synthetic primer

<400> SEQUENCE: 164
tgaacacaga ccactcacca tg                                              22

<210> SEQ ID NO 165
<211> LENGTH: 21
<212> TYPE: DNA
<213> ORGANISM: Artificial Sequence
<220> FEATURE:
<223> OTHER INFORMATION: mIgG2b-a synthetic primer

<400> SEQUENCE: 165
gggccagtgg atagactgat g                                               21

<210> SEQ ID NO 166
<211> LENGTH: 22
<212> TYPE: DNA
<213> ORGANISM: Artificial Sequence
<220> FEATURE:
<223> OTHER INFORMATION: IGKV4-1-a synthetic primer

<400> SEQUENCE: 166
gcattgtgaa ctgagctaca ac                                              22

<210> SEQ ID NO 167
<211> LENGTH: 22
<212> TYPE: DNA
<213> ORGANISM: Artificial Sequence
<220> FEATURE:
<223> OTHER INFORMATION: IgK-d synthetic primer

<400> SEQUENCE: 167
gacatcgtga tgacccagtc tc                                              22

<210> SEQ ID NO 168
<211> LENGTH: 24
<212> TYPE: DNA
<213> ORGANISM: Artificial Sequence
<220> FEATURE:
<223> OTHER INFORMATION: rIgK-a synthetic primer

<400> SEQUENCE: 168
agatacagtt ggtgcagcat cagc                                            24

<210> SEQ ID NO 169
<211> LENGTH: 30
<212> TYPE: DNA
<213> ORGANISM: Artificial Sequence
<220> FEATURE:
<223> OTHER INFORMATION: 13HcS-EcoR synthetic primer

<400> SEQUENCE: 169
ggaattccat ggaatgtaac tggatacttc                                      30

<210> SEQ ID NO 170
<211> LENGTH: 30
<212> TYPE: DNA
<213> ORGANISM: Artificial Sequence
<220> FEATURE:
<223> OTHER INFORMATION: 13HcA-Nhe synthetic primer

<400> SEQUENCE: 170
```

```
ctagctagcg ctggagacgg tgactgaggt                                              30
```

<210> SEQ ID NO 171
<211> LENGTH: 29
<212> TYPE: DNA
<213> ORGANISM: Artificial Sequence
<220> FEATURE:
<223> OTHER INFORMATION: 13LcS-EcoR synthetic primer

<400> SEQUENCE: 171

```
ggaattccat ggagacagac acactcctg                                               29
```

<210> SEQ ID NO 172
<211> LENGTH: 30
<212> TYPE: DNA
<213> ORGANISM: Artificial Sequence
<220> FEATURE:
<223> OTHER INFORMATION: 13LcA-BsiW synthetic primer

<400> SEQUENCE: 172

```
caccgtacgt ttgatttcca gcttggtccc                                              30
```

<210> SEQ ID NO 173
<211> LENGTH: 5
<212> TYPE: PRT
<213> ORGANISM: Artificial Sequence
<220> FEATURE:
<223> OTHER INFORMATION: Synthetic peptide F1024 Heavy chain CDR1

<400> SEQUENCE: 173

Asp Tyr Ala Met Asn
1               5

<210> SEQ ID NO 174
<211> LENGTH: 17
<212> TYPE: PRT
<213> ORGANISM: Artificial Sequence
<220> FEATURE:
<223> OTHER INFORMATION: Synthetic peptide F1024 Heavy chain CDR2

<400> SEQUENCE: 174

Trp Ile Asn Thr Gln Thr Gly Lys Pro Thr Tyr Ala Asp Asp Phe Lys
1               5                   10                  15

Gln

<210> SEQ ID NO 175
<211> LENGTH: 16
<212> TYPE: PRT
<213> ORGANISM: Artificial Sequence
<220> FEATURE:
<223> OTHER INFORMATION: Synthetic peptide F1024 Heavy chain CDR3

<400> SEQUENCE: 175

Ser Thr Phe Tyr Tyr Ser Ser Tyr Ile Tyr Gly Trp Tyr Phe Asp Phe
1               5                   10                  15

<210> SEQ ID NO 176
<211> LENGTH: 11
<212> TYPE: PRT
<213> ORGANISM: Artificial Sequence
<220> FEATURE:
<223> OTHER INFORMATION: Synthetic peptide F1024 light chain CDR1

<400> SEQUENCE: 176

Lys Ala Ser Gln Asn Val Gly Ser Asn Val Asp
1               5                   10

<210> SEQ ID NO 177
<211> LENGTH: 7
<212> TYPE: PRT
<213> ORGANISM: Artificial Sequence
<220> FEATURE:
<223> OTHER INFORMATION: Synthetic peptide F1024 light chain CDR2

<400> SEQUENCE: 177

Lys Ala Ser Asn Arg Tyr Thr
1               5

<210> SEQ ID NO 178
<211> LENGTH: 10
<212> TYPE: PRT
<213> ORGANISM: Artificial Sequence
<220> FEATURE:
<223> OTHER INFORMATION: Synthetic peptide F1024 light chain CDR3

<400> SEQUENCE: 178

Met Gln Ser Asn Thr Asn Pro Pro Trp Thr
1               5                   10

<210> SEQ ID NO 179
<211> LENGTH: 30
<212> TYPE: DNA
<213> ORGANISM: Artificial Sequence
<220> FEATURE:
<223> OTHER INFORMATION: P294H-S1 synthetic primer

<400> SEQUENCE: 179
agactgaaca gggcgcacca gcctgacgag                                      30

<210> SEQ ID NO 180
<211> LENGTH: 30
<212> TYPE: DNA
<213> ORGANISM: Artificial Sequence
<220> FEATURE:
<223> OTHER INFORMATION: P294H-A1 synthetic primer

<400> SEQUENCE: 180
cagctcgtca ggctggtgcg ccctgttcag                                      30

<210> SEQ ID NO 181
<211> LENGTH: 21
<212> TYPE: DNA
<213> ORGANISM: Artificial Sequence
<220> FEATURE:
<223> OTHER INFORMATION: H1043Sdmt synthetic primer

<400> SEQUENCE: 181
cagggcggcg caggctgacg a                                               21

<210> SEQ ID NO 182
<211> LENGTH: 21
<212> TYPE: DNA
<213> ORGANISM: Artificial Sequence
<220> FEATURE:
<223> OTHER INFORMATION: H1043Admt synthetic primer

<400> SEQUENCE: 182
tcgtcagcct gcgccgccct g                                               21

<210> SEQ ID NO 183
<211> LENGTH: 30
<212> TYPE: DNA
<213> ORGANISM: Artificial Sequence -continued

```
<220> FEATURE:
<223> OTHER INFORMATION: Q295A-S1 synthetic primer

<400> SEQUENCE: 183
agggcgccgg ctcctgacga gctgcccgag                                30

<210> SEQ ID NO 184
<211> LENGTH: 30
<212> TYPE: DNA
<213> ORGANISM: Artificial Sequence
<220> FEATURE:
<223> OTHER INFORMATION: Q295A-A1 synthetic primer

<400> SEQUENCE: 184
ctcgtcagga gccggcgccc tgttcagtct                                30

<210> SEQ ID NO 185
<211> LENGTH: 30
<212> TYPE: DNA
<213> ORGANISM: Artificial Sequence
<220> FEATURE:
<223> OTHER INFORMATION: P296H-S1 synthetic primer

<400> SEQUENCE: 185
aacagggcgc cgcagcacga cgagctgccc                                30

<210> SEQ ID NO 186
<211> LENGTH: 30
<212> TYPE: DNA
<213> ORGANISM: Artificial Sequence
<220> FEATURE:
<223> OTHER INFORMATION: P296H-A1 Synthetic primer

<400> SEQUENCE: 186
ctcgggcagc tcgtcgtgct gcggcgccct                                30

<210> SEQ ID NO 187
<211> LENGTH: 27
<212> TYPE: DNA
<213> ORGANISM: Artificial Sequence
<220> FEATURE:
<223> OTHER INFORMATION: D2-R15A-s synthetic primer

<400> SEQUENCE: 187
ggcccctgcg cagccttcat ccagctc                                   27

<210> SEQ ID NO 188
<211> LENGTH: 27
<212> TYPE: DNA
<213> ORGANISM: Artificial Sequence
<220> FEATURE:
<223> OTHER INFORMATION: D2-R15A-a synthetic primer

<400> SEQUENCE: 188
gatgaaggct gcgcaggggc cccggac                                   27

<210> SEQ ID NO 189
<211> LENGTH: 21
<212> TYPE: DNA
<213> ORGANISM: Artificial Sequence
<220> FEATURE:
<223> OTHER INFORMATION: IgG4-w synthetic primer

<400> SEQUENCE: 189
aatgtcttct catgctccgt g                                         21
```

<210> SEQ ID NO 190
<211> LENGTH: 23
<212> TYPE: DNA
<213> ORGANISM: Artificial Sequence
<220> FEATURE:
<223> OTHER INFORMATION: pEF2ce-27 synthetic primer

<400> SEQUENCE: 190
catcaatgta tcttatcatc tct                    23

<210> SEQ ID NO 191
<211> LENGTH: 20
<212> TYPE: DNA
<213> ORGANISM: Artificial Sequence
<220> FEATURE:
<223> OTHER INFORMATION: TM-b synthetic primer

<400> SEQUENCE: 191
tttccccggc gcctgcacgc                        20

<210> SEQ ID NO 192
<211> LENGTH: 21
<212> TYPE: DNA
<213> ORGANISM: Artificial Sequence
<220> FEATURE:
<223> OTHER INFORMATION: TM-g  synthetic primer

<400> SEQUENCE: 192
tcctggacgg aggccgctca g                      21

<210> SEQ ID NO 193
<211> LENGTH: 29
<212> TYPE: DNA
<213> ORGANISM: Artificial Sequence
<220> FEATURE:
<223> OTHER INFORMATION: TMD 123456 synthetic primer

<400> SEQUENCE: 193
gggatcctgc agcgtggaga acggcggct              29

<210> SEQ ID NO 194
<211> LENGTH: 29
<212> TYPE: DNA
<213> ORGANISM: Artificial Sequence
<220> FEATURE:
<223> OTHER INFORMATION: TMD23456

<400> SEQUENCE: 194
gggatccacc gcatccgcga cgcagtcct              29

<210> SEQ ID NO 195
<211> LENGTH: 29
<212> TYPE: DNA
<213> ORGANISM: Artificial Sequence
<220> FEATURE:
<223> OTHER INFORMATION: TMD 3456 synthetic primer

<400> SEQUENCE: 195
gggatccgag gacgtggatg actgcatac              29

<210> SEQ ID NO 196
<211> LENGTH: 29
<212> TYPE: DNA
<213> ORGANISM: Artificial Sequence
<220> FEATURE:
<223> OTHER INFORMATION: TMD456 synthetic primer

<400> SEQUENCE: 196

```
gggatccgtg gagcccgtgg acccgtgct                                              29

<210> SEQ ID NO 197
<211> LENGTH: 35
<212> TYPE: DNA
<213> ORGANISM: Artificial Sequence
<220> FEATURE:
<223> OTHER INFORMATION: TMdomain2-Not1Bgl2 synthetic primer

<400> SEQUENCE: 197
ggagatctgc ggccgctcaa cagtcggtgc caatg                                       35

<210> SEQ ID NO 198
<211> LENGTH: 35
<212> TYPE: DNA
<213> ORGANISM: Artificial Sequence
<220> FEATURE:
<223> OTHER INFORMATION: TMdomain3-Not1Bgl2 synthetic primer

<400> SEQUENCE: 198
ggagatctgc ggccgctcac gaatgcacga gcccc                                       35

<210> SEQ ID NO 199
<211> LENGTH: 33
<212> TYPE: DNA
<213> ORGANISM: Artificial Sequence
<220> FEATURE:
<223> OTHER INFORMATION: TM(M388L)-s synthetic primer

<400> SEQUENCE: 199
ccgcacaggt gccagctgtt ttgcaaccag act                                         33

<210> SEQ ID NO 200
<211> LENGTH: 33
<212> TYPE: DNA
<213> ORGANISM: Artificial Sequence
<220> FEATURE:
<223> OTHER INFORMATION: TM(M388L)-a synthetic primer

<400> SEQUENCE: 200
agtctggttg caaaacagct ggcacctgtg cgg                                         33

<210> SEQ ID NO 201
<211> LENGTH: 15
<212> TYPE: DNA
<213> ORGANISM: Artificial Sequence
<220> FEATURE:
<223> OTHER INFORMATION: LinkerSG-4-s synthetic primer
<220> FEATURE:
<221> NAME/KEY: misc_feature
<222> LOCATION: (1)..(1)
<223> OTHER INFORMATION: phosphorylation

<400> SEQUENCE: 201
gatctggagg tggag                                                             15

<210> SEQ ID NO 202
<211> LENGTH: 15
<212> TYPE: DNA
<213> ORGANISM: Artificial Sequence
<220> FEATURE:
<223> OTHER INFORMATION: LinkerSG-4-a synthetic primer
<220> FEATURE:
<221> NAME/KEY: misc_feature
<222> LOCATION: (1)..(1)
<223> OTHER INFORMATION: phosphorylation

<400> SEQUENCE: 202
```

```
gatcctccac ctcca                                              15

<210> SEQ ID NO 203
<211> LENGTH: 5
<212> TYPE: DNA
<213> ORGANISM: Artificial Sequence
<220> FEATURE:
<223> OTHER INFORMATION: Synthetic Linker

<400> SEQUENCE: 203 ggggs                                                          5

<210> SEQ ID NO 204
<211> LENGTH: 7
<212> TYPE: DNA
<213> ORGANISM: Artificial Sequence
<220> FEATURE:
<223> OTHER INFORMATION: Synthetic Linker

<400> SEQUENCE: 204 gsggggs                                                        7

<210> SEQ ID NO 205
<211> LENGTH: 12
<212> TYPE: DNA
<213> ORGANISM: Artificial Sequence
<220> FEATURE:
<223> OTHER INFORMATION: Synthetic Linker

<400> SEQUENCE: 205
gsggggsggg gs                                                 12

<210> SEQ ID NO 206
<211> LENGTH: 17
<212> TYPE: DNA
<213> ORGANISM: Artificial Sequence
<220> FEATURE:
<223> OTHER INFORMATION: Synthetic Linker

<400> SEQUENCE: 206
gsggggsggg gsggggs                                            17

<210> SEQ ID NO 207
<211> LENGTH: 35
<212> TYPE: DNA
<213> ORGANISM: Artificial Sequence
<220> FEATURE:
<223> OTHER INFORMATION: F1024H-kozak synthetic primer

<400> SEQUENCE: 207
ggggaattcg ccgccaccat ggattggttg tggaa                        35

<210> SEQ ID NO 208
<211> LENGTH: 20
<212> TYPE: DNA
<213> ORGANISM: Artificial Sequence
<220> FEATURE:
<223> OTHER INFORMATION: IgG4-1 synthetic primer

<400> SEQUENCE: 208
gctgtgctct cggaggtgct                                         20

<210> SEQ ID NO 209
<211> LENGTH: 20
<212> TYPE: DNA
<213> ORGANISM: Artificial Sequence
```

<220> FEATURE:
<223> OTHER INFORMATION: Synthetic Primer

<400> SEQUENCE: 209
gcggcagtat gctgacacgg                                              20

<210> SEQ ID NO 210
<211> LENGTH: 30
<212> TYPE: DNA
<213> ORGANISM: Artificial Sequence
<220> FEATURE:
<223> OTHER INFORMATION: Synthetic Primer

<400> SEQUENCE: 210
gataacctga cactggacgg gaatcccttc                                   30

<210> SEQ ID NO 211
<211> LENGTH: 20
<212> TYPE: DNA
<213> ORGANISM: Artificial Sequence
<220> FEATURE:
<223> OTHER INFORMATION: Synthetic Primer

<400> SEQUENCE: 211
gccatccaga atctagcgct                                              20

<210> SEQ ID NO 212
<211> LENGTH: 30
<212> TYPE: DNA
<213> ORGANISM: Artificial Sequence
<220> FEATURE:
<223> OTHER INFORMATION: Synthetic Primer

<400> SEQUENCE: 212
gaagggattc ccgtccagtg tcaggttatc                                   30

<210> SEQ ID NO 213
<211> LENGTH: 22
<212> TYPE: DNA
<213> ORGANISM: Artificial Sequence
<220> FEATURE:
<223> OTHER INFORMATION: Synthetic Primer

<400> SEQUENCE: 213
attagccaga agtcagatgc tc                                           22

<210> SEQ ID NO 214
<211> LENGTH: 19
<212> TYPE: DNA
<213> ORGANISM: Artificial Sequence
<220> FEATURE:
<223> OTHER INFORMATION: Synthetic Primer

<400> SEQUENCE: 214
gggcattggc cacaccagc                                               19

<210> SEQ ID NO 215
<211> LENGTH: 543
<212> TYPE: PRT
<213> ORGANISM: Artificial Sequence
<220> FEATURE:
<223> OTHER INFORMATION: Synthetic fusion protein F1024S-D2(4)

<400> SEQUENCE: 215

Met Asp Trp Leu Trp Asn Leu Leu Phe Leu Met Val Val Ala Gln Ser
1               5                   10                  15

```
Ala Gln Ala Gln Ile Gln Leu Val Gln Ser Gly Pro Glu Leu Lys Lys
            20                  25                  30

Pro Gly Glu Ser Val Lys Ile Ser Cys Lys Ala Ser Gly Tyr Thr Phe
        35                  40                  45

Thr Asp Tyr Ala Met Asn Trp Val Lys Gln Ala Pro Gly Asn Gly Leu
50                      55                  60

Lys Trp Met Gly Trp Ile Asn Thr Gln Thr Gly Lys Pro Thr Tyr Ala
65                  70                  75                  80

Asp Asp Phe Lys Gln Arg Phe Val Phe Ser Leu Glu Thr Ser Ala Ser
                85                  90                  95

Thr Ala Tyr Leu Gln Ile Asn Asn Leu Asn Ile Glu Asp Thr Ala Thr
            100                 105                 110

Tyr Phe Cys Thr Arg Ser Thr Phe Tyr Ser Ser Tyr Ile Tyr Gly
        115                 120                 125

Trp Tyr Phe Asp Phe Trp Gly Pro Gly Thr Met Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Lys Thr
    210                 215                 220

Tyr Thr Cys Asn Val Asp His Lys Pro Ser Asn Thr Lys Val Asp Lys
225                 230                 235                 240

Arg Val Glu Ser Lys Tyr Gly Pro Pro Gly Pro Ser Gly Pro Ala Pro
                245                 250                 255

Glu Phe Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser Gln Glu Asp Pro Glu Val Gln Phe Asn Trp Tyr Val Asp
290                 295                 300

Gly Val Glu Val His Asn Ala Lys Thr Lys Pro Arg Glu Glu Gln Phe
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
            340                 345                 350

Pro Ser Ser Ile Glu Lys Thr Ile Ser Lys Ala Lys Gly Gln Pro Arg
        355                 360                 365

Glu Pro Gln Val Tyr Thr Leu Pro Pro Ser Gln Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Arg Leu Thr Val Asp Lys Ser Arg Trp Gln Glu Gly Asn Val Phe Ser
        435                 440                 445
```

-continued

Cys Ser Val Met His Glu Ala Leu His Asn His Tyr Thr Gln Lys Ser
        450                 455                 460

Leu Ser Leu Ser Leu Gly Lys Gly Ser Thr Val Ala Ala Cys Asn Leu
465                 470                 475                 480

Pro Ile Val Ser Gly Pro Cys Thr Ala Phe Ile Lys Leu Trp Ala Phe
                485                 490                 495

Asp Ala Val Lys Gly Lys Cys Val Leu Phe Pro Tyr Gly Gly Cys Gln
                500                 505                 510

Gly Asn Gly Asn Lys Phe Asp Ser Glu Lys Glu Cys Arg Glu Tyr Cys
                515                 520                 525

Gly Val Pro Gly Asp Gly Asp Glu Glu Leu Leu Arg Phe Ser Asn
                530                 535                 540

<210> SEQ ID NO 216
<211> LENGTH: 673
<212> TYPE: PRT
<213> ORGANISM: Artificial Sequence
<220> FEATURE:
<223> OTHER INFORMATION: Synthetic fusion protein F1024S-TM23456L

<400> SEQUENCE: 216

Met Asp Trp Leu Trp Asn Leu Leu Phe Leu Met Val Val Ala Gln Ser
1               5                   10                  15

Ala Gln Ala Gln Ile Gln Leu Val Gln Ser Gly Pro Glu Leu Lys Lys
                20                  25                  30

Pro Gly Glu Ser Val Lys Ile Ser Cys Lys Ala Ser Gly Tyr Thr Phe
            35                  40                  45

Thr Asp Tyr Ala Met Asn Trp Val Lys Gln Ala Pro Gly Asn Gly Leu
50                  55                  60

Lys Trp Met Gly Trp Ile Asn Thr Gln Thr Gly Lys Pro Thr Tyr Ala
65                  70                  75                  80

Asp Asp Phe Lys Gln Arg Phe Val Phe Ser Leu Glu Thr Ser Ala Ser
                85                  90                  95

Thr Ala Tyr Leu Gln Ile Asn Asn Leu Asn Ile Glu Asp Thr Ala Thr
            100                 105                 110

Tyr Phe Cys Thr Arg Ser Thr Phe Tyr Tyr Ser Ser Tyr Ile Tyr Gly
        115                 120                 125

Trp Tyr Phe Asp Phe Trp Gly Pro Gly Thr Met Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Lys Thr
    210                 215                 220

Tyr Thr Cys Asn Val Asp His Lys Pro Ser Asn Thr Lys Val Asp Lys
225                 230                 235                 240

Arg Val Glu Ser Lys Tyr Gly Pro Pro Gly Pro Ser Gly Pro Ala Pro
                245                 250                 255

Glu Phe Leu Gly Gly Pro Ser Val Phe Leu Phe Pro Pro Lys Pro Lys
            260                 265                 270

-continued

```
Asp Thr Leu Met Ile Ser Arg Thr Pro Glu Val Thr Cys Val Val Val
        275                 280                 285

Asp Val Ser Gln Glu Asp Pro Glu Val Gln Phe Asn Trp Tyr Val Asp
290                 295                 300

Gly Val Glu Val His Asn Ala Lys Thr Lys Pro Arg Glu Glu Gln Phe
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
                340                 345                 350

Pro Ser Ser Ile Glu Lys Thr Ile Ser Lys Ala Lys Gly Gln Pro Arg
        355                 360                 365

Glu Pro Gln Val Tyr Thr Leu Pro Pro Ser Gln Glu Glu Met Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
        420                 425                 430

Arg Leu Thr Val Asp Lys Ser Arg Trp Gln Glu Gly Asn Val Phe Ser
        435                 440                 445

Cys Ser Val Met His Glu Ala Leu His Asn His Tyr Thr Gln Lys Ser
450                 455                 460

Leu Ser Leu Ser Leu Gly Lys Gly Ser Thr Ala Ser Ala Thr Gln Ser
465                 470                 475                 480

Cys Asn Asp Leu Cys Glu His Phe Cys Val Pro Asn Pro Asp Gln Pro
                485                 490                 495

Gly Ser Tyr Ser Cys Met Cys Glu Thr Gly Tyr Arg Leu Ala Ala Asp
        500                 505                 510

Gln His Arg Cys Glu Asp Val Asp Asp Cys Ile Leu Glu Pro Ser Pro
        515                 520                 525

Cys Pro Gln Arg Cys Val Asn Thr Gln Gly Gly Phe Glu Cys His Cys
530                 535                 540

Tyr Pro Asn Tyr Asp Leu Val Asp Gly Glu Cys Val Glu Pro Val Asp
545                 550                 555                 560

Pro Cys Phe Arg Ala Asn Cys Glu Tyr Gln Cys Gln Pro Leu Asn Gln
                565                 570                 575

Thr Ser Tyr Leu Cys Val Cys Ala Glu Gly Phe Ala Pro Ile Pro His
        580                 585                 590

Glu Pro His Arg Cys Gln Leu Phe Cys Asn Gln Thr Ala Cys Pro Ala
        595                 600                 605

Asp Cys Asp Pro Asn Thr Gln Ala Ser Cys Glu Cys Pro Glu Gly Tyr
610                 615                 620

Ile Leu Asp Asp Gly Phe Ile Cys Thr Asp Ile Asp Glu Cys Glu Asn
625                 630                 635                 640

Gly Gly Phe Cys Ser Gly Val Cys His Asn Leu Pro Gly Thr Phe Glu
                645                 650                 655

Cys Ile Cys Gly Pro Asp Ser Ala Leu Ala Arg His Ile Gly Thr Asp
        660                 665                 670

Cys

<210> SEQ ID NO 217
<211> LENGTH: 543
```

```
<212> TYPE: PRT
<213> ORGANISM: Artificial Sequence
<220> FEATURE:
<223> OTHER INFORMATION: Synthetic humanized F1024S-D2(3)

<400> SEQUENCE: 217

Met Asp Trp Thr Trp Ser Ile Leu Phe Leu Val Ala Ala Thr Gly
1               5                   10                  15

Thr Tyr Ser Gln Val Gln Leu Val Gln Ser Gly His Glu Val Lys Gln
            20                  25                  30

Pro Gly Ala Ser Val Lys Val Ser Cys Lys Ala Ser Gly Tyr Ser Phe
            35                  40                  45

Thr Asp Tyr Ala Met Asn Trp Val Lys Gln Ala Pro Gly Gln Gly Leu
        50                  55                  60

Glu Trp Met Gly Trp Ile Asn Thr Gln Thr Gly Lys Pro Thr Tyr Ala
65                  70                  75                  80

Asp Asp Phe Lys Gln Arg Phe Val Phe Ser Met Asp Thr Ser Ala Ser
                85                  90                  95

Thr Ala Tyr Leu Gln Ile Ser Ser Leu Lys Ala Glu Asp Met Ala Met
            100                 105                 110

Tyr Tyr Cys Ala Arg Ser Thr Phe Tyr Ser Ser Tyr Ile Tyr Gly
            115                 120                 125

Trp Tyr Phe Asp Phe Trp Gly Gln Gly Thr Met Val Thr Val Ser Ser
        130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Lys Thr
        210                 215                 220

Tyr Thr Cys Asn Val Asp His Lys Pro Ser Asn Thr Lys Val Asp Lys
225                 230                 235                 240

Arg Val Glu Ser Lys Tyr Gly Pro Pro Gly Pro Ser Gly Pro Ala Pro
                245                 250                 255

Glu Phe Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser Gln Glu Asp Pro Glu Val Gln Phe Asn Trp Tyr Val Asp
        290                 295                 300

Gly Val Glu Val His Asn Ala Lys Thr Lys Pro Arg Glu Glu Gln Phe
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
            340                 345                 350

Pro Ser Ser Ile Glu Lys Thr Ile Ser Lys Ala Lys Gly Gln Pro Arg
        355                 360                 365

Glu Pro Gln Val Tyr Thr Leu Pro Pro Ser Gln Glu Glu Met Thr Lys
        370                 375                 380

Asn Gln Val Ser Leu Thr Cys Leu Val Lys Gly Phe Tyr Pro Ser Asp
```

```
            385                 390                 395                 400
Ile Ala Val Glu Trp Glu Ser Asn Gly Gln Pro Glu Asn Asn Tyr Lys
                    405                 410                 415

Thr Thr Pro Pro Val Leu Asp Ser Asp Gly Ser Phe Phe Leu Tyr Ser
                420                 425                 430

Arg Leu Thr Val Asp Lys Ser Arg Trp Gln Glu Gly Asn Val Phe Ser
            435                 440                 445

Cys Ser Val Met His Glu Ala Leu His Asn His Tyr Thr Gln Lys Ser
        450                 455                 460

Leu Ser Leu Ser Leu Gly Lys Gly Ser Thr Val Ala Ala Cys Asn Leu
465                 470                 475                 480

Pro Ile Val Ser Gly Pro Cys Arg Ala Phe Ile Lys Leu Trp Ala Phe
                485                 490                 495

Asp Ala Val Lys Gly Lys Cys Val Leu Phe Pro Tyr Gly Gly Cys Gln
                500                 505                 510

Gly Asn Gly Asn Lys Phe Asp Ser Glu Lys Glu Cys Arg Glu Tyr Cys
            515                 520                 525

Gly Val Pro Gly Asp Gly Asp Glu Glu Leu Leu Arg Phe Ser Asn
        530                 535                 540

<210> SEQ ID NO 218
<211> LENGTH: 235
<212> TYPE: PRT
<213> ORGANISM: Artificial Sequence
<220> FEATURE:
<223> OTHER INFORMATION: Synthetic humanized F1024S-D2(3)

<400> SEQUENCE: 218

Met Glu Ala Pro Ala Gln Leu Leu Phe Leu Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Lys Ala Ser Gln Asn
        35                  40                  45

Val Gly Ser Asn Val Asp Trp Tyr Gln Gln Lys Pro Gly Gln Ala Pro
    50                  55                  60

Arg Leu Leu Ile Tyr Lys Ala Ser Asn Arg Tyr Thr Gly Ile Pro Ala
65                  70                  75                  80

Arg Phe Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Met Gln Ser Asn
            100                 105                 110

Thr Asn Pro Pro Trp Thr Phe Gly Gln Gly Thr Lys Val Glu Ile Lys
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220
```

```
Pro Val Thr Lys Ser Phe Asn Arg Gly Glu Cys
225                 230                 235

<210> SEQ ID NO 219
<211> LENGTH: 125
<212> TYPE: PRT
<213> ORGANISM: Artificial Sequence
<220> FEATURE:
<223> OTHER INFORMATION: Synthetic peptide

<400> SEQUENCE: 219

Gln Ile Gln Leu Val Gln Ser Gly Pro Glu Leu Lys Lys Pro Gly Glu
1               5                   10                  15

Ser Val Lys Ile Ser Cys Lys Ala Ser Gly Tyr Thr Phe Thr Asp Tyr
                20                  25                  30

Ala Met Asn Trp Val Lys Gln Ala Pro Gly Asn Gly Leu Lys Trp Met
            35                  40                  45

Gly Trp Ile Asn Thr Gln Thr Gly Lys Pro Thr Tyr Ala Asp Asp Phe
        50                  55                  60

Lys Gln Arg Phe Val Phe Ser Leu Glu Thr Ser Ala Ser Thr Ala Tyr
65                  70                  75                  80

Leu Gln Ile Asn Asn Leu Asn Ile Glu Asp Thr Ala Thr Tyr Phe Cys
                85                  90                  95

Thr Arg Ser Thr Phe Tyr Tyr Ser Ser Tyr Ile Tyr Gly Trp Tyr Phe
                100                 105                 110

Asp Phe Trp Gly Pro Gly Thr Ser Val Thr Val Ser Ser
            115                 120                 125

<210> SEQ ID NO 220
<211> LENGTH: 125
<212> TYPE: PRT
<213> ORGANISM: Artificial Sequence
<220> FEATURE:
<223> OTHER INFORMATION: Synthetic peptide

<400> SEQUENCE: 220

Gln Val Gln Leu Val Gln Ser Gly His Glu Val Lys Gln Pro Gly Ala
1               5                   10                  15

Ser Val Lys Val Ser Cys Lys Ala Ser Gly Tyr Ser Phe Thr Asp Tyr
                20                  25                  30

Ala Met Asn Trp Val Pro Gln Ala Pro Gly Gln Gly Leu Glu Trp Met
            35                  40                  45

Gly Trp Ile Asn Thr Gln Thr Gly Lys Pro Thr Tyr Ala Asp Asp Phe
        50                  55                  60

Lys Gln Arg Phe Val Phe Ser Met Asp Thr Ser Ala Ser Thr Ala Tyr
65                  70                  75                  80

Leu Gln Ile Ser Ser Leu Lys Ala Glu Asp Met Ala Met Tyr Tyr Cys
                85                  90                  95

Ala Arg Ser Thr Phe Tyr Tyr Ser Ser Tyr Ile Tyr Gly Trp Tyr Phe
                100                 105                 110

Asp Phe Trp Gly Gln Gly Thr Ser Val Thr Val Ser Ser
            115                 120                 125

<210> SEQ ID NO 221
<211> LENGTH: 125
<212> TYPE: PRT
<213> ORGANISM: Artificial Sequence
<220> FEATURE:
<223> OTHER INFORMATION: Synthetic peptide
```

-continued

```
<400> SEQUENCE: 221

Gln Val Gln Leu Gln Glu Ser Gly Pro Gly Leu Val Arg Pro Ser Gln
1               5                   10                  15

Thr Leu Ser Leu Thr Cys Thr Val Ser Gly Thr Phe Ser Asp Tyr
            20                  25                  30

Ala Met Asn Trp Val Arg Gln Pro Pro Gly Arg Gly Leu Glu Trp Ile
        35                  40                  45

Gly Trp Ile Asn Thr Gln Thr Gly Lys Pro Thr Tyr Ala Asp Asp Phe
    50                  55                  60

Lys Gln Arg Val Thr Met Leu Val Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Thr Phe Tyr Tyr Ser Ser Tyr Ile Tyr Gly Trp Tyr Phe
            100                 105                 110

Asp Phe Trp Gly Gln Gly Ser Leu Val Thr Val Ser Ser
        115                 120                 125

<210> SEQ ID NO 222
<211> LENGTH: 125
<212> TYPE: PRT
<213> ORGANISM: Artificial Sequence
<220> FEATURE:
<223> OTHER INFORMATION: Synthetic peptide

<400> SEQUENCE: 222

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Met Asn Trp Val Arg Gln Ala Pro Gly Gln Gly Leu Glu Trp Met
        35                  40                  45

Gly Trp Ile Asn Thr Gln Thr Gly Lys Pro Thr Tyr Ala Asp Asp Phe
    50                  55                  60

Lys Gln Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Ile Tyr Tyr Cys
                85                  90                  95

Ala Arg Ser Thr Phe Tyr Tyr Ser Ser Tyr Ile Tyr Gly Trp Tyr Phe
            100                 105                 110

Asp Phe Trp Gly Gln Gly Thr Leu Val Thr Val Ser Ser
        115                 120                 125

<210> SEQ ID NO 223
<211> LENGTH: 110
<212> TYPE: PRT
<213> ORGANISM: Artificial Sequence
<220> FEATURE:
<223> OTHER INFORMATION: Synthetic peptide

<400> SEQUENCE: 223

Asp Ile Val Met Thr Gln Ser Pro Thr Ser Ile Ser Ile Ser Val Gly
1               5                   10                  15

Glu Arg Val Thr Met Asn Cys Lys Ala Ser Gln Asn Val Gly Ser Asn
            20                  25                  30

Val Asp Trp Tyr Gln Gln Lys Thr Gly Gln Ser Pro Lys Leu Leu Ile
        35                  40                  45

Tyr Lys Ala Ser Asn Arg Tyr Thr Gly Val Pro Asp Arg Phe Thr Gly
```

```
                    50                  55                  60

Ser Gly Ser Gly Thr Asp Phe Thr Phe Thr Ile Ser Asn Met Gln Ala
 65                  70                  75                  80

Val Asp Leu Ala Val Tyr Tyr Cys Met Gln Ser Asn Thr Asn Pro Pro
                 85                  90                  95

Trp Thr Phe Gly Gly Gly Thr Lys Leu Glu Leu Lys Arg Thr
                100                 105                 110

<210> SEQ ID NO 224
<211> LENGTH: 110
<212> TYPE: PRT
<213> ORGANISM: Artificial Sequence
<220> FEATURE:
<223> OTHER INFORMATION: Synthetic peptide

<400> SEQUENCE: 224

Glu Ile Val Met Thr Gln Ser Pro Ala Thr Leu Ser Val Ser Pro Gly
 1               5                  10                  15

Glu Arg Ala Thr Leu Ser Cys Lys Ala Ser Gln Asn Val Gly Ser Asn
                20                  25                  30

Val Asp Trp Tyr Gln Gln Lys Pro Gly Gln Ala Pro Arg Leu Leu Ile
             35                  40                  45

Tyr Lys Ala Ser Asn Arg Tyr Thr Gly Ile Pro Ala Arg Phe Ser Gly
         50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Met Gln Ser Asn Thr Asn Pro Pro
                 85                  90                  95

Trp Thr Phe Gly Gln Gly Thr Lys Val Glu Ile Lys Arg Thr
                100                 105                 110

<210> SEQ ID NO 225
<211> LENGTH: 110
<212> TYPE: PRT
<213> ORGANISM: Artificial Sequence
<220> FEATURE:
<223> OTHER INFORMATION: Synthetic peptide

<400> SEQUENCE: 225

Asp Ile Gln Met Thr Gln Ser Pro Ser Ser Ile Ser Ala Ser Val Gly
 1               5                  10                  15

Asp Arg Val Thr Ile Thr Cys Lys Ala Ser Gln Asn Val Gly Ser Asn
                20                  25                  30

Val Asp Trp Tyr Gln Gln Lys Pro Gly Lys Ala Pro Lys Leu Leu Ile
             35                  40                  45

Tyr Lys Ala Ser Asn Arg Tyr Thr Gly Val Pro Ser Arg Phe Ser Gly
         50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Met Gln Ser Asn Thr Asn Pro Pro
                 85                  90                  95

Trp Thr Phe Gly Gln Gly Thr Lys Val Glu Ile Lys Arg Thr
                100                 105                 110

<210> SEQ ID NO 226
<211> LENGTH: 110
<212> TYPE: PRT
<213> ORGANISM: Artificial Sequence
<220> FEATURE:
<223> OTHER INFORMATION: Synthetic peptide
```

<400> SEQUENCE: 226

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asn Val Gly Ser Asn
            20                  25                  30

Val Asp Trp Tyr Gln Gln Lys Pro Gly Lys Ala Pro Lys Leu Leu Met
        35                  40                  45

Tyr Lys Ala Ser Asn Arg Tyr Thr Gly Val Pro Ser Arg Phe Ile Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Met Gln Ser Asn Thr Asn Pro Pro
                85                  90                  95

Trp Thr Phe Gly Gln Gly Thr Lys Val Glu Val Lys Arg Thr
            100                 105                 110

<210> SEQ ID NO 227
<211> LENGTH: 125
<212> TYPE: PRT
<213> ORGANISM: Artificial Sequence
<220> FEATURE:
<223> OTHER INFORMATION: Synthetic peptide

<400> SEQUENCE: 227

Gln Val Gln Leu Val Gln Ser Gly His Glu Val Lys Gln Pro Gly Ala
1               5                   10                  15

Ser Val Lys Val Ser Cys Lys Ala Ser Gly Tyr Ser Phe Thr Asp Tyr
            20                  25                  30

Ala Met Asn Trp Val Pro Gln Ala Pro Gly Gln Gly Leu Glu Trp Met
        35                  40                  45

Gly Trp Ile Asn Thr Gln Thr Gly Lys Pro Thr Tyr Ala Asp Asp Phe
    50                  55                  60

Lys Gln Arg Phe Val Phe Ser Met Asp Thr Ser Ala Ser Thr Ala Tyr
65                  70                  75                  80

Leu Gln Ile Ser Ser Leu Lys Ala Glu Asp Met Ala Met Tyr Tyr Cys
                85                  90                  95

Ala Arg Ser Thr Phe Tyr Tyr Ser Ser Tyr Ile Tyr Gly Trp Tyr Phe
            100                 105                 110

Asp Phe Trp Gly Gln Gly Thr Ser Val Thr Val Ser Ser
        115                 120                 125

<210> SEQ ID NO 228
<211> LENGTH: 125
<212> TYPE: PRT
<213> ORGANISM: Artificial Sequence
<220> FEATURE:
<223> OTHER INFORMATION: Synthetic peptide

<400> SEQUENCE: 228

Gln Val Gln Leu Val Gln Ser Gly His Glu Val Lys Gln Pro Gly Ala
1               5                   10                  15

Ser Val Lys Val Ser Cys Lys Ala Ser Gly Tyr Ser Phe Thr Asp Tyr
            20                  25                  30

Ala Met Asn Trp Val Lys Gln Ala Pro Gly Asn Gly Leu Lys Trp Met
        35                  40                  45

Gly Trp Ile Asn Thr Gln Thr Gly Lys Pro Thr Tyr Ala Asp Asp Phe
    50                  55                  60

```
Lys Gln Arg Phe Val Phe Ser Met Asp Thr Ser Ala Ser Thr Ala Tyr
 65                  70                  75                  80

Leu Gln Ile Ser Ser Leu Lys Ala Glu Asp Met Ala Met Tyr Tyr Cys
                 85                  90                  95

Ala Arg Ser Thr Phe Tyr Tyr Ser Tyr Ile Tyr Gly Trp Tyr Phe
            100                 105                 110

Asp Phe Trp Gly Gln Gly Thr Ser Val Thr Val Ser Ser
            115                 120                 125

<210> SEQ ID NO 229
<211> LENGTH: 125
<212> TYPE: PRT
<213> ORGANISM: Artificial Sequence
<220> FEATURE:
<223> OTHER INFORMATION: Synthetic peptide

<400> SEQUENCE: 229

Gln Val Gln Leu Val Gln Ser Gly His Glu Val Lys Gln Pro Gly Ala
 1               5                  10                  15

Ser Val Lys Val Ser Cys Lys Ala Ser Gly Tyr Ser Phe Thr Asp Tyr
                 20                  25                  30

Ala Met Asn Trp Val Lys Gln Ala Pro Gly Gln Gly Leu Glu Trp Met
             35                  40                  45

Gly Trp Ile Asn Thr Gln Thr Gly Lys Pro Thr Tyr Ala Asp Asp Phe
         50                  55                  60

Lys Gln Arg Phe Val Phe Ser Met Asp Thr Ser Ala Ser Thr Ala Tyr
 65                  70                  75                  80

Leu Gln Ile Ser Ser Leu Lys Ala Glu Asp Met Ala Met Tyr Tyr Cys
                 85                  90                  95

Ala Arg Ser Thr Phe Tyr Tyr Ser Tyr Ile Tyr Gly Trp Tyr Phe
            100                 105                 110

Asp Phe Trp Gly Gln Gly Thr Ser Val Thr Val Ser Ser
            115                 120                 125

<210> SEQ ID NO 230
<211> LENGTH: 125
<212> TYPE: PRT
<213> ORGANISM: Artificial Sequence
<220> FEATURE:
<223> OTHER INFORMATION: Synthetic peptide

<400> SEQUENCE: 230

Gln Val Gln Leu Gln Glu Ser Gly Pro Gly Leu Val Arg Pro Ser Gln
 1               5                  10                  15

Thr Leu Ser Leu Thr Cys Thr Val Ser Gly Ser Thr Phe Ser Asp Tyr
                 20                  25                  30

Ala Met Asn Trp Val Arg Gln Pro Pro Gly Arg Gly Leu Glu Trp Ile
             35                  40                  45

Gly Trp Ile Asn Thr Gln Thr Gly Lys Pro Thr Tyr Ala Asp Asp Phe
         50                  55                  60

Lys Gln Arg Val Thr Met Leu Val Asp Thr Ser Lys Asn Gln Phe Ser
 65                  70                  75                  80

Leu Arg Leu Ser Ser Val Thr Ala Ala Asp Thr Ala Val Tyr Tyr Cys
                 85                  90                  95

Ala Arg Ser Thr Phe Tyr Tyr Ser Tyr Ile Tyr Gly Trp Tyr Phe
            100                 105                 110

Asp Phe Trp Gly Gln Gly Ser Leu Val Thr Val Ser Ser
            115                 120                 125
```

```
<210> SEQ ID NO 231
<211> LENGTH: 125
<212> TYPE: PRT
<213> ORGANISM: Artificial Sequence
<220> FEATURE:
<223> OTHER INFORMATION: Synthetic peptide

<400> SEQUENCE: 231

Gln Ile Gln Leu Val Gln Ser Gly Pro Glu Leu Lys Lys Pro Gly Glu
1               5                   10                  15

Ser Val Lys Ile Ser Cys Lys Ala Ser Gly Ser Thr Phe Ser Asp Tyr
            20                  25                  30

Ala Met Asn Trp Val Arg Gln Pro Pro Gly Arg Gly Leu Glu Trp Ile
        35                  40                  45

Gly Trp Ile Asn Thr Gln Thr Gly Lys Pro Thr Tyr Ala Asp Asp Phe
    50                  55                  60

Lys Gln Arg Val Thr Met Leu Val Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Thr Phe Tyr Tyr Ser Ser Tyr Ile Tyr Gly Trp Tyr Phe
            100                 105                 110

Asp Phe Trp Gly Gln Gly Ser Leu Val Thr Val Ser Ser
        115                 120                 125

<210> SEQ ID NO 232
<211> LENGTH: 125
<212> TYPE: PRT
<213> ORGANISM: Artificial Sequence
<220> FEATURE:
<223> OTHER INFORMATION: Synthetic peptide

<400> SEQUENCE: 232

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Met Asn Trp Val Arg Gln Ala Pro Gly Gln Gly Leu Glu Trp Met
        35                  40                  45

Gly Trp Ile Asn Thr Gln Thr Gly Lys Pro Thr Tyr Ala Asp Asp Phe
    50                  55                  60

Lys Gln Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Ile Tyr Tyr Cys
                85                  90                  95

Ala Arg Ser Thr Phe Tyr Tyr Ser Ser Tyr Ile Tyr Gly Trp Tyr Phe
            100                 105                 110

Asp Phe Trp Gly Gln Gly Thr Leu Val Thr Val Ser Ser
        115                 120                 125

<210> SEQ ID NO 233
<211> LENGTH: 125
<212> TYPE: PRT
<213> ORGANISM: Artificial Sequence
<220> FEATURE:
<223> OTHER INFORMATION: Synthetic peptide

<400> SEQUENCE: 233

Gln Ile Gln Leu Val Gln Ser Gly Pro Glu Leu Lys Lys Pro Gly Glu
1               5                   10                  15
```

```
Ser Val Lys Ile Ser Cys Lys Ala Ser Gly Tyr Thr Phe Thr Asp Tyr
            20                  25                  30

Ala Met Asn Trp Val Arg Gln Ala Pro Gly Gln Gly Leu Glu Trp Met
            35                  40                  45

Gly Trp Ile Asn Thr Gln Thr Gly Lys Pro Thr Tyr Ala Asp Asp Phe
 50                  55                  60

Lys Gln Arg Val Thr Ile Thr Ala Asp Glu Ser Thr Asn Thr Ala Tyr
 65                  70                  75                  80

Met Glu Leu Ser Ser Leu Arg Ser Glu Asp Thr Ala Ile Tyr Tyr Cys
                85                  90                  95

Ala Arg Ser Thr Phe Tyr Tyr Ser Ser Tyr Ile Tyr Gly Trp Tyr Phe
                100                 105                 110

Asp Phe Trp Gly Gln Gly Thr Leu Val Thr Val Ser Ser
            115                 120                 125

<210> SEQ ID NO 234
<211> LENGTH: 91
<212> TYPE: PRT
<213> ORGANISM: Eschericia coli
<220> FEATURE:
<221> NAME/KEY: mat_peptide
<222> LOCATION: (22)..(91)

<400> SEQUENCE: 234

Met Lys Gln Ser Thr Ile Ala Leu Ala Leu Leu Pro Leu Leu Phe Thr
 -20                 -15                 -10

Pro Val Thr Lys Ala Thr Val Ala Ala Cys Asn Leu Pro Ile Val Arg
 -5                  -1   1                   5                  10

Gly Pro Cys Arg Ala Phe Ile Gln Leu Trp Ala Phe Asp Ala Val Lys
            15                  20                  25

Gly Lys Cys Val Leu Phe Pro Tyr Gly Gly Cys Gln Gly Asn Gly Asn
            30                  35                  40

Lys Phe Glu Ser Glu Lys Glu Cys Arg Glu Tyr Cys Gly Val Pro Gly
            45                  50                  55

Asp Gly Asp Glu Glu Leu Leu Arg Phe Ser Asn
 60                  65                  70

<210> SEQ ID NO 235
<211> LENGTH: 91
<212> TYPE: PRT
<213> ORGANISM: Eschericia coli
<220> FEATURE:
<221> NAME/KEY: mat_peptide
<222> LOCATION: (22)..(91)

<400> SEQUENCE: 235

Met Lys Gln Ser Thr Ile Ala Leu Ala Leu Leu Pro Leu Leu Phe Thr
 -20                 -15                 -10

Pro Val Thr Lys Ala Asp Asp Ala Ala Cys Asn Leu Pro Ile Val Arg
 -5                  -1   1                   5                  10

Gly Pro Cys Arg Ala Phe Ile Lys Leu Trp Ala Phe Asp Ala Val Lys
            15                  20                  25

Gly Lys Cys Val Leu Phe Pro Tyr Gly Gly Cys Gln Gly Asn Gly Asn
            30                  35                  40

Lys Phe Tyr Ser Glu Lys Glu Cys Arg Glu Tyr Cys Gly Val Pro Gly
            45                  50                  55

Asp Gly Asp Glu Glu Leu Leu Arg Phe Ser Asn
 60                  65                  70
```

-continued

```
<210> SEQ ID NO 236
<211> LENGTH: 89
<212> TYPE: PRT
<213> ORGANISM: Eschericia coli
<220> FEATURE:
<221> NAME/KEY: mat_peptide
<222> LOCATION: (22)..(89)

<400> SEQUENCE: 236

Met Lys Gln Ser Thr Ile Ala Leu Ala Leu Leu Pro Leu Leu Phe Thr
    -20                 -15                 -10

Pro Val Thr Lys Ala Ala Ala Cys Asn Leu Pro Ile Val Arg Gly Pro
 -5              -1   1               5                  10

Cys Arg Ala Phe Ile Arg Leu Trp Ala Phe Asp Ala Val Lys Gly Lys
             15                  20                  25

Cys Val Leu Phe Pro Tyr Gly Gly Cys Gln Gly Asn Gly Asn Lys Phe
             30                  35                  40

Tyr Ser Glu Lys Glu Cys Arg Glu Tyr Cys Gly Val Pro Gly Asp Gly
             45                  50                  55

Asp Glu Glu Leu Leu Arg Phe Ser Asn
 60                  65

<210> SEQ ID NO 237
<211> LENGTH: 89
<212> TYPE: PRT
<213> ORGANISM: Eschericia coli
<220> FEATURE:
<221> NAME/KEY: mat_peptide
<222> LOCATION: (22)..(89)

<400> SEQUENCE: 237

Met Lys Gln Ser Thr Ile Ala Leu Ala Leu Leu Pro Leu Leu Phe Thr
    -20                 -15                 -10

Pro Val Thr Lys Ala Ala Ala Cys Asn Leu Pro Ile Val Arg Gly Pro
 -5              -1   1               5                  10

Cys Arg Ala Phe Ile Lys Leu Trp Ala Phe Asp Ala Val Lys Gly Lys
             15                  20                  25

Cys Val Leu Phe Pro Tyr Gly Gly Cys Gln Gly Asn Gly Asn Lys Phe
             30                  35                  40

Glu Ser Glu Lys Glu Cys Arg Glu Tyr Cys Gly Val Pro Gly Asp Gly
             45                  50                  55

Asp Glu Glu Leu Leu Arg Phe Ser Asn
 60                  65

<210> SEQ ID NO 238
<211> LENGTH: 89
<212> TYPE: PRT
<213> ORGANISM: Eschericia coli
<220> FEATURE:
<221> NAME/KEY: mat_peptide
<222> LOCATION: (22)..(89)

<400> SEQUENCE: 238

Met Lys Gln Ser Thr Ile Ala Leu Ala Leu Leu Pro Leu Leu Phe Thr
    -20                 -15                 -10

Pro Val Thr Lys Ala Ala Ala Cys Asn Leu Pro Ile Val Glu Gly Pro
 -5              -1   1               5                  10

Cys Arg Ala Phe Ile Gln Leu Trp Ala Phe Asp Ala Val Lys Gly Lys
             15                  20                  25

Cys Val Leu Phe Pro Tyr Gly Gly Cys Gln Gly Asn Gly Asn Lys Phe
             30                  35                  40
```

Glu Ser Glu Lys Glu Cys Arg Glu Tyr Cys Gly Val Pro Gly Asp Gly
        45                  50                  55

Asp Glu Glu Leu Leu Arg Phe Ser Asn
 60                  65

<210> SEQ ID NO 239
<211> LENGTH: 89
<212> TYPE: PRT
<213> ORGANISM: Eschericia coli
<220> FEATURE:
<221> NAME/KEY: mat_peptide
<222> LOCATION: (22)..(89)

<400> SEQUENCE: 239

Met Lys Gln Ser Thr Ile Ala Leu Ala Leu Leu Pro Leu Leu Phe Thr
        -20                 -15                 -10

Pro Val Thr Lys Ala Ala Ala Cys Asn Leu Pro Ile Val Arg Gly Pro
 -5              -1   1               5                   10

Cys Arg Ala Phe Ile Arg Leu Trp Ala Phe Asp Ala Val Lys Gly Lys
             15                  20                  25

Cys Val Leu Phe Pro Tyr Gly Gly Cys Gln Gly Asn Gly Asn Lys Phe
         30                  35                  40

Glu Ser Glu Lys Glu Cys Arg Glu Tyr Cys Gly Val Pro Gly Asp Gly
        45                  50                  55

Asp Glu Glu Leu Leu Arg Phe Ser Asn
 60                  65

<210> SEQ ID NO 240
<211> LENGTH: 101
<212> TYPE: PRT
<213> ORGANISM: Eschericia coli
<220> FEATURE:
<221> NAME/KEY: mat_peptide
<222> LOCATION: (34)..(101)

<400> SEQUENCE: 240

Met Lys Gln Ser Thr Ile Ala Leu Ala Leu Leu Pro Leu Leu Phe Thr
        -30                 -25                 -20

Pro Val Thr Lys Ala Ala Val Leu Pro Gln Glu Glu Glu Gly Ser Gly
        -15                 -10                 -5

Met Ala Ala Cys Asn Leu Pro Ile Val Arg Gly Pro Cys Arg Ala Phe
 -1  1               5                   10                  15

Ile Lys Leu Trp Ala Phe Asp Ala Val Lys Gly Lys Cys Val Leu Phe
             20                  25                  30

Pro Tyr Gly Gly Cys Gln Gly Asn Gly Asn Lys Phe Asp Ser Glu Lys
         35                  40                  45

Glu Cys Arg Glu Tyr Cys Gly Val Pro Gly Asp Gly Asp Glu Glu Leu
         50                  55                  60

Leu Arg Phe Ser Asn
         65

<210> SEQ ID NO 241
<211> LENGTH: 101
<212> TYPE: PRT
<213> ORGANISM: Eschericia coli
<220> FEATURE:
<221> NAME/KEY: mat_peptide
<222> LOCATION: (34)..(101)

<400> SEQUENCE: 241

Met Lys Gln Ser Thr Ile Ala Leu Ala Leu Leu Pro Leu Leu Phe Thr

-continued

```
                -30                 -25                 -20
Pro Val Thr Lys Ala Ala Val Leu Pro Gln Glu Glu Glu Gly Ser Gly
        -15                 -10                  -5

Met Ala Ala Cys Asn Leu Pro Ile Val Arg Gly Pro Cys Arg Ala Phe
 -1  1               5                  10                  15

Ile Arg Leu Trp Ala Phe Asp Ala Val Lys Gly Lys Cys Val Leu Phe
                 20                  25                  30

Pro Tyr Gly Gly Cys Gln Gly Asn Gly Asn Lys Phe Asp Ser Glu Lys
             35                  40                  45

Glu Cys Arg Glu Tyr Cys Gly Val Pro Gly Asp Gly Asp Glu Glu Leu
             50                  55                  60

Leu Arg Phe Ser Asn
             65

<210> SEQ ID NO 242
<211> LENGTH: 101
<212> TYPE: PRT
<213> ORGANISM: Eschericia coli
<220> FEATURE:
<221> NAME/KEY: mat_peptide
<222> LOCATION: (34)..(101)

<400> SEQUENCE: 242

Met Lys Gln Ser Thr Ile Ala Leu Ala Leu Leu Pro Leu Leu Phe Thr
                -30                 -25                 -20

Pro Val Thr Lys Ala Ala Val Leu Pro Gln Glu Glu Glu Gly Ser Gly
        -15                 -10                  -5

Met Ala Ala Cys Asn Leu Pro Ile Val Gln Gly Pro Cys Arg Ala Phe
 -1  1               5                  10                  15

Ile Lys Leu Trp Ala Phe Asp Ala Val Lys Gly Lys Cys Val Leu Phe
                 20                  25                  30

Pro Tyr Gly Gly Cys Gln Gly Asn Gly Asn Lys Phe Asp Ser Glu Lys
             35                  40                  45

Glu Cys Arg Glu Tyr Cys Gly Val Pro Gly Asp Gly Asp Glu Glu Leu
             50                  55                  60

Leu Arg Phe Ser Asn
             65

<210> SEQ ID NO 243
<211> LENGTH: 101
<212> TYPE: PRT
<213> ORGANISM: Eschericia coli
<220> FEATURE:
<221> NAME/KEY: mat_peptide
<222> LOCATION: (34)..(101)

<400> SEQUENCE: 243

Met Lys Gln Ser Thr Ile Ala Leu Ala Leu Leu Pro Leu Leu Phe Thr
                -30                 -25                 -20

Pro Val Thr Lys Ala Ala Val Leu Pro Gln Glu Glu Glu Gly Ser Gly
        -15                 -10                  -5

Met Ala Ala Cys Asn Leu Pro Ile Val Asp Gly Pro Cys Arg Ala Phe
 -1  1               5                  10                  15

Ile Lys Leu Trp Ala Phe Asp Ala Val Lys Gly Lys Cys Val Leu Phe
                 20                  25                  30

Pro Tyr Gly Gly Cys Gln Gly Asn Gly Asn Lys Phe Asp Ser Glu Lys
             35                  40                  45

Glu Cys Arg Glu Tyr Cys Gly Val Pro Gly Asp Gly Asp Glu Glu Leu
             50                  55                  60
```

```
Leu Arg Phe Ser Asn
        65

<210> SEQ ID NO 244
<211> LENGTH: 101
<212> TYPE: PRT
<213> ORGANISM: Eschericia coli
<220> FEATURE:
<221> NAME/KEY: mat_peptide
<222> LOCATION: (34)..(101)

<400> SEQUENCE: 244

Met Lys Gln Ser Thr Ile Ala Leu Ala Leu Leu Pro Leu Leu Phe Thr
            -30                 -25                 -20

Pro Val Thr Lys Ala Ala Val Leu Pro Gln Glu Glu Glu Gly Ser Gly
        -15                 -10                  -5

Met Ala Ala Cys Asn Leu Pro Ile Val Leu Gly Pro Cys Arg Ala Phe
 -1   1               5                  10                  15

Ile Lys Leu Trp Ala Phe Asp Ala Val Lys Gly Lys Cys Val Leu Phe
                20                  25                  30

Pro Tyr Gly Gly Cys Gln Gly Asn Gly Asn Lys Phe Asp Ser Glu Lys
            35                  40                  45

Glu Cys Arg Glu Tyr Cys Gly Val Pro Gly Asp Gly Asp Glu Glu Leu
        50                  55                  60

Leu Arg Phe Ser Asn
        65

<210> SEQ ID NO 245
<211> LENGTH: 101
<212> TYPE: PRT
<213> ORGANISM: Eschericia coli
<220> FEATURE:
<221> NAME/KEY: mat_peptide
<222> LOCATION: (34)..(101)

<400> SEQUENCE: 245

Met Lys Gln Ser Thr Ile Ala Leu Ala Leu Leu Pro Leu Leu Phe Thr
            -30                 -25                 -20

Pro Val Thr Lys Ala Ala Val Leu Pro Gln Glu Glu Glu Gly Ser Gly
        -15                 -10                  -5

Met Ala Ala Cys Asn Leu Pro Ile Val Glu Gly Pro Cys Arg Ala Phe
 -1   1               5                  10                  15

Ile Lys Leu Trp Ala Phe Asp Ala Val Lys Gly Lys Cys Val Leu Phe
                20                  25                  30

Pro Tyr Gly Gly Cys Gln Gly Asn Gly Asn Lys Phe Glu Ser Glu Lys
            35                  40                  45

Glu Cys Arg Glu Tyr Cys Gly Val Pro Gly Asp Gly Asp Glu Glu Leu
        50                  55                  60

Leu Arg Phe Ser Asn
        65

<210> SEQ ID NO 246
<211> LENGTH: 68
<212> TYPE: PRT
<213> ORGANISM: Eschericia coli
<220> FEATURE:
<221> NAME/KEY: mat_peptide
<222> LOCATION: (34)..(68)

<400> SEQUENCE: 246

Ala Ala Cys Asn Leu Pro Ile Val Ser Gly Pro Cys Arg Ala Phe Ile
```

```
                  -30              -25                -20
Lys Leu Trp Ala Phe Asp Ala Val Lys Gly Lys Cys Val Leu Phe Pro
        -15              -10                -5

Tyr Gly Gly Cys Gln Gly Asn Gly Asn Lys Phe Asp Ser Lys Glu
 -1  1           5               10                   15

Cys Arg Glu Tyr Cys Gly Val Pro Gly Asp Gly Asp Glu Glu Leu Leu
                20              25                   30

Arg Phe Ser Asn
            35

<210> SEQ ID NO 247
<211> LENGTH: 68
<212> TYPE: PRT
<213> ORGANISM: Eschericia coli
<220> FEATURE:
<221> NAME/KEY: misc_feature
<223> OTHER INFORMATION: AN68 polypeptide

<400> SEQUENCE: 247

Ala Ala Cys Asn Leu Pro Ile Val Arg Gly Pro Cys Arg Ala Phe Ile
 1               5                  10                  15

Gln Leu Trp Ala Phe Asp Ala Val Lys Gly Lys Cys Val Leu Phe Pro
            20                  25                  30

Tyr Gly Gly Cys Gln Gly Asn Gly Asn Lys Phe Tyr Ser Glu Lys Glu
            35                  40                  45

Cys Arg Glu Tyr Cys Gly Val Pro Gly Asp Gly Asp Glu Glu Leu Leu
            50                  55                  60

Arg Phe Ser Asn
65

<210> SEQ ID NO 248
<211> LENGTH: 68
<212> TYPE: PRT
<213> ORGANISM: Eschericia coli
<220> FEATURE:
<221> NAME/KEY: mat_peptide
<222> LOCATION: (34)..(68)

<400> SEQUENCE: 248

Ala Ala Cys Asn Leu Pro Ile Val Asn Gly Pro Cys Arg Ala Phe Ile
              -30              -25                -20

Lys Leu Trp Ala Phe Asp Ala Val Lys Gly Lys Cys Val Leu Phe Pro
        -15              -10                -5

Tyr Gly Gly Cys Gln Gly Asn Gly Asn Lys Phe Asp Ser Glu Lys Glu
 -1  1           5               10                   15

Cys Arg Glu Tyr Cys Gly Val Pro Gly Asp Gly Asp Glu Glu Leu Leu
                20              25                   30

Arg Phe Ser Asn
            35

<210> SEQ ID NO 249
<211> LENGTH: 68
<212> TYPE: PRT
<213> ORGANISM: Eschericia coli
<220> FEATURE:
<221> NAME/KEY: mat_peptide
<222> LOCATION: (34)..(68)

<400> SEQUENCE: 249

Ala Ala Cys Asn Leu Pro Ile Val Ala Gly Pro Cys Arg Ala Phe Ile
              -30              -25                -20
```

```
Lys Leu Trp Ala Phe Asp Ala Val Lys Gly Lys Cys Val Leu Phe Pro
        -15                 -10                  -5
Tyr Gly Gly Cys Gln Gly Asn Gly Asn Lys Phe Asp Ser Glu Lys Glu
 -1  1               5                  10                   15
Cys Arg Glu Tyr Cys Gly Val Pro Gly Asp Gly Glu Glu Leu Leu
             20                  25                  30
Arg Phe Ser Asn
            35
```

<210> SEQ ID NO 250
<211> LENGTH: 89
<212> TYPE: PRT
<213> ORGANISM: Eschericia coli
<220> FEATURE:
<221> NAME/KEY: mat_peptide
<222> LOCATION: (22)..(89)

<400> SEQUENCE: 250

```
Met Lys Gln Ser Thr Ile Ala Leu Ala Leu Leu Pro Leu Leu Phe Thr
    -20                 -15                 -10
Pro Val Thr Lys Ala Ala Ala Cys Asn Leu Pro Ile Val Arg Gly Pro
 -5              -1  1               5                   10
Cys Arg Ala Phe Ile Gln Leu Trp Ala Phe Asp Ala Val Lys Gly Lys
             15                  20                  25
Cys Val Leu Phe Pro Tyr Gly Gly Cys Gln Gly Asn Gly Asn Lys Phe
            30                  35                  40
Glu Ser Glu Lys Glu Cys Arg Glu Tyr Cys Gly Val Pro Gly Asp Gly
            45                  50                  55
Asp Glu Glu Leu Leu Arg Phe Ser Asn
 60                  65
```

<210> SEQ ID NO 251
<211> LENGTH: 89
<212> TYPE: PRT
<213> ORGANISM: Eschericia coli
<220> FEATURE:
<221> NAME/KEY: mat_peptide
<222> LOCATION: (22)..(89)

<400> SEQUENCE: 251

```
Met Lys Gln Ser Thr Ile Ala Leu Ala Leu Leu Pro Leu Leu Phe Thr
    -20                 -15                 -10
Pro Val Thr Lys Ala Ala Ala Cys Asn Leu Pro Ile Val Arg Gly Pro
 -5              -1  1               5                   10
Cys Arg Ala Phe Ile Lys Leu Trp Ala Phe Asp Ala Val Lys Gly Lys
             15                  20                  25
Cys Val Leu Phe Pro Tyr Gly Gly Cys Gln Gly Asn Gly Asn Lys Phe
            30                  35                  40
Tyr Ser Glu Lys Glu Cys Arg Glu Tyr Cys Gly Val Pro Gly Asp Gly
            45                  50                  55
Asp Glu Glu Leu Leu Arg Phe Ser Asn
 60                  65
```